United States Patent [19]

Williams et al.

[11] Patent Number: 5,256,626

[45] Date of Patent: Oct. 26, 1993

[54] HERBICIDAL COMPOSITIONS SAFENED BY 5-HETEROCYCLIC-SUBSTITUTED OXAZOLIDINE DIHALOACETAMIDES COMPOUNDS

[75] Inventors: Eric L. Williams, St. Peters; Steven M. Massey, Maryland Heights; Brett H. Bussler, St. Peters; Ronald J. Brinker, St. Louis, all of Mo.

[73] Assignee: Monsanto Company, St. Louis, Mo.

[21] Appl. No.: 725,136

[22] Filed: Jul. 3, 1991

Related U.S. Application Data

[60] Division of Ser. No. 212,621, Jul. 1, 1988, which is a continuation-in-part of Ser. No. 84,786, Aug. 13, 1987, abandoned.

[51] Int. Cl.$^5$ .............................. A01N 25/32
[52] U.S. Cl. ........................ 504/107; 504/104; 504/105; 504/106; 504/108; 504/206; 504/212; 504/214; 504/227; 504/253; 504/244; 504/260; 504/265; 504/275; 504/276; 504/280; 504/283; 504/300; 504/314; 504/340; 504/341; 504/342
[58] Field of Search ............... 71/88, 118; 504/107, 504/104, 105, 106

[56] References Cited

U.S. PATENT DOCUMENTS

| | | | |
|---|---|---|---|
| 4,483,706 | 11/1984 | Teach | 71/88 |
| 4,531,966 | 7/1985 | Green | 71/93 |
| 4,900,350 | 2/1990 | Ronchi | 71/88 |

FOREIGN PATENT DOCUMENTS

| | | | |
|---|---|---|---|
| 8667002 | 7/1987 | Australia | 548/216 |
| 0136016 | 4/1985 | European Pat. Off. | |
| 0190105 | 8/1986 | European Pat. Off. | 548/216 |
| 2806265 | 1/1980 | Fed. Rep. of Germany | |
| 8408583 | 5/1985 | South Africa | |
| 873821 | 12/1987 | South Africa | 548/216 |

Primary Examiner—Allen J. Robinson
Assistant Examiner—Brian Bembenick
Attorney, Agent, or Firm—William I. Andress

[57] ABSTRACT

The disclosure herein relates to a new family of haloalkyl oxazolidinyl derivatives as antidotal compounds to reduce injury to crop plants by a variety of herbicides. The antidotal compounds are characterized particularly by having heterocyclyl or spiroheterocyclyl radicals attached to the 5-position of haloalkyl oxazolidine compounds and are especially useful as in-can antidotes against injury by acetanilide and thiocarbamate herbicides to corn, sorghum, soybeans, wheat, rice and other crops.

81 Claims, No Drawings

HERBICIDAL COMPOSITIONS SAFENED BY 5-HETEROCYCLIC-SUBSTITUTED OXAZOLIDINE DIHALOACETAMIDES COMPOUNDS

This application is a division of copending application U.S. Ser.No. 07/212,621, filed Jul, 1, 1988, (pending) which is a continuation-in-part of application U.S. Ser. No. 084,786, filed Aug. 13, 1987, now abandoned.

FIELD OF THE INVENTION

Herbicide antidotes are well-known crop protection chemicals. Of particular interest herein is a class of certain 5-heterocyclic-substituted oxazolidine and thiazolidine dihaloacetamide compounds found effective as antidotes for protecting crop plants from herbicide injury.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antidotes" or "safeners".

There are described in the literature various dihaloacyl oxazolidinyl and thiazolidinyl compounds containing a variety of substitutions on the oxazolidinyl or thiazolidinyl moiety, which compounds are known as antidotes, or safeners, for various herbicidal compounds in various crops. For example, a number of patents describe such dihaloacyl oxazolidinyl compounds having as substituents on the oxazolidinyl ring hydrogen, alkyl, cycloalkyl, spirocycloalkyl, alkoxyalkyl, alkanol, heterocycyl, aryl or aryloxyalkyl moieties, which compounds are used as antidotes for herbicides such as α-haloacetanilides or thiocarbamates in various crops. Typical of such patents are U.S. Pat. Nos. 3,959,304, 3,989,503, 4,072,688, 4,137,070, 4,124,372, 4,186,130, 4,197,110, 4,249,932, 4,256,481, 4,618,361 and 4,708,735 and EP Nos. 0054278, 0,147,365, 190,105 and 0,234,036, None of the above patents or any other known to the inventors herein disclose any dihaloacyl oxazolidinyl or thiazolidinyl compounds directly substituted with a heterocyclic radical in the 5-position. The above EP 190,105 discloses one dichloroacetyl oxazolidine compound having a furyl radical in the 2-position; that compound is not within the generic scope of the defined dichloroacetyl oxazolidine antidotes in that patent. The EP 0,234,036 discloses a great variety of dichloroacetic acid amide derivatives including various heterocyclic radicals such as 1, 3-oxazolidines which may be further substituted in non-designated positions with any of a plurality of radicals including the pyridyl and piperidinyl radicals, but the patent fails to exemplify any such compounds.

An effective herbicide must provide a relatively high level of control of grassy or broadleaf weeds, or both, in the presence of crops in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

SUMMARY OF THE INVENTION

A novel family of compounds useful as antidotes against herbicide injury to crops is provided by 5-heterocyclic-substituted oxazolidine dihaloacetamide compounds embraced by the general formula:

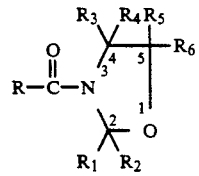

and agriculturally-acceptable salts thereof wherein
R is haloalkyl;
R, is $C_{1-4}$ alkyl, haloalkyl or phenyl;
$R_2$-$R_5$ are H or $C_{1-4}$ alkyl;
$R_6$ is a saturated or unsaturated $C_{5-10}$ heterocyclic radical containing 1 or 2 oxygen, nitrogen or sulfur atoms, optionally substituted with a $C_{1-4}$ alkyl or haloalkyl radical or halogen atom or with oxygen on a ring nitrogen atom; and
$R_5$ and $R_6$ may be combined to form a spiroheterocyclic ring as defined for the $R_6$ radical.

The term "haloalkyll" embraces radicals wherein any one or more of the carbon atoms, preferably from 1 to 4 in number, is substituted with one or more halo groups, preferably selected from bromo, chloro and fluoro. Specifically embraced by the term "haloalkyll" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Preferred haloalkyl R members are dihalomethyl, particularly dichloromethyl, while the preferred haloalkyl $R_1$ member is a tri-halogenated methyl radical, preferably trifluoromethyl.

Where the term "alkyll" is used either alone or in compound form (as in "haloalkyll"), it is intended to embrace linear or branched radicals having up to four carbon atoms, the preferred members being methyl and ethyl.

Also included in this invention are the stereo and optical isomers of compounds within the class defined by the above formula.

The heterocyclic $R_6$ member, alone or combined with the $R_5$ member to form a spiroheterocyclic radical through the 5-position carbon atom of the oxazolidinyl radical, can be saturated or unsaturated and contains five to ten ring members of which at least one member is a heterocyclic oxygen, nitrogen or sulfur atom. The heterocyclic ring may contain as many as four hetero atoms which may be the same or mixtures of said hetero atoms. The heterocyclic members of preference are the furanyl, thienyl and pyridinyl radicals. The heterocyclic ring may be substituted with one or more $C_{1-4}$ alkyl or haloalkyl radicals or with a halogen, preferably chloro, atom and with oxygen on a nitrogen hetero atom. As an $R_6$ member per se the heterocyclic ring must be attached directly to the 5-position of the oxazolidinone ring without any intervening moieties therebetween, e.g., an alkylene group.

It is further within the purview of this invention that in alternative embodiments, the oxazolidinyl radical may be substituted with a heterocyclic or spiroheterocyclic ring at the 2- and/or 4- carbon atoms, as described above for such substitutions on the 5- position carbon atom.

By "agriculturally-acceptable salts" of the compounds defined by the above formula is meant a salt or salts which readily ionize in aqueous media to form a cation of said compounds and a salt anion, which salts have no deleterious effect on the antidotal properties of said compounds or of the herbicidal properties of a given herbicide and which permit formulation of the herbicide-antidote composition without undue problems of mixing, suspension, stability, applicator equipment use, packaging, etc.

By "antidotally-effective" is meant the amount of antidote required to reduce the phytotoxicity level or effect of a herbicide, preferably by at least 10% or 15%, but naturally the greater the reduction in herbicidal injury the better.

By "herbicidally-effective" is meant the amount of herbicide required to effect a meaningful injury or destruction to a significant portion of affected undesirable plants or weeds. Although of no hard and fast rule, it is desirable from a commercial viewpoint that 80-85% or more of the weeds be destroyed, although commercially significant suppression of weed growth can occur at much lower levels, particularly with some very noxious, herbicide-resistant plants.

The preferred species of antidotal compounds according to this invention are
oxazolidine, 3-(dichloroacetyl)-5-(2-thienyl)-2,2-dimethyl-.
oxazolidine, 3-(dichloroacetyl)-5-(2-furanyl)-2,2-dimethyl-, and
oxazolidine, 3-(dichloroacetyl)-5-(3-pyridyly-2,2-dimethyl-.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

As further detailed infra, while not necessary, the composition containing the herbicide-antidote combination may also contain other additaments, e.g., biocides such as insecticides, fungicides, nematocides, miticides, etc., fertilizers, inert formulation aids, e.g., surfactants, emulsifiers, defoamers, dyes, etc.

Herbicides which may be used with benefit in combination with an antidote of the described class include preferably thiocarbamates (including dithiocarbamates), acetamides, heterocyclyl phenyl ethers (especially phenoxypyrazoles), imidazolinones, pyridines, and sulfonylureas. It is within the purview of this invention that the novel class of antidotal compounds be used with other classes of herbicides, e.g., triazines, ureas, diphenyl ethers, nitroanilines, thiazoles, isoxazoles, etc., the individual members of which classes may be derivatives having one or more substituents selected from a wide variety of radicals. Such combinations can be used to obtain selective weed control with low crop injury in several varieties of monocotyledonous crop plants such as corn, grain sorghum (milo), and cereals such as wheat, rice, barley, oats, and rye, as well as several varieties of dicotyledonous crop plants including oilseed crops such as soybeans and cotton. Particular utility for the antidotal compounds of this invention has been experienced with various herbicides in corn, sorghum and soybeans.

Examples of important thiocarbamate herbicides are the following:
cis-/trans-2,3-dichloroallyl-diisopropylthiolcarbamate (common name "diallate");
ethyl dipropylthiocarbamate (common name "EPTC");
S-ethyl diisobutyl (thiocarbamate) (common name "butylate");
S-propyl dipropyl(thiocarbamate) (common name "vernolate");
2,3,3-trichloroallyl-diisopropylthiolcarbamate (common name "triallate");

Examples of important acetamide herbicides are the following:
2-chloro-N-isopropylacetanilide (common name "propachlor");
2-chloro-1',6'-diethyl-N-(methoxymethyl)-acetanilide (common name "alachlor");
2-chloro-2',6'-diethyl-N-(butoxymethyl)-acetanilide (common name "butachlor");
2- chloro-N-(ethoxymethyl)-6'-ethyl-α-acetetoluidide (common name "acetochlor");
ethyl ester of N-chloroacetyl-N-(2,6-diethylphenyl)glycine (common name "diethatyl ethyl");
2-chloro-N-(2,6-dimethylphenyl)-N-(2-methoxyethyl)acetamide (common name "dimethachlor");
2-chloro-N-(2-methoxy-l-methylethyl)-6'-ethyl-o-acetotoluidide (common name "metolachlor");
2-chloro-2'-methyl-6'-methoxy-N-(isopropoxymethyl)acetanilide;

2-chloro-2',6'-dimethyl-N-(1-pyrazol-1-yl-methyl)-acetanilide (common name "metazachlor");
2-chloro-N(2,6-dimethyl-1-cyclohexen-1-yl)-N-(1H-pyrazol-1-ylmethyl)acetamide;
2-chloro-6'-trifluoromethyl-N-(isopropoxymethyl)acetanilide;
2-chloro-2'-methyl-6'-trifluoromethyl-N-(ethoxymethyl)acetanilide;
2-chloro-2'-ethyl-6'-trifluoromethyl-N-(1-pyrazolyl-1-ylmethyl)acetanilide;
2-chloro-N-isopropyl-1-(3,5,5-trimethylcyclohexen-1-yl)acetamide (common name "trimexachlor").

Examples of important pyridine herbicides include:
3-pyridinecarboxylic acid, 2-(difluoromethyl)-5-(4,5-dihydro-2-thiazolyl)-4-(2-methylpropyl)-6-(trifluoromethyl)-, methyl ester;
3-pyridinecarboxylic acid, 2-(difluoromethyl)-4-(2-methylpropyl)-5-(lH-pyrazol-l-ylcarbonyl)-6-(trifluoromethyl)-, methyl ester;
3,5-pyridine dicarbothioic acid, 2-(difluoromethyl)-4-(2-methylpropyl)-6-(trifluoromethyl)-, S,S-dimethyl ester;
3,5-pyridinedicarboxylic acid, 2-(difluoromethyl)-4-(2-methylpropyl)-6-trifluoromethyl, dimethyl ester.

Examples of important heterocyclyl phenyl ethers include:
5-(trifluoromethyl)-4-chloro-3-(3'-[l-ethoxycarbonyl]-ethoxy-4'-nitrophenoxy)-1-methylpyrazol;
5-(trifluoromethyl)-4-chloro-3-(3'-methoxy-4'-nitrophenoxy)-1-methylpyrazole;
5-(trifluoromethyl)-4-chloro-3(3'-[l-butoxycarbonyl]-ethoxy-41-nitrophenoxy)-4-methylpyrazol;
5-(trifluoromethyl)4-chloro-3-(3'-methylsulfamoylcarboroyl-1-propoxy-4'-nitrophenoxy)-4-methylpyrazol;
5-(trifluoromethyl)-4-chloro-3-(3'-propoxycarbonylmethyloxime-4'-nitrophenoxy)-1-methylpyrazole;
(±)-2-[4-[[5-(trifluoromethyl)-2-pyridinyl]oxy]phenoxy]propanoic acid (9CI).

Examples of important sulfonylureas include:
Benzenesulfonamide, 2-chloro-N-[[(4-methoxy-6-methyl-1, 3, 5-triazin-2-yl) amino]carbonyl];
Benzoic acid, 2-[[[[(4-chloro-6-methoxy-2-pyrimidinyl) amino]carbonyl]amino]sulfonyl]-ethyl ester;
2-thiophenecarboxylic acid, 3-[[[[(4,6-dimethoxy-1,3,5-triazin-2-yl)amino]carbonyl]amino]sulfonyl]-, methyl ester;
Benzoic acid, 2-[[[[(4, 6-dimethyl-2-pyrimidinyl) amino]carbonyl]amino]sulfonyl]methyl ester;
Benzenesulfonamide, 2-(2-chloroethoxy)-N-[[(4-methoxy-6-methyl-1, 3, 5-triazin-2-yl) amino]carbonyl];
Benzoic acid, 2-[[[[(4-methoxy-6-methyl-1,3,5-triazin-2-yl) amino]carbonyl]amino]sulfonyl]-methyl ester;

Examples of important imidazolinone herbicides include:
3-Quinolinecarboxylic acid, 2-[4,5-dihydro-4-methyl-4-(l-methylethyl)-5-oxo-1H-imidazol-2yl]-;
3-pyridinecarboxylic acid, 2-[4,5-dihydro-4-methyl-4-(l-methylethyl)-5-oxo-1H-imidazol-2-yl]-;
Benzoic Acid, 2-[4,5-dihydro-4-methyl-4-(1-methylethyl)-5-oxo-1H-imidazol-2- yl]-4(or 5)-methyl-;
3-pyridinecarboxylic acid, 5-ethyl-2-4,5-dihydro[4-methyl-4-(1-methylethyl)-5-oxo-1H-i az ol-2-yl]-;
3-pyridinecarboxylic acid, 2-[4,5-dihydro-4-methyl-4-(l-methylethyl)-5-oxo-1H-imidazol-2-yl]-5-methyl-, ammonium salt.

Examples of other important herbicides include:
2-Chloro-4-(ethylamino)-6-(isopropylamino)-sym-triazine;
4-Amino-6-tertbutyl-3-(methylthio)-AS-triazine-5(4H)one;
Trifluoro-2,6-dinitro-N,N-dipropyl-p-toluidine;
Benzeneamine, N-(1-ethylpropyl)-3, 4-dimethyl-2,6-dinitro-;
2-Pyrrolidinone, 3-chloro-4-(chloromethyl)-1-[3-(trifluoromethyl) phenyl], trans-;
3-Isoxazolidinone, 2-[(2-chlorophenyl) methyl]-4, 4-dimethyl-;
2-Imidazolidinone, 3-[5-(1,1-dimethylethyl)-3-isoxazolyl]-4-hydroxy-l-methyl-;
2-Chloro-4-(1-cyano-l-methylethylamino)-6-ethylamino-1,3,5-triazine;
2-Methoxy-3, 6-dichlorobenzoic acid, dimethylamine salt;
Methyl 5-(2,4-dichlorophenoxy)-2-nitrobenzoate;
1'-(Carboethoxy)ethyl 5-[2-chloro-4-(trifluoromethyl) phenoxy]-2-nitrobenzoate;
Ammonium-DL-homoalanin-4-yl (methyl) phosphinate;
2-(3,4-Dichlorophenyl)-4-methyl-1,2,4-oxadiazolidine-3,5-dione.

The herbicides of particular and preferred interest in compositions with antidotes according to this invention include each of the above-mentioned species from different chemical classes of compounds exemplified as important herbicides, particularly those of current commercial interest and use and those which may be determined of commercial utility;
alachlor,
acetochlor,
butachlor,
metolachlor,
metazochlor,
2-chloro-2'-methyl-6'-methoxy-N-(isopropoxymethyl)acetanilide,
2-chloro-2'-methyl-6'-trifluoromethyl-N-(ethoxymethyl)acetanilide, and
2-chloro-2',6'-dimethyl-N-(2-methoxyethyl)-acetanilide.

All of the above specifically-named herbicides are known in the art, except the heterocyclyl phenyl ethers which are disclosed and claimed in copending application Ser. No. 07/175,460(abandoned) assigned to the assignee herein.

Combinations may be made of any one or more of the described antidote compounds with any one or more of the herbicide compounds mentioned herein.

Of particular importance and preference herein, a number of the antidotal compounds of the invention have been found to be especially versatile as "in-can" safeners or antidotes for use with a plurality of herbicides in a plurality of crops. Of special mention here is the use of the antidotes, oxazolidine, 3-(dichloroacetyl)-5-(2-furanyl)-2,2-dimethyl-; oxazolidine, 3-(dichloroacetyl)-5-(3-pyridyl)-2,2-dimethyl- and oxazolidine, 3-(dichloroacetyl)-5-(2-thienyl)-2,2-dimethyl-, to reduce the phytotoxicity of alachlor (active ingredient in LASSO ® herbicide) in corn and grain sorghum. The just-named antidotes have similarly been found to be particularly efficacious against acetochlor (active ingredient in HARNESS ® herbicide) in corn, sorghum and soybeans. And some of these antidotes, particularly the 5-(2-thienyl)oxazolidine compound, have also exhibited antidotal properties against butachlor (active ingredient in MACHETE® herbicide) in rice, particularly at higher rates, e.g., 8.96 kg/ha.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous manner, but more complex, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides in various crops than in others. Thus, while a given antidotal compound may have no crop protective ability against a given herbicide in a given crop, that same antidotal compound may have a very high crop protective ability against the same given herbicide in a different crop or against a different herbicide in the same crop. This is an expected phenomenon.

DETAILED DESCRIPTION OF THE INVENTION

Antidote Compound Preparation

The antidote compounds of the invention may be prepared by the following exemplary general procedures described in Examples 1–38.

These examples are presented for purposes of illustration only and are not intended as a restriction on the scope of the invention. All parts are by weight unless otherwise indicated.

Table I sets forth analytical data for 38 specific compounds prepared in accordance with these procedures.

Example 1

Preparation of 3-(Dichloroacetyl)-2,2-Dimethyl-5-(2-Thienyl)-oxazolidine

2-Thiophenecarboxaldehyde (28.3g, 0.252 mol) was added to a mixture of cyanotrimethylsilane (25 g, 0.252 mol) and zinc iodide (1 mg), and the mixture was stirred at room temperature under nitrogen for 2 hours. The resulting silylcyanohydrin was distilled directly from the pot (BP 95° C. @1.5 torr) yielding 50.9g (96%) of a pale yellow oil.

The silylcyanohydrin (0.241 mol) was taken up in 100 mL of anhydrous ether and was added dropwise to 13.7g (0.361 mol) of lithium aluminum hydride in 400 mL of anhydrous ether under nitrogen cooled in an ice bath. The green colored reaction was stirred overnight then cooled in an ice bath, and was carefully quenched with 20 mL of water followed by 20 mL of 10% NaOH. After stirring for 30 min. anhydrous sodium sulfate was added and the mixture was filtered through celite. The filter cake was rinsed with THF and the filtrate was concentrated to give a solid which was recrystallized from methylene chloride - ether to give 25g (72%) of α-(aminomethyl)-2-thiophenemethanol; MP 80°–82° C.

Twelve grams (12.0g, 83.8 mmol) of the product in the preceding paragraph and acetone (9.7g, 0.168 mol) in 85 mL of 1,2-dichloroethane were refluxed for 2 hours using a reverse water separator. Resulting mixture was concentrated giving an oil which was distilled to give 12.33g (80%) of 2,2-dimethyl-5-(2-thienyl)-oxazolidine, as a pale yellow oil (BP 102°–105° C. @1.5 torr).

To a stirred mixture of 4.0 g (21.83 mmol) of the product of the preceding paragraph in a biphasic mixture of 40 mL of methylene chloride ($CH_2Cl_2$) and 20 mL of 10% NAOH cooled in an ice bath was added 2.5 mL (26.19 mmol) of dichloroacetyl chloride dropwise. The mixture was stirred for 20 min. and the layers separated. The aqueous layer was extracted with $CH_2Cl_2$ and the combined organic layers dried over anhydrous magnesium sulfate ($MgSO_4$). The product was purified by chromatography on silica gel (Waters Prep. 500A, 10% ethyl-acetate-hexanes) and recrystallization from methylcyclohexane to give 3.87g (60%) of the title compound. MP 104°–105° C.

Examples 2–5

Following substantially the same procedure described in Example 1, but substituting the appropriate heterocyclic aldehyde, the antidotal compounds of Examples 2–5 were prepared. These compounds are identified by structure and physical properties in Table 1 herein.

Example 6

Example 6 is prepared using the same basic procedure as Example 1 with the following modifications. The starting material for Example 1, 2-thiophenecarboxaldehyde, is replaced by 3-furaldehyde. In addition, a benzene reflux is used to azeotrope water rather than 1,2-dichloroethane when forming the oxazolidine ring with acetone. The dichloroacetylation step is effected by placing 11.2 grams (0.067 mol) 2,2-dimethyl-5-(3-furan)-oxazolidine in methylene chloride at 0° C. with 9.5 g (0.094 mol) triethylamine and adding dropwise 11.8 grams (0.08 mol) dichloroacetyl chloride. The reaction mixture is washed with water and the organics dried with $MgSO_4$. Concentration and chromatography with 10% ethylacetate-hexanes gives 5.1 grams (65%) of white solid; m.p. 90°–91° C.

Examples 7–12

Following the same procedure described in Example 6, but substituting the appropriate heterocyclic aldehyde, the antidotal compounds of Examples 7–12 were prepared. These compounds are described by structure and physical properties in Table 1 herein.

Example 13

Following the procedure described in Example 1, but substituting diethyl ketone for acetone, the compound identified as Example 13 in Table 1 was prepared and characterized.

Examples 14 and 15

The compounds of Examples 14 and 15 in Table 1 were prepared in accordance with the basic procedure of Example 1 above, substituting 2-furaldehyde and 3,-methyl-2-thiophenecarboxaldehyde, respectively, for 2-thiophenecarboxaldehyde and acetaldehyde for acetone, and with the following additional modification in Example 14. In Example 14 the oxazolidine ring is formed by placing 5.0 grams (0.04 mol) 1-furanmethanol alpha-(aminomethyl)- and 1.8 grams (0.04 mol) acetaldehyde in methylene chloride in the presence Of $MgSO_4$ for 2 hours. After filtration and then cooling to 0° C., 4.3 g (0.06 mol) pyridine was added. After the addition of 6.9 grams (0.05 mol) dichloroacetyl chloride the reaction mixture is washed with water and the organics are dried over MgSOhd. Concentration and chromatography with 10% ethyl acetate-hexanes gives 2.0 grams (19%) of colorless oil.

Example 16

Following substantially the same procedure as in Example 14, but substituting propionaldehyde instead of acetaldehyde, the product identified as Example 16 in Table 1 was produced.

Example 17

In similar manner, when the procedure of Example 14 was repeated using benzaldehyde instead of acetaldehyde, there was obtained the product of Example 17 as identified in Table 1.

Examples 18 and 19

To prepare antidotal compounds according to the invention having mixed halogen atoms at the 3-haloacyl position, the procedure of Example 6 was repeated, but substituting bromochloroacetyl chloride as the acylating agent instead of dichloroacetyl chloride. In this manner, the compounds identified in Table 1 as Examples 18 and 19 were prepared and characterized.

Example 20

Pyridine, 3-[3-(dichloroacetyl)-2,2-dimethyl-5-oxazolidinyl]-

To a cooled stirring solution of 15 grams (0.25 mol) nitromethane and 0.35 gram (0.005 mol) diethylamine in 26 milliliters of ethanol was added dropwise 10 grams (0.093 mol) 3-pyridine carboxaldehyde. The reaction was stirred for 3 hours at 0° C. then warmed to ambient temperature. Concentration yielded crude 1-(3-pyridyl)-2-nitroethanol.

The above product was dissolved in ethyl alcohol and added to 8 grams of 10% palladium on carbon. The mixture was hydrogenated in a Parr Shaker at 45 psi until 3 mol equivalents of hydrogen were reacted. Filtration through celite and concentration yielded a crude 2-(3-pyridyl)-2-hydroxy-1-aminoethane.

The product of the preceding paragraph and 10.9 grams (0.19 mol) acetone were stirred in 150 milliliters benzene and refluxed for 4 hours in a Dean-Stark apparatus to remove water. The reaction mixture was decanted from any solid and concentrated to a crude pyridine, 3-(2,2-dimethyloxazolidinyl)-.

The oxazolidinyl compound of the preceding step and 10.3 grams (0.102 mol) triethylamine were stirred at 0° C. in $CH_2Cl_2$. 12.9 grams (0.088 mol) dichloroacetyl chloride were added dropwise and the reaction mixture was stirred for 30 minutes at 0° C. The reaction mixture was warmed to ambient temperature and stirred for 1 hour. The reaction was worked up by washing with water, separation and drying the organics with $Na_2SO_4$. Filtration and concentration yielded crude product which when chromatographed with 60% ethylacetate-hexanes gave 7% overall yield of the title compound (1.8 grams, cream colored solid, M.P. 111°-113° C.).

The product of this example can also be prepared according to the procedure of Example 1.

Example 21

Three (3) grams (0.01 mol) of the product of Example 20 and 1.1 gram (0.013 mol) of $NaHCO_3$ were stirred in $CH_2Cl_2$. To this mixture was added 2.15 grams (0.01 mol) of m-chloroperbenzoic acid in two portions and stirred for one hour. The reaction mixture was washed with water and dried with $MgSO_4$. The $MgSO_4$ was filtered and the $CH_2Cl_2$ was removed to yield a white solid. Flash chromatography using 20% methanol, 30% ethylacetate 50% hexanes was done on the crude product. After concentration and placing under high vacuum for 24 hours at room temperature an amorphous solid was collected. (MP=64°-70° C., 2.5 grams, 82% yield). The product was identified as pyridineoxide, 2-[3-(dichloroacetyl)2,2-dimethyl-5-oxazolidinyl]-.

Example 22

Two (2) grams (0.007 mol) of the product of Example 20 were dissolved in $CH_2Cl_2$ and 1.2 gram (0.007 mol) of methyl trifluoromethyl sulfonate was added dropwise. A colorless solid precipitated after 30 minutes which was filtered and collected under nitrogen. 2.7 grams (86% yield) of product was collected (M.P. 151°-153° C.) and identified as pyridinium, 3-[3-(dichloroacetyl)-2,2-dimethyl-5-oxazolidinyl]-1-methyl-, salt of trifluoromethane sulfonic acid (1:1).

Example 23

Caution: This procedure uses HCN which is highly toxic and requires special handling.

19.2 grams (0.2 mol) of freshly distilled 2-furaldehyde and 40 milligrains of mandelonitrile lyase (4.1.2.10) were dissolved in 480 milliliters of 50% methanol-acetate buffer (pH =5.2) 7.1 grams (0.26 mol) of HCN were added over 10 minutes with vigorous stirring to this reaction mixture. The reaction mixture was stirred for 40 minutes at room temperature and then placed under vacuum for 15 minutes to remove excess HCN. Extraction was effected using CHC13 (3×150 mls) and then the organics were dried using $MgSO_4$. After filtration and concentration, 21 grams of 83% enantiomerically pure oil, 2-(1-hydroxy-2-cyanoethyl)-furan (S) was collected. Optical rotation $[\alpha]21/D = +28.5°$ (C=5, chloroform; Lit value $[\alpha]20/D = +30.6°$ C. neat)

Seven (7.0) grams (0.057 mol) of the above product were dissolved in anhydrous ethyl ether and added dropwise to 74 milliliters of 1M ethyl ether solution of lithium aluminum hydride (LAH) under nitrogen. The reaction mixture was stirred 5 hours and then the excess LAH was destroyed by adding dropwise 5 milliliters of $H_2O$ and 5 milliliters of 10% NAOH (aq). The mixture was filtered and concentrated to give 4 grams of colorless solid (55% yield). Recrystallization from ethyl acetate - hexane yielded 2-(1-hydroxy-2-amino-ethyl)-furan (S) with a melting point equal to 74°-77° C. Optical rotation $[\alpha]21/D = -23.60$ (C=5, chloroform; Lit value $[\alpha]21/D = -28°$ C=5, chloroform)

Two (2.0) grams (0.016 mol) of the product of the preceding paragraph, 1.8 grams (0.031 mol) of acetone and 50 milliliters of benzene were stirred together at reflux for 40 hours in a Dean Stark apparatus. After 0.2 milliliters of $H_2O$ was removed, the reaction was cooled and concentrated to collect 2.58 grams (96% yield) of amber oil, 2,2-dimethyl-5-(2-furyl)oxazolidine (S).

2.58 grams (0.015 mol) of the above oxazolidine compound was dissolved in $CH_2Cl_2$ and cooled to 0° C. at which time 2.18 grams (0.02 mol) of triethylamine was added in one portion with stirring. Dropwise addition of 2.17 grams (0.019 mol) of dichloroacetyl chloride was effected and the reaction was stirred for an additional 30 minutes at 0° C. The reaction was warmed to room temperature, washed with water and the organics were dried with $Na_2SO_4$. Filtration and concentration yielded 5.0 grams of dark oil which was chromatographed using 10% ethyl acetate-hexane. 2.5 grams of colorless product were collected and identified as oxazolidine, 3-(dichloroacetyl)-5-(2-furanyl)-2,2-dimethyl-, (S); (m.p.=116°-119° C., yield =60%). Optical rotation $[\alpha]21/D = +10.8°$ (C=5, chloroform).

Example 24

Six grams (0.05 mol) of 2-(1-hydroxy-l-amino-ethyl)-furan, 2.8 grams (0.05 mol) acetic acid and 10.6 grams (0.1 mol) 1,1,1-trifluoromethyl acetone were refluxed in benzene for 1.5 hours while removing water via a Dean-Stark apparatus. The reaction mixture was concentrated and the acetic acid was removed on a Kugelrohr without heating, and then the product was distilled over at 80°-100° C. (high vacuum). 8.4 grams of colorless oil was collected (76% yield) and identified as oxazolidine, 5-(2-furanyl)-2-methyl-2-trifluoromethyl-.

One (1.0) gram (0.005 mol) of the above oxazolidine and 0.7 gram (0.005 mol) dichloroacetyl chloride were refluxed in toluene for 4 hours. The reaction mixture was concentrated and flash chromatography was run with 5% ethyl acetate-hexanes on the crude product. Three-fourth (0.75) gram (45% yield) of white solid, was collected and identified as oxazolidine, 3-(dichloroacetyl)-2-methyl-5-(2-furanyl)-2-(trifluoromethyl)-; m.p.=97°-100° C. as a mixture of diasteroisomers.

Examples 25 and 26

Following substantially the same procedure described in Example 24, but substituting 2-(1-hydroxy-1-aminoethyl)-thiophene for the -furanyl analog, 3.3 g (5.6% yield) of white solid was separated and identified as an isomeric mixture of cis- and transoxazolidine, 3-(dichloroacetyl)-2-methyl-5-(2-thienyl),-2-(trifluoromethyl)-. The diastereoisomers were separated by chromatography using 10% ethylacetate and hexanes. The isomeric compounds were recovered in a ratio of 2:1 (trans-:cis-). MP of the trans-isomer, 89°-90° C. and of the cis-isomer, 96°-97° C. The structures of these isomers were tentatively assigned by NMR and molecular modeling.

Example 27

This example describes the preparation of an antidotal compound according to the invention wherein the $R_5$ and $R_6$ members of the above generic formula are combined with the 5-carbon atom of the oxazolidine ring to form a six-membered spiroheterocyclic radical.

The process of Example 6 was repeated, except the 3-furaldehyde of that example was replaced by tetrahydrothiopyran-4-one as the starting heterocyclic radical donor. After reaction and workup as described in Example 6, there was recovered 4.5 g 56% yield) of a white-colored solid MP 137°-139° C., which was identified as 1-oxa-8-thia-3-azaspiro [4.5]-decane, 3-(dichloroacetyl)-2,2-dimethyl-.

Example 28

This example describes the preparation of an antidotal compound wherein the $R_5$ and $R_6$ members of the above generic formula are combined with the 5-carbon atom of the oxazolidinyl ring to form a 5-membered spiroheterocyclic radical.

The process according to Example 6 was repeated, except the 3-furaldehyde of that example was replaced by tetrahydrothiophene-3-one as the heterocyclic radical donor starting material. After reaction and workup as described in Example 6, 5.5g (65% yield) of a white-colored solid MP 128°-130° C., was recovered. The compound was identified as 1-oxa-7-thia-3-azaspiro [4.4]-nonane, 3-(dichloroacetyl)-2,2-di-methyl-.

Example 29

The process of Example 14 was repeated, except in this example, the starting material of Example 14 was replaced by tetrahydrothiopyran-4-one. After reaction and workup, 5.Og (65% yield) of a white-colored solid, MP 109°-111° C. was recovered. The compound was identified as 1-oxa-8-thia-3-azaspiro [4.5]-decane, 3-(dichloroacetyl)-2-methyl-.

Example 30

The process of Example 14 was followed, except the starting material of Example 14 was replaced by tetrahydrothiophene and the acetaldehyde was replaced by propionaldehyde. After workup, 5.8 g (53% yield) of a colorless oil was recovered. The compound was identified as 1-oxa-7-thia-3-azaspiro [4.4]-nonane, 3-(dichloroacetyl)-2-ethyl-.

Example 31

This example describes the preparation of an antidotal compound according to the invention, characterized by an alkyl substitution in the 4-position and by a 5-furanyl substitution.

The process of Example 20 was again repeated, except in this process 2-furaldehyde was used in place of the 3-pyridinecarboxaldehyde of Example 20 and nitroethane was used instead of nitromethane in the first step of the action.

After workup, 0.4 g (3% yield) of a white-colored solid, MP 128°-131° C. was recovered. The compound was identified as oxazolidine, 3-(3-dichloroacetyl)-5-(2-furanyl)-2,2,4-trimethyl-.

Example 32

Another antidotal compound exemplary of those of this invention is characterized by substitution of a pyrazinyl radical in the 5-position of the oxazolidine ring.

The process of this example followed that of Example 20, but for the substitution of 2-pyrazine-carboxaldehyde for the 3-pyridinecarboxaldehyde of Example 20.

After reaction and workup, 0.9 g (5% yield) of a tan-colored solid, MP 94°-96° C. was recovered. The product was identified as pyrazine, 3-[3-(dichloroacetyl)-2,2-dimethyl-5-oxazolidinyl]-.

Example 33

To a solution of 9.2 mL (0.105 mol) of oxalyl chloride in 200 mL of anhydrous methylene chloride under nitrogen at −78° C. was added 7.8 mL (0.11 mol) of anhydrous dimethylsulfoxide dropwise over several minutes. Following the addition the mixture was allowed to warm to −35° C. and after five minutes was recooled to −78° C. A solution of 10.2g (0.10 mol) of tetrahydrofurfural alcohol in 100 mL of anhydrous methylene chloride was added. The reaction was warmed to −35° C. then 70 mL (0.50 mol) of triethylamine was added over a five minute period. The reaction was recooled to −78° C. and was stirred at that temperature for two hours. The mixture was then filtered followed by washing the filtrate with 350 mL of 5% hydrochloric acid. The aqueous layers were backwashed with two portions of methylene chloride. The combined organic phases were dried over anhydrous magnesium sulfate and concentrated (>10° C., 100 torr) to ca. 20 mL volume to give a mixture of the desired aldehyde and methylene chloride. This mixture is treated with 13.3 mL (0.10 mol) of trimethylsilylcyanide and 10 mg of zinc iodide. The mildly exothermic reaction is stirred under nitrogen at room temperature for one hour followed by concentration in vacuo. The resulting oily silyl cyanohydrin was taken up in 150 mL of anhydrous ether. Cooled mixture in an ice bath under nitrogen followed by the addition of 100 mL of a 1M lithium aluminum hydride solution in ether. The reaction is mechanically stirred at room temperature for two hours and is then recooled with an ice bath followed by the cautious dropwise addition of 3 mL of water then 6 mL of a 10% sodium hydroxide solution. Diluted mixture with 200 mL of tetrahydrofuran and stirred at room temperature for 45 minutes. Anhydrous sodium sulfate was added to absorb excess water followed by filtration through celite and concentration in vacuo to give the amino alcohol as an amber oil. The amino alcohol was dissolved in 100 mL of acetone. About 5 g of anhydrous magnesium sulfate was added followed by stirring overnight at room temperature. Filtration and concentration in vacuo gave the oxazolidine as an amber oil. The oxazolidine was dissolved in 150 mL of methylene chloride followed by the addition of 75 mL of 10% sodium hydroxide. The mixture was cooled in an ice bath and was treated with 9.6 mL (0.10 mol) of dichloroacetyl chloride. The reaction was vigorously stirred for 45 minutes. The layers were then separated and the organic phase was dried over anhydrous magnesium sulfate. Thin layer chromatography (ethyl acetate:hexanes=1;1) and gas chromatography show the presence of the title product as a mixture of two diasteromers. The mixture was resolved by flash chromatography on silica gel (ethyl acetate:hexanes 1:4). The two diasteromers were isolated: (A) 3.46 g of the less polar isomer was isolated as a yellow oil n25/D=1.4991. Anal. calc'd for $C_{11}H_{17}Cl_2NO_3$: C,46.82; H,6.07; Cl,25.13. Found: C,46.52; H,6.01; Cl,25.01. (B) 2.00g of the more polar isomer as a yellow oil n25/D=1.5021. Anal. Calc'd for $C_{11}H_{17}Cl_2NO_3$: C,46.82; H,6.07; Cl25.13. Found: C,46.58; H,6.00; Cl,24.97. The overall yield for the fix steps is 19%. The product was identified as 3-(dichloroacetyl)-2,2-dimethyl-5-(tetrahydro-2-furanyl)-oxazolidine.

Example 34

Using the same basic procedure described in Example 6, but substituting monochloroacetyl chloride in the last step, the compound oxazolidine, 3-(chloroacetyl)-5-(2-furanyl)-2, 2-dimethyl was prepared.

Example 35

Following the procedure of Example 6, but substituting trichloroacetyl chloride in the last step of the reaction there was prepared oxazolidine, 5-(2-furanyl)-2,2-dimethyl-3-(trichloracetyl)-.

Example 36

Using the same procedure as Example 6, but substituting 2-thiophene-methanol for tetrahydrofurfuralalcohol and using monofluoroacetyl chloride in the last step, the compound oxazolidine, 3-(fluoroacetyl) 2,2-dimethyl-5-(2-thienyl) was prepared. MP 65°–67° C.

Example 37

The compound oxazolidine, 3-(dichloracetyl)-5-(2-thienyl)- was prepared using the same basic procedure as Example 6 with the following modifications: the cyclization of the 2-thiophenemethanol, alpha-(aminomethyl)-, with formaldehyde to form the oxazolidine ring was effected by dissolving the 2-thiophenemethanol, alpha-(aminomethyl)-, in water and then adding the formaldehyde in one portion. The resulting oil that drops out is extracted with methylene chloride and dried with anhydrous magnesium sulfate ($MgSO_4$). Filtration and concentration gave a crude product which was acetylated with dichloroacetyl chloride to give the above compound.

Example 38

The same basic procedure as in example 6 was repeated with the following modifications: the cyclization of the 2-benzofuranmethanol, alpha-(aminomethyl)-, with acetone was effected by stirring the two together at ambient temperature until a homogeneous solution resulted. After which the solution was dried with anhydrous magnesium sulfate ($MgSO_4$). Filtration and concentration gave a crude product that was acetylated to yield oxazolidine, 5-(2-benzofuranyl)-3-(dichloroacetyl)-2, 2-dimethyl- MP115°–117° C.

Various other compounds within the above generic formula and analogs thereof are specifically contemplated as within the scope of the invention. For example, compounds according to the above formula where the oxygen atom of the oxazolidinyl radical is replaced by a sulfur atom (to form the thiazolidinyl analog) and the R–R$_6$ members are as defined above may be found to have varying degrees of antidotal activity against various herbicides in various crops. Particularly contemplated are such thiazolidinyl compounds wherein R is dichloromethyl, the $R_1$–$R_5$ members hydrogen or $C_{1-4}$ alkyl and the $R_6$ member is a thienyl, furanyl, pyranyl, pyrazinyl or pyridinyl radical or the 5,5-spiro analogs thereof. Exemplary species include thiazolidine, 3-(dichloroacetyl)-5-(2-furanyl),-2,2-dimethyl-; thiazolidine, 3-(dichloroacetyl)-5-(2-thienyl)-2,2-dimethyl-; thiazolidine, 3-(dichloroacetyl-2,2-dimethyl-5-(l-methyl-1H-pyrrol-2-yl)-; thiazolidinyl, 3-(dichloroacetyl)-5-(3-pyridyl)-2,2-dimethyl-and thiazolidinyl, 3-(dichloroacetyl)-5-(2-pyrazyl)-2,2-dimethyl-. As with the oxazolidinyl analogs, the foregoing thiazolidinyl compounds and analogs thereof may be characterized as having H or other lower alkyl groups in the $R_1$–$R_5$ positions.

The antidotal compounds prepared in accordance with the foregoing working examples are listed in Table 1. The specific compounds are listed in the first column by example/antidote number ("Ex./ Antidote No.") followed by structural features according to the generic formula at the head of the table and by process yield and physical characteristics in the remaining columns.

TABLE 1
| Ex./Antidote No. | R | $R_1$ | $R_2$ | $R_3$ | $R_4$ | $R_5$ | $R_6$ | Yield (Wt. %) | MP (°C.) | Elem. | Anal. Cal'd. | Anal. F'nd |
|---|---|---|---|---|---|---|---|---|---|---|---|---|
| 1 | —CHCl$_2$ | —CH$_3$ | —CH$_3$ | H | H | H | 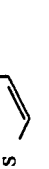 | 60 | 104–105 | C H Cl | 44.91 4.45 24.10 | 45.02 4.49 24.04 |
| 2 | —CHCl$_2$ | —CH$_3$ | —CH$_3$ | H | H | H | 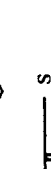 | 26 | 91–93 | C H Cl | 46.76 4.91 23.00 | 46.85 4.96 22.95 |
| 3 | —CHCl$_2$ | —CH$_3$ | —CH$_3$ | H | H | H |  | 50 | 95–96 | C H Cl | 47.50 4.71 25.49 | 47.64 4.72 25.42 |
| 4 | —CHCl$_2$ | —CH$_3$ | —CH$_3$ | H | H | H |  | 47 | 94–96 | C H Cl | 46.76 4.91 23.00 | 46.81 4.95 22.92 |
| 5 | —CHCl$_2$ | —CH$_3$ | —CH$_3$ | H | H | H |  | 47 | 84–87 | C H Cl | 44.91 4.45 24.10 | 44.98 4.46 24.01 |
| 6 | —CHCl$_2$ | —CH$_3$ | —CH$_3$ | H | H | H |  | 65 | 90–91 | C H Cl | 47.50 4.71 25.49 | 46.42 4.64 24.55 |
| 7 | —CHCl$_2$ | —CH$_3$ | —CH$_3$ | H | H | H |  | 77 | 82–84 | C H N | 46.76 4.91 4.54 | 46.82 5.02 4.46 |
| 8 | —CHCl$_2$ | —CH$_3$ | —CH$_3$ | H | H | H |  | 71 | 78–80 | C H N | 49.33 5.18 4.79 | 49.43 5.26 4.71 |

TABLE 1-continued
structure: R-C(=O)-N(R5)-C(R3)(R4)-C(R1)(R2)-O-R6... (general formula shown)
| Ex./Antidote No. | R | $R_1$ | $R_2$ | $R_3$ | $R_4$ | $R_5$ | $R_6$ | Yield (Wt. %) | MP (°C.) | Elem. | Anal. Cal'd. | F'nd |
|---|---|---|---|---|---|---|---|---|---|---|---|---|
| 9 | —CHCl$_2$ | —CH$_3$ | —CH$_3$ | H | H | H |  | 53 | 100-102-84 | C H N | 52.50 5.32 9.24 | 51.55 5.35 9.20 |
| 10 | —CHCl$_2$ | —CH$_3$ | —CH$_3$ | H | H | H |  | 57 | 107-108 | C H N | 49.50 5.54 9.62 | 39.32 5.60 9.59 |
| 11 | —CHCl$_2$ | —CH$_3$ | —CH$_3$ | H | H | H |  | 9 | 65-68 | C H N | 48.45 5.32 4.35 | 48.53 5.38 4.31 |
| 12 | —CHCl$_2$ | —CH$_3$ | —CH$_3$ | H | H | H |  | 9 | 115-116 | C H N | 33.23 2.53 7.05 | 33.21 2.57 7.04 |
| 13 | —CHCl$_2$ | —CH$_2$CH$_3$ | —CH$_2$CH$_3$ | H | H | H |  | 39 | 80-82 | C H N | 48.45 5.32 22.00 | 48.52 5.35 21.92 |
| 14 | —CHCl$_2$ | —CH$_3$ | —CH$_3$ | H | H | H |  | 19 | $N_D^{26}$ 1.5300 | C H N | 48.45 4.20 5.30 | 45.10 4.29 5.20 |
| 15 | —CHCl$_2$ | —CH$_3$ | —CH$_3$ | H | H | H |  | 63 | $N_D^{26}$ 1.5530 | C H N | 44.91 4.45 4.76 | 45.18 4.51 4.84 |

TABLE 1-continued $$\underset{R_1}{\overset{R_3}{\underset{R_1}{\overset{R_4}{\underset{R_2}{\overset{R_5}{\underset{O}{\overset{R_6}{\rightleftharpoons}}}}}}}}$$

| Ex./Antidote No. | R | $R_1$ | $R_2$ | $R_3$ | $R_4$ | $R_5$ | $R_6$ | Yield (Wt. %) | MP (°C.) | Elem. | Anal. Cal'd. | F'nd |
|---|---|---|---|---|---|---|---|---|---|---|---|---|
| 16 | —CHCl$_2$ | —C$_2$H$_5$ | —CH$_3$ | H | H | H | furan | 32 | $n_D^{24}$ 1.5160 | C<br>H<br>N | 47.50<br>4.71<br>5.04 | 47.41<br>4.69<br>4.87 |
| 17 | —CHCl$_2$ | —⟨⟩ | H | H | H | H | furan | 32 | 126–103 | C<br>H<br>N | 40.96<br>4.06<br>4.34 | 41.13<br>4.11<br>4.37 |
| 18 | —CHBrCl | —CH$_3$ | —CH$_3$ | H | H | H | furan | 45 | 102–103 | C<br>H<br>N | 40.96<br>4.06<br>4.34 | 41.13<br>4.11<br>4.37 |
| 19 | —CHBrCl | —CH$_3$ | —CH$_3$ | H | H | H | thiophene | 42 | 101–102.5 | C<br>H<br>N | 39.01<br>3.87<br>4.14 | 39.11<br>3.89<br>4.11 |
| 20 | —CHCl$_2$ | —CH$_3$ | —CH$_3$ | H | H | H | pyridine | 11 | 111–112 | C<br>H<br>N | 49.84<br>4.88<br>9.69 | 49.92<br>4.90<br>9.68 |
| 21 | —CHCl$_2$ | —CH$_3$ | —CH$_3$ | H | H | H | pyridine N-oxide | 82 | 64–70 | C<br>H<br>N | 47.23<br>4.62<br>9.18 | 46.49<br>4.84<br>8.69 |

TABLE 1-continued

R-C(=O)-N(R3R4-C(R1)(R2)-C(R5)(R6)... structure

| Ex./Antidote No. | R | $R_1$ | $R_2$ | $R_3$ | $R_4$ | $R_5$ | $R_6$ | Yield (Wt. %) | MP (°C.) | Elem. | Anal. Cal'd. | F'nd |
|---|---|---|---|---|---|---|---|---|---|---|---|---|
| 22 | —CHCl$_2$ | —CH$_3$ | —CH$_3$ | H | H | H | 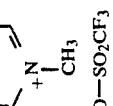 —O—SO$_2$CF$_3$ | 86 | 151–153 | C<br>H<br>N | 37.10<br>3.78<br>6.18 | 37.19<br>3.82<br>6.14 |
| 23 | —CHCl$_2$ | —CH$_3$ | —CH$_3$ | H | H | H | 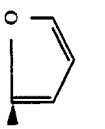 | 60 | 116–119 | C<br>H<br>N | 47.50<br>4.71<br>5.04 | 47.51<br>4.74<br>5.00 |
| 24 | —CHCl$_2$ | —CF$_3$ | —CH$_3$ | H | H | H | 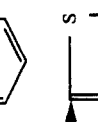 | 45 | 97–100 | C<br>H<br>N | 39.78<br>3.04<br>4.22 | 39.94<br>3.07<br>4.27 |
| 25 | —CHCl$_2$ | …CF$_3$ | …CH$_3$ | H | H | H | 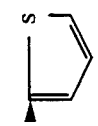 | 37 | 89–90 | C<br>H<br>N | 37.95<br>2.90<br>4.02 | 38.01<br>2.91<br>4.02 |
| 26 | —CHCl$_2$ | —CF$_3$ | —CH$_3$ | H | H | H | 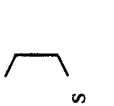 | 19 | 96–97 | C<br>H<br>N | 37.95<br>2.90<br>4.02 | 38.00<br>2.92<br>4.01 |
| 27 | —CHCl$_2$ | —CH$_3$ | —CH$_3$ | H | H | H |  | 56 | 137–139 | C<br>H<br>N | 44.30<br>5.75<br>4.70 | 44.48<br>5.73<br>4.69 |
| 28 | —CHCl$_2$ | —CH$_3$ | —CH$_3$ | H | H | H |  | 65 | 128–130 | C<br>H<br>N | 42.26<br>5.32<br>4.93 | 42.54<br>5.47<br>4.91 |

TABLE 1-continued $$\underset{R-\overset{\underset{\displaystyle\|}{O}}{C}-N}{\overset{R_3\ R_4\ R_5}{\underset{R_1\ R_2}{|\ |\ |}}}\overset{R_6}{\underset{O}{|}}$$

| Ex./Antidote No. | R | $R_1$ | $R_2$ | $R_3$ | $R_4$ | $R_5$ | $R_6$ | Yield (Wt. %) | MP (°C.) | Elem. | Anal. Cal'd. | F'nd |
|---|---|---|---|---|---|---|---|---|---|---|---|---|
| 29 | —CHCl$_2$ | —CH$_3$ | H | H | H | H | (thiane) | 65 | 109–111 | C H N | 42.26 5.32 4.93 | 42.55 5.47 4.91 |
| 30 | —CHCl$_2$ | —C$_2$H$_5$ | H | H | H | H | (thiane) | 53 | $N_D^{26}$ 1.5406 | C H N | 42.26 5.32 4.93 | 42.58 5.21 4.82 |
| 31 | —CHCl$_2$ | —CH$_3$ | —CH$_3$ | H | —CH$_3$ | H | (pyran) | 3 | 128–131 | C H N | 49.33 4.19 4.79 | 49.35 5.19 4.77 |
| 32 | —CHCl$_2$ | —CH$_3$ | —CH$_3$ | H | H | H | (pyrazine) | 5 | 94–96 | C H N | 45.53 4.53 14.49 | 44.95 4.47 14.30 |
| 33(A) | —CHCl$_2$ | —CH$_3$ | —CH$_3$ | H | H | H | (dioxane) | ⎱ 19 | Yellow Oil $N_D^{25}$ 1.5021 | C H N | 46.82 6.07 25.13 | 46.52 6.01 25.01 |
| 33(B) | —CHCl$_2$ | —CH$_3$ | —CH$_3$ | H | H | H | (pyran) | ⎰ | Yellow Oil $N_D^{25}$ 1.5021 | C H N | 46.82 6.07 25.12 | 46.58 6.00 24.97 |
| 34 | —CH$_2$Cl | —CH$_3$ | —CH$_3$ | H | H | H | (pyran) | 73 | 67–69 | C H N | 54.22 5.75 5.75 | 54.10 5.85 5.69 |
| 35 | —CCl$_3$ | —CH$_3$ | —CH$_3$ | H | H | H | (pyran) | 70 | 90–92 | C H N | 42.27 3.87 4.48 | 42.32 3.88 4.43 |

TABLE 1-continued
Structure: R—C(=O)—N(—C(R3)(R4)—C(R5)(R6)—O—C(R1)(R2)—)
| Ex./Antidote No. | R | R1 | R2 | R3 | R4 | R5 | R6 | Yield (Wt. %) | MP (°C.) | Elem. | Anal. Cal'd | Anal. F'nd |
|---|---|---|---|---|---|---|---|---|---|---|---|---|
| 36 | —CH2F | —CH3 | —CH3 | H | H | H | (thienyl) | 88 | 65–67 | C<br>H<br>N | 54.30<br>5.80<br>5.76 | 54.16<br>5.83<br>5.74 |
| 37 | —CHCl2 | H | H | H | H | H | (thienyl) | | $N_D^{20}$ 1.5790 | C<br>H<br>N | 40.62<br>3.41<br>5.26 | 40.66<br>3.43<br>5.22 |
| 38 | —CHCl2 | —CH3 | —CH3 | H | H | H | (benzofuryl) | 38 | 115–117 | C<br>H<br>N | 54.90<br>4.61<br>4.27 | 54.98<br>4.62<br>4.26 |
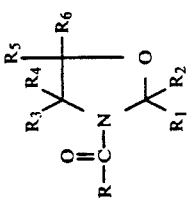

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will physically combine to form a "composition" of those agents.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-60:1 (preferably 1:5-to-30:1) parts by weight may be employed. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.1 to about 12 kilograms/hectare. The preferred range of rate of application is from about 0.4 to about 10 kg/ha. Preferably, antidote application rates range from about 0.5 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples 39–42 in greenhouse testing. Measurements of biological response as reported in Tables 2–5 were made in the following manner. A visual comparison was made between a crop plant treated with herbicide alone and crop plant having no herbicide or antidote treatment. A number was assigned to this visual comparison indicating the percent injury or inhibition to the herbicide-alone treated crop plant (column "WO" in Tables 2–5 indicating herbicide "without" antidote). Also, a visual comparison was made between the crop plant treated with herbicide + antidote combination and the crop plant having no herbicide or antidote treatment. A number was assigned to this visual comparison indicating the percent injury or inhibition to the herbicide+antidote treated crop plant (column "W" in Tables 2-5 indicating herbicide "with" antidote). Where treatments involved weed plant species, observations of response to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables 2-5 are data in parenthesis showing "safening effect" (defined below) for the herbicide+antidote combinations calculated from the plant inhibition numbers. These tables show crop or weed column headings under which there are no data. The lack of such data is not an indication of a failed test; rather it is merely an indication that the particular herbicide+antidote rate combination was not tested with that crop or weed. Summarized below is key information for interpreting data reported in Tables 2-5:

| Herbicide No. | Name |
|---|---|
| 1. | 2,3,3-trichloroallyl-N,N-diisopropyl-thiocarbamate(triallate) |
| 2. | 2-chloro-2',6'-diethyl-N-(methoxymethyl)-acetanilide (alachlor) |
| 3. | 2-chloro-2',6'-diethyl-N-(butoxymethyl)-acetanilide (butachlor) |
| 4. | 2-chloro-2',methyl-6'-methoxy-N-(isopropoxymethyl)acetanilide |
| 5. | 3,5-pyridinecarboxylic acid, 2-(difluoromethyl)-4-(2-methylpropyl)-6-trifluoromethyl, dimethyl ester |
| 6. | ethyl dipropylthiocarbamate |
| 7. | $\alpha,\alpha,\alpha$-trifluoro-2,6-dinitro-N,N-dipropyl-p-toluidine |
| 8. | 2-chloro-N-(2-methoxyethyl)-o,o-aceto-xylidide |
| 9. | 2-chloro-N-(2-methoxy-1-methylethyl)-6'-ethyl-o-acetstoluidide |
| 10. | 2-chloro-2', 6'-dimethyl-N-(1-pyrazol-1-ylmethyl)acetanilide |
| 11. | 2-chloro-2'-methyl-6'-trifluoromethyl-N-(ethoxymethyl)acetanilide |
| 12. | 2-pyrrolidinone, 3-chloro-4-(chloromethyl)-1-[3-(trifluoromethyl)phenyl]-, trans- |
| 13. | 2-chloro-N-(ethoxymethyl)-6'-ethyl-o-acetotoluide |
| 14. | cis-trans-2,3-dichloroallyl N-benzyl-dithiocarbamate |

Antidote No. = Compound in corresponding Example No.
Rate = kilograms/hectare (kg/ha).
W = % Plant Inhibition caused by combination of herbicide and antidote.
WO = % Plant Inhibition caused by herbicide alone.
Data reported in parentheses = % Safening Effect
$$(\text{---}) = \frac{WO - W}{WO} \times 100$$

Example 39

The following procedure shows interaction between a herbicide and antidote when the antidote is applied in a soil furrow containing crop seed and the herbicide is incorporated in a soil cover layer. Containers were filled and compacted with fumigated slit loam soil to a depth of about 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded furrows of the third container. Antidote application rate was 0.55 mg active compound per inch of furrow (0.22 mg/cm). This rate was comparable to a plot application rate of 0.28 kilogram per hectare (kg/ha), based on 76 cm (30") spaced-apart furrows. Then, each of the second and third containers was filled and leveled with a cover layer of soil having incorporated therein the selected herbicide at a predetermined concentration. The first container was filled and leveled with soil containing no herbicide. The containers were then placed on a bench in a greenhouse and sub-irrigated as required for the duration of the test. Plant response was observed about three weeks after initial treatment. Results are reported in Table 2.

TABLE 2

% PLANT INHIBITION AND % SAFENING EFFECT ( )

| HERB. NO. | RATE | ANTIDOTE NO. | RATE | Sorghum W | Sorghum WO | Wheat W | Wheat WO | Rice W | Rice WO | Soybean W | Soybean WO | Corn W | Corn WO |
|---|---|---|---|---|---|---|---|---|---|---|---|---|---|
| 1 | .56 | 1 | .28 | | | 90 (5) | 95 | | | | | | |
| 1 | .56 | 2 | .28 | | | 85 (10) | 95 | | | | | | |
| 1 | .56 | 3 | .28 | | | 95 (0) | 95 | | | | | | |
| 1 | .56 | 4 | .28 | | | 80 (15) | 95 | | | | | | |
| 1 | .56 | 5 | .28 | | | 80 (15) | 95 | | | | | | |
| 1 | .56 | 13 | .28 | | | 95 (0) | 95 | | | | | | |
| 1 | .56 | 6 | .28 | | | 95 (5) | 100 | | | | | | |
| 2 | 2.24 | 1 | .28 | 25 (73) | 95 | 15 (75) | 60 | | | | | | |
| 2 | 2.24 | 2 | .28 | 15 (85) | 100 | 30 (57) | 70 | | | | | | |
| 2 | 2.24 | 3 | .28 | 55 (42) | 95 | 85 (15) | 100 | | | | | | |
| 2 | 2.24 | 4 | .28 | 45 (52) | 95 | 50 (28) | 70 | | | | | | |
| 2 | 2.24 | 5 | .28 | 15 | 95 | 10 | 65 | | | | | | |

TABLE 2-continued

% PLANT INHIBITION AND % SAFENING EFFECT ( )

| HERB. NO. | RATE | ANTI-DOTE NO. | RATE | Sorghum W | WO | Wheat W | WO | Rice W | WO | Soybean W | WO | Corn W | WO |
|---|---|---|---|---|---|---|---|---|---|---|---|---|---|
| 2 | 2.24 | 13 | .28 | 35 (84) | 100 | 50 (84) | 85 | | | | | | |
| 2 | 2.24 | 6 | .28 | 35 (65) | 95 | 90 (41) | 95 | | | | | | |
| 2 | 2.24 | 27 | .28 | 45 (63) | 95 | (5) | | | | | | | |
| 2 | 2.24 | 7 | .28 | 35 (52) | 95 | | | | | | | | |
| 2 | 2.24 | 28 | .28 | 25 (63) | 95 | | | | | | | | |
| 2 | 2.24 | 8 | .28 | 10 (73) | 95 | | | | | | | | |
| 2 | 2.24 | 29 | .28 | 30 (89) | 100 | | | | | | | | |
| 2 | 2.24 | 14 | .28 | 20 (70) | 100 | | | | | | | | |
| 2 | 2.24 | 30 | .28 | 60 (80) | 100 | | | | | | | | |
| 2 | 2.24 | 15 | .28 | 30 (40) | 100 | | | | | | | | |
| 2 | 2.24 | 16 | .28 | 25 (70) | 100 | | | | | | | | |
| 2 | 2.24 | 9 | .28 | 40 (75) | 100 | | | | | | | | |
| 2 | 2.24 | 10 | .28 | 15 (60) | 100 | | | | | | | | |
| 2 | 2.24 | 11 | .28 | 15 (85) | 85 | | | | | | | | |
| 2 | 2.24 | 17 | .28 | 20 (82) | 90 | | | | | | | | |
| 2 | 2.24 | 20 | .28 | 15 (77) | 90 | | | | | | | | |
| 2 | 2.24 | 12 | .28 | 50 (83) | 95 | | | | | | | | |
| 2 | 2.24 | 18 | .28 | 35 (47) | 97 | | | | | | | | |
| 2 | 2.24 | 24 | .28 | 50 (63) | 98 | | | | | | | | |
| 2 | 2.24 | 19 | .28 | 35 (48) | 98 | | | | | | | | |
| 2 | 2.24 | 22 | .28 | 95 (64) | 92 | | | | | | | | |
| 3 | 4.48 | 1 | .28 | (0) | | | | 0 (100) | 80 | | | | |
| 3 | 4.48 | 2 | .28 | | | | | 90 (47) | 95 | | | | |
| 3 | 4.48 | 3 | .28 | | | | | 85 (10) | 95 | | | | |
| 3 | 4.48 | 4 | .28 | | | | | 70 (26) | 95 | | | | |
| 3 | 4.48 | 5 | .28 | | | | | 90 (5) | 95 | | | | |
| 3 | 4.48 | 13 | .28 | | | | | 55 (35) | 85 | | | | |
| 3 | 4.48 | 6 | .28 | | | | | 90 | 95 | | | | |
| 4 | 2.24 | 1 | .28 | | | | | | | 30 (25) | 40 | 5 (94) | 95 |
| 4 | 2.24 | 2 | .28 | | | | | | | 30 (57) | 70 | 10 (89) | 95 |
| 4 | 2.24 | 3 | .28 | | | | | | | 95 (0) | 90 | 5 (94) | 95 |
| 4 | 2.24 | 4 | .28 | | | | | | | 70 (12) | 80 | 15 (81) | 80 |
| 4 | 2.24 | 5 | .28 | | | | | | | 80 (0) | 55 | 45 (47) | 85 |
| 4 | 2.24 | 13 | .28 | | | | | | | 40 (27) | 55 | 35 (61) | 90 |
| 4 | 2.24 | 6 | .28 | | | | | | | 80 (0) | 75 | 5 (94) | 95 |
| 5 | .07 | 1 | .28 | | | 95 (5) | 100 | 90 (10) | 100 | | | | |
| 5 | .14 | 1 | .28 | | | | | | | 65 (0) | 50 | 100 (0) | 100 |
| 5 | .07 | 2 | .28 | | | 100 (0) | 100 | 90 (5) | 95 | | | | |

TABLE 2-continued

| | | | | % PLANT INHIBITION AND % SAFENING EFFECT ( ) | | | | | | | | | |
|---|---|---|---|---|---|---|---|---|---|---|---|---|---|
| HERB. | | ANTI-DOTE | | Sorghum | | Wheat | | Rice | | Soybean | | Corn | |
| NO. | RATE | NO. | RATE | W | WO | W | WO | W | WO | W | WO | W | WO |
| 5 | .14 | 2 | .28 | | | | | | | 55 (0) | 55 | 85 (10) | 95 |
| 5 | .07 | 3 | .28 | | | 50 (44) | 90 | 95 (0) | 95 | | | | |
| 5 | .14 | 3 | .28 | | | | | | | 40 (46) | 75 | 95 (0) | 95 |
| 5 | .07 | 4 | .28 | | | 90 (0) | 65 | 95 (0) | 95 | | | | |
| 5 | .14 | 4 | .28 | | | | | | | 70 (0) | 60 | 95 (0) | 95 |
| 5 | .07 | 5 | .28 | | | 95 (0) | 80 | 95 (0) | 90 | | | | |
| 5 | .14 | 5 | .28 | | | | | | | 65 (0) | 60 | 95 (0) | 85 |
| 5 | .07 | 13 | .28 | | | 85 (0) | 80 | 35 (58) | 85 | | | | |
| 5 | .14 | 13 | .28 | | | | | | | 45 (0) | 45 | 55 (38) | 90 |
| 5 | .07 | 6 | .28 | | | 90 (5) | 95 | 95 (0) | 95 | | | | |
| 5 | .14 | 6 | .28 | | | | | | | 75 (16) | 90 | 95 (0) | 95 |
| 5 | .07 | 27 | .28 | | | 95 (5) | 100 | 75 (16) | 90 | | | | |
| 5 | .14 | 27 | .28 | | | | | | | 60 (0) | 50 | 95 (0) | 95 |
| 5 | .07 | 7 | .28 | | | 95 (5) | 100 | 95 (0) | 90 | | | | |
| 5 | .14 | 7 | .28 | | | | | | | 65 (0) | 50 | 95 (0) | 95 |
| 5 | .07 | 28 | .28 | | | 100 (0) | 100 | 95 (0) | 90 | | | | |
| 5 | .14 | 28 | .28 | | | | | | | 20 (60) | 50 | 95 (0) | 95 |
| 5 | .07 | 8 | .28 | | | 100 (0) | 95 | 95 (0) | 90 | | | | |
| 5 | .14 | 8 | .28 | | | | | | | 60 (25) | 80 | 90 (5) | 95 |
| 5 | .07 | 29 | .28 | | | 100 (0) | 95 | 95 (0) | 95 | | | | |
| 5 | .14 | 29 | .28 | | | | | | | 85 (0) | 85 | 95 (0) | 95 |
| 5 | .07 | 14 | .28 | | | 90 (5) | 95 | 95 (0) | 95 | | | | |
| 5 | .14 | 14 | .28 | | | | | | | 65 (13) | 75 | 95 (0) | 95 |
| 5 | .07 | 30 | .28 | | | 95 (0) | 95 | 95 (0) | 95 | | | | |
| 5 | .14 | 30 | .28 | | | | | | | 40 (46) | 75 | 95 (0) | 95 |
| 5 | .07 | 15 | .28 | | | 100 (0) | 95 | 95 (0) | 95 | | | | |
| 5 | .14 | 15 | .28 | | | | | | | 75 (0) | 75 | 95 (0) | 95 |
| 5 | .07 | 16 | .28 | | | 100 (0) | 95 | 95 (0) | 95 | | | | |
| 5 | .14 | 16 | .28 | | | | | | | 70 (17) | 85 | 95 (0) | 95 |
| 5 | .07 | 9 | .28 | | | 100 (0) | 100 | 95 (0) | 95 | | | | |
| 5 | .14 | 9 | .28 | | | | | | | 65 (7) | 70 | 95 (0) | 95 |
| 5 | .07 | 10 | .28 | | | 95 (5) | 100 | 85 (10) | 95 | | | | |
| 5 | .14 | 10 | .28 | | | | | | | 55 (0) | 50 | 75 (21) | 95 |
| 5 | .07 | 11 | .28 | | | 100 (0) | 95 | 30 (68) | 95 | | | | |
| 5 | .14 | 11 | .28 | | | | | | | 30 (40) | 50 | 95 (0) | 85 |
| 5 | .07 | 17 | .28 | | | 100 (0) | 100 | 70 (30) | 100 | | | | |
| 5 | .14 | 17 | .28 | | | | | | | 25 (64) | 70 | 85 (5) | 90 |
| 5 | .07 | 20 | .28 | | | 100 (0) | 100 | 90 (10) | 100 | | | | |
| 5 | .14 | 20 | .28 | | | | | | | 65 | 70 | 100 | 90 |

TABLE 2-continued

| | | | | % PLANT INHIBITION AND % SAFENING EFFECT ( ) | | | | | | | | | |
|---|---|---|---|---|---|---|---|---|---|---|---|---|---|
| HERB. | | ANTI-DOTE | | Sorghum | | Wheat | | Rice | | Soybean | | Corn | |
| NO. | RATE | NO. | RATE | W | WO | W | WO | W | WO | W | WO | W | WO |
|  |  |  |  |  |  |  |  |  |  |  | (7) |  | (0) |
| 5 | .07 | 12 | .28 |  |  | 95 | 95 (0) | 65 | 95 (31) |  |  |  |  |
| 5 | .14 | 12 | .28 |  |  |  |  |  |  | 50 | 80 (81) | 70 | 95 (26) |

Example 40

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a bench in a greenhouse and sub-irrigated as required for the duration of the test. Plant response was observed about three weeks after initial treatment. Results are reported in Table 3.

TABLE 3

| HERB. NO. | HERB. RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 6 | .56 | 1 | .56 | 85 | 95 | | | | | | | | | 95 | 95 | | | | |
| 6 | .56 | 1 | 2.24 | 80 (10) | 95 | | | | | | | | | 95 (0) | 95 | | | | |
| 6 | .56 | 1 | 8.96 | 75 (15) | 95 | | | | | | | | | 75 (0) | 95 | | | | |
| 6 | 2.24 | 1 | .56 | 100 (21) | 100 | | | | | | | | | 100 (21) | 100 | | | | |
| 6 | 2.24 | 1 | 2.24 | 95 (0) | 100 | | | | | | | | | 100 (0) | 100 | | | | |
| 6 | 2.24 | 1 | 8.96 | 95 (5) | 100 | | | | | | | | | 95 (0) | 100 | | | | |
| 6 | 3.36 | 1 | .56 | | | | | | | 95 (5) | 100 | 70 (0) | 40 | | | | | | |
| 6 | 3.36 | 1 | 2.24 | | | | | | | 95 (5) | 100 | 45 (0) | 40 | | | | | | |
| 6 | 3.36 | 1 | 8.96 | | | | | | | 95 (5) | 100 | 70 (0) | 40 | | | | | | |
| 6 | 6.72 | 1 | .56 | | | | | | | 95 (5) | 100 | 15 (81) | 82 | | | | | | |
| 6 | 6.72 | 1 | 2.24 | | | | | | | 95 (5) | 100 | 85 (0) | 82 | | | | | | |
| 6 | 6.72 | 1 | 8.96 | | | | | | | 95 (5) | 100 | 50 (39) | 82 | | | | | | |
| 6 | .56 | 3 | .56 | 85 (10) | 95 | | | | | | | | | 95 (0) | 95 | | | | |
| 6 | .56 | 3 | 2.24 | 85 (10) | 95 | | | | | | | | | 95 (0) | 95 | | | | |
| 6 | .56 | 3 | 8.96 | 75 (21) | 95 | | | | | | | | | 85 (10) | 95 | | | | |
| 6 | 2.24 | 3 | .56 | 95 (5) | 100 | | | | | | | | | 100 (0) | 100 | | | | |
| 6 | 2.24 | 3 | 2.24 | 95 (5) | 100 | | | | | | | | | 95 (5) | 100 | | | | |
| 6 | 2.24 | 3 | 8.96 | 95 (5) | 100 | | | | | | | | | 95 (5) | 100 | | | | |
| 6 | 3.36 | 3 | .56 | | | | | | | 95 (5) | 100 | 70 (0) | 40 | | | | | | |
| 6 | 3.36 | 3 | 2.24 | | | | | | | 95 (5) | 100 | 30 (25) | 40 | | | | | | |
| 6 | 3.36 | 3 | 8.96 | | | | | | | 95 (5) | 100 | 75 (0) | 40 | | | | | | |
| 6 | 6.72 | 3 | .56 | | | | | | | 95 (5) | 100 | 0 (100) | 82 | | | | | | |
| 6 | 6.72 | 3 | 2.24 | | | | | | | 95 (5) | 100 | 70 (14) | 82 | | | | | | |
| 6 | 6.72 | 3 | 8.96 | | | | | | | 100 (0) | 100 | 70 (14) | 82 | | | | | | |

% PLANT INHIBITION AND % SAFENING EFFECT ( )

TABLE 3-continued

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 6 | .56 | 20 | .56 | 75 | 95 | | | | | | | | | 95 | 95 | | | | |
| 6 | .56 | 20 | 2.24 | 70 (21) | 95 | | | | | | | | | 95 (0) | 95 | | | | |
| 6 | .56 | 20 | 8.96 | 75 (26) | 95 | | | | | | | | | 95 (0) | 95 | | | | |
| 6 | 2.24 | 20 | .56 | 95 (21) | 100 | | | | | | | | | 100 (0) | 100 | | | | |
| 6 | 2.24 | 20 | 2.24 | 95 (5) | 100 | | | | | | | | | 95 (5) | 100 | | | | |
| 6 | 2.24 | 20 | 8.96 | 95 (5) | 100 | | | | | | | | | 100 (0) | 100 | | | | |
| 6 | 3.36 | 20 | .56 | | | | | | | 95 (5) | 100 | 70 (0) | 40 | | | | | | |
| 6 | 3.36 | 20 | 2.24 | | | | | | | 95 (5) | 100 | 0 (100) | 40 | | | | | | |
| 6 | 3.36 | 20 | 8.96 | | | | | | | 95 (5) | 100 | 60 (0) | 40 | | | | | | |
| 6 | 6.72 | 20 | .56 | | | | | | | 100 (0) | 100 | 100 (0) | 82 | | | | | | |
| 6 | 6.72 | 20 | 2.24 | | | | | | | 95 (5) | 100 | 30 (63) | 82 | | | | | | |
| 6 | 6.72 | 20 | 8.96 | | | | | | | 95 (5) | 100 | 50 (39) | 82 | | | | | | |
| 1 | .28 | 1 | .56 | | | 95 (0) | 95 | | | | | | | | | 100 (0) | 100 | | |
| 1 | .28 | 1 | 2.24 | | | 95 (0) | 95 | | | | | | | | | 100 (0) | 100 | | |
| 1 | .28 | 1 | 8.96 | | | 90 (5) | 95 | | | | | | | | | 100 (0) | 100 | | |
| 1 | 1.12 | 1 | .56 | | | 100 (0) | 100 | | | | | | | | | 100 (0) | 100 | | |
| 1 | 1.12 | 1 | 2.24 | | | 95 (5) | 100 | | | | | | | | | 100 (0) | 100 | | |
| 1 | 1.12 | 1 | 8.96 | | | 95 (5) | 100 | | | | | | | | | 100 (0) | 100 | | |
| 1 | .28 | 3 | .56 | | | 95 (0) | 95 | | | | | | | | | 100 (0) | 100 | | |
| 1 | .28 | 3 | 2.24 | | | 90 (5) | 95 | | | | | | | | | 100 (0) | 100 | | |
| 1 | .28 | 3 | 8.96 | | | 95 (0) | 95 | | | | | | | | | 100 (0) | 100 | | |
| 1 | 1.12 | 3 | .56 | | | 100 (5) | 100 | | | | | | | | | 100 (0) | 100 | | |
| 1 | 1.12 | 3 | 2.24 | | | 100 (0) | 100 | | | | | | | | | 100 (0) | 100 | | |
| 1 | 1.12 | 3 | 8.96 | | | 100 (0) | 100 | | | | | | | | | 100 (0) | 100 | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 1 | .28 | 20 | .56 | 70 | 97 | 90 (5) | 95 | | | | | | | | | 100 | (0) 100 | | |
| 1 | .28 | 20 | 2.24 | 50 | 42 | 70 (26) | 95 | | | | | | | | | 100 | (0) 100 | | |
| 1 | .28 | 20 | 8.96 | 5 | 53 | 95 (0) | 95 | | | | | | | | | 100 | (0) 100 | | |
| 1 | 1.12 | 20 | .56 | 45 | 97 | 95 (5) | 100 | | | | | | | | | 100 | (0) 100 | | |
| 1 | 1.12 | 20 | 2.24 | 5 | 25 | 100 (5) | 100 | | | | | | | | | 100 | (0) 100 | | |
| 1 | 1.12 | 20 | 8.96 | 40 | 32 | 95 (5) | 100 | | | | | | | | | 100 | (0) 100 | | |
| 2 | .56 | 1 | .14 | 0 | 42 | | | | | | | | | 100 | (0) 100 | | | | |
| 2 | .56 | 1 | .56 | 10 | 25 | | | | | | | | | 100 | (0) 100 | | | | |
| 2 | .56 | 1 | .56 | 10 | 53 | | | | | | | | | 98 | (0) 95 | | | | |
| 2 | .56 | 1 | .56 | 70 | 97 | | | | | | | | | 100 | (0) 98 | | | | |
| 2 | .56 | 1 | .56 | 10 | 32 | | | | | | | | | 100 | (0) 100 | | | | |
| 2 | .56 | 1 | .56 | 15 | 97 | | | | | | | | | 100 | (0) 98 | | | | |
| 2 | .56 | 1 | .56 | 15 | 90 | | | | | | | | | 98 | (0) 95 | | | | |
| 2 | .56 | 1 | .56 | 60 | 90 | | | | | | | | | 95 | (5) 100 | | | | |
| 2 | .56 | 1 | .56 | 0 | 95 | | | | | | | | | 100 | (5) 100 | | | | |
| 2 | .56 | 1 | .56 | 0 | 77 | | | | | | | | | 95 | (0) 100 | | | | |
| 2 | .56 | 1 | .56 | 20 | 60 | | | | | | | | | 100 | (5) 100 | | | | |
| 2 | .56 | 1 | .56 | 20 | 83 | | | | | | | | | 100 | (0) 98 | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 1 | .56 | 10 | 93 | | | | | | | | | 100 | 100 | | | | |
| 2 | .56 | 1 | .56 | 10 (89) | 60 | | | | | | | | | 95 (0) | 100 | | | | |
| 2 | .56 | 1 | .56 | 25 (83) | 90 | | | | | | | | | 95 (5) | 95 | | | | |
| 2 | .56 | 1 | .56 | 5 (72) | 80 | | | | | | | | | 95 (0) | 100 | | | | |
| 2 | .56 | 1 | .56 | 0 (93) | 93 | | | | | | | | | 100 (5) | 100 | | | | |
| 2 | .56 | 1 | .56 | 5 (100) | 75 | | | | | | | | | 100 (0) | 100 | | | | |
| 2 | .56 | 1 | .56 | 15 (93) | 35 | | | | | | | | | 95 (0) | 90 | | | | |
| 2 | .56 | 1 | .56 | 10 (57) | 95 | | | | | | | | | 100 (0) | 100 | | | | |
| 2 | .56 | 1 | .56 | 20 (89) | 65 | | | | | | | | | 100 (0) | 95 | | | | |
| 2 | .56 | 1 | .56 | 5 (69) | 85 | | | | | | | | | 100 (0) | 100 | | | | |
| 2 | .56 | 1 | .56 | 5 (94) | 95 | | | | | | | | | 95 (5) | 100 | | | | |
| 2 | .56 | 1 | .56 | 10 (94) | 85 | | | | | | | | | 100 (0) | 100 | | | | |
| 2 | .56 | 1 | .56 | 55 (88) | 95 | | | | | | | | | 100 (0) | 100 | | | | |
| 2 | .56 | 1 | .56 | 25 (42) | 95 | | | | | | | | | 100 (0) | 100 | | | | |
| 2 | .56 | 1 | .56 | 10 (73) | 70 | | | | | | | | | 95 (5) | 100 | | | | |
| 2 | .56 | 1 | .56 | 5 (85) | 90 | | | | | | | | | 95 (0) | 95 | | | | |
| 2 | .56 | 1 | .56 | 10 (88) | 80 | | | | | | | | | 95 (0) | 95 | | | | |
| 2 | .56 | 1 | .56 | 15 (81) | 90 | | | | | | | | | 95 (5) | 100 | | | | |
| 2 | .56 | 1 | .56 | 5 (94) | 80 | | | | | | | | | 95 (5) | 100 | | | | |
| 2 | .56 | 1 | .56 | 10 (87) | 90 | | | | | | | | | 95 (5) | 95 | | | | |
| 2 | .56 | 1 | .56 | 15 (84) | 95 | | | | | | | | | 95 (0) | 100 | | | | |
| 2 | .56 | 1 | .56 | 30 (0) | 28 | | | | | | | | | 95 (5) | 95 | | | | |
| 2 | .56 | 1 | .56 | 20 (76) | 85 | | | | | | | | | 95 (0) | 100 | | | | |
| 2 | .56 | 1 | .56 | 30 (68) | 95 | | | | | | | | | 100 (0) | 100 | | | | |
| 2 | .56 | 1 | .56 | 10 (66) | 30 | | | | | | | | | 95 (0) | 95 | | | | |

TABLE 3-continued

| | | | | | | | | | | | | | | | | | | | |
|---|---|---|---|---|---|---|---|---|---|---|---|---|---|---|---|---|---|---|---|
| | | | | colspan="16" | % PLANT INHIBITION AND % SAFENING EFFECT ( ) | | | | | | | | | | |
| HERB. NO. | RATE | ANTI-DOTE NO. | RATE | Sorghum W | | WO | Wheat W | WO | Corn W | WO | Barnyard Grass W | WO | Rice W | WO | Foxtail Green W | | WO | Wild Oats W | WO | Soybean W | WO |
| 2 | .56 | 1 | .56 | 20 | (63) | 55 | | | | | | | | | 95 | | 95 | | | | WO |
| 2 | .56 | 1 | .56 | 0 | (100) | 95 | | | | | | | | | 100 | (0) | 100 | | | | |
| 2 | .56 | 1 | .56 | 10 | (85) | 70 | | | | | | | | | 95 | (5) | 100 | | | | |
| 2 | .56 | 1 | .56 | 35 | (63) | 95 | | | | | 100 | 100 | | | | | | | | | |
| 2 | .56 | 1 | .56 | 5 | (94) | 95 | | | | | | (0) | | | 100 | (0) | 100 | | | | |
| 2 | .56 | 1 | .56 | 15 | (81) | 80 | | | | | | | | | 95 | (5) | 95 | | | | |
| 2 | .56 | 1 | .56 | 25 | (73) | 95 | | | | | | | | | 100 | (0) | 100 | | | | |
| 2 | .56 | 1 | .56 | 45 | (47) | 85 | | | | | | | | | 100 | (0) | 95 | | | | |
| 2 | .56 | 1 | .56 | 25 | (66) | 75 | | | | | | | | | 95 | (0) | 95 | | | | |
| 2 | .56 | 1 | .56 | 30 | (66) | 90 | | | | | | | | | 100 | (5) | 100 | | | | |
| 2 | .56 | 1 | .56 | 65 | (30) | 93 | | | | | | | | | 100 | (0) | 100 | | | | |
| 2 | .56 | 1 | .56 | 30 | (68) | 95 | | | | | | | | | 100 | (0) | 100 | | | | |
| 2 | .56 | 1 | .56 | 0 | (100) | 85 | | | | | | | | | 100 | (0) | 100 | | | | |
| 2 | .56 | 1 | 2.24 | 30 | (69) | 97 | | | | | | | | | 98 | (2) | 95 | | | | |
| 2 | .56 | 1 | 2.24 | 30 | (37) | 32 | | | | | | | | | 95 | (0) | (98) | | | | |
| 2 | .56 | 1 | 2.24 | 20 | (100) | 53 | | | | | | | | | 98 | (0) | 100 | | | | |
| 2 | .56 | 1 | 2.24 | 0 | (0) | 25 | | | | | | | | | 100 | (0) | 100 | | | | |
| 2 | .56 | 1 | 2.24 | 25 | (28) | 42 | | | | | | | | | 100 | (0) | 100 | | | | |
| 2 | .56 | 1 | 2.24 | 30 | (57) | 95 | | | | | | | | | 100 | (0) | 100 | | | | |
| 2 | .56 | 1 | 2.24 | 40 | (43) | 97 | | | | | | | | | 100 | (0) | 100 | | | | |
| 2 | .56 | 1 | 2.24 | 55 | (83) | 90 | | | | | | | | | 85 | (15) | 100 | | | | |
| 2 | .56 | 1 | 2.24 | 15 | (77) | 90 | | | | | | | | | 100 | (0) | 100 | | | | |
| 2 | .56 | 1 | 2.24 | 20 | (78) | 95 | | | | | | | | | 100 | (0) | 100 | | | | |
| 2 | .56 | 1 | 2.24 | 20 | (46) | 93 | | | | | | | | | 100 | (0) | 100 | | | | |
| 2 | .56 | 1 | 2.24 | 50 | | | | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 1 | 2.24 | 30 (60) | 75 | | | | | | | | | 95 | 95 | | | | |
| 2 | .56 | 1 | 2.24 | 20 (78) | 95 | | | | | | | | | 100 (0) | 100 | | | | |
| 2 | .56 | 1 | 2.24 | 35 (50) | 70 | | | | | | | | | 100 (0) | 100 | | | | |
| 2 | .56 | 1 | 2.24 | 15 (83) | 90 | | | | | | | | | 95 (0) | 95 | | | | |
| 2 | .56 | 1 | 2.24 | 10 (87) | 80 | | | | | | | | | 95 (5) | 100 | | | | |
| 2 | .56 | 1 | 2.24 | 30 (64) | 85 | | | | | | | | | 95 (0) | 95 | | | | |
| 2 | .56 | 1 | 2.24 | 35 (63) | 95 | | | | | | | | | 95 (5) | 100 | | | | |
| 2 | .56 | 1 | 2.24 | 40 (52) | 85 | | | | | | | | | 100 (0) | 100 | | | | |
| 2 | .56 | 1 | 2.24 | 5 (94) | 95 | | | | | 100 (0) | 100 | | | 100 (0) | 100 | | | | |
| 2 | .56 | 1 | 2.24 | 30 (68) | 30 | | | | | | | | | 90 (5) | 95 | | | | |
| 2 | .56 | 1 | 2.24 | 10 (66) | 90 | | | | | | | | | 100 (0) | 100 | | | | |
| 2 | .56 | 1 | 2.24 | 20 (77) | 95 | | | | | | | | | 100 (0) | 100 | | | | |
| 2 | .56 | 1 | 2.24 | 15 (84) | 55 | | | | | | | | | 95 (5) | 95 | | | | |
| 2 | .56 | 1 | 2.24 | 35 (36) | 85 | | | | | | | | | 95 (0) | 100 | | | | |
| 2 | .56 | 1 | 2.24 | 15 (82) | 28 | | | | | | | | | 90 (0) | 95 | | | | |
| 2 | .56 | 1 | 2.24 | 20 (28) | 80 | | | | | | | | | 100 (10) | 95 | | | | |
| 2 | .56 | 1 | 2.24 | 15 (81) | 95 | | | | | | | | | 100 (0) | 100 | | | | |
| 2 | .56 | 1 | 2.24 | 40 (57) | 80 | | | | | | | | | 100 (0) | 100 | | | | |
| 2 | .56 | 1 | 2.24 | 5 (93) | 93 | | | | | | | | | 95 (0) | 95 | | | | |
| 2 | .56 | 1 | 2.24 | 0 (100) | 90 | | | | | | | | | 100 (0) | 100 | | | | |
| 2 | .56 | 1 | 2.24 | 15 (83) | 85 | | | | | | | | | 95 (5) | 100 | | | | |
| 2 | .56 | 1 | 2.24 | 5 (94) | 70 | | | | | | | | | 100 (0) | 100 | | | | |
| 2 | .56 | 1 | 2.24 | 35 (50) | 70 | | | | | | | | | 90 (10) | 100 | | | | |
| 2 | .56 | 1 | 2.24 | 30 (68) | 95 | | | | | | | | | 100 (0) | 100 | | | | |

TABLE 3-continued

% PLANT INHIBITION AND % SAFENING EFFECT ( )

| HERB. NO. | RATE | ANTI- DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 1 | 2.24 | 5 | 95 | | | | | | | | | 95 | (5) | 100 | | | |
| 2 | .56 | 1 | 2.24 | 15 | (94) 100 | | | | | | | | | 100 | (0) | 100 | | | |
| 2 | .56 | 1 | 2.24 | 5 | (85) 75 | | | | | | | | | 100 | (0) | 100 | | | |
| 2 | .56 | 1 | 2.24 | 20 | (93) 80 | | | | | | | | | 100 | (0) | 100 | | | |
| 2 | .56 | 1 | 2.24 | 20 | (75) 65 | | | | | | | | | 95 | (0) | 95 | | | |
| 2 | .56 | 1 | 2.24 | 10 | (69) 60 | | | | | | | | | 100 | (0) | 100 | | | |
| 2 | .56 | 1 | 2.24 | 0 | (83) 83 | | | | | | | | | 100 | (0) | 98 | | | |
| 2 | .56 | 1 | 2.24 | 20 | (100) 95 | | | | | | | | | 95 | (0) | 100 | | | |
| 2 | .56 | 1 | 2.24 | 0 | (78) 95 | | | | | | | | | 100 | (5) | 100 | | | |
| 2 | .56 | 1 | 2.24 | 15 | (100) 35 | | | | | | | | | 90 | (0) | 90 | | | |
| 2 | .56 | 1 | 2.24 | 30 | (57) 90 | | | | | | | | | 95 | (0) | 95 | | | |
| 2 | .56 | 1 | 2.24 | 15 | (66) 85 | | | | | | | | | 95 | (0) | 100 | | | |
| 2 | .56 | 1 | 2.24 | 0 | (82) 93 | | | | | | | | | 100 | (5) | 100 | | | |
| 2 | .56 | 1 | 2.24 | 0 | (100) 77 | | | | | | | | | 100 | (0) | 100 | | | |
| 2 | .56 | 1 | 2.24 | 25 | (100) 60 | | | | | | | | | 95 | (0) | 100 | | | |
| 2 | .56 | 1 | 8.96 | 0 | (58) 95 | | | | | | | | | 100 | (5) | 100 | | | |
| 2 | .56 | 1 | 8.96 | 25 | (100) 60 | | | | | | | | | 90 | (10) | 100 | | | |
| 2 | .56 | 1 | 8.96 | 0 | (58) 85 | | | | | | | | | 95 | (5) | 100 | | | |
| 2 | .56 | 1 | 8.96 | 10 | (100) 35 | | | | | | | | | 100 | (0) | 90 | | | |
| 2 | .56 | 1 | 8.96 | 20 | (71) 77 | | | | | | | | | 100 | (0) | 100 | | | |
| 2 | .56 | 1 | 8.96 | 10 | (74) 95 | | | | | | | | | 100 | (0) | 100 | | | |
| 2 | .56 | 1 | 8.96 | 10 | (89) 95 | | | | | | | | | 95 | (0) | 100 | | | |
| 2 | .56 | 1 | 8.96 | 0 | (89) 93 | | | | | | | | | 95 | (5) | 100 | | | |
| 2 | .56 | 1 | 8.96 | 5 | (100) 65 | | | | | | | | | 100 | (5) | 95 | | | |
| 2 | .56 | 1 | | | (92) | | | | | | | | | | (0) | | | | |

TABLE 3-continued

% PLANT INHIBITION AND % SAFENING EFFECT ( )

| HERB. NO. | RATE | ANTI-DOTE NO. | RATE | Sorghum W | Sorghum ( ) | Sorghum WO | Wheat W | Wheat WO | Corn W | Corn WO | Barnyard Grass W | Barnyard Grass ( ) | Barnyard Grass WO | Rice W | Rice WO | Foxtail Green W | Foxtail Green ( ) | Foxtail Green WO | Wild Oats W | Wild Oats WO | Soybean W | Soybean WO |
|---|---|---|---|---|---|---|---|---|---|---|---|---|---|---|---|---|---|---|---|---|---|---|
| 2 | .56 | 1 | 8.96 | 10 |  | 70 |  |  |  |  |  |  |  |  |  | 100 |  | 100 |  |  |  |  |
| 2 | .56 | 1 | 8.96 | 10 | (85) | 75 |  |  |  |  |  |  |  |  |  | 90 | (0) | 100 |  |  |  |  |
| 2 | .56 | 1 | 8.96 | 5 | (86) | 85 |  |  |  |  |  |  |  |  |  | 95 | (10) | 100 |  |  |  |  |
| 2 | .56 | 1 | 8.96 | 30 | (94) | 95 |  |  |  |  | 100 | (0) | 100 |  |  | 95 | (5) | 100 |  |  |  |  |
| 2 | .56 | 1 | 8.96 | 50 | (68) | 55 |  |  |  |  |  |  |  |  |  | 95 | (0) | 95 |  |  |  |  |
| 2 | .56 | 1 | 8.96 | 30 | (9) | 80 |  |  |  |  |  |  |  |  |  | 95 | (5) | 100 |  |  |  |  |
| 2 | .56 | 1 | 8.96 | 10 | (62) | 28 |  |  |  |  |  |  |  |  |  | 90 | (5) | 95 |  |  |  |  |
| 2 | .56 | 1 | 8.96 | 0 | (64) | 90 |  |  |  |  |  |  |  |  |  | 95 | (5) | 100 |  |  |  |  |
| 2 | .56 | 1 | 8.96 | 15 | (100) | 95 |  |  |  |  |  |  |  |  |  | 95 | (5) | 100 |  |  |  |  |
| 2 | .56 | 1 | 8.96 | 10 | (84) | 80 |  |  |  |  |  |  |  |  |  | 90 | (10) | 100 |  |  |  |  |
| 2 | .56 | 1 | 8.96 | 15 | (87) | 70 |  |  |  |  |  |  |  |  |  | 100 | (0) | 100 |  |  |  |  |
| 2 | .56 | 1 | 8.96 | 5 | (78) | 90 |  |  |  |  |  |  |  |  |  | 95 | (0) | 95 |  |  |  |  |
| 2 | .56 | 1 | 8.96 | 30 | (94) | 93 |  |  |  |  |  |  |  |  |  | 100 | (0) | 100 |  |  |  |  |
| 2 | .56 | 1 | 8.96 | 10 | (67) | 75 |  |  |  |  |  |  |  |  |  | 100 | (0) | 95 |  |  |  |  |
| 2 | .56 | 1 | 8.96 | 20 | (86) | 95 |  |  |  |  |  |  |  |  |  | 95 | (5) | 100 |  |  |  |  |
| 2 | .56 | 1 | 8.96 | 25 | (78) | 90 |  |  |  |  |  |  |  |  |  | 95 | (5) | 100 |  |  |  |  |
| 2 | .56 | 1 | 8.96 | 15 | (72) | 90 |  |  |  |  |  |  |  |  |  | 95 | (5) | 100 |  |  |  |  |
| 2 | .56 | 1 | 8.96 | 30 | (83) | 85 |  |  |  |  |  |  |  |  |  | 95 | (5) | 100 |  |  |  |  |
| 2 | .56 | 1 | 8.96 | 15 | (64) | 30 |  |  |  |  |  |  |  |  |  | 95 | (0) | 95 |  |  |  |  |
| 2 | .56 | 1 | 8.96 | 30 | (50) | 95 |  |  |  |  |  |  |  |  |  | 95 | (0) | 100 |  |  |  |  |
| 2 | .56 | 1 | 8.96 | 10 | (68) | 100 |  |  |  |  |  |  |  |  |  | 80 | (5) | 95 |  |  |  |  |
| 2 | .56 | 1 | 8.96 | 0 | (90) | 80 |  |  |  |  |  |  |  |  |  | 85 | (20) | 95 |  |  |  |  |
| 2 | .56 | 1 | 8.96 | 20 | (100) | 95 |  |  |  |  |  |  |  |  |  | 95 | (10) | 100 |  |  |  |  |
| 2 | .56 | 1 | 8.96 | 20 | (78) | 95 |  |  |  |  |  |  |  |  |  | 95 | (5) | 100 |  |  |  |  |
|   |      |   |      |   | (78) |   |   |   |   |   |   |   |   |   |   |   | (5) |   |   |   |   |   |

TABLE 3-continued

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 1 | 8.96 | 0 | 85 | | | | | | | | | 95 | 100 | | | | |
| 2 | .56 | 1 | 8.96 | 25 | (100) 95 | | | | | | | | | 100 (5) | 100 | | | | |
| 2 | .56 | 1 | 8.96 | 20 | (73) 80 | | | | | | | | | 95 (0) | 100 | | | | |
| 2 | .56 | 1 | 8.96 | 20 | (75) 83 | | | | | | | | | 95 (5) | 98 | | | | |
| 2 | .56 | 1 | 8.96 | 10 | (75) 95 | | | | | | | | | 100 (3) | 100 | | | | |
| 2 | .56 | 1 | 8.96 | 20 | (89) 90 | | | | | | | | | 95 (0) | 95 | | | | |
| 2 | .56 | 1 | 8.96 | 0 | (77) 95 | | | | | | | | | 95 (0) | 100 | | | | |
| 2 | .56 | 1 | 8.96 | 10 | (100) 90 | | | | | | | | | 95 (5) | 100 | | | | |
| 2 | .56 | 1 | 8.96 | 10 | (88) 60 | | | | | | | | | 90 (10) | 100 | | | | |
| 2 | .56 | 1 | 8.96 | 25 | (83) 85 | | | | | | | | | 95 (5) | 100 | | | | |
| 2 | .56 | 1 | 8.96 | 10 | (70) 93 | | | | | | | | | 100 (0) | 100 | | | | |
| 2 | 1.12 | 1 | 2.24 | | (89) | 95 | (0) 95 | | | | | | | 100 (0) | 100 | | | | |
| 2 | 1.12 | 1 | 8.96 | | | 80 | (15) 95 | | | | | | | 100 (0) | 98 | | | | |
| 2 | 2.24 | 1 | .14 | 50 | (46) 93 | | | | | | | | | 100 (0) | 100 | | | | |
| 2 | 2.24 | 1 | .14 | 10 | (89) 95 | | | | | | | | | 100 (0) | 100 | | | | |
| 2 | 2.24 | 1 | .14 | 80 | (0) 77 | | | | | | | | | 100 (0) | 100 | | | | |
| 2 | 2.24 | 1 | .14 | 40 | (56) 92 | | | | | | | | | 100 (0) | 100 | | | | |
| 2 | 2.24 | 1 | .14 | 60 | (40) 100 | | | | | | | | | 100 (0) | 100 | | | | |
| 2 | 2.24 | 1 | .14 | 25 | (46) 47 | | | | | | | | | 100 (0) | 100 | | | | |
| 2 | 2.24 | 1 | .14 | 30 | (69) 98 | | | | | | | | | 100 (0) | 100 | | | | |
| 2 | 2.24 | 1 | .14 | 5 | (94) 97 | | | | | | | | | 100 (0) | 100 | | | | |
| 2 | 2.24 | 1 | .14 | 85 | (8) 93 | | | | | | | | | 100 (0) | 100 | | | | |
| 2 | 2.24 | 1 | .14 | 30 | (62) 80 | | | | | | | | | 100 (0) | 100 | | | | |
| 2 | 2.24 | 1 | .14 | 85 | (13) 98 | | | | | | | | | 100 (0) | 100 | | | | |

TABLE 3-continued

| | | | | % PLANT INHIBITION AND % SAFENING EFFECT ( ) | | | | | | | | | | | | | | | | |
|---|---|---|---|---|---|---|---|---|---|---|---|---|---|---|---|---|---|---|---|---|
| HERB. NO. | HERB RATE | ANTI-DOTE NO. | ANTI-DOTE RATE | Sorghum | | Wheat | | Corn | | Barnyard Grass | | Rice | | Foxtail Green | | Wild Oats | | Soybean | | | |
| | | | | W | WO | W | WO | W | WO | W | WO | W | WO | W | WO | W | WO | W | WO | | |
| 2 | 2.24 | 1 | .14 | 60 | 100 | | | | | | | | | 100 | 100 | | | | | | |
| 2 | 2.24 | 1 | .14 | 15 | (40) 92 | | | | | | | | | 98 | (0) 98 | | | | | | |
| 2 | 2.24 | 1 | .14 | 60 | (83) 100 | | | | | | | | | 100 | (0) 100 | | | | | | |
| 2 | 2.24 | 1 | .14 | 85 | (40) 100 | | | | | | | | | 100 | (0) 100 | | | | | | |
| 2 | 2.24 | 1 | .14 | 20 | (15) 90 | | | | | | | | | 100 | (0) 100 | | | | | | |
| 2 | 2.24 | 1 | .14 | 85 | (77) 93 | | | | | | | | | 100 | (0) 100 | | | | | | |
| 2 | 2.24 | 1 | .56 | 35 | (8) 93 | | | | | | | | | 100 | (0) 100 | | | | | | |
| 2 | 2.24 | 1 | .56 | 35 | (62) 92 | | | | | | | | | 98 | (0) 98 | | | | | | |
| 2 | 2.24 | 1 | .56 | 15 | (61) 95 | | | | | | | | | 100 | (0) 100 | | | | | | |
| 2 | 2.24 | 1 | .56 | 60 | (84) 100 | | | | | | | | | 100 | (0) 100 | | | | | | |
| 2 | 2.24 | 1 | .56 | 95 | (40) 100 | | | | | | | | | 100 | (0) 100 | | | | | | |
| 2 | 2.24 | 1 | .56 | 40 | (5) 47 | | | | | | | | | 100 | (0) 100 | | | | | | |
| 2 | 2.24 | 1 | .56 | 5 | (14) 80 | | | | | | | | | 100 | (0) 100 | | | | | | |
| 2 | 2.24 | 1 | .56 | 80 | (93) 98 | | | | 100 | (0) 100 | | | 100 | (0) 100 | | | | | | |
| 2 | 2.24 | 1 | .56 | 15 | (18) 97 | | | | | | | | | 100 | (0) 100 | | | | | | |
| 2 | 2.24 | 1 | .56 | 20 | (84) 92 | | | | | | | | | 100 | (0) 100 | | | | | | |
| 2 | 2.24 | 1 | .56 | 75 | (78) 100 | | | | | | | | | 100 | (0) 100 | | | | | | |
| 2 | 2.24 | 1 | .56 | 30 | (25) 77 | | | | | | | | | 100 | (0) 100 | | | | | | |
| 2 | 2.24 | 1 | .56 | 45 | (61) 100 | | | | | | | | | 100 | (0) 100 | | | | | | |
| 2 | 2.24 | 1 | .56 | 75 | (55) 98 | | | | | | | | | 100 | (0) 100 | | | | | | |
| 2 | 2.24 | 1 | .56 | 55 | (23) 95 | | | | | | | | | | | | | | | | |
| 2 | 2.24 | 1 | .56 | 10 | (42) 95 | | | | | | | | | 100 | (0) 100 | | | | | | |
| 2 | 2.24 | 1 | .56 | 15 | (89) 95 | | | | | | | | | 100 | (0) 100 | | | | | | |
| 2 | 2.24 | 1 | .56 | 55 | (84) 95 | | | | | | | | | 100 | (0) 100 | | | | | | |
| 2 | 2.24 | 1 | .56 | 55 | (42) | | | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 1 | .56 | 35 (61) | 90 | | | | | | | | | 100 (0) | 100 | | | | |
| 2 | 2.24 | 1 | .56 | 55 (45) | 100 | | | | | | | | | 100 (0) | 100 | | | | |
| 2 | 2.24 | 1 | .56 | 5 (95) | 100 | | | | | | | | | 100 (0) | 100 | | | | |
| 2 | 2.24 | 1 | .56 | 15 (84) | 95 | | | | | | | | | 100 (0) | 100 | | | | |
| 2 | 2.24 | 1 | .56 | 30 (68) | 95 | | | | | | | | | 100 (0) | 100 | | | | |
| 2 | 2.24 | 1 | .56 | 35 (63) | 95 | | | | | | | | | 95 (5) | 100 | | | | |
| 2 | 2.24 | 1 | .56 | 60 (36) | 95 | 90 (0) | 73 | | | | | | | | | | | | |
| 2 | 2.24 | 1 | .56 | 15 (83) | 92 | | | | | | | | | 100 (0) | 100 | | | | |
| 2 | 2.24 | 1 | .56 | 30 (68) | 95 | | | | | | | | | 100 (0) | 100 | | | | |
| 2 | 2.24 | 1 | .56 | 40 (57) | 95 | | | | | | | | | 100 (0) | 100 | | | | |
| 2 | 2.24 | 1 | .56 | 40 (50) | 80 | | | | | | | | | 100 (0) | 95 | | | | |
| 2 | 2.24 | 1 | .56 | 35 (63) | 95 | | | | | | | | | 100 (0) | 100 | | | | |
| 2 | 2.24 | 1 | .56 | 25 (73) | 95 | | | | | | | | | 100 (0) | 100 | | | | |
| 2 | 2.24 | 1 | .56 | 10 (89) | 95 | | | | | | | | | 100 (0) | 100 | | | | |
| 2 | 2.24 | 1 | .56 | 0 (100) | 62 | | | | | | | | | 100 (0) | 100 | | | | |
| 2 | 2.24 | 1 | .56 | 30 (66) | 90 | | | | | | | | | 100 (0) | 100 | | | | |
| 2 | 2.24 | 1 | .56 | 40 (57) | 95 | | | | | | | | | 100 (0) | 100 | | | | |
| 2 | 2.24 | 1 | .56 | 20 (78) | 95 | | | | | | | | | 100 (0) | 100 | | | | |
| 2 | 2.24 | 1 | .56 | 10 (89) | 95 | | | | | | | | | 100 (0) | 100 | | | | |
| 2 | 2.24 | 1 | .56 | 50 (47) | 95 | | | | | | | | | 100 (0) | 100 | | | | |
| 2 | 2.24 | 1 | .56 | 40 (55) | 90 | | | | | | | | | 100 (0) | 100 | | | | |
| 2 | 2.24 | 1 | .56 | 25 (73) | 95 | | | | | | | | | 95 (5) | 100 | | | | |
| 2 | 2.24 | 1 | .56 | 75 (21) | 95 | | | | | | | | | 100 (0) | 100 | | | | |
| 2 | 2.24 | 1 | .56 | 60 (40) | 100 | | | | | | | | | 100 (0) | 100 | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 1 | .56 | 40 | 95 |  |  |  |  |  |  | 95 | (5) | 100 |  |  |  |  |
| 2 | 2.24 | 1 | .56 | 55 | (57) 100 |  |  |  |  |  |  | 100 | (0) | 100 |  |  |  |  |
| 2 | 2.24 | 1 | .56 | 5 | (45) 80 |  |  |  |  |  |  | 100 | (0) | 100 |  |  |  |  |
| 2 | 2.24 | 1 | .56 | 20 | (93) 95 |  |  |  |  |  |  | 100 | (0) | 100 |  |  |  |  |
| 2 | 2.24 | 1 | .56 | 10 | (78) 85 |  |  |  |  |  |  | 100 | (0) | 100 |  |  |  |  |
| 2 | 2.24 | 1 | .56 | 40 | (88) 95 |  |  |  |  |  |  | 100 | (0) | 100 |  |  |  |  |
| 2 | 2.24 | 1 | .56 | 60 | (57) 95 |  |  |  |  |  |  | 100 | (0) | 100 |  |  |  |  |
| 2 | 2.24 | 1 | .56 | 5 | (36) 85 |  |  |  |  |  |  | 100 | (0) | 100 |  |  |  |  |
| 2 | 2.24 | 1 | .56 | 65 | (94) 95 |  |  |  |  |  |  | 100 | (0) | 100 |  |  |  |  |
| 2 | 2.24 | 1 | .56 | 30 | (31) 85 |  |  |  |  |  |  | 100 | (0) | 100 |  |  |  |  |
| 2 | 2.24 | 1 | .56 | 35 | (64) 95 |  |  |  |  |  |  | 100 | (0) | 100 |  |  |  |  |
| 2 | 2.24 | 1 | .56 | 40 | (63) 95 |  |  |  |  |  |  | 100 | (0) | 100 |  |  |  |  |
| 2 | 2.24 | 1 | .56 | 15 | (57) 100 |  |  |  |  |  |  | 100 | (0) | 100 |  |  |  |  |
| 2 | 2.24 | 1 | .56 | 20 | (85) 95 |  |  |  |  |  |  | 100 | (0) | 100 |  |  |  |  |
| 2 | 2.24 | 1 | .56 | 5 | (78) 85 |  |  |  |  |  |  | 100 | (0) | 100 |  |  |  |  |
| 2 | 2.24 | 1 | .56 | 20 | (94) 80 |  |  |  |  |  |  | 100 | (0) | 100 |  |  |  |  |
| 2 | 2.24 | 1 | 2.24 | 0 | (100) 98 |  |  |  |  |  |  | 100 | (0) | 100 |  |  |  |  |
| 2 | 2.24 | 1 | 2.24 | 10 | (75) 77 |  |  |  |  |  |  | 100 | (0) | 100 |  |  |  |  |
| 2 | 2.24 | 1 | 2.24 | 20 | (87) 100 |  |  |  |  |  |  | 100 | (0) | 100 |  |  |  |  |
| 2 | 2.24 | 1 | 2.24 | 55 | (80) 100 |  |  |  |  |  |  | 100 | (0) | 100 |  |  |  |  |
| 2 | 2.24 | 1 | 2.24 | 65 | (45) 98 |  |  |  |  |  |  | 100 | (0) | 100 |  |  |  |  |
| 2 | 2.24 | 1 | 2.24 | 25 | (33) 97 |  |  |  |  |  |  | 95 | (5) | 100 |  |  |  |  |
|  |  |  |  |  | (74) |  |  |  |  |  |  |  |  |  |  |  |  |

TABLE 3-continued

| | | | | % PLANT INHIBITION AND % SAFENING EFFECT ( ) | | | | | | | | | | | | | | |
|---|---|---|---|---|---|---|---|---|---|---|---|---|---|---|---|---|---|---|
| | | | | Sorghum | | Wheat | | Corn | | Barnyard Grass | | Rice | | Foxtail Green | | Wild Oats | | Soybean |
| HERB. NO. | RATE | ANTI-DOTE NO. | RATE | W | WO | W | WO | W | WO | W | WO | W | WO | W | WO | W | WO | W WO |
| 2 | 2.24 | 1 | 2.24 | 15 (83) | 93 | | | | | | | | | 100 (0) | 98 | | | |
| 2 | 2.24 | 1 | 2.24 | 20 (78) | 92 | | | | | | | | | 98 (0) | 98 | | | |
| 2 | 2.24 | 1 | 2.24 | 35 (65) | 100 | | | | | | | | | 100 (0) | 100 | | | |
| 2 | 2.24 | 1 | 2.24 | 30 (68) | 95 | | | | | | | | | 100 (0) | 100 | | | |
| 2 | 2.24 | 1 | 2.24 | 10 (78) | 47 | | | | | | | | | 100 (0) | 100 | | | |
| 2 | 2.24 | 1 | 2.24 | 15 (83) | 93 | | | | | | | | | 100 (0) | 100 | | | |
| 2 | 2.24 | 1 | 2.24 | 60 (40) | 100 | | | | | | | | | 100 (0) | 100 | | | |
| 2 | 2.24 | 1 | 2.24 | 45 (51) | 92 | | | | | | | | | 100 (0) | 100 | | | |
| 2 | 2.24 | 1 | 2.24 | 0 (100) | 80 | | | | | | | | | 100 (0) | 100 | | | |
| 2 | 2.24 | 1 | 2.24 | 10 (87) | 80 | | | | | | | | | 100 (0) | 100 | | | |
| 2 | 2.24 | 1 | 2.24 | 10 (89) | 95 | | | | | | | | | 100 (0) | 100 | | | |
| 2 | 2.24 | 1 | 2.24 | 40 (59) | 98 | | | | | | | | | 100 (0) | 100 | | | |
| 2 | 2.24 | 1 | 2.24 | 15 (82) | 85 | | | | | | | | | 100 (0) | 100 | | | |
| 2 | 2.24 | 1 | 2.24 | 30 (68) | 95 | | | | | | | | | 100 (0) | 100 | | | |
| 2 | 2.24 | 1 | 2.24 | 70 (26) | 95 | | | | | | | | | 100 (0) | 100 | | | |
| 2 | 2.24 | 1 | 2.24 | 40 (57) | 85 | | | | | | | | | 95 (5) | 100 | | | |
| 2 | 2.24 | 1 | 2.24 | 5 (94) | 95 | | | | | | | | | 100 (0) | 100 | | | |
| 2 | 2.24 | 1 | 2.24 | 30 (68) | 100 | | | | | | | | | 100 (0) | 100 | | | |
| 2 | 2.24 | 1 | 2.24 | 25 (75) | 95 | | | | | | | | | 95 (5) | 100 | | | |
| 2 | 2.24 | 1 | 2.24 | 45 (52) | 85 | | | | | | | | | 100 (0) | 100 | | | |
| 2 | 2.24 | 1 | 2.24 | 45 (47) | 85 | | | | | | | | | 100 (0) | 100 | | | |
| 2 | 2.24 | 1 | 2.24 | 20 (76) | 95 | | | | | | | | | 100 (0) | 100 | | | |
| 2 | 2.24 | 1 | 2.24 | 10 (89) | 95 | | | | | | | | | 100 (0) | 100 | | | |
| 2 | 2.24 | 1 | 2.24 | 15 (85) | 100 | | | | | | | | | 100 (0) | 100 | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 1 | 2.24 | 55 | 95 | | | | | | | | | 100 | (0) | 100 | | | |
| 2 | 2.24 | 1 | 2.24 | 5 | (42) 100 | | | | | | | | | 100 | (0) | 100 | | | |
| 2 | 2.24 | 1 | 2.24 | 30 | (95) 100 | | | | | | | | | 100 | (0) | 100 | | | |
| 2 | 2.24 | 1 | 2.24 | 40 | (70) 95 | | | | | | | | | 100 | (0) | 100 | | | |
| 2 | 2.24 | 1 | 2.24 | 40 | (57) 95 | | | | | | | | | 95 | (5) | 100 | | | |
| 2 | 2.24 | 1 | 2.24 | 15 | (57) 80 | | | | | | | | | 100 | (0) | 100 | | | |
| 2 | 2.24 | 1 | 2.24 | 35 | (81) 95 | | | | | | | | | 100 | (0) | 100 | | | |
| 2 | 2.24 | 1 | 2.24 | 10 | (63) 95 | | | | | | | | | 100 | (0) | 100 | | | |
| 2 | 2.24 | 1 | 2.24 | 65 | (89) 95 | | | | | | | | | 100 | (0) | 100 | | | |
| 2 | 2.24 | 1 | 2.24 | 20 | (31) 100 | | | | | | | | | 100 | (0) | 100 | | | |
| 2 | 2.24 | 1 | 2.24 | 10 | (80) 90 | | | | | | | | | 100 | (0) | 100 | | | |
| 2 | 2.24 | 1 | 2.24 | 30 | (88) 95 | | | | | | | | | 100 | (0) | 100 | | | |
| 2 | 2.24 | 1 | 2.24 | 20 | (68) 95 | | | | | | | | | 100 | (0) | 100 | | | |
| 2 | 2.24 | 1 | 2.24 | 35 | (78) 95 | | | | | | | | | 100 | (0) | 100 | | | |
| 2 | 2.24 | 1 | 2.24 | 15 | (63) 62 | | | | | | | | | 95 | (0) | 95 | | | |
| 2 | 2.24 | 1 | 2.24 | 20 | (75) 80 | 80 | | | | 100 | | | | 100 | (0) | 100 | | | |
| 2 | 2.24 | 1 | 2.24 | 65 | (75) 95 | | (0) | | | | (0) | | | 100 | (0) | 100 | | | |
| 2 | 2.24 | 1 | 2.24 | 10 | (31) 92 | | 73 | | | | 100 | | | 100 | (0) | 100 | | | |
| 2 | 2.24 | 1 | 2.24 | 30 | (89) 90 | | | | | | | | | 100 | (0) | 100 | | | |
| 2 | 2.24 | 1 | 2.24 | 10 | (88) 95 | | | | | | | | | 100 | (0) | 100 | | | |
| 2 | 2.24 | 1 | 2.24 | 35 | (63) 95 | | | | | | | | | 100 | (0) | 100 | | | |
| 2 | 2.24 | 1 | 2.24 | 35 | (63) 95 | | | | | | | | | 100 | (0) | 100 | | | |
| 2 | 2.24 | 1 | 2.24 | 30 | (68) 95 | | | | | | | | | | (0) | | | | |
| 2 | 2.24 | 1 | 2.24 | 30 | (68) 95 | | | | | | | | | 100 | (0) | 100 | | | |
| 2 | 2.24 | 1 | 2.24 | 35 | (63) 95 | | | | | | | | | | | | | | |

TABLE 3-continued

| | | | | | % PLANT INHIBITION AND % SAFENING EFFECT ( ) | | | | | | | | | | | | |
|---|---|---|---|---|---|---|---|---|---|---|---|---|---|---|---|---|---|
| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
| 2 | 2.24 | 1 | 2.24 | 20 | 90 | | | | | | | | | 100 | 100 | | | | |
| 2 | 2.24 | 1 | 2.24 | 30 | 95 (77) | | | | | | | | | 100 (0) | 100 | | | | |
| 2 | 2.24 | 1 | 2.24 | 0 | 95 (68) | | | | | | | | | 100 (0) | 100 | | | | |
| 2 | 2.24 | 1 | 2.24 | 35 | 95 (100) | | | | | | | | | 100 (0) | 100 | | | | |
| 2 | 2.24 | 1 | 2.24 | 45 | 95 (63) | | | | | | | | | 100 (0) | 100 | | | | |
| 2 | 2.24 | 1 | 2.24 | 30 | 95 (52) | | | | | | | | | 100 (0) | 100 | | | | |
| 2 | 2.24 | 1 | 2.24 | 15 | 100 (68) | | | | | | | | | 100 (0) | 100 | | | | |
| 2 | 2.24 | 1 | 2.24 | 45 | 95 (85) | | | | | | | | | | | | | | |
| 2 | 2.24 | 1 | 4.48 | 20 | 95 (52) | 40 | 73 (45) | | | | | | | 100 (0) | 100 | | | | |
| 2 | 2.24 | 1 | 8.96 | 20 | 95 (78) | | | | | | | | | 100 (0) | 100 | | | | |
| 2 | 2.24 | 1 | 8.96 | 15 | 95 (78) | | | | | | | | | 100 (0) | 100 | | | | |
| 2 | 2.24 | 1 | 8.96 | 20 | 95 (84) | | | | | | | | | 100 (0) | 100 | | | | |
| 2 | 2.24 | 1 | 8.96 | 20 | 95 (78) | | | | | | | | | 100 (0) | 100 | | | | |
| 2 | 2.24 | 1 | 8.96 | 20 | 95 (78) | | | | | | | | | 100 (0) | 100 | | | | |
| 2 | 2.24 | 1 | 8.96 | 15 | 95 (84) | | | | | | | | | 100 (0) | 100 | | | | |
| 2 | 2.24 | 1 | 8.96 | 15 | 95 (84) | | | | | | | | | 100 (0) | 100 | | | | |
| 2 | 2.24 | 1 | 8.96 | 10 | 95 (89) | | | | | 100 | 100 (0) | | | 95 (5) | 100 | | | | |
| 2 | 2.24 | 1 | 8.96 | 20 | 62 (67) | | | | | | | | | 100 (0) | 100 | | | | |
| 2 | 2.24 | 1 | 8.96 | 15 | 90 (83) | | | | | | | | | 100 (0) | 100 | | | | |
| 2 | 2.24 | 1 | 8.96 | 35 | 95 (63) | | | | | | | | | | | | | | |
| 2 | 2.24 | 1 | 8.96 | 15 | 95 (84) | | | | | | | | | 100 (0) | 100 | | | | |
| 2 | 2.24 | 1 | 8.96 | 40 | 95 (57) | | | | | | | | | | | | | | |
| 2 | 2.24 | 1 | 8.96 | 25 | 80 (68) | | | | | | | | | 100 (0) | 100 | | | | |
| 2 | 2.24 | 1 | 8.96 | 35 | 95 (63) | | | | | | | | | 100 (0) | 100 | | | | |

TABLE 3-continued

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 1 | 8.96 | 30 | 95 | | | | | | | | | 100 | 100 | | | | |
| 2 | 2.24 | 1 | 8.96 | 10 (68) | 95 | | | | | | | | | 100 (0) | 100 | | | | |
| 2 | 2.24 | 1 | 8.96 | 20 (89) | 100 | | | | | | | | | 100 (0) | 100 | | | | |
| 2 | 2.24 | 1 | 8.96 | 20 (80) | 85 | | | | | | | | | 100 (0) | 100 | | | | |
| 2 | 2.24 | 1 | 8.96 | 40 (76) | 100 | | | | | | | | | 100 (0) | 100 | | | | |
| 2 | 2.24 | 1 | 8.96 | 25 (60) | 100 | | | | | | | | | 100 (0) | 100 | | | | |
| 2 | 2.24 | 1 | 8.96 | 10 (75) | 95 | | | | | | | | | 100 (0) | 100 | | | | |
| 2 | 2.24 | 1 | 8.96 | 55 (89) | 95 | | | | | | | | | 100 (0) | 100 | | | | |
| 2 | 2.24 | 1 | 8.96 | 35 (42) | 95 | | | | | | | | | 100 (0) | 100 | | | | |
| 2 | 2.24 | 1 | 8.96 | 10 (63) | 85 | | | | | | | | | 100 (0) | 100 | | | | |
| 2 | 2.24 | 1 | 8.96 | 25 (88) | 80 | | | | | | | | | 100 (0) | 100 | | | | |
| 2 | 2.24 | 1 | 8.96 | 15 (68) | 98 | | | | | | | | | 100 (0) | 100 | | | | |
| 2 | 2.24 | 1 | 8.96 | 35 (84) | 85 | | | | | | | | | 100 (0) | 100 | | | | |
| 2 | 2.24 | 1 | 8.96 | 10 (58) | 100 | | | | | | | | | 100 (0) | 100 | | | | |
| 2 | 2.24 | 1 | 8.96 | 5 (90) | 85 | | | | | | | | | 100 (0) | 100 | | | | |
| 2 | 2.24 | 1 | 8.96 | 15 (94) | 95 | | | | | | | | | 100 (0) | 100 | | | | |
| 2 | 2.24 | 1 | 8.96 | 35 (84) | 100 | | | | | | | | | 100 (0) | 100 | | | | |
| 2 | 2.24 | 1 | 8.96 | 25 (65) | 95 | | | | | | | | | 100 (0) | 100 | | | | |
| 2 | 2.24 | 1 | 8.96 | 0 (73) | 95 | | | | | | | | | 100 (0) | 100 | | | | |
| 2 | 2.24 | 1 | 8.96 | 55 (100) | 95 | | | | | | | | | 100 (0) | 100 | | | | |
| 2 | 2.24 | 1 | 8.96 | 55 (42) | 95 | | | | | | | | | 100 (0) | 100 | | | | |
| 2 | 2.24 | 1 | 8.96 | 45 (42) | 95 | | | | | | | | | 100 (0) | 100 | | | | |
| 2 | 2.24 | 1 | 8.96 | 10 (52) | 95 | | | | | | | | | 100 (0) | 100 | | | | |
| 2 | 2.24 | 1 | 8.96 | 20 (89) | 95 | | | | | | | | | 100 (0) | 100 | | | | |
| 2 | 2.24 | 1 | 8.96 | 20 (78) | 95 | | | | | | | | | 100 (0) | 100 | | | | |

TABLE 3-continued

| HERB. NO. | HERB RATE | ANTI-DOTE NO. | ANTIDOTE RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 1 | 8.96 | 35 | 90 (61) | | | | | | | | | 100 | 100 (0) | | | | |
| 2 | 2.24 | 1 | 8.96 | 30 | 80 (62) | | | | | | | | | 100 | 95 (0) | | | | |
| 2 | 2.24 | 1 | 8.96 | 10 | 92 (89) | | | | | | | | | 100 | 100 (0) | | | | |
| 2 | 2.24 | 1 | 8.96 | 35 | 95 (63) | | | | | | | | | 100 | 100 (0) | | | | |
| 2 | 2.24 | 1 | 8.96 | 0 | 95 (100) | | | | | | | | | 100 | 100 (0) | | | | |
| 2 | 2.24 | 1 | 8.96 | 35 | 100 (65) | | | | | | | | | 100 | 100 (0) | | | | |
| 2 | 2.24 | 1 | 2.24 | | | 95 | 95 (0) | | | | | | | 100 | 100 (0) | | | | |
| 2 | 2.24 | 1 | 8.96 | | | 90 | 95 (5) | | | | | | | 100 | 95 (0) | | | | |
| 2 | .56 | 2 | .56 | 25 | 85 (70) | | | | | | | | | 100 | 95 (0) | | | | |
| 2 | .56 | 2 | .56 | 20 | 65 (69) | | | | | | | | | 95 | 95 (0) | | | | |
| 2 | .56 | 2 | .56 | 10 | 95 (89) | | | | | | | | | 95 | 100 (5) | | | | |
| 2 | .56 | 2 | .56 | 20 | 30 (33) | | | | | | | | | 95 | 95 (0) | | | | |
| 2 | .56 | 2 | .56 | 5 | 85 (94) | | | | | | | | | 100 | 100 (0) | | | | |
| 2 | .56 | 2 | .56 | 15 | 95 (84) | | | | | | | | | 100 | 100 (0) | | | | |
| 2 | .56 | 2 | 2.24 | 10 | 85 (88) | | | | | | | | | 95 | 100 (5) | | | | |
| 2 | .56 | 2 | 2.24 | 65 | 85 (23) | | | | | | | | | 100 | 100 (0) | | | | |
| 2 | .56 | 2 | 2.24 | 0 | 30 (100) | | | | | | | | | 95 | 95 (0) | | | | |
| 2 | .56 | 2 | 2.24 | 25 | 95 (73) | | | | | | | | | 100 | 100 (0) | | | | |
| 2 | .56 | 2 | 2.24 | 20 | 65 (69) | | | | | | | | | 95 | 95 (5) | | | | |
| 2 | .56 | 2 | 2.24 | 20 | 95 (78) | | | | | | | | | 95 | 100 (0) | | | | |
| 2 | .56 | 2 | 8.96 | 25 | 85 (70) | | | | | | | | | 100 | 95 (5) | | | | |
| 2 | .56 | 2 | 8.96 | 30 | 85 (64) | | | | | | | | | 100 | 100 (0) | | | | |
| 2 | .56 | 2 | 8.96 | 20 | 30 (33) | | | | | | | | | 95 | 95 (0) | | | | |
| 2 | .56 | 2 | 8.96 | 0 | 95 (100) | | | | | | | | | 95 | 100 (5) | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 2 | 8.96 | 15 | 65 | | | | | | | | | 95 | 95 | | | | |
| 2 | .56 | 2 | 8.96 | 15 | (76) 95 | | | | | | | | | 95 | (5) 100 | | | | |
| 2 | 2.24 | 2 | .56 | 10 | (84) 95 | | | | | | | | | 100 | (0) 100 | | | | |
| 2 | 2.24 | 2 | .56 | 25 | (89) 85 | | | | | | | | | 100 | (0) 100 | | | | |
| 2 | 2.24 | 2 | .56 | 35 | (70) 95 | | | | | | | | | 100 | (0) 100 | | | | |
| 2 | 2.24 | 2 | .56 | 10 | (63) 80 | | | | | | | | | 100 | (0) 95 | | | | |
| 2 | 2.24 | 2 | .56 | 40 | (87) 90 | | | | | | | | | 100 | (0) 100 | | | | |
| 2 | 2.24 | 2 | .56 | 45 | (55) 95 | | | | | | | | | 100 | (0) 100 | | | | |
| 2 | 2.24 | 2 | 2.24 | 40 | (52) 95 | | | | | | | | | 100 | (0) 100 | | | | |
| 2 | 2.24 | 2 | 2.24 | 25 | (57) 95 | | | | | | | | | 100 | (0) 95 | | | | |
| 2 | 2.24 | 2 | 2.24 | 5 | (73) 80 | | | | | | | | | 100 | (0) 100 | | | | |
| 2 | 2.24 | 2 | 2.24 | 50 | (93) 90 | | | | | | | | | 100 | (0) 100 | | | | |
| 2 | 2.24 | 2 | 2.24 | 30 | (44) 85 | | | | | | | | | 10 | (90) 100 | | | | |
| 2 | 2.24 | 2 | 2.24 | 40 | (64) 95 | | | | | | | | | 100 | (0) 100 | | | | |
| 2 | 2.24 | 2 | 8.96 | 25 | (57) 90 | | | | | | | | | 100 | (0) 100 | | | | |
| 2 | 2.24 | 2 | 8.96 | 25 | (72) 95 | | | | | | | | | 100 | (0) 100 | | | | |
| 2 | 2.24 | 2 | 8.96 | 25 | (73) 80 | | | | | | | | | 100 | (0) 95 | | | | |
| 2 | 2.24 | 2 | 8.96 | 15 | (68) 85 | | | | | | | | | 100 | (0) 100 | | | | |
| 2 | 2.24 | 2 | 8.96 | 40 | (82) 95 | | | | | | | | | 100 | (0) 100 | | | | |
| 2 | 2.24 | 2 | 8.96 | 10 | (57) 95 | | | | | | | | | 100 | (0) 100 | | | | |
| 2 | 2.24 | 2 | 8.96 | 25 | (89) 97 | | | | | | | | | 95 | (0) 95 | | | | |
| 2 | .56 | 3 | .14 | 70 | (27) 53 | | | | | | | | | 100 | (0) 100 | | | | |
| 2 | .56 | 3 | .14 | 0 | (100) 32 | | | | | | | | | 100 | (0) 98 | | | | |
| 2 | .56 | 3 | .14 | 35 | (0) 25 | | | | | | | | | | | | | | |
| 2 | .56 | 3 | .14 | 0 | (100) | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 3 | .14 | 5 | 42 | | | | | | | | | 100 | 100 | | | | |
| 2 | .56 | 3 | .14 | 85 | (88) | | | | | | | | | 100 | (0) 100 | | | | |
| 2 | .56 | 3 | .56 | 75 | (12) 97 | | | | | | | | | 100 | (0) 100 | | | | |
| 2 | .56 | 3 | .56 | 95 | (22) 97 | | | | | | | | | 100 | (0) 100 | | | | |
| 2 | .56 | 3 | .56 | 10 | (2) 32 | | | | | | | | | 100 | (0) 100 | | | | |
| 2 | .56 | 3 | .56 | 30 | (68) 53 | | | | | | | | | 95 | (0) 95 | | | | |
| 2 | .56 | 3 | .56 | 15 | (43) 42 | | | | | | | | | 100 | (0) 100 | | | | |
| 2 | .56 | 3 | .56 | 20 | (64) 25 | | | | | | | | | 100 | (0) 98 | | | | |
| 2 | .56 | 3 | .56 | 5 | (20) 85 | | | | | | | | | 95 | (0) 95 | | | | |
| 2 | .56 | 3 | .56 | 40 | (94) 95 | | | | | | | | | 100 | (0) 100 | | | | |
| 2 | .56 | 3 | .56 | 20 | (57) 65 | | | | | | | | | 95 | (0) 95 | | | | |
| 2 | .56 | 3 | .56 | 15 | (69) 95 | | | | | | | | | 95 | (5) 100 | | | | |
| 2 | .56 | 3 | .56 | 10 | (84) 30 | | | | | | | | | 95 | (0) 95 | | | | |
| 2 | .56 | 3 | 2.24 | 10 | (66) 97 | | | | | | | | | 100 | (0) 100 | | | | |
| 2 | .56 | 3 | 2.24 | 5 | (89) 25 | | | | | | | | | 98 | (2) 98 | | | | |
| 2 | .56 | 3 | 2.24 | 65 | (80) 97 | | | | | | | | | 100 | (0) 100 | | | | |
| 2 | .56 | 3 | 2.24 | 5 | (32) 32 | | | | | | | | | 98 | (0) 100 | | | | |
| 2 | .56 | 3 | 2.24 | 10 | (84) 53 | | | | | | | | | 95 | (0) 95 | | | | |
| 2 | .56 | 3 | 2.24 | 10 | (81) 42 | | | | | | | | | 100 | (0) 100 | | | | |
| 2 | .56 | 3 | 2.24 | 10 | (76) 65 | | | | | | | | | 95 | (0) 95 | | | | |
| 2 | .56 | 3 | 2.24 | 20 | (84) 30 | | | | | | | | | 95 | (0) 95 | | | | |
| 2 | .56 | 3 | 2.24 | 10 | (33) 95 | | | | | | | | | 100 | (0) 100 | | | | |
| 2 | .56 | 3 | 2.24 | 30 | (89) 95 | | | | | | | | | 100 | (0) 100 | | | | |
| 2 | .56 | 3 | 2.24 | 20 | (68) 85 | | | | | | | | | 100 | (0) 95 | | | | |
| | | | | | (76) | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 3 | 8.96 | 25 | 85 | | | | | | | | | 100 | 95 | | | | |
| 2 | .56 | 3 | 8.96 | 5 | (70) 65 | | | | | | | | | 95 | (0) 95 | | | | |
| 2 | .56 | 3 | 8.96 | 20 | (92) 95 | | | | | | | | | 100 | (0) 100 | | | | |
| 2 | .56 | 3 | 8.96 | 30 | (78) 30 | | | | | | | | | 95 | (0) 95 | | | | |
| 2 | .56 | 3 | 8.96 | 15 | (0) 95 | | | | | | | | | 100 | (0) 100 | | | | |
| 2 | 2.24 | 3 | .14 | 55 | (84) 92 | | | | | | | | | 100 | (0) 98 | | | | |
| 2 | 2.24 | 3 | .14 | 85 | (40) 100 | | | | | | | | | 100 | (0) 100 | | | | |
| 2 | 2.24 | 3 | .14 | 85 | (15) 100 | | | | | | | | | 100 | (0) 100 | | | | |
| 2 | 2.24 | 3 | .14 | 40 | (15) 93 | | | | | | | | | 100 | (0) 98 | | | | |
| 2 | 2.24 | 3 | .14 | 95 | (56) 98 | | | | | | | | | 100 | (0) 100 | | | | |
| 2 | 2.24 | 3 | .14 | 55 | (3) 77 | | | | | | | | | 100 | (0) 100 | | | | |
| 2 | 2.24 | 3 | .14 | 30 | (28) 47 | | | | | | | | | 100 | (0) 100 | | | | |
| 2 | 2.24 | 3 | .14 | 45 | (36) 80 | | | | | | | | | 100 | (0) 100 | | | | |
| 2 | 2.24 | 3 | .14 | 30 | (43) 90 | | | | | | | | | 100 | (0) 100 | | | | |
| 2 | 2.24 | 3 | .56 | 35 | (66) 90 | | | | | | | | | 100 | (0) 100 | | | | |
| 2 | 2.24 | 3 | .56 | 0 | (61) 47 | | | | | | | | | 100 | (0) 100 | | | | |
| 2 | 2.24 | 3 | .56 | 10 | (100) 80 | | | | | | | | | 100 | (0) 100 | | | | |
| 2 | 2.24 | 3 | .56 | 85 | (87) 98 | | | | | | | | | 100 | (0) 98 | | | | |
| 2 | 2.24 | 3 | .56 | 55 | (13) 92 | | | | | | | | | 98 | (2) 100 | | | | |
| 2 | 2.24 | 3 | .56 | 15 | (40) 77 | | | | | | | | | 100 | (0) 98 | | | | |
| 2 | 2.24 | 3 | .56 | 25 | (80) 93 | | | | | | | | | 100 | (0) 100 | | | | |
| 2 | 2.24 | 3 | .56 | 85 | (73) 100 | | | | | | | | | 100 | (0) 100 | | | | |
| 2 | 2.24 | 3 | .56 | 95 | (15) 100 | | | | | | | | | 100 | (0) 95 | | | | |
| 2 | 2.24 | 3 | .56 | 15 | (5) 80 | | | | | | | | | 100 | (0) | | | | |
| 2 | 2.24 | 3 | | | (81) | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 3 | .56 | 50 | 95 | | | | | | | | | 100 | 100 | | | | |
| 2 | 2.24 | 3 | .56 | 40 | 90 (47) | | | | | | | | | 100 | 100 | | | | |
| 2 | 2.24 | 3 | .56 | 20 | 85 (55) | | | | | | | | | 100 | 100 | | | | |
| 2 | 2.24 | 3 | .56 | 50 | 95 (76) | | | | | | | | | 100 | 100 | | | | |
| 2 | 2.24 | 3 | 2.24 | 55 | 100 (47) | | | | | | | | | 100 | 100 | | | | |
| 2 | 2.24 | 3 | 2.24 | 80 | 98 (45) | | | | | | | | | 100 | 100 | | | | |
| 2 | 2.24 | 3 | 2.24 | 40 | 92 (18) | | | | | | | | | 98 | 98 | | | | |
| 2 | 2.24 | 3 | 2.24 | 45 | 93 (56) | | | | | | | | | 100 | 98 | | | | |
| 2 | 2.24 | 3 | 2.24 | 80 | 100 (51) | | | | | | | | | 100 | 100 | | | | |
| 2 | 2.24 | 3 | 2.24 | 20 | 90 (20) | | | | | | | | | 100 | 100 | | | | |
| 2 | 2.24 | 3 | 2.24 | 50 | 80 (77) | | | | | | | | | 100 | 100 | | | | |
| 2 | 2.24 | 3 | 2.24 | 45 | 47 (37) | | | | | | | | | 100 | 100 | | | | |
| 2 | 2.24 | 3 | 2.24 | 25 | 77 (4) | | | | | | | | | 100 | 100 | | | | |
| 2 | 2.24 | 3 | 2.24 | 20 | 95 (67) | | | | | | | | | 100 | 100 | | | | |
| 2 | 2.24 | 3 | 2.24 | 15 | 85 (78) | | | | | | | | | 100 | 95 | | | | |
| 2 | 2.24 | 3 | 2.24 | 40 | 95 (82) | | | | | | | | | 100 | 100 | | | | |
| 2 | 2.24 | 3 | 2.24 | 10 | 80 (57) | | | | | | | | | 100 | 100 | | | | |
| 2 | 2.24 | 3 | 2.24 | 15 | 90 (87) | | | | | | | | | 100 | 95 | | | | |
| 2 | 2.24 | 3 | 8.96 | 35 | 95 (83) | | | | | | | | | 100 | 100 | | | | |
| 2 | 2.24 | 3 | 8.96 | 10 | 90 (63) | | | | | | | | | 100 | 100 | | | | |
| 2 | 2.24 | 3 | 8.96 | 10 | 85 (88) | | | | | | | | | 100 | 100 | | | | |
| 2 | 2.24 | 3 | 8.96 | 15 | 80 (88) | | | | | | | | | 100 | 95 | | | | |
| 2 | 2.24 | 3 | 8.96 | 50 | 95 (81) | | | | | | | | | 100 | 100 | | | | |
| 2 | .56 | 3 | .56 | 40 | 90 (47) | | | | | | | | | 100 | 100 | | | | |
| 2 | | 4 | | | (55) | | | | | | | | | 95 | 100 | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 4 | 2.24 | 20 (77) | 90 | | | | | | | | | 95 (5) | 100 | | | | |
| 2 | .56 | 4 | 8.96 | 30 (66) | 90 | | | | | | | | | 95 (5) | 100 | | | | |
| 2 | 2.24 | 4 | .56 | 40 (57) | 95 | | | | | | | | | 100 (0) | 100 | | | | |
| 2 | 2.24 | 4 | 2.24 | 60 (36) | 95 | | | | | | | | | 100 (0) | 100 | | | | |
| 2 | 2.24 | 4 | 8.96 | 50 (47) | 95 | | | | | | | | | 95 (5) | 100 | | | | |
| 2 | .56 | 5 | .56 | 30 (66) | 90 | | | | | | | | | 95 (5) | 100 | | | | |
| 2 | .56 | 5 | 2.24 | 25 (72) | 90 | | | | | | | | | 95 (5) | 100 | | | | |
| 2 | .56 | 5 | 8.96 | 40 (55) | 90 | | | | | | | | | 95 (5) | 100 | | | | |
| 2 | 2.24 | 5 | .56 | 50 (47) | 95 | | | | | | | | | 100 (0) | 100 | | | | |
| 2 | 2.24 | 5 | 2.24 | 30 (68) | 95 | | | | | | | | | 100 (0) | 100 | | | | |
| 2 | 2.24 | 5 | 8.96 | 20 (78) | 95 | | | | | | | | | 100 (0) | 100 | | | | |
| 2 | .56 | 13 | .56 | 55 (42) | 95 | | | | | | | | | 100 (0) | 100 | | | | |
| 2 | .56 | 13 | .56 | 65 (31) | 95 | | | | | | | | | 100 (0) | 100 | | | | |
| 2 | .56 | 13 | 2.24 | 35 (63) | 95 | | | | | | | | | 100 (0) | 100 | | | | |
| 2 | .56 | 13 | 2.24 | 35 (63) | 95 | | | | | | | | | 95 (5) | 100 | | | | |
| 2 | .56 | 13 | 8.96 | 60 (36) | 95 | | | | | | | | | 90 (10) | 100 | | | | |
| 2 | .56 | 13 | 8.96 | 30 (68) | 95 | | | | | | | | | 100 (0) | 100 | | | | |
| 2 | 2.24 | 13 | .56 | 85 (10) | 95 | | | | | | | | | 100 (0) | 100 | | | | |
| 2 | 2.24 | 13 | .56 | 95 (0) | 95 | | | | | | | | | 100 (0) | 100 | | | | |
| 2 | 2.24 | 13 | 2.24 | 50 (47) | 95 | | | | | | | | | 100 (0) | 100 | | | | |
| 2 | 2.24 | 13 | 2.24 | 65 (31) | 95 | | | | | | | | | 100 (0) | 100 | | | | |
| 2 | 2.24 | 13 | 8.96 | 50 (47) | 95 | | | | | | | | | 100 (0) | 100 | | | | |
| 2 | 2.24 | 13 | 8.96 | 60 (36) | 95 | | | | | | | | | 100 (0) | 95 | | | | |
| 2 | .56 | 27 | .56 | 20 (69) | 65 | | | | | | | | | 100 (0) | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 27 | .56 | 25 | 30 | | | | | 95 | | | | | 95 | | | | |
| 2 | .56 | 27 | 2.24 | 10 (16) | 30 | | | | | 95 | | | | (0) | 95 | | | | |
| 2 | .56 | 27 | 2.24 | 15 (66) | 65 | | | | | 95 | | | | (0) | 95 | | | | |
| 2 | .56 | 27 | 8.96 | 15 (76) | 30 | | | | | 95 | | | | (0) | 95 | | | | |
| 2 | .56 | 27 | 8.96 | 15 (50) | 65 | | | | | 90 | | | | (0) | 95 | | | | |
| 2 | .56 | 27 | .56 | 30 (76) | 80 | | | | | 95 | | | | (5) | 95 | | | | |
| 2 | 2.24 | 27 | .56 | 55 (62) | 85 | | | | | 100 | | | | (0) | 100 | | | | |
| 2 | 2.24 | 27 | 2.24 | 60 (35) | 80 | | | | | 100 | | | | (0) | 95 | | | | |
| 2 | 2.24 | 27 | 2.24 | 40 (25) | 85 | | | | | 95 | | | | (0) | 100 | | | | |
| 2 | 2.24 | 27 | 8.96 | 5 (52) | 80 | | | | | 95 | | | | (5) | 95 | | | | |
| 2 | 2.24 | 27 | 8.96 | 35 (93) | 85 | | | | | 100 | | | | (0) | 100 | | | | |
| 2 | 2.24 | 27 | .56 | 40 (58) | 85 | | | | | 100 | | | | (0) | 95 | | | | |
| 2 | .56 | 7 | .56 | 40 (52) | 30 | | | | | 90 | | | | (5) | 95 | | | | |
| 2 | .56 | 7 | .56 | 5 (83) | 85 | | | | | 100 | | | | (0) | 95 | | | | |
| 2 | .56 | 7 | 2.24 | 25 (70) | 30 | | | | | 95 | | | | (0) | 95 | | | | |
| 2 | .56 | 7 | 2.24 | 10 (66) | 30 | | | | | 100 | | | | (0) | 95 | | | | |
| 2 | .56 | 7 | 8.96 | 10 (88) | 85 | | | | | 95 | | | | (0) | 100 | | | | |
| 2 | .56 | 7 | 8.96 | 15 (50) | 30 | | | | | 100 | | | | (0) | 100 | | | | |
| 2 | 2.24 | 7 | .56 | 30 (66) | 90 | | | | | 100 | | | | (0) | 95 | | | | |
| 2 | 2.24 | 7 | .56 | 30 (62) | 80 | | | | | 100 | | | | (0) | 100 | | | | |
| 2 | 2.24 | 7 | 2.24 | 15 (83) | 90 | | | | | 100 | | | | (0) | 95 | | | | |
| 2 | 2.24 | 7 | 2.24 | 20 (75) | 80 | | | | | 95 | | | | (0) | 95 | | | | |
| 2 | 2.24 | 7 | 8.96 | 0 (100) | 80 | | | | | 95 | | | | (0) | 100 | | | | |
| 2 | 2.24 | 7 | 8.96 | 35 (61) | 90 | | | | | 100 | | | | (0) | 95 | | | | |
| 2 | .56 | 28 | .56 | 10 (66) | 30 | | | | | 95 | | | | (0) | 95 | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 28 | .56 | 20 | 65 | | | | | | | | | 100 | 95 | | | | |
| 2 | .56 | 28 | 2.24 | 20 | (69) 30 | | | | | | | | | 95 | (0) 95 | | | | |
| 2 | .56 | 28 | 8.96 | 30 | (33) 65 | | | | | | | | | 95 | (0) 95 | | | | |
| 2 | .56 | 28 | 8.96 | 10 | (53) 30 | | | | | | | | | 95 | (0) 95 | | | | |
| 2 | .56 | 28 | 8.96 | 20 | (66) 65 | | | | | | | | | 95 | (0) 95 | | | | |
| 2 | 2.24 | 28 | .56 | 55 | (69) 85 | | | | | | | | | 100 | (0) 100 | | | | |
| 2 | 2.24 | 28 | .56 | 50 | (35) 80 | | | | | | | | | 100 | (0) 95 | | | | |
| 2 | 2.24 | 28 | 2.24 | 50 | (37) 85 | | | | | | | | | 100 | (0) 100 | | | | |
| 2 | 2.24 | 28 | 2.24 | 35 | (41) 80 | | | | | | | | | 100 | (0) 95 | | | | |
| 2 | 2.24 | 28 | 8.96 | 40 | (56) 85 | | | | | | | | | 95 | (5) 100 | | | | |
| 2 | 2.24 | 28 | 8.96 | 20 | (52) 80 | | | | | | | | | 100 | (0) 95 | | | | |
| 2 | .56 | 8 | .56 | 10 | (75) 65 | | | | | | | | | 95 | (0) 95 | | | | |
| 2 | .56 | 8 | 2.24 | 10 | (84) 65 | | | | | | | | | 95 | (0) 95 | | | | |
| 2 | .56 | 8 | 8.96 | 20 | (84) 65 | | | | | | | | | 100 | (0) 95 | | | | |
| 2 | 2.24 | 8 | .56 | 20 | (69) 85 | | | | | | | | | 100 | (0) 100 | | | | |
| 2 | 2.24 | 8 | 2.24 | 30 | (76) 85 | | | | | | | | | 100 | (0) 100 | | | | |
| 2 | 2.24 | 8 | 8.96 | 15 | (64) 85 | | | | | | | | | 100 | (0) 100 | | | | |
| 2 | .56 | 29 | .56 | 35 | (82) 65 | | | | | | | | | 95 | (0) 95 | | | | |
| 2 | .56 | 29 | 2.24 | 50 | (46) 65 | | | | | | | | | 100 | (0) 95 | | | | |
| 2 | .56 | 29 | 8.96 | 15 | (23) 65 | | | | | | | | | 95 | (0) 95 | | | | |
| 2 | 2.24 | 29 | .56 | 80 | (76) 85 | | | | | | | | | 100 | (0) 100 | | | | |
| 2 | 2.24 | 29 | 2.24 | 70 | (5) 85 | | | | | | | | | 95 | (5) 100 | | | | |
| 2 | 2.24 | 29 | 8.96 | 65 | (17) 85 | | | | | | | | | 100 | (0) 100 | | | | |
| 2 | .56 | 14 | .56 | 10 | (23) 65 | | | | | | | | | 100 | (0) 100 | | | | |
| 2 | .56 | 14 | .56 | 10 | (84) 65 | | | | | | | | | 95 | (0) 95 | | | | |

TABLE 3-continued
% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 14 | 2.24 | 30 | 65 | | | | | | | | | 95 | 95 | | | | |
| 2 | .56 | 14 | 8.96 | 15 | (53) 65 | | | | | | | | | (0) | 95 | | | | |
| 2 | 2.24 | 14 | .56 | 30 | (76) 85 | | | | | | | | | (0) | 100 | | | | |
| 2 | 2.24 | 14 | 2.24 | 25 | (64) 85 | | | | | | | | | (5) | 100 | | | | |
| 2 | 2.24 | 14 | 8.96 | 30 | (70) 85 | | | | | | | | | (0) | 100 | | | | |
| 2 | .56 | 30 | .56 | 45 | (64) 65 | | | | | | | | | (0) | 95 | | | | |
| 2 | .56 | 30 | .56 | 55 | (30) 85 | | | | | | | | | (0) | 95 | | | | |
| 2 | .56 | 30 | 2.24 | 25 | (35) 85 | | | | | | | | | (0) | 95 | | | | |
| 2 | .56 | 30 | 2.24 | 25 | (70) 65 | | | | | | | | | (0) | 95 | | | | |
| 2 | .56 | 30 | 8.96 | 40 | (61) 85 | | | | | | | | | (0) | 95 | | | | |
| 2 | .56 | 30 | 8.96 | 30 | (52) 65 | | | | | | | | | (0) | 95 | | | | |
| 2 | .56 | 30 | .56 | 70 | (53) 90 | | | | | | | | | (5) | 100 | | | | |
| 2 | .56 | 30 | .56 | 85 | (22) 85 | | | | | | | | | (0) | 100 | | | | |
| 2 | 2.24 | 30 | 2.24 | 85 | (0) 85 | | | | | | | | | (0) | 100 | | | | |
| 2 | 2.24 | 30 | 2.24 | 75 | (0) 90 | | | | | | | | | (0) | 100 | | | | |
| 2 | 2.24 | 30 | 8.96 | 55 | (16) 90 | | | | | | | | | (0) | 100 | | | | |
| 2 | 2.24 | 30 | 8.96 | 65 | (38) 85 | | | | | | | | | (0) | 100 | | | | |
| 2 | .56 | 15 | .56 | 35 | (23) 65 | | | | | | | | | (0) | 95 | | | | |
| 2 | .56 | 15 | .56 | 40 | (46) 85 | | | | | | | | | (0) | 95 | | | | |
| 2 | .56 | 15 | 2.24 | 30 | (52) 65 | | | | | | | | | (0) | 95 | | | | |
| 2 | .56 | 15 | 2.24 | 20 | (53) 85 | | | | | | | | | (0) | 95 | | | | |
| 2 | .56 | 15 | 8.96 | 20 | (76) 65 | | | | | | | | | (5) | 95 | | | | |
| 2 | .56 | 15 | 8.96 | 40 | (69) 85 | | | | | | | | | (0) | 95 | | | | |
| 2 | 2.24 | 15 | .56 | 35 | (52) 90 | | | | | | | | | (0) | 100 | | | | |
| 2 | | | | | (61) | | | | | | | | | (0) | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 15 | .56 | 35 | 85 | | | | | | | | | 100 | (0) | | | | 100 |
| 2 | 2.24 | 15 | 2.24 | 45 | (58) 90 | | | | | | | | | 100 | (0) | | | | 100 |
| 2 | 2.24 | 15 | 2.24 | 40 | (50) 85 | | | | | | | | | 100 | (0) | | | | 100 |
| 2 | 2.24 | 15 | 8.96 | 30 | (52) 90 | | | | | | | | | 100 | (0) | | | | 100 |
| 2 | 2.24 | 15 | 8.96 | 40 | (66) 85 | | | | | | | | | 100 | (0) | | | | 100 |
| 2 | .56 | 16 | .56 | 15 | (52) 65 | | | | | | | | | 90 | (0) | | | | 95 |
| 2 | .56 | 16 | 2.24 | 15 | (76) 65 | | | | | | | | | 90 | (5) | | | | 95 |
| 2 | .56 | 16 | 8.96 | 15 | (76) 65 | | | | | | | | | 90 | (5) | | | | 95 |
| 2 | 2.24 | 16 | .56 | 40 | (76) 85 | | | | | | | | | 100 | (0) | | | | 100 |
| 2 | 2.24 | 16 | 2.24 | 20 | (52) 85 | | | | | | | | | 95 | (5) | | | | 100 |
| 2 | 2.24 | 16 | 8.96 | 40 | (76) 85 | | | | | | | | | 95 | (5) | | | | 100 |
| 2 | .56 | 9 | .56 | 0 | (52) 85 | | | | | | | | | 100 | (0) | | | | 100 |
| 2 | .56 | 9 | 2.24 | 15 | (100) 85 | | | | | | | | | 100 | (0) | | | | 100 |
| 2 | .56 | 9 | 8.96 | 0 | (82) 85 | | | | | | | | | 100 | (0) | | | | 100 |
| 2 | 2.24 | 9 | .56 | 35 | (100) 95 | | | | | | | | | 100 | (0) | | | | 100 |
| 2 | 2.24 | 9 | 2.24 | 5 | (63) 95 | | | | | | | | | 100 | (0) | | | | 100 |
| 2 | 2.24 | 9 | 8.96 | 20 | (94) 95 | | | | | | | | | 100 | (0) | | | | 100 |
| 2 | .56 | 10 | .56 | 25 | (78) 80 | | | | | | | | | 100 | (0) | | | | 100 |
| 2 | .56 | 10 | 2.24 | 15 | (68) 80 | | | | | | | | | 100 | (0) | | | | 100 |
| 2 | .56 | 10 | 8.96 | 10 | (81) 80 | | | | | | | | | 100 | (0) | | | | 100 |
| 2 | 2.24 | 10 | .56 | 70 | (87) 95 | | | | | | | | | 100 | (0) | | | | 100 |
| 2 | 2.24 | 10 | 2.24 | 35 | (26) 95 | | | | | | | | | 100 | (0) | | | | 100 |
| 2 | 2.24 | 10 | 8.96 | 30 | (63) 95 | | | | | | | | | 100 | (0) | | | | 100 |
| 2 | .56 | 11 | .56 | 30 | (68) 85 | | | | | | | | | 100 | (0) | | | | 95 |
| 2 | | | | 30 | (64) | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 11 | 2.24 | 40 | 85 | | | | | | | | | 100 | 95 | | | | |
| 2 | .56 | 11 | 8.96 | 100 | (52) 85 | | | | | | | | | 100 | (0) 95 | | | | |
| 2 | 2.24 | 11 | .56 | 90 | (0) 90 | | | | | | | | | 100 | (0) 100 | | | | |
| 2 | 2.24 | 11 | 2.24 | 50 | (0) 90 | | | | | | | | | 100 | (0) 100 | | | | |
| 2 | 2.24 | 11 | 8.96 | 35 | (44) 90 | | | | | | | | | 100 | (0) 100 | | | | |
| 2 | .56 | 17 | .56 | 60 | (61) 85 | | | | | | | | | 100 | (0) 100 | | | | |
| 2 | .56 | 17 | 2.24 | 45 | (29) 85 | | | | | | | | | 100 | (0) 100 | | | | |
| 2 | .56 | 17 | 8.96 | 35 | (47) 85 | | | | | | | | | 100 | (0) 100 | | | | |
| 2 | 2.24 | 17 | .56 | 95 | (58) 95 | | | | | | | | | 100 | (0) 100 | | | | |
| 2 | 2.24 | 17 | 2.24 | 90 | (0) 95 | | | | | | | | | 100 | (0) 100 | | | | |
| 2 | 2.24 | 17 | 8.96 | 65 | (5) 95 | | | | | | | | | 98 | (0) 95 | | | | |
| 2 | .56 | 20 | .14 | 5 | (31) 53 | | | | | | | | | 98 | (0) 100 | | | | |
| 2 | .56 | 20 | .14 | 5 | (90) 32 | | | | | | | | | 100 | (2) 98 | | | | |
| 2 | .56 | 20 | .14 | 10 | (84) 25 | | | | | | | | | 90 | (0) 100 | | | | |
| 2 | .56 | 20 | .56 | 10 | (60) 32 | | | | | | | | | 98 | (10) 95 | | | | |
| 2 | .56 | 20 | .56 | 0 | (68) 53 | | | | | | | | | 100 | (0) 98 | | | | |
| 2 | .56 | 20 | .56 | 15 | (100) 25 | | | | | | | | | 90 | (0) 100 | | | | |
| 2 | .56 | 20 | 2.24 | 30 | (40) 85 | | | | | | | | | 100 | (10) 98 | | | | |
| 2 | .56 | 20 | 2.24 | 5 | (64) 32 | | | | | | | | | 95 | (0) 95 | | | | |
| 2 | .56 | 20 | 2.24 | 5 | (84) 25 | | | | | | | | | 95 | (5) 100 | | | | |
| 2 | .56 | 20 | 2.24 | 0 | (80) 53 | | | | | | | | | 100 | (0) 100 | | | | |
| 2 | .56 | 20 | 8.96 | 15 | (100) 85 | | | | | | | | | 100 | (0) 100 | | | | |
| 2 | .56 | 20 | 8.96 | 15 | (82) 85 | | | | | | | | | | | | | | |
| 2 | 2.24 | 20 | .14 | 20 | (74) 77 | | | | | | | | | | | | | | |

TABLE 3-continued

| | | | | % PLANT INHIBITION AND % SAFENING EFFECT ( ) | | | | | | | | | | | | | | | |
|---|---|---|---|---|---|---|---|---|---|---|---|---|---|---|---|---|---|---|---|
| | | | | Sorghum | | Wheat | | Corn | | Barnyard Grass | | Rice | | Foxtail Green | | Wild Oats | | Soybean | |
| HERB. NO. | RATE | ANTI-DOTE NO. | RATE | W | WO | W | WO | W | WO | W | WO | W | WO | W | WO | W | WO | W | WO |
| 2 | 2.24 | 20 | .14 | 10 | 47 | | | | | | | | | 100 | 100 | | | | |
| 2 | 2.24 | 20 | .14 | 10 | 92 (78) | | | | | | | | | 98 | 98 | | | | |
| 2 | 2.24 | 20 | .56 | 10 | 47 (89) | | | | | | | | | 100 | 100 | | | | |
| 2 | 2.24 | 20 | .56 | 25 | 77 (78) | | | | | | | | | 100 | 100 | | | | |
| 2 | 2.24 | 20 | .56 | 25 | 92 (67) | | | | | | | | | 100 | 98 | | | | |
| 2 | 2.24 | 20 | .56 | 5 | 95 (72) | | | | | | | | | 100 | 100 | | | | |
| 2 | 2.24 | 20 | 2.24 | 10 | 92 (94) | | | | | | | | | 98 | 98 | | | | |
| 2 | 2.24 | 20 | 2.24 | 20 | 77 (89) | | | | | | | | | 100 | 100 | | | | |
| 2 | 2.24 | 20 | 2.24 | 30 | 47 (74) | | | | | | | | | 100 | 100 | | | | |
| 2 | 2.24 | 20 | 2.24 | 30 | 95 (36) | | | | | | | | | 100 | 100 | | | | |
| 2 | 2.24 | 20 | 8.96 | 25 | 95 (68) | | | | | | | | | 100 | 100 | | | | |
| 2 | 2.24 | 12 | .14 | 40 | 90 (73) | | | | | | | | | 100 | 100 | | | | |
| 2 | 2.24 | 12 | .14 | 55 | 97 (55) | | | | | | | | | 100 | 100 | | | | |
| 2 | 2.24 | 12 | .56 | 20 | 97 (79) | | | | | | | | | 100 | 100 | | | | |
| 2 | 2.24 | 12 | .56 | 25 | 97 (74) | | | | | | | | | 100 | 100 | | | | |
| 2 | 2.24 | 12 | 2.24 | 55 | 90 (38) | | | | | | | | | 100 | 100 | | | | |
| 2 | 2.24 | 12 | 2.24 | 0 | 97 (100) | | | | | | | | | 100 | 100 | | | | |
| 2 | 2.24 | 18 | .14 | 30 | 90 (66) | | | | | | | | | 100 | 100 | | | | |
| 2 | 2.24 | 18 | .14 | 70 | 92 (23) | | | | | | | | | 100 | 100 | | | | |
| 2 | 2.24 | 18 | .56 | 70 | 92 (23) | | | | | | | | | 100 | 100 | | | | |
| 2 | 2.24 | 18 | 2.24 | 30 | 92 (67) | | | | | | | | | 100 | 100 | | | | |
| 2 | .56 | 24 | .14 | 65 | 97 (32) | | | | | | | | | 100 | 100 | | | | |
| 2 | .56 | 24 | .56 | 40 | 97 (58) | | | | | | | | | 100 | 100 | | | | |
| 2 | .56 | 24 | 2.24 | 20 | 97 (79) | | | | | | | | | 100 | 100 | | | | |
| 2 | 2.24 | 24 | .14 | 85 | 100 (15) | | | | | | | | | 100 | 100 | | | | |

TABLE 3-continued

% PLANT INHIBITION AND % SAFENING EFFECT ()

| HERB. NO. | RATE | ANTI-DOTE NO. | ANTI RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | 2.24 | 24 | .14 | 75 | 98 (23) |  |  |  |  |  |  |  |  | 100 | 100 (0) |  |  |  |  |
| 2 | 2.24 | 24 | .56 | 75 | 98 (23) |  |  |  |  |  |  |  |  | 100 | 100 (0) |  |  |  |  |
| 2 | 2.24 | 24 | .56 | 90 | 100 (10) |  |  |  |  |  |  |  |  | 100 | 100 (0) |  |  |  |  |
| 2 | 2.24 | 24 | 2.24 | 85 | 100 (15) |  |  |  |  |  |  |  |  | 100 | 100 (0) |  |  |  |  |
| 2 | 2.24 | 24 | 2.24 | 85 | 98 (13) |  |  |  |  |  |  |  |  | 100 | 100 (0) |  |  |  |  |
| 2 | .56 | 26 | .14 | 50 | 42 (0) |  |  |  |  |  |  |  |  | 100 | 100 (0) |  |  |  |  |
| 2 | .56 | 26 | .56 | 10 | 42 (76) |  |  |  |  |  |  |  |  | 100 | 100 (0) |  |  |  |  |
| 2 | .56 | 26 | 2.24 | 5 | 80 (88) |  |  |  |  |  |  |  |  | 100 | 100 (0) |  |  |  |  |
| 2 | 2.24 | 26 | .14 | 5 | 80 (93) |  |  |  |  |  |  |  |  | 100 | 100 (0) |  |  |  |  |
| 2 | 2.24 | 26 | .56 | 30 | 80 (62) |  |  |  |  |  |  |  |  | 100 | 100 (0) |  |  |  |  |
| 2 | 2.24 | 26 | 2.24 | 5 | 97 (93) |  |  |  |  |  |  |  |  | 100 | 100 (0) |  |  |  |  |
| 2 | .56 | 19 | .14 | 80 | 97 (17) |  |  |  |  |  |  |  |  | 100 | 100 (0) |  |  |  |  |
| 2 | .56 | 19 | .56 | 55 | 97 (43) |  |  |  |  |  |  |  |  | 100 | 100 (0) |  |  |  |  |
| 2 | .56 | 19 | 2.24 | 35 | 98 (63) |  |  |  |  |  |  |  |  | 100 | 100 (0) |  |  |  |  |
| 2 | 2.24 | 19 | .14 | 100 | 100 (0) |  |  |  |  |  |  |  |  | 100 | 100 (0) |  |  |  |  |
| 2 | 2.24 | 19 | .14 | 95 | 100 (5) |  |  |  |  |  |  |  |  | 100 | 100 (0) |  |  |  |  |
| 2 | 2.24 | 19 | .56 | 95 | 100 (5) |  |  |  |  |  |  |  |  | 100 | 100 (0) |  |  |  |  |
| 2 | 2.24 | 19 | .56 | 80 | 98 (18) |  |  |  |  |  |  |  |  | 100 | 100 (0) |  |  |  |  |
| 2 | 2.24 | 19 | 2.24 | 75 | 98 (23) |  |  |  |  |  |  |  |  | 100 | 100 (0) |  |  |  |  |
| 2 | 2.24 | 19 | 2.24 | 80 | 100 (20) |  |  |  |  |  |  |  |  | 100 | 100 (0) |  |  |  |  |
| 2 | .56 | 23 | .14 | 85 | 97 (12) |  |  |  |  |  |  |  |  | 100 | 100 (0) |  |  |  |  |
| 2 | .56 | 23 | .14 | 10 | 42 (76) |  |  |  |  |  |  |  |  | 100 | 100 (0) |  |  |  |  |
| 2 | .56 | 23 | .56 | 15 | 97 (84) |  |  |  |  |  |  |  |  | 100 | 100 (0) |  |  |  |  |
| 2 | .56 | 23 | .56 | 25 | 42 (40) |  |  |  |  |  |  |  |  | 100 | 100 (0) |  |  |  |  |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 2 | .56 | 23 | 2.24 | 5 | 42 | | | | | | | | | 100 | | | | | |
| 2 | .56 | 23 | 2.24 | 40 | (88) 97 | | | | | | | | | 100 | (0) 100 | | | | |
| 2 | .56 | 23 | .14 | 50 | (58) 80 | | | | | | | | | 100 | (0) 100 | | | | |
| 2 | 2.24 | 23 | .14 | 95 | (37) 98 | | | | | | | | | 100 | (0) 100 | | | | |
| 2 | 2.24 | 23 | .56 | 45 | (3) 80 | | | | | | | | | 100 | (0) 100 | | | | |
| 2 | 2.24 | 23 | .56 | 90 | (43) 98 | | | | | | | | | 100 | (0) 100 | | | | |
| 2 | 2.24 | 23 | 2.24 | 85 | (8) 98 | | | | | | | | | 100 | (0) 100 | | | | |
| 2 | 2.24 | 23 | 2.24 | 0 | (13) 80 | | | | | | | | | 100 | (0) 100 | | | | |
| 2 | .56 | 22 | .14 | 55 | (100) 32 | | | | | | | | | 98 | (2) 100 | | | | |
| 2 | .56 | 22 | .56 | 80 | (0) 32 | | | | | | | | | 95 | (5) 100 | | | | |
| 2 | .56 | 22 | 2.24 | 10 | (0) 32 | | | | | | | | | 90 | (10) 100 | | | | |
| 2 | 2.24 | 22 | .14 | 70 | (68) 77 | | | | | | | | | 100 | (0) 100 | | | | |
| 2 | 2.24 | 22 | .56 | 80 | (9) 77 | | | | | | | | | 98 | (2) 100 | | | | |
| 2 | 2.24 | 22 | 2.24 | 95 | (0) 77 | | | | | | | | | 100 | (0) 100 | | | | |
| 7 | .56 | 1 | .56 | | | | | | | 100 | (0) 100 | 60 | (0) 60 | | | | | | |
| 7 | .56 | 1 | 2.24 | | | | | | | 100 | (0) 100 | 90 | (0) 60 | | | | | | |
| 7 | .56 | 1 | 8.96 | | | | | | | 100 | (0) 100 | 50 | (16) 60 | | | | | | |
| 7 | 1.12 | 1 | .56 | | | | | | | 100 | (0) 100 | 90 | (0) 85 | | | | | | |
| 7 | 1.12 | 1 | 2.24 | | | | | | | 100 | (0) 100 | 80 | (5) 85 | | | | | | |
| 7 | 1.12 | 1 | 8.96 | | | | | | | 100 | (0) 100 | 95 | (0) 85 | | | | | | |
| 3 | 1.12 | 1 | .56 | | | 25 | | (32) | 37 | 100 | | | | | | | | | |
| 3 | 1.12 | 1 | 2.24 | | | 25 | | (32) | 37 | 100 | | | | | | | | | |
| 3 | 1.12 | 1 | 2.24 | | | 95 | | (0) | 95 | 100 | | | | | | | | | |
| 3 | 1.12 | 1 | 8.96 | | | 15 | | (59) | 37 | 100 | | | | | | | | | |

TABLE 3-continued

| | | | | % PLANT INHIBITION AND % SAFENING EFFECT ( ) | | | | | | | | | | | | | | |
|---|---|---|---|---|---|---|---|---|---|---|---|---|---|---|---|---|---|---|
| HERB. NO. | RATE | ANTI-DOTE NO. | RATE | Sorghum | | Wheat | | Corn | | Barnyard Grass | | Rice | | Foxtail Green | | Wild Oats | | Soybean | |
| | | | | W | WO | W | WO | W | WO | W | WO | W | WO | W | WO | W | WO | W | WO |
| 3 | 1.12 | 1 | 8.96 | | | | | 95 (0) | 95 | 100 (0) | 100 | | | | | | | | |
| 3 | 4.48 | 1 | .56 | | | | | 90 (0) | 85 | 100 (0) | 100 | | | | | | | | |
| 3 | 4.48 | 1 | 2.24 | | | | | 55 (35) | 85 | 100 (0) | 100 | | | | | | | | |
| 3 | 4.48 | 1 | 2.24 | | | | | 90 (10) | 100 | 100 (0) | 100 | | | | | | | | |
| 3 | 4.48 | 1 | 8.96 | | | | | 50 (41) | 85 | 100 (0) | 100 | | | | | | | | |
| 3 | 4.48 | 1 | 8.96 | | | | | 90 (10) | 100 | 100 (0) | 100 | | | | | | | | |
| 3 | 1.12 | 2 | .56 | | | | | 35 (12) | 40 | 100 (0) | 100 | | | | | | | | |
| 3 | 1.12 | 2 | 2.24 | | | | | 20 (50) | 40 | 100 (0) | 100 | | | | | | | | |
| 3 | 1.12 | 2 | 8.96 | | | | | 10 (75) | 40 | 100 (0) | 100 | | | | | | | | |
| 3 | 4.48 | 2 | .56 | | | | | 80 (11) | 90 | 100 (0) | 100 | | | | | | | | |
| 3 | 4.48 | 2 | 2.24 | | | | | 85 (5) | 90 | 100 (0) | 100 | | | | | | | | |
| 3 | 4.48 | 2 | 8.96 | | | | | 80 (11) | 90 | 100 (0) | 100 | | | | | | | | |
| 3 | 1.12 | 3 | .56 | | | | | 50 (0) | 37 | 95 (5) | 100 | | | | | | | | |
| 3 | 1.12 | 3 | 2.24 | | | | | 45 (0) | 37 | 100 (0) | 100 | | | | | | | | |
| 3 | 1.12 | 3 | 8.96 | | | | | 25 (32) | 37 | 100 (0) | 100 | | | | | | | | |
| 3 | 4.48 | 3 | .56 | | | | | 85 (0) | 85 | 100 (0) | 100 | | | | | | | | |
| 3 | 4.48 | 3 | 2.24 | | | | | 75 (11) | 85 | 100 (0) | 100 | | | | | | | | |
| 3 | 4.48 | 3 | 8.96 | | | | | 70 (17) | 85 | 100 (0) | 100 | | | | | | | | |
| 3 | 1.12 | 20 | .56 | | | | | 45 (0) | 37 | 100 (0) | 100 | | | | | | | | |
| 3 | 1.12 | 20 | 2.24 | | | | | 50 (0) | 37 | 100 (0) | 100 | | | | | | | | |
| 3 | 1.12 | 20 | 8.96 | | | | | 10 (72) | 37 | 100 (0) | 100 | | | | | | | | |
| 3 | 4.48 | 20 | .56 | | | | | 90 (0) | 85 | 100 (0) | 100 | | | | | | | | |
| 3 | 4.48 | 20 | 2.24 | | | | | 85 (0) | 85 | 100 (0) | 100 | | | | | | | | |
| 3 | 4.48 | 20 | 8.96 | | | | | 80 (5) | 85 | 100 (0) | 100 | | | | | | | | |

TABLE 3-continued

| | | | | Sorghum | | Wheat | | Corn | | Barnyard Grass | | Rice | | Foxtail Green | | Wild Oats | | Soybean | |
|---|---|---|---|---|---|---|---|---|---|---|---|---|---|---|---|---|---|---|---|
| HERB. NO. | RATE | ANTI-DOTE NO. | RATE | W | WO | W | WO | W | WO | W | WO | W | WO | W | WO | W | WO | W | WO |
| 8 | .56 | | | 65 | 75 | | | | | | | | | | | | | | |
| 8 | .56 | 1 | .56 | 90 | (13) 75 | | | | | | | | | | | | | | |
| 8 | .56 | 1 | 2.24 | 5 | (0) 75 | | | | | | | | | | | | | | |
| 8 | .56 | 1 | 8.96 | | (93) 75 | | | | | | | | | | | | | | |
| 8 | 2.24 | 1 | .56 | 100 | (0) 100 | | | | | 100 | (0) | 50 | (46) | 100 | (0) | 100 | | | |
| 8 | 2.24 | 1 | 2.24 | 90 | (0) 100 | | | | | 100 | (0) | 30 | (67) | 100 | (0) | 100 | | | |
| 8 | 2.24 | 1 | 2.24 | | (10) 100 | | | | | | | | | | | | | | |
| 8 | 2.24 | 1 | 8.96 | 100 | (0) 100 | | | | | 100 | (0) | 65 | (30) | 100 | (0) | 100 | | | |
| 8 | 2.24 | 1 | 8.96 | | | | | | | 100 | (0) | 95 | (0) | 100 | (0) | 100 | | | |
| 8 | 8.96 | 1 | .56 | | | | | | | 100 | (0) | 95 | (0) | 100 | (0) | 100 | | | |
| 8 | 8.96 | 1 | 2.24 | | | | | | | 100 | (0) | 40 | (55) | 100 | (0) | 100 | | | |
| 8 | 8.96 | 1 | 8.96 | | | | | | | | | | | | | | | | |
| 8 | .56 | 3 | .56 | 50 | (33) 75 | | | | | 100 | (0) | 85 | (8) | 100 | (0) | 100 | | | |
| 8 | .56 | 3 | 2.24 | 90 | (0) 75 | | | | | | | | | | | | | | |
| 8 | .56 | 3 | 8.96 | 25 | (66) 75 | | | | | | | | | | | | | | |
| 8 | 2.24 | 3 | .56 | 95 | (5) 100 | | | | | 100 | (0) | 65 | (30) | 100 | (0) | | | | |
| 8 | 2.24 | 3 | .56 | | | | | | | 100 | (0) | 25 | (73) | 100 | (0) | | | | |
| 8 | 2.24 | 3 | 2.24 | 100 | (0) 100 | | | | | 100 | (0) | 75 | (16) | 100 | (0) | | | | |
| 8 | 2.24 | 3 | 2.24 | | | | | | | 100 | (0) | 60 | (33) | 100 | (0) | | | | |
| 8 | 2.24 | 3 | 8.96 | 95 | (5) 100 | | | | | 100 | (0) | 65 | (27) | | | | | | |
| 8 | 2.24 | 3 | 8.96 | | | | | | | | | | | | | | | | |
| 8 | 8.96 | 3 | .56 | | | | | | | | | | | | | | | | |
| 8 | 8.96 | 3 | 2.24 | | | | | | | | | | | | | | | | |
| 8 | 8.96 | 3 | 8.96 | | | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 8 | .56 | 20 | .56 | 25 | 75 | | | | | | | | | 100 | 100 | | | | |
| 8 | .56 | 20 | 2.24 | 45 | (66) | | | | | | | | | 100 | (0) | | | | |
| 8 | .56 | 20 | 8.96 | 30 | (40) | | | | | | | | | 100 | (0) | | | | |
| 8 | 2.24 | 20 | .56 | | (60) | | | | | 100 | (0) | | (24) | 100 | (0) | | | | |
| 8 | 2.24 | 20 | .56 | 95 | 100 | | | | | | | | | | | | | | |
| 8 | 2.24 | 20 | 2.24 | 50 | (5) | | | | | | | | | 100 | (0) | | | | |
| 8 | 2.24 | 20 | 2.24 | | 100 | | | | | 100 | (0) | | (46) | | | | | | |
| 8 | 2.24 | 20 | 8.96 | | (50) | | | | | 100 | (0) | | (24) | 100 | (0) | | | | |
| 8 | 2.24 | 20 | 8.96 | | 100 | | | | | | | | | | | | | | |
| 8 | 8.96 | 20 | .56 | 70 | (30) | | | | | 100 | (0) | 95 | 90 (0) | | | | | | |
| 8 | 8.96 | 20 | 2.24 | | | | | | | 100 | (0) | 30 | 90 (66) | | | | | | |
| 8 | 8.96 | 20 | 8.96 | | | | | | | 100 | (0) | 75 | 90 (16) | | | | | | |
| 9 | 2.24 | 1 | .56 | | | | | | | 100 | (0) | 20 | 62 (67) | | | | | | |
| 9 | 2.24 | 1 | 2.24 | | | | | | | 100 | (0) | 15 | 62 (75) | | | | | | |
| 9 | 2.24 | 1 | 8.96 | | | | | | | 100 | (0) | 100 | 62 (0) | | | | | | |
| 9 | 8.96 | 1 | .56 | | | | | | | 100 | (0) | 85 | 80 (0) | | | | | | |
| 9 | 8.96 | 1 | 2.24 | | | | | | | 100 | (0) | 50 | 80 (37) | | | | | | |
| 9 | 8.96 | 1 | 8.96 | | | | | | | 100 | (0) | 70 | 80 (12) | | | | | | |
| 9 | 2.24 | 3 | .56 | | | | | | | 100 | (0) | 0 | 62 (100) | | | | | | |
| 9 | 2.24 | 3 | 2.24 | | | | | | | 100 | (0) | 0 | 62 (100) | | | | | | |
| 9 | 2.24 | 3 | 8.96 | | | | | | | 100 | (0) | 0 | 62 (100) | | | | | | |
| 9 | 8.96 | 3 | .56 | | | | | | | 100 | (0) | 0 | 80 (100) | | | | | | |
| 9 | 8.96 | 3 | 2.24 | | | | | | | 100 | (0) | 0 | 80 (100) | | | | | | |
| 9 | 8.96 | 3 | 8.96 | | | | | | | 100 | (0) | 0 | 80 (100) | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 9 | 2.24 | 20 | .56 | | | | | | | 100 (0) | 100 | 50 (19) | 62 | | | | | | |
| 9 | 2.24 | 20 | 2.24 | | | | | | | 100 (0) | 100 | 60 (3) | 62 | | | | | | |
| 9 | 2.24 | 20 | 8.96 | | | | | | | 100 (0) | 100 | 30 (51) | 62 | | | | | | |
| 9 | 8.96 | 20 | .56 | | | | | | | 100 (0) | 100 | 85 (0) | 80 | | | | | | |
| 9 | 8.96 | 20 | 2.24 | | | | | | | 100 (0) | 100 | 60 (25) | 80 | | | | | | |
| 9 | 8.96 | 20 | 8.96 | | | | | | | 100 (0) | 100 | 70 (12) | 80 | | | | | | |
| 14 | .56 | 1 | .56 | 25 (65) | 73 | | | | | | | | | 95 (3) | 98 | | | | |
| 14 | .56 | 1 | 2.24 | 0 (100) | 73 | | | | | | | | | 95 (3) | 98 | | | | |
| 14 | .56 | 1 | 8.96 | 0 (100) | 73 | | | | | | | | | 95 (3) | 98 | | | | |
| 14 | 2.24 | 1 | .56 | 75 (21) | 95 | | | | | | | | | 100 (0) | 100 | | | | |
| 14 | 2.24 | 1 | 2.24 | 45 (52) | 95 | | | | | | | | | 100 (0) | 100 | | | | |
| 14 | 2.24 | 1 | 8.96 | 5 (94) | 95 | | | | | | | | | 100 (0) | 100 | | | | |
| 14 | .56 | 3 | .56 | 40 (45) | 73 | | | | | | | | | 95 (3) | 98 | | | | |
| 14 | .56 | 3 | 2.24 | 15 (79) | 73 | | | | | | | | | 100 (0) | 98 | | | | |
| 14 | .56 | 3 | 8.96 | 15 (79) | 73 | | | | | | | | | 100 (0) | 98 | | | | |
| 14 | 2.24 | 3 | .56 | 75 (21) | 95 | | | | | | | | | 100 (0) | 100 | | | | |
| 14 | 2.24 | 3 | 2.24 | 55 (42) | 95 | | | | | | | | | 100 (0) | 100 | | | | |
| 14 | 2.24 | 3 | 8.96 | 35 (63) | 95 | | | | | | | | | 100 (0) | 98 | | | | |
| 14 | .56 | 20 | .56 | 5 (93) | 73 | | | | | | | | | 95 (3) | 98 | | | | |
| 14 | .56 | 20 | 2.24 | 5 (93) | 73 | | | | | | | | | 100 (0) | 98 | | | | |
| 14 | .56 | 20 | 8.96 | 0 (100) | 73 | | | | | | | | | 100 (0) | 100 | | | | |
| 14 | 2.24 | 20 | .56 | 30 (68) | 95 | | | | | | | | | 100 (0) | 100 | | | | |
| 14 | 2.24 | 20 | 2.24 | 15 (84) | 95 | | | | | | | | | 100 (0) | 100 | | | | |
| 14 | 2.24 | 20 | 8.96 | 40 (57) | 95 | | | | | | | | | 100 (0) | 100 | | | | |

TABLE 3-continued

% PLANT INHIBITION AND % SAFENING EFFECT ( )

| HERB. NO. | RATE | ANTI-DOTE NO. | ANTI-DOTE RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 4 | .56 | 1 | .56 | | | | | | | 100 (0) | 100 | 40 (38) | 65 | | | | | | |
| 4 | .56 | 1 | .56 | 80 (17) | 97 | | | | | 100 (0) | 100 | 15 (76) | 65 | 100 (0) | 100 | | | | |
| 4 | .56 | 1 | 2.24 | 25 (74) | 97 | | | | | 100 (0) | 100 | 25 (73) | 95 | 100 (0) | 100 | | | | |
| 4 | .56 | 1 | 2.24 | | | | | | | 100 (0) | 100 | 50 (23) | 65 | | | | | | |
| 4 | .56 | 1 | 8.96 | 15 (84) | 97 | | | | | 100 (0) | 100 | 5 (94) | 95 | | | | | | |
| 4 | .56 | 1 | 8.96 | | | | | | | 100 (0) | 100 | 65 (7) | 70 | 100 (0) | 100 | | | | |
| 4 | .56 | 1 | 8.96 | | | | | | | 100 (0) | 100 | 90 (0) | 70 | 100 (0) | 100 | | | | |
| 4 | 2.24 | 1 | .56 | | | | | | | 100 (0) | 100 | 30 (70) | 100 | 100 (0) | 100 | | | | |
| 4 | 2.24 | 1 | .56 | 95 (5) | 100 | | | | | 100 (0) | 100 | 15 (78) | 70 | | | | | | |
| 4 | 2.24 | 1 | 2.24 | 85 (15) | 100 | | | | | 100 (0) | 100 | 5 (95) | 100 | | | | | | |
| 4 | 2.24 | 1 | 2.24 | | | | | | | 100 (0) | 100 | 15 (81) | 80 | | | | | | |
| 4 | 2.24 | 1 | 2.24 | | | | | | | 100 (0) | 100 | 5 (93) | 80 | | | | | | |
| 4 | 2.24 | 1 | 8.96 | 80 (20) | 100 | | | | | 100 (0) | 100 | 0 (100) | 80 | | | | | | |
| 4 | 2.24 | 1 | 8.96 | | | | | | | 100 (0) | 100 | | | | | 40 | | 55 | |
| 4 | 2.24 | 1 | 8.96 | | | | | | | 100 (0) | 100 | 15 (84) | 95 | | | 35 | | (27) 55 | |
| 4 | .56 | 2 | .56 | | | | | | | 100 (0) | 100 | 5 (94) | 95 | | | 45 | | (36) 55 | |
| 4 | .56 | 2 | 2.24 | | | | | | | 100 (0) | 100 | | | | | | | (18) | |
| 4 | .56 | 2 | 8.96 | | | | | | | | | | | | | | | | |
| 4 | 1.12 | 2 | .56 | | | | | | | | | | | | | | | | |
| 4 | 1.12 | 2 | 2.24 | | | | | | | | | | | | | | | | |
| 4 | 1.12 | 2 | 8.96 | | | | | | | | | | | | | | | | |
| 4 | 2.24 | 2 | .56 | | | | | | | | | | | | | | | | |
| 4 | 2.24 | 2 | 2.24 | | | | | | | | | | | | | | | | |

TABLE 3-continued

% PLANT INHIBITION AND % SAFENING EFFECT ( )

| HERB. NO. | HERB. RATE | ANTI-DOTE NO. | ANTI-DOTE RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 4 | 2.24 | 2 | 8.96 | | | | | | | 100 | 100 (0) | 5 | 95 (94) | | | | | | |
| 4 | 4.48 | 2 | .56 | | | | | | | 100 | 100 (0) | | | | | | | 70 | 80 (12) |
| 4 | 4.48 | 2 | 2.24 | | | | | | | 100 | 100 (0) | | | | | | | 80 | 80 (0) |
| 4 | 4.48 | 2 | 8.96 | | | | | | | 100 | 100 (0) | | | | | | | 70 | 80 (12) |
| 4 | .56 | 3 | .56 | 80 | 97 (17) | | | | | | | | | | | | | | |
| 4 | .56 | 3 | .56 | | (12) | | | | | 100 | 100 (0) | (100) | 65 | | | | | | |
| 4 | .56 | 3 | .56 | | | | | | | 100 | 100 (0) | (100) | 70 | | | | | | |
| 4 | .56 | 3 | 2.24 | | | | | | | 100 | 100 (0) | (100) | 65 | | | | | | |
| 4 | .56 | 3 | 2.24 | 85 | 97 (12) | | | | | | | | | | | | | | |
| 4 | .56 | 3 | 2.24 | | | | | | | 100 | 100 (0) | (100) | 70 | 100 | 100 (0) | | | | |
| 4 | .56 | 3 | 8.96 | 70 | 97 (27) | | | | | 100 | 100 (0) | (100) | 65 | 100 | 100 (0) | | | | |
| 4 | .56 | 3 | 8.96 | | | | | | | 100 | 100 (0) | (78) | 70 | 54 | 100 (46) | | | | |
| 4 | .56 | 3 | 8.96 | | | | | | | 95 | 100 (5) | | | | | | | | |
| 4 | .56 | 3 | .56 | 95 | 100 (5) | | | | | 100 | 100 (0) | (100) | 70 | 100 | 100 (0) | | | | |
| 4 | 2.24 | 3 | .56 | | | | | | | 100 | 100 (0) | (100) | 90 | | | | | | |
| 4 | 2.24 | 3 | .56 | | | | | | | 100 | 100 (0) | (88) | 70 | 100 | 100 (0) | | | | |
| 4 | 2.24 | 3 | 2.24 | 95 | 100 (5) | | | | | 100 | 100 (0) | (100) | 70 | | | | | | |
| 4 | 2.24 | 3 | 2.24 | | | | | | | 100 | 100 (0) | (100) | 90 | | | | | | |
| 4 | 2.24 | 3 | 2.24 | | | | | | | 100 | 100 (5) | (92) | 70 | 100 | 100 (0) | | | | |
| 4 | 2.24 | 3 | 8.96 | 90 | 100 (10) | | | | | 95 | 100 (5) | (88) | 90 | | | | | | |
| 4 | 2.24 | 3 | 8.96 | | | | | | | 100 | 100 (0) | (100) | 70 | 100 | 100 (0) | | | | |
| 4 | 2.24 | 3 | 8.96 | | | | | | | 100 | 100 (0) | (100) | 70 | | | | | | |
| 4 | .56 | 4 | .56 | | | | | | | | | | | | | | | | |
| 4 | .56 | 4 | 2.24 | | | | | | | | | | | | | | | | |

TABLE 3-continued

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 4 | .56 | 4 | 8.96 | | | | | | | 100 | 100 | 0 (100) | 70 | | | | | | |
| 4 | 2.24 | 4 | .56 | | | | | | | 100 | 100 | 10 (88) | 90 | | | | | | |
| 4 | 2.24 | 4 | 2.24 | | | | | | | 100 | 100 | 15 (83) | 90 | | | | | | |
| 4 | 2.24 | 4 | 8.96 | | | | | | | 95 | 100 | 5 (94) | 90 | | | | | | |
| 4 | .56 | 5 | .56 | | | | | | | 100 | 100 | 30 (60) | 75 | | | | | | |
| 4 | .56 | 5 | 2.24 | | | | | | | 100 | 100 | 15 (80) | 75 | | | | | | |
| 4 | .56 | 5 | 8.96 | | | | | | | 100 | 100 | 15 (80) | 75 | | | | | | |
| 4 | 2.24 | 5 | .56 | | | | | | | 100 | 100 | 35 (63) | 95 | | | | | | |
| 4 | 2.24 | 5 | 2.24 | | | | | | | 100 | 100 | 10 (89) | 95 | | | | | | |
| 4 | 2.24 | 5 | 8.96 | | | | | | | 100 | 100 | 10 (89) | 95 | | | | | | |
| 4 | .56 | 13 | .56 | | | | | | | 100 | 100 | 5 (94) | 85 | | | | | | |
| 4 | .56 | 13 | 2.24 | | | | | | | 100 | 100 | 5 (94) | 85 | | | | | | |
| 4 | .56 | 13 | 8.96 | | | | | | | 100 | 100 | 0 (100) | 85 | | | | | | |
| 4 | 2.24 | 13 | .56 | | | | | | | 100 | 100 | 65 (31) | 95 | | | | | | |
| 4 | 2.24 | 13 | 2.24 | | | | | | | 100 | 100 | 10 (89) | 95 | | | | | | |
| 4 | 2.24 | 13 | 8.96 | | | | | | | 100 | 100 | 5 (94) | 95 | | | | | | |
| 4 | .56 | 20 | .56 | 60 | 97 (38) | | | | | 100 | 100 | 20 (69) | 65 | 100 | 100 (0) | | | | |
| 4 | .56 | 20 | .56 | | | | | | | 100 | 100 | 55 (15) | 65 | | | | | | |
| 4 | .56 | 20 | 2.24 | | | | | | | | | | | | | | | | |
| 4 | .56 | 20 | 2.24 | 40 | 97 (58) | | | | | | | | | 100 | 100 (0) | | | | |
| 4 | .56 | 20 | 8.96 | | | | | | | 100 | 100 | 20 (69) | 65 | | | | | | |
| 4 | .56 | 20 | 8.96 | 10 | 97 (89) | | | | | | | | | 100 | 100 (0) | | | | |
| 4 | 2.24 | 20 | .56 | 85 | 100 (15) | | | | | | | | | 100 | 100 (0) | | | | |
| 4 | 2.24 | 20 | .56 | | | | | | | 100 | 100 | 30 (57) | 70 | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 4 | 2.24 | 20 | 2.24 | 60 (40) | 100 | | | | | 100 (0) | 100 | 70 (0) | 70 | 100 (0) | 100 | | | | |
| 4 | 2.24 | 20 | 8.96 | 60 (40) | 100 | | | | | 100 (0) | 100 | 25 (64) | 70 | 100 (0) | 100 | | | | |
| 4 | 2.24 | 1 | .56 | | | | | | | 100 (0) | 100 | 30 (68) | 95 | | | | | | |
| 10 | 2.24 | 1 | 2.24 | | | | | | | 100 (0) | 100 | 50 (47) | 95 | | | | | | |
| 10 | 2.24 | 1 | 8.96 | | | | | | | 100 (0) | 100 | 50 (47) | 95 | | | | | | |
| 10 | 8.96 | 1 | .56 | | | | | | | 100 (0) | 100 | 90 (0) | 85 | | | | | | |
| 10 | 8.96 | 1 | 2.24 | | | | | | | 100 (0) | 100 | 40 (52) | 85 | | | | | | |
| 10 | 8.96 | 1 | 8.96 | | | | | | | 100 (0) | 100 | 30 (64) | 95 | | | | | | |
| 10 | 2.24 | 3 | .56 | | | | | | | 100 (0) | 100 | 10 (89) | 95 | | | | | | |
| 10 | 2.24 | 3 | 2.24 | | | | | | | 100 (0) | 100 | 10 (89) | 95 | | | | | | |
| 10 | 2.24 | 3 | 8.96 | | | | | | | 100 (0) | 100 | 5 (94) | 85 | | | | | | |
| 10 | 8.96 | 3 | .56 | | | | | | | 100 (0) | 100 | 15 (82) | 85 | | | | | | |
| 10 | 8.96 | 3 | 2.24 | | | | | | | 100 (0) | 100 | 75 (11) | 85 | | | | | | |
| 10 | 8.96 | 3 | 8.96 | | | | | | | 100 (0) | 100 | 60 (29) | 95 | | | | | | |
| 10 | 2.24 | 20 | .56 | | | | | | | 100 (0) | 100 | 25 (73) | 95 | | | | | | |
| 10 | 2.24 | 20 | 2.24 | | | | | | | 100 (0) | 100 | 45 (52) | 95 | | | | | | |
| 10 | 2.24 | 20 | 8.96 | | | | | | | 100 (0) | 100 | 30 (68) | 85 | | | | | | |
| 10 | 8.96 | 20 | .56 | | | | | | | 100 (0) | 100 | 85 (0) | 85 | | | | | | |
| 10 | 8.96 | 20 | 2.24 | | | | | | | 100 (0) | 100 | 90 (0) | 85 | | | | | | |
| 10 | 8.96 | 20 | 8.96 | | | | | | | 100 (0) | 100 | 85 (0) | 85 | | | | | | |
| 11 | .56 | 1 | .56 | 40 (56) | 93 | | | | | | | | | 100 (0) | 100 | | | | |
| 11 | .56 | 1 | 2.24 | 60 (35) | 93 | | | | | | | | | 100 (0) | 100 | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 11 | .56 | 1 | 8.96 | 0 | 93 (100) | | | | | | | | | 95 (5) | 100 | | | | |
| 11 | 2.24 | 1 | .56 | | | | | | | 100 (0) | 100 | 20 (66) | 60 | | | | | | |
| 11 | 2.24 | 1 | .56 | 95 | 98 (3) | | | | | | | | | | | | | | |
| 11 | 2.24 | 1 | 2.24 | 85 | 98 (13) | | | | | | | | | | | | | | |
| 11 | 2.24 | 1 | 2.24 | | | | | | | 100 (0) | 100 | 35 (41) | 60 | 100 (0) | 100 | | | | |
| 11 | 2.24 | 1 | 8.96 | | | | | | | 100 (0) | 100 | 60 (0) | 60 | 100 (0) | 100 | | | | |
| 11 | 2.24 | 1 | 8.96 | 90 | 98 (8) | | | | | | | | | | | | | | |
| 11 | 8.96 | 1 | .56 | | | | | | | 100 (0) | 100 | 30 (69) | 97 | 100 (0) | 100 | | | | |
| 11 | 8.96 | 1 | 2.24 | | | | | | | 100 (0) | 100 | 65 (32) | 97 | | | | | | |
| 11 | 8.96 | 1 | 8.96 | | | | | | | 100 (0) | 100 | 35 (63) | 97 | | | | | | |
| 11 | .56 | 3 | .56 | 50 | 93 (46) | | | | | | | | | 100 (0) | 100 | | | | |
| 11 | 2.24 | 3 | 2.24 | 40 | 93 (56) | | | | | | | | | 100 (0) | 100 | | | | |
| 11 | 2.24 | 3 | 8.96 | 60 | 93 (35) | | | | | | | | | 95 (5) | 100 | | | | |
| 11 | 2.24 | 3 | .56 | 95 | 98 (3) | | | | | | | | | 100 (0) | 100 | | | | |
| 11 | 2.24 | 3 | .56 | | | | | | | 100 (0) | 100 | 0 (100) | 60 | | | | | | |
| 11 | 2.24 | 3 | 2.24 | | | | | | | 100 (0) | 100 | 0 (100) | 60 | | | | | | |
| 11 | 2.24 | 3 | 2.24 | 95 | 98 (3) | | | | | | | | | 100 (0) | 100 | | | | |
| 11 | 2.24 | 3 | 8.96 | | | | | | | 100 (0) | 100 | 0 (100) | 60 | | | | | | |
| 11 | 2.24 | 3 | 8.96 | 95 | 98 (3) | | | | | | | | | 100 (0) | 100 | | | | |
| 11 | 8.96 | 3 | .56 | | | | | | | 100 (0) | 100 | 0 (100) | 97 | | | | | | |
| 11 | 8.96 | 3 | 2.24 | | | | | | | 100 (0) | 100 | 5 (94) | 97 | | | | | | |
| 11 | 8.96 | 3 | 8.96 | | | | | | | 100 (0) | 100 | 0 (100) | 97 | | | | | | |
| 11 | .56 | 20 | .56 | 60 | 93 (35) | | | | | | | | | 100 (0) | 100 | | | | |
| 11 | .56 | 20 | 2.24 | 40 | 93 (56) | | | | | | | | | 100 (0) | 100 | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 11 | .56 | 20 | 8.96 | 40 | 93 | | | | | | | | | 95 | 100 | | | | |
| 11 | 2.24 | 20 | .56 | 85 | (56) 98 | | | | | | | | | 100 | (5) 100 | | | | |
| 11 | 2.24 | 20 | .56 | | (13) | | | | | 100 | (0) 100 | | | 100 | (0) 100 | | | | |
| 11 | 2.24 | 20 | 2.24 | 85 | 98 | | | | | 100 | (0) 100 | | (100) 60 | 100 | (0) 100 | | | | |
| 11 | 2.24 | 20 | 2.24 | | (13) | | | | | 100 | (0) 100 | 55 | (8) 60 | | | | | | |
| 11 | 2.24 | 20 | 8.96 | 75 | (23) 98 | | | | | 100 | (0) 100 | 40 | (33) 60 | | (0) 100 | | | | |
| 11 | 8.96 | 20 | .56 | | | | | | | 100 | (0) 100 | 70 | (27) 97 | | | | | | |
| 11 | 8.96 | 20 | 2.24 | | | | | | | 100 | (0) 100 | 75 | (22) 97 | | | | | | |
| 11 | 8.96 | 20 | 8.96 | | | | | | | 100 | (0) 100 | 45 | (53) 97 | | | | | | |
| 5 | .03 | 3 | .56 | | | 60 | 95 | | | | | | | 95 | 85 | | | | |
| 5 | .03 | 3 | 2.24 | | | 95 | (36) 95 | | | | | | | 90 | (0) 85 | | | | |
| 5 | .03 | 3 | 8.96 | | | 30 | (0) 95 | | | | | | | 100 | (0) 85 | | | | |
| 5 | .07 | 3 | .56 | | | 100 | (68) 100 | | | | | | | 95 | (0) 95 | | | | |
| 5 | .07 | 3 | 2.24 | | | 80 | (0) 100 | | | | | | | 95 | (0) 95 | | | | |
| 5 | .07 | 3 | 8.96 | | | 100 | (20) 100 | | | | | | | 100 | (0) 95 | | | | |
| 5 | .03 | 13 | .56 | | | | (0) | 95 | (0) 95 | 100 | (0) 100 | | | | | | | | |
| 5 | .03 | 13 | 2.24 | | | | | 95 | (0) 95 | 100 | (0) 100 | | | | | | | | |
| 5 | .03 | 13 | 8.96 | | | | | 95 | (0) 95 | 100 | (0) 100 | | | | | | | | |
| 5 | .07 | 13 | .56 | | | | | 95 | (5) 100 | 100 | (0) 100 | | | | | | | | |
| 5 | .07 | 13 | 2.24 | | | | | 95 | (5) 100 | 100 | (0) 100 | | | | | | | | |
| 5 | .07 | 13 | 8.96 | | | | | 95 | (5) 100 | 100 | (0) 100 | | | | | | | | |
| 12 | .56 | 1 | .56 | 60 | 65 | | | | | | | | | 100 | (0) 100 | | | | |
| 12 | .56 | 1 | 2.24 | 65 | (7) 65 | | | | | | | | | 100 | (0) 100 | | | | |
| | | | | | (0) | | | | | | | | | | | | | | |

TABLE 3-continued

% PLANT INHIBITION AND % SAFENING EFFECT ( )

| HERB. NO. | RATE | ANTI-DOTE NO. | RATE | Sorghum W | Sorghum WO | Wheat W | Wheat WO | Corn W | Corn WO | Barnyard Grass W | Barnyard Grass WO | Rice W | Rice WO | Foxtail Green W | Foxtail Green WO | Wild Oats W | Wild Oats WO | Soybean W | Soybean WO |
|---|---|---|---|---|---|---|---|---|---|---|---|---|---|---|---|---|---|---|---|
| 12 | .56 | 1 | 8.96 | 55 | 65 | | | | | | | | | 100 | 100 | | | | |
| 12 | 2.24 | 1 | .56 | 100 (15) | 100 | | | | | | | | | 100 (0) | 100 | | | | |
| 12 | 2.24 | 1 | 2.24 | 100 (0) | 100 | | | | | | | | | 100 (0) | 100 | | | | |
| 12 | 2.24 | 1 | 8.96 | 95 (5) | 100 | | | | | | | | | 100 (0) | 100 | | | | |
| 12 | 4.48 | 1 | .56 | | | | | | | 100 (0) | 100 | 75 (0) | 72 | | | | | | |
| 12 | 4.48 | 1 | 2.24 | | | | | | | 100 (0) | 100 | 80 (0) | 72 | | | | | | |
| 12 | 4.48 | 1 | 8.96 | | | | | | | 100 (0) | 100 | 80 (0) | 85 | 100 (0) | 100 | | | | |
| 12 | .56 | 3 | .56 | 65 (0) | 65 | | | | | 100 (0) | 100 | 90 (0) | 85 | 100 (0) | 100 | | | | |
| 12 | .56 | 3 | 2.24 | 50 (23) | 65 | | | | | 100 (0) | 100 | 85 (0) | 85 | 100 (0) | 100 | | | | |
| 12 | .56 | 3 | 8.96 | 95 (0) | 65 | | | | | | | | | 100 (0) | 100 | | | | |
| 12 | 2.24 | 3 | .56 | 95 (5) | 100 | | | | | 100 (0) | 100 | 70 (2) | 72 | 10 (90) | 100 | | | | |
| 12 | 2.24 | 3 | 2.24 | 100 (0) | 100 | | | | | 100 (0) | 100 | 70 (2) | 72 | | | | | | |
| 12 | 2.24 | 3 | 8.96 | | | | | | | 100 (0) | 100 | 85 (0) | 72 | 100 (0) | 100 | | | | |
| 12 | 2.24 | 3 | 2.24 | 95 (5) | 100 | | | | | 100 (0) | 100 | 75 (11) | 85 | 100 (0) | 100 | | | | |
| 12 | 4.48 | 3 | .56 | | | | | | | 100 (0) | 100 | 80 (5) | 85 | | | | | | |
| 12 | 4.48 | 3 | 2.24 | | | | | | | 100 (0) | 100 | 70 (17) | 85 | | | | | | |
| 12 | 4.48 | 3 | 8.96 | | | | | | | | | | | 100 (0) | 100 | | | | |
| 12 | .56 | 20 | .56 | 30 (53) | 65 | | | | | | | | | 100 (0) | 100 | | | | |
| 12 | .56 | 20 | 2.24 | 65 (0) | 65 | | | | | | | | | 100 (0) | 100 | | | | |

TABLE 3-continued

| | | | | % PLANT INHIBITION AND % SAFENING EFFECT ( ) | | | | | | | | | | | | | | |
|---|---|---|---|---|---|---|---|---|---|---|---|---|---|---|---|---|---|---|
| | | | | Sorghum | | Wheat | | Corn | | Barnyard Grass | | Rice | | Foxtail Green | | Wild Oats | | Soybean |
| HERB. NO. | RATE | ANTI-DOTE NO. | RATE | W | WO | W | WO | W | WO | W | WO | W | WO | W | WO | W | WO | W WO |
| 12 | .56 | 20 | 8.96 | 55 | 65 | | | | | | | | | | | | | |
| 12 | 2.24 | 20 | .56 | | (15) | | | | | 100 | 100 (0) | 80 | 72 (0) | 100 | 100 (0) | | | |
| 12 | 2.24 | 20 | .56 | 95 | 100 | | | | | | | | | | | | | |
| 12 | 2.24 | 20 | 2.24 | | (5) | | | | | 100 | 100 (0) | 75 | 72 (0) | 100 | 100 (0) | | | |
| 12 | 2.24 | 20 | 2.24 | 95 | 100 | | | | | | | | | | | | | |
| 12 | 2.24 | 20 | 8.96 | | (5) | | | | | 100 | 100 (0) | 75 | 72 (0) | 100 | 100 (0) | | | |
| 12 | 2.24 | 20 | 8.96 | 85 | 100 | | | | | | | | | | | | | |
| 12 | 4.48 | 20 | .56 | | (15) | | | | | 100 | 100 (0) | 80 | 85 (5) | | | | | |
| 12 | 4.48 | 20 | 2.24 | | | | | | | 100 | 100 (0) | 80 | 85 (5) | | | | | |
| 12 | 4.48 | 20 | 8.96 | | | | | | | 100 | 100 (0) | 85 | 85 (0) | | | | | |

Example 41

The following procedure shows interaction between herbicide and antidote when applied together as a mixture before emergence of the crop and weed species. Containers were filled and compacted with fumigated silt loam top soil to a depth of about 1.3 cm from the top of the container. A first container was designated as an untreated control, a second container was designated as a herbicide control, and a third container was designated as a herbicide+antidote test container. Each of the containers was seeded with both crop plant and weed species. The herbicide and the herbicide+antidote test mixture were applied to the seeded containers either by a procedure of topical application to a soil layer placed over the seed bed followed by watering to achieve incorporation, or by a procedure of incorporation into soil and then placement of the treated soil into the container over the seed bed. The containers were then placed on a greenhouse bench, and sub-irrigated as required for the duration of the test. Plant response was observed about three weeks after initial treatment. Results are reported in Table 4.

TABLE 4

% PLANT INHIBITION AND % SAFENING EFFECT ( )

| HERB. NO. | RATE | ANTIDOTE NO. | RATE | Sorghum W | Sorghum WO | Foxtail Green W | Foxtail Green WO | Crabgrass Large W | Crabgrass Large WO | Barnyard Grass W | Barnyard Grass WO | Corn W | Corn WO |
|---|---|---|---|---|---|---|---|---|---|---|---|---|---|
| 2 | .56 | 1 | .03 | 60 (31) | 87 | 98 (2) | 100 | | | 100 (0) | 100 | | |
| 2 | .56 | 1 | .03 | 20 (45) | 37 | 100 (0) | 100 | | | 100 (0) | 100 | | |
| 2 | .56 | 1 | .07 | 25 (73) | 95 | 100 (0) | 100 | | | 100 (0) | 100 | | |
| 2 | .56 | 1 | .14 | 13 (83) | 78 | 100 (0) | 100 | | | 95 (0) | 95 | | |
| 2 | .56 | 1 | .14 | 15 (83) | 90 | 100 (0) | 100 | | | 95 (0) | 95 | | |
| 2 | .56 | 1 | .14 | 10 (87) | 77 | 100 (0) | 100 | | | 100 (0) | 100 | | |
| 2 | .56 | 1 | .14 | 23 (74) | 90 | 95 (0) | 95 | | | 100 (0) | 100 | | |
| 2 | .56 | 1 | .14 | 20 (77) | 87 | 100 (0) | 100 | | | 100 (0) | 100 | | |
| 2 | .56 | 1 | .14 | 10 (85) | 70 | | | | | | | | |
| 2 | .56 | 1 | .14 | 13 (84) | 83 | | | | | | | | |
| 2 | .56 | 1 | .14 | 5 (94) | 95 | 100 (0) | 100 | | | 100 (0) | 100 | | |
| 2 | .56 | 1 | .14 | 10 (89) | 92 | 100 (0) | 100 | | | 100 (0) | 100 | | |
| 2 | .56 | 1 | .14 | 43 (0) | 37 | 100 (0) | 100 | | | 100 (0) | 100 | | |
| 2 | .56 | 1 | .14 | 18 (80) | 93 | 100 (0) | 90 | | | 100 (0) | 100 | | |
| 2 | .56 | 1 | .56 | 0 (100) | 78 | 98 (2) | 100 | | | 98 (0) | 95 | | |
| 2 | .56 | 1 | .56 | 20 (74) | 77 | 100 (0) | 100 | | | 100 (0) | 100 | | |
| 2 | .56 | 1 | .56 | 18 (80) | 92 | 100 (0) | 100 | | | 100 (0) | 100 | | |
| 2 | .56 | 1 | .56 | 15 (59) | 37 | 98 (2) | 100 | | | 98 (2) | 100 | | |
| 2 | .56 | 1 | .56 | 8 (91) | 95 | 100 (0) | 100 | | | 100 (0) | 100 | | |
| 2 | .56 | 1 | .56 | 0 (100) | 93 | 95 (0) | 90 | | | 95 (5) | 100 | | |
| 2 | .56 | 1 | .56 | 48 (49) | 95 | 100 (0) | 100 | | | 98 (2) | 100 | | |
| 2 | .56 | 1 | .56 | 13 (81) | 70 | | | | | | | | |
| 2 | .56 | 1 | .56 | 0 (100) | 87 | 100 (0) | 100 | | | 100 (0) | 100 | | |
| 2 | .56 | 1 | .56 | 8 (90) | 83 | | | | | | | | |
| 2 | .56 | 1 | .56 | 8 (91) | 90 | 85 (10) | 95 | | | 100 (0) | 100 | | |
| 2 | .56 | 1 | .56 | 30 (66) | 90 | 100 (0) | 100 | | | 100 (0) | 95 | | |
| 2 | .56 | 1 | 1.12 | 8 (91) | 95 | 100 (0) | 100 | | | 100 (0) | 100 | | |
| 2 | .56 | 1 | 2.24 | 18 (80) | 93 | 95 (0) | 90 | | | 100 (0) | 100 | | |
| 2 | .56 | 1 | 2.24 | 10 (89) | 92 | 100 (0) | 100 | | | 100 (0) | 100 | | |
| 2 | .56 | 1 | 2.24 | 5 (92) | 70 | | | | | | | | |
| 2 | .56 | 1 | 2.24 | 5 (93) | 77 | 100 (0) | 100 | | | 100 (0) | 100 | | |
| 2 | .56 | 1 | 2.24 | 5 | 83 | | | | | | | | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | | | Sorghum | | Foxtail Green | | Crabgrass Large | | Barnyard Grass | | Corn | |
| HERB. NO. | RATE | ANTIDOTE NO. | RATE | W | WO | W | WO | W | WO | W | WO | W | WO |
| 2 | .56 | 1 | 2.24 | 13 (93) | 95 | 100 (0) | 100 | | | 100 (0) | 100 | | |
| 2 | .56 | 1 | 2.24 | 5 (86) | 78 | 100 (0) | 100 | | | 100 (0) | 95 | | |
| 2 | .56 | 1 | 2.24 | 13 (93) | 90 | 85 (10) | 95 | | | 100 (0) | 100 | | |
| 2 | .56 | 1 | 2.24 | 23 (85) | 90 | 100 (0) | 100 | | | 100 (0) | 95 | | |
| 2 | 1.12 | 1 | .03 | 83 (74) | 95 | 100 (0) | 100 | | | 100 (0) | 100 | | |
| 2 | 1.12 | 1 | .03 | 83 (12) | 65 | 100 (0) | 100 | | | 100 (0) | 100 | | |
| 2 | 1.12 | 1 | .07 | 28 (0) | 95 | 100 (0) | 100 | | | 100 (0) | 100 | | |
| 2 | 1.12 | 1 | .14 | 33 (70) | 65 | 100 (0) | 100 | | | 100 (0) | 100 | | |
| 2 | 1.12 | 1 | .14 | 8 (49) | 98 | 100 (0) | 100 | | | 100 (0) | 100 | | |
| 2 | 1.12 | 1 | .14 | 28 (91) | 90 | 100 (0) | 100 | | | 100 (0) | 100 | | |
| 2 | 1.12 | 1 | .14 | 33 (68) | 95 | 95 (3) | 98 | | | 100 (0) | 100 | | |
| 2 | 1.12 | 1 | .14 | 43 (65) | 95 | 100 (0) | 100 | | | 100 (0) | 100 | | |
| 2 | 1.12 | 1 | .14 | 28 (54) | 95 | 95 (0) | 95 | | | 100 (0) | 100 | | |
| 2 | 1.12 | 1 | .14 | 40 (70) | 95 | 100 (0) | 100 | | | 100 (0) | 100 | | |
| 2 | 1.12 | 1 | .14 | 8 (57) | 85 | | | | | | | | |
| 2 | 1.12 | 1 | .14 | 20 (90) | 85 | | | | | | | | |
| 2 | 1.12 | 1 | .14 | 53 (76) | 93 | 100 (0) | 100 | | | 100 (0) | 100 | | |
| 2 | 1.12 | 1 | .14 | 28 (43) | 95 | 100 (0) | 100 | | | 100 (0) | 100 | | |
| 2 | 1.12 | 1 | .56 | 8 (70) | 85 | | | | | | | | |
| 2 | 1.12 | 1 | .56 | 8 (90) | 95 | 100 (0) | 100 | | | 100 (0) | 100 | | |
| 2 | 1.12 | 1 | .56 | 13 (91) | 85 | | | | | | | | |
| 2 | 1.12 | 1 | .56 | 18 (84) | 95 | 100 (0) | 100 | | | 100 (0) | 100 | | |
| 2 | 1.12 | 1 | .56 | 13 (81) | 90 | 100 (0) | 100 | | | 100 (0) | 100 | | |
| 2 | 1.12 | 1 | .56 | 5 (85) | 98 | 100 (0) | 100 | | | 98 (2) | 100 | | |
| 2 | 1.12 | 1 | .56 | 33 (94) | 95 | 100 (0) | 100 | | | 100 (0) | 100 | | |
| 2 | 1.12 | 1 | .56 | 43 (65) | 100 | 100 (0) | 100 | | | 100 (0) | 100 | | |
| 2 | 1.12 | 1 | .56 | 25 (57) | 65 | 100 (0) | 100 | | | 100 (0) | 100 | | |
| 2 | 1.12 | 1 | .56 | 25 (61) | 95 | 100 (0) | 95 | | | 100 (0) | 100 | | |
| 2 | 1.12 | 1 | .56 | 18 (73) | 95 | 95 (3) | 98 | | | 100 (0) | 100 | | |
| 2 | 1.12 | 1 | .56 | 30 (81) | 93 | 100 (0) | 100 | | | 100 (0) | 100 | | |
| 2 | 1.12 | 1 | 1.12 | 53 (67) | 100 | 100 (0) | 100 | | | 100 (0) | 100 | | |
| 2 | 1.12 | 1 | 2.24 | 8 (47) | 95 | 100 (0) | 100 | | | 100 (0) | 100 | | |
| 2 | 1.12 | 1 | 2.24 | 28 (91) | 93 | 100 (0) | 100 | | | 100 (0) | 100 | | |
| 2 | 1.12 | 1 | 2.24 | 5 (69) | 90 | 100 (0) | 100 | | | 100 (0) | 100 | | |
| 2 | 1.12 | 1 | 2.24 | 18 (94) | 95 | 95 (0) | 95 | | | 95 (5) | 100 | | |
| 2 | 1.12 | 1 | 2.24 | 5 (81) | 85 | | | | | | | | |
| 2 | 1.12 | 1 | 2.24 | 5 (94) | 98 | 100 (0) | 100 | | | 98 (2) | 100 | | |
| 2 | 1.12 | 1 | 2.24 | 70 (94) | 100 | 100 (0) | 100 | | | 100 (0) | 100 | | |
| | | | | (30) | | | | | | | | | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 2 | 1.12 | 1 | 2.24 | 35 (63) | 95 | 98 (0) | 98 | | | 100 (0) | 100 | | |
| 2 | 1.12 | 1 | 2.24 | 20 (76) | 85 | | | | | | | | |
| 2 | 2.24 | 1 | .03 | 85 (5) | 90 | 100 (0) | 100 | | | 100 (0) | 100 | | |
| 2 | 2.24 | 1 | .03 | 95 (2) | 97 | 100 (0) | 100 | | | 100 (0) | 100 | | |
| 2 | 2.24 | 1 | .07 | 60 (39) | 99 | 100 (0) | 100 | | | 100 (0) | 100 | | |
| 2 | 2.24 | 1 | .14 | 93 (4) | 97 | 100 (0) | 100 | | | 100 (0) | 100 | | |
| 2 | 2.24 | 1 | .14 | 70 (28) | 98 | 100 (0) | 100 | | | 98 (2) | 100 | | |
| 2 | 2.24 | 1 | .14 | 38 (61) | 98 | 98 (0) | 98 | | | 100 (0) | 100 | | |
| 2 | 2.24 | 1 | .14 | 75 (24) | 99 | 100 (0) | 100 | | | 100 (0) | 100 | | |
| 2 | 2.24 | 1 | .14 | 40 (57) | 95 | 95 (5) | 100 | | | 100 (0) | 100 | | |
| 2 | 2.24 | 1 | .14 | 73 (24) | 97 | 100 (0) | 100 | | | 100 (0) | 100 | | |
| 2 | 2.24 | 1 | .14 | 40 (58) | 97 | 100 (0) | 100 | | | 100 (0) | 100 | | |
| 2 | 2.24 | 1 | .14 | 18 (80) | 93 | 98 (2) | 100 | | | 100 (0) | 100 | | |
| 2 | 2.24 | 1 | .14 | 33 (57) | 78 | | | | | | | | |
| 2 | 2.24 | 1 | .14 | 55 (38) | 90 | 100 (0) | 100 | | | 100 (0) | 100 | | |
| 2 | 2.24 | 1 | .14 | 35 (61) | 90 | | | | | | | | |
| 2 | 2.24 | 1 | .56 | 78 (13) | 90 | 100 (0) | 100 | | | 100 (0) | 100 | | |
| 2 | 2.24 | 1 | .56 | 20 (79) | 98 | 100 (0) | 100 | | | 100 (0) | 100 | | |
| 2 | 2.24 | 1 | .56 | 33 (66) | 98 | 100 (0) | 98 | | | 100 (0) | 100 | | |
| 2 | 2.24 | 1 | .56 | 33 (63) | 90 | | | | | | | | |
| 2 | 2.24 | 1 | .56 | 15 (84) | 97 | 100 (0) | 100 | | | 100 (0) | 100 | | |
| 2 | 2.24 | 1 | .56 | 23 (75) | 95 | 100 (0) | 100 | | | 100 (0) | 100 | | |
| 2 | 2.24 | 1 | .56 | 75 (22) | 97 | 100 (0) | 100 | | | 100 (0) | 100 | | |
| 2 | 2.24 | 1 | .56 | 38 (60) | 97 | 100 (0) | 100 | | | 100 (0) | 100 | | |
| 2 | 2.24 | 1 | .56 | 5 (93) | 78 | | | | | | | | |
| 2 | 2.24 | 1 | .56 | 93 (7) | 100 | 100 (0) | 100 | | | 100 (0) | 100 | | |
| 2 | 2.24 | 1 | .56 | 8 (91) | 93 | 100 (0) | 100 | | | 100 (0) | 100 | | |
| 2 | 2.24 | 1 | .56 | 13 (86) | 99 | 100 (0) | 100 | | | 100 (0) | 100 | | |
| 2 | 2.24 | 1 | 1.12 | 70 (30) | 100 | 100 (0) | 100 | | | 100 (0) | 100 | | |
| 2 | 2.24 | 1 | 2.24 | 63 (37) | 100 | 100 (0) | 100 | | | 100 (0) | 100 | | |
| 2 | 2.24 | 1 | 2.24 | 28 (71) | 97 | 100 (0) | 100 | | | 100 (0) | 100 | | |
| 2 | 2.24 | 1 | 2.24 | 0 (100) | 78 | | | | | | | | |
| 2 | 2.24 | 1 | 2.24 | 28 (71) | 98 | 100 (0) | 100 | | | 100 (0) | 100 | | |
| 2 | 2.24 | 1 | 2.24 | 33 (64) | 93 | 100 (0) | 100 | | | 100 (0) | 100 | | |
| 2 | 2.24 | 1 | 2.24 | 25 (74) | 97 | 100 (0) | 100 | | | 100 (0) | 100 | | |
| 2 | 2.24 | 1 | 2.24 | 40 (57) | 95 | 100 (0) | 100 | | | 100 (0) | 100 | | |
| 2 | 2.24 | 1 | 2.24 | 33 (63) | 90 | | | | | | | | |
| 2 | 2.24 | 1 | 2.24 | 28 (71) | 98 | 100 (0) | 98 | | | 100 (0) | 100 | | |
| 2 | .56 | 2 | .07 | 5 | 58 | 98 | 100 | | | 100 | 100 | | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 2 | .56 | 2 | .14 | 15 (91) | 58 | 100 (2) | 100 | | | 100 (0) | 100 | | |
| 2 | .56 | 2 | .14 | 13 (74) | 77 | 100 (0) | 100 | | | 100 (0) | 100 | | |
| 2 | .56 | 2 | .14 | 35 (83) | 95 | 100 (0) | 100 | | | 100 (0) | 100 | | |
| 2 | .56 | 2 | .14 | 38 (63) | 87 | 100 (0) | 100 | | | 100 (0) | 100 | | |
| 2 | .56 | 2 | .14 | 5 (56) | 92 | 100 (0) | 100 | | | 100 (0) | 100 | | |
| 2 | .56 | 2 | .14 | 33 (94) | 90 | 95 (5) | 100 | | | 95 (0) | 95 | | |
| 2 | .56 | 2 | .56 | 10 (63) | 58 | 100 (0) | 100 | | | 100 (0) | 100 | | |
| 2 | .56 | 2 | .56 | 5 (82) | 77 | 100 (0) | 100 | | | 100 (0) | 100 | | |
| 2 | .56 | 2 | .56 | 30 (93) | 87 | 98 (2) | 100 | | | 100 (0) | 100 | | |
| 2 | .56 | 2 | .56 | 13 (65) | 95 | 100 (0) | 100 | | | 100 (0) | 100 | | |
| 2 | .56 | 2 | .56 | 43 (86) | 92 | 100 (0) | 100 | | | 100 (0) | 100 | | |
| 2 | .56 | 2 | .56 | 15 (53) | 90 | 95 (5) | 100 | | | 100 (0) | 95 | | |
| 2 | .56 | 2 | 2.24 | 8 (83) | 77 | 100 (0) | 100 | | | 100 (0) | 100 | | |
| 2 | .56 | 2 | 2.24 | 18 (89) | 87 | 98 (2) | 100 | | | 100 (0) | 100 | | |
| 2 | .56 | 2 | 2.24 | 15 (79) | 95 | 100 (0) | 100 | | | 100 (0) | 100 | | |
| 2 | .56 | 2 | 2.24 | 58 (84) | 92 | 100 (0) | 100 | | | 100 (0) | 100 | | |
| 2 | .56 | 2 | 2.24 | 33 (36) | 90 | 98 (2) | 100 | | | 95 (0) | 95 | | |
| 2 | 1.12 | 2 | .07 | 13 (63) | 72 | 100 (0) | 98 | | | 100 (0) | 100 | | |
| 2 | 1.12 | 2 | .14 | 5 (81) | 90 | 100 (0) | 100 | | | 100 (0) | 100 | | |
| 2 | 1.12 | 2 | .14 | 23 (94) | 72 | 100 (0) | 98 | | | 100 (0) | 100 | | |
| 2 | 1.12 | 2 | .14 | 63 (68) | 98 | 100 (0) | 100 | | | 100 (0) | 100 | | |
| 2 | 1.12 | 2 | .14 | 48 (35) | 100 | 100 (0) | 100 | | | 100 (0) | 100 | | |
| 2 | 1.12 | 2 | .14 | 30 (52) | 93 | 100 (0) | 100 | | | 98 (2) | 100 | | |
| 2 | 1.12 | 2 | .14 | 20 (67) | 95 | 100 (0) | 100 | | | 100 (0) | 100 | | |
| 2 | 1.12 | 2 | .56 | 0 (78) | 72 | 100 (0) | 98 | | | 100 (0) | 100 | | |
| 2 | 1.12 | 2 | .56 | 10 (100) | 90 | 100 (0) | 100 | | | 100 (0) | 100 | | |
| 2 | 1.12 | 2 | .56 | 18 (88) | 93 | 100 (0) | 100 | | | 100 (0) | 100 | | |
| 2 | 1.12 | 2 | .56 | 70 (80) | 98 | 100 (0) | 100 | | | 100 (0) | 100 | | |
| 2 | 1.12 | 2 | .56 | 45 (28) | 95 | 100 (0) | 100 | | | 100 (0) | 100 | | |
| 2 | 1.12 | 2 | .56 | 23 (52) | 100 | 100 (0) | 100 | | | 100 (0) | 100 | | |
| 2 | 1.12 | 2 | 2.24 | 0 (77) | 90 | 100 (0) | 100 | | | 100 (0) | 100 | | |
| 2 | 1.12 | 2 | 2.24 | 45 (100) | 100 | 100 (0) | 100 | | | 100 (0) | 100 | | |
| 2 | 1.12 | 2 | 2.24 | 35 (55) | 98 | 100 (0) | 100 | | | 100 (0) | 100 | | |
| 2 | 1.12 | 2 | 2.24 | 33 (64) | 93 | 100 (0) | 100 | | | 100 (0) | 100 | | |
| 2 | 1.12 | 2 | 2.24 | 30 (64) | 95 | 100 (0) | 100 | | | 100 (0) | 100 | | |
| 2 | 2.24 | 2 | .07 | 60 (68) | 97 | 100 (0) | 100 | | | 100 (0) | 100 | | |
| 2 | 2.24 | 2 | .14 | 25 (38) | 97 | 100 (0) | 100 | | | 100 (0) | 100 | | |
| 2 | 2.24 | 2 | .14 | 45 (74) | 97 | 100 (0) | 100 | | | 100 (0) | 100 | | |
| | | | | (53) | | (0) | | | | (0) | | | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 2 | 2.24 | 2 | .14 | 25 (74) | 98 | 100 (0) | 100 | | | 100 (0) | 100 | | |
| 2 | 2.24 | 2 | .14 | 78 (19) | 97 | 100 (0) | 100 | | | 100 (0) | 100 | | |
| 2 | 2.24 | 2 | .14 | 88 (10) | 98 | 100 (0) | 100 | | | 100 (0) | 100 | | |
| 2 | 2.24 | 2 | .14 | 53 (47) | 100 | 100 (0) | 100 | | | 100 (0) | 100 | | |
| 2 | 2.24 | 2 | .56 | 23 (76) | 97 | 100 (0) | 100 | | | 100 (0) | 100 | | |
| 2 | 2.24 | 2 | .56 | 8 (91) | 97 | 100 (0) | 100 | | | 100 (0) | 100 | | |
| 2 | 2.24 | 2 | .56 | 65 (33) | 98 | 100 (0) | 100 | | | 100 (0) | 100 | | |
| 2 | 2.24 | 2 | .56 | 23 (76) | 97 | 100 (0) | 100 | | | 100 (0) | 100 | | |
| 2 | 2.24 | 2 | .56 | 63 (37) | 100 | 100 (0) | 100 | | | 100 (0) | 100 | | |
| 2 | 2.24 | 2 | .56 | 43 (56) | 98 | 100 (0) | 100 | | | 100 (0) | 100 | | |
| 2 | 2.24 | 2 | 2.24 | 25 (74) | 97 | 100 (0) | 100 | | | 100 (0) | 100 | | |
| 2 | 2.24 | 2 | 2.24 | 45 (55) | 100 | 100 (0) | 100 | | | 100 (0) | 100 | | |
| 2 | 2.24 | 2 | 2.24 | 15 (84) | 97 | 100 (0) | 100 | | | 100 (0) | 100 | | |
| 2 | 2.24 | 2 | 2.24 | 25 (74) | 98 | 100 (0) | 100 | | | 100 (0) | 100 | | |
| 2 | 2.24 | 2 | 2.24 | 58 (40) | 98 | 100 (0) | 100 | | | 100 (0) | 100 | | |
| 2 | .56 | 3 | .03 | 60 (0) | 37 | 98 (2) | 100 | | | 98 (2) | 100 | | |
| 2 | .56 | 3 | .03 | 35 (59) | 87 | 100 (0) | 100 | | | 100 (0) | 100 | | |
| 2 | .56 | 3 | .04 | 5 (94) | 88 | 98 (2) | 100 | | | 95 (5) | 100 | | |
| 2 | .56 | 3 | .07 | 43 (54) | 95 | 98 (2) | 100 | | | 100 (0) | 100 | | |
| 2 | .56 | 3 | .07 | 45 (22) | 58 | 98 (2) | 100 | | | 100 (0) | 100 | | |
| 2 | .56 | 3 | .14 | 15 (80) | 77 | 100 (0) | 100 | | | 100 (0) | 100 | | |
| 2 | .56 | 3 | .14 | 8 (90) | 88 | 98 (2) | 100 | | | 98 (2) | 100 | | |
| 2 | .56 | 3 | .14 | 25 (32) | 37 | 100 (0) | 100 | | | 98 (2) | 100 | | |
| 2 | .56 | 3 | .14 | 30 (65) | 87 | 100 (0) | 100 | | | 100 (0) | 100 | | |
| 2 | .56 | 3 | .14 | 38 (60) | 95 | 100 (0) | 100 | | | 100 (0) | 100 | | |
| 2 | .56 | 3 | .14 | 23 (60) | 58 | 100 (0) | 100 | | | 100 (0) | 100 | | |
| 2 | .56 | 3 | .14 | 68 (28) | 95 | 100 (0) | 100 | | | 100 (0) | 100 | | |
| 2 | .56 | 3 | .14 | 10 (89) | 92 | 100 (0) | 100 | | | 100 (0) | 100 | | |
| 2 | .56 | 3 | .14 | 33 (62) | 87 | 100 (0) | 100 | | | 100 (0) | 100 | | |
| 2 | .56 | 3 | .14 | 13 (85) | 90 | 95 (5) | 100 | | | 100 (0) | 95 | | |
| 2 | .56 | 3 | .56 | 13 (64) | 37 | 100 (0) | 100 | | | 100 (0) | 100 | | |
| 2 | .56 | 3 | .56 | 15 (74) | 58 | 100 (0) | 100 | | | 100 (0) | 100 | | |
| 2 | .56 | 3 | .56 | 0 (100) | 88 | 100 (0) | 100 | | | 100 (0) | 100 | | |
| 2 | .56 | 3 | .56 | 0 (100) | 77 | 100 (0) | 100 | | | 100 (0) | 100 | | |
| 2 | .56 | 3 | .56 | 13 (86) | 95 | 100 (0) | 100 | | | 100 (0) | 100 | | |
| 2 | .56 | 3 | .56 | 20 (77) | 87 | 100 (0) | 100 | | | 100 (0) | 100 | | |
| 2 | .56 | 3 | .56 | 40 (55) | 90 | 98 (2) | 100 | | | 95 (0) | 95 | | |
| 2 | .56 | 3 | .56 | 15 (84) | 95 | 100 (0) | 100 | | | 100 (0) | 100 | | |
| 2 | .56 | 3 | .56 | 13 | 92 | 100 | 100 | | | 100 | 100 | | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | | | Sorghum | | Foxtail Green | | Crabgrass Large | | Barnyard Grass | | Corn | |
| HERB. NO. | RATE | ANTIDOTE NO. | RATE | W | WO | W | WO | W | WO | W | WO | W | WO |
| 2 | .56 | 3 | .56 | 28 | 87 | 100 | 100 | | | 100 | 100 | | |
| | | | | (85) | | (0) | | | | (0) | | | |
| 2 | .56 | 3 | 2.24 | 5 | 77 | 100 | 100 | | | 100 | 100 | | |
| | | | | (67) | | (0) | | | | (0) | | | |
| 2 | .56 | 3 | 2.24 | 43 | 95 | 98 | 100 | | | 95 | 100 | | |
| | | | | (93) | | (0) | | | | (5) | | | |
| 2 | .56 | 3 | 2.24 | 8 | 90 | 95 | 100 | | | 95 | 95 | | |
| | | | | (54) | | (2) | | | | (0) | | | |
| 2 | .56 | 3 | 2.24 | 0 | 87 | 98 | 100 | | | 100 | 100 | | |
| | | | | (91) | | (5) | | | | (0) | | | |
| 2 | .56 | 3 | 2.24 | 8 | 92 | 100 | 100 | | | 100 | 100 | | |
| | | | | (100) | | (2) | | | | (0) | | | |
| 2 | 1.12 | 3 | .03 | 40 | 65 | 100 | 100 | | | 100 | 100 | | |
| | | | | (91) | | (0) | | | | (0) | | | |
| 2 | 1.12 | 3 | .03 | 70 | 95 | 100 | 100 | | | 100 | 100 | | |
| | | | | (38) | | (0) | | | | (0) | | | |
| 2 | 1.12 | 3 | .04 | 23 | 87 | 100 | 100 | | | 100 | 100 | | |
| | | | | (26) | | (0) | | | | (0) | | | |
| 2 | 1.12 | 3 | .07 | 40 | 72 | 100 | 98 | | | 100 | 100 | | |
| | | | | (73) | | (0) | | | | (0) | | | |
| 2 | 1.12 | 3 | .07 | 43 | 95 | 100 | 100 | | | 100 | 100 | | |
| | | | | (44) | | (0) | | | | (0) | | | |
| 2 | 1.12 | 3 | .14 | 90 | 65 | 98 | 100 | | | 98 | 100 | | |
| | | | | (54) | | (0) | | | | (0) | | | |
| 2 | 1.12 | 3 | .14 | 8 | 90 | 100 | 100 | | | 100 | 100 | | |
| | | | | (0) | | (2) | | | | (2) | | | |
| 2 | 1.12 | 3 | .14 | 50 | 95 | 100 | 100 | | | 100 | 100 | | |
| | | | | (91) | | (0) | | | | (0) | | | |
| 2 | 1.12 | 3 | .14 | 43 | 95 | 100 | 100 | | | 100 | 100 | | |
| | | | | (47) | | (0) | | | | (0) | | | |
| 2 | 1.12 | 3 | .14 | 28 | 87 | 100 | 100 | | | 100 | 100 | | |
| | | | | (54) | | (0) | | | | (0) | | | |
| 2 | 1.12 | 3 | .14 | 15 | 72 | 100 | 98 | | | 100 | 100 | | |
| | | | | (67) | | (0) | | | | (0) | | | |
| 2 | 1.12 | 3 | .14 | 25 | 95 | 100 | 100 | | | 100 | 100 | | |
| | | | | (79) | | (0) | | | | (0) | | | |
| 2 | 1.12 | 3 | .14 | 55 | 93 | 100 | 100 | | | 100 | 100 | | |
| | | | | (73) | | (0) | | | | (0) | | | |
| 2 | 1.12 | 3 | .14 | 33 | 98 | 100 | 100 | | | 98 | 100 | | |
| | | | | (40) | | (0) | | | | (2) | | | |
| 2 | 1.12 | 3 | .14 | 65 | 100 | 100 | 100 | | | 100 | 100 | | |
| | | | | (66) | | (0) | | | | (0) | | | |
| 2 | 1.12 | 3 | .56 | 60 | 65 | 100 | 100 | | | 100 | 100 | | |
| | | | | (35) | | (0) | | | | (0) | | | |
| 2 | 1.12 | 3 | .56 | 15 | 87 | 100 | 100 | | | 100 | 100 | | |
| | | | | (7) | | (0) | | | | (0) | | | |
| 2 | 1.12 | 3 | .56 | 15 | 72 | 100 | 98 | | | 100 | 100 | | |
| | | | | (82) | | (0) | | | | (0) | | | |
| 2 | 1.12 | 3 | .56 | 70 | 95 | 100 | 100 | | | 100 | 100 | | |
| | | | | (79) | | (0) | | | | (0) | | | |
| 2 | 1.12 | 3 | .56 | 20 | 90 | 100 | 100 | | | 100 | 100 | | |
| | | | | (26) | | (0) | | | | (0) | | | |
| 2 | 1.12 | 3 | .56 | 15 | 95 | 100 | 100 | | | 100 | 100 | | |
| | | | | (77) | | (0) | | | | (0) | | | |
| 2 | 1.12 | 3 | .56 | 23 | 98 | 100 | 100 | | | 100 | 100 | | |
| | | | | (84) | | (0) | | | | (0) | | | |
| 2 | 1.12 | 3 | .56 | 38 | 93 | 100 | 100 | | | 95 | 100 | | |
| | | | | (76) | | (0) | | | | (5) | | | |
| 2 | 1.12 | 3 | .56 | 75 | 100 | 100 | 100 | | | 100 | 100 | | |
| | | | | (59) | | (0) | | | | (0) | | | |
| 2 | 1.12 | 3 | .56 | 15 | 95 | 100 | 100 | | | 98 | 100 | | |
| | | | | (25) | | (0) | | | | (2) | | | |
| 2 | 1.12 | 3 | 2.24 | 20 | 90 | 100 | 100 | | | 100 | 100 | | |
| | | | | (84) | | (0) | | | | (0) | | | |
| 2 | 1.12 | 3 | 2.24 | 28 | 100 | 100 | 100 | | | 100 | 100 | | |
| | | | | (77) | | (0) | | | | (0) | | | |
| 2 | 1.12 | 3 | 2.24 | 15 | 95 | 100 | 100 | | | 100 | 100 | | |
| | | | | (72) | | (0) | | | | (0) | | | |
| 2 | 1.12 | 3 | 2.24 | 35 | 93 | 100 | 100 | | | 100 | 100 | | |
| | | | | (84) | | (0) | | | | (0) | | | |
| 2 | 1.12 | 3 | 2.24 | 15 | 98 | 98 | 100 | | | 100 | 100 | | |
| | | | | (62) | | (0) | | | | (0) | | | |
| 2 | 2.24 | 3 | .03 | 90 | 90 | 98 | 100 | | | 100 | 100 | | |
| | | | | (84) | | (2) | | | | (0) | | | |
| 2 | 2.24 | 3 | .03 | 93 | 97 | 100 | 100 | | | 100 | 100 | | |
| | | | | (0) | | (2) | | | | (0) | | | |
| | | | | (4) | | (0) | | | | (0) | | | |

TABLE 4-continued

| | | | | % PLANT INHIBITION AND % SAFENING EFFECT ( ) | | | | | | | | |
|---|---|---|---|---|---|---|---|---|---|---|---|---|
| | | ANTIDOTE | | Sorghum | | Foxtail Green | | Crabgrass Large | | Barnyard Grass | | Corn |
| HERB. NO. | RATE | NO. | RATE | W | WO | W | WO | W | WO | W | WO | W | WO |
| 2 | 2.24 | 3 | .04 | 25 (58) | 60 | 100 (0) | 100 | | | 100 (0) | 100 | | |
| 2 | 2.24 | 3 | .07 | 95 (4) | 99 | 100 (0) | 100 | | | 100 (0) | 100 | | |
| 2 | 2.24 | 3 | .07 | 68 (29) | 97 | 100 (0) | 100 | | | 100 (0) | 100 | | |
| 2 | 2.24 | 3 | .14 | 63 (35) | 97 | 100 (0) | 100 | | | 100 (0) | 100 | | |
| 2 | 2.24 | 3 | .14 | 88 (2) | 90 | 100 (0) | 100 | | | 100 (0) | 100 | | |
| 2 | 2.24 | 3 | .14 | 45 (54) | 99 | 100 (0) | 100 | | | 100 (0) | 100 | | |
| 2 | 2.24 | 3 | .14 | 45 (25) | 60 | 100 (0) | 100 | | | 100 (0) | 100 | | |
| 2 | 2.24 | 3 | .14 | 63 (35) | 97 | 98 (2) | 100 | | | 100 (0) | 100 | | |
| 2 | 2.24 | 3 | .14 | 53 (45) | 97 | 100 (0) | 100 | | | 100 (0) | 100 | | |
| 2 | 2.24 | 3 | .14 | 35 (64) | 98 | 100 (0) | 100 | | | 100 (0) | 100 | | |
| 2 | 2.24 | 3 | .14 | 85 (12) | 97 | 100 (0) | 100 | | | 100 (0) | 100 | | |
| 2 | 2.24 | 3 | .14 | 50 (50) | 100 | 100 (0) | 100 | | | 100 (0) | 100 | | |
| 2 | 2.24 | 3 | .14 | 80 (18) | 98 | 100 (0) | 100 | | | 100 (0) | 100 | | |
| 2 | 2.24 | 3 | .56 | 33 (65) | 97 | 100 (0) | 100 | | | 100 (0) | 100 | | |
| 2 | 2.24 | 3 | .56 | 35 (61) | 90 | 100 (0) | 100 | | | 100 (0) | 100 | | |
| 2 | 2.24 | 3 | .56 | 25 (58) | 60 | 100 (0) | 100 | | | 100 (0) | 100 | | |
| 2 | 2.24 | 3 | .56 | 63 (35) | 97 | 100 (0) | 100 | | | 100 (0) | 100 | | |
| 2 | 2.24 | 3 | .56 | 53 (46) | 99 | 100 (0) | 100 | | | 100 (0) | 100 | | |
| 2 | 2.24 | 3 | .56 | 20 (79) | 97 | 100 (0) | 100 | | | 100 (0) | 100 | | |
| 2 | 2.24 | 3 | .56 | 73 (27) | 100 | 100 (0) | 100 | | | 100 (0) | 100 | | |
| 2 | 2.24 | 3 | .56 | 78 (20) | 98 | 100 (0) | 100 | | | 100 (0) | 100 | | |
| 2 | 2.24 | 3 | .56 | 35 (64) | 98 | 100 (0) | 100 | | | 100 (0) | 100 | | |
| 2 | 2.24 | 3 | .56 | 55 (43) | 97 | 100 (0) | 100 | | | 98 (2) | 100 | | |
| 2 | 2.24 | 3 | 2.24 | 20 (79) | 97 | 100 (0) | 100 | | | 100 (0) | 100 | | |
| 2 | 2.24 | 3 | 2.24 | 25 (74) | 98 | 100 (0) | 100 | | | 100 (0) | 100 | | |
| 2 | 2.24 | 3 | 2.24 | 55 (45) | 100 | 100 (0) | 100 | | | 100 (0) | 100 | | |
| 2 | 2.24 | 3 | 2.24 | 55 (43) | 98 | 100 (0) | 100 | | | 100 (0) | 100 | | |
| 2 | 2.24 | 3 | 2.24 | 80 (17) | 97 | 100 (0) | 100 | | | 100 (0) | 100 | | |
| 2 | .56 | 4 | .14 | 58 (38) | 95 | 100 (0) | 100 | | | 100 (0) | 100 | | |
| 2 | .56 | 4 | .14 | 33 (63) | 90 | 100 (0) | 100 | | | 98 (0) | 95 | | |
| 2 | .56 | 4 | .56 | 48 (49) | 95 | 100 (0) | 100 | | | 98 (2) | 100 | | |
| 2 | .56 | 4 | .56 | 20 (77) | 90 | 100 (0) | 100 | | | 98 (0) | 95 | | |
| 2 | .56 | 4 | 2.24 | 20 (78) | 95 | 98 (2) | 100 | | | 100 (0) | 100 | | |
| 2 | .56 | 4 | 2.24 | 28 (68) | 90 | 100 (0) | 100 | | | 95 (0) | 95 | | |
| 2 | 1.12 | 4 | .14 | 60 (40) | 100 | 100 (0) | 100 | | | 100 (0) | 100 | | |
| 2 | 1.12 | 4 | .14 | 33 (64) | 93 | 98 (2) | 100 | | | 98 (2) | 100 | | |
| 2 | 1.12 | 4 | .56 | 63 (37) | 100 | 100 (0) | 100 | | | 100 (0) | 100 | | |
| 2 | 1.12 | 4 | .56 | 30 (67) | 93 | 100 (0) | 100 | | | 100 (0) | 100 | | |
| 2 | 1.12 | 4 | 2.24 | 50 | 100 | 100 | 100 | | | 100 | 100 | | |

TABLE 4-continued

% PLANT INHIBITION AND % SAFENING EFFECT ( )

| HERB. NO. | RATE | ANTIDOTE NO. | RATE | Sorghum W | Sorghum WO | Foxtail Green W | Foxtail Green WO | Crabgrass Large W | Crabgrass Large WO | Barnyard Grass W | Barnyard Grass WO | Corn W | Corn WO |
|---|---|---|---|---|---|---|---|---|---|---|---|---|---|
| 2 | 1.12 | 4 | 2.24 | 63 (50) | 93 | 100 (0) | 100 | | | 100 (0) | 100 | | |
| 2 | 2.24 | 4 | .14 | 70 (32) | 100 | 100 (0) | 100 | | | 100 (0) | 100 | | |
| 2 | 2.24 | 4 | .14 | 53 (30) | 97 | 100 (0) | 100 | | | 100 (0) | 100 | | |
| 2 | 2.24 | 4 | .56 | 53 (45) | 97 | 100 (0) | 100 | | | 100 (0) | 100 | | |
| 2 | 2.24 | 4 | .56 | 65 (45) | 100 | 100 (0) | 100 | | | 100 (0) | 100 | | |
| 2 | 2.24 | 4 | 2.24 | 50 (35) | 97 | 100 (0) | 100 | | | 100 (0) | 100 | | |
| 2 | 2.24 | 4 | 2.24 | 50 (48) | 100 | 100 (0) | 100 | | | 100 (0) | 100 | | |
| 2 | .56 | 5 | .14 | 35 (50) | 95 | 100 (0) | 100 | | | 100 (0) | 100 | | |
| 2 | .56 | 5 | .14 | 78 (63) | 90 | 100 (0) | 100 | | | 90 (5) | 95 | | |
| 2 | .56 | 5 | .56 | 38 (13) | 90 | 100 (0) | 100 | | | 100 (0) | 95 | | |
| 2 | .56 | 5 | .56 | 40 (57) | 95 | 100 (0) | 100 | | | 95 (5) | 100 | | |
| 2 | .56 | 5 | 2.24 | 23 (57) | 95 | 100 (0) | 100 | | | 100 (0) | 100 | | |
| 2 | .56 | 5 | 2.24 | 5 (75) | 90 | 100 (0) | 100 | | | 98 (0) | 95 | | |
| 2 | 1.12 | 5 | .14 | 58 (94) | 100 | 100 (0) | 100 | | | 100 (0) | 100 | | |
| 2 | 1.12 | 5 | .14 | 38 (42) | 93 | 100 (0) | 100 | | | 95 (5) | 100 | | |
| 2 | 1.12 | 5 | .56 | 35 (59) | 93 | 100 (0) | 100 | | | 100 (0) | 100 | | |
| 2 | 1.12 | 5 | .56 | 53 (62) | 100 | 100 (0) | 100 | | | 100 (0) | 100 | | |
| 2 | 1.12 | 5 | 2.24 | 23 (47) | 100 | 100 (0) | 100 | | | 100 (0) | 100 | | |
| 2 | 1.12 | 5 | 2.24 | 28 (77) | 93 | 100 (0) | 100 | — | | 100 (0) | 100 | | |
| 2 | 2.24 | 5 | .14 | 73 (69) | 97 | 100 (0) | 100 | | | 100 (0) | 100 | | |
| 2 | 2.24 | 5 | .14 | 85 (24) | 100 | 100 (0) | 100 | | | 100 (0) | 100 | | |
| 2 | 2.24 | 5 | .56 | 73 (15) | 97 | 100 (0) | 100 | | | 100 (0) | 100 | | |
| 2 | 2.24 | 5 | .56 | 73 (24) | 100 | 100 (0) | 100 | | | 100 (0) | 100 | | |
| 2 | 2.24 | 5 | 2.24 | 68 (27) | 100 | 100 (0) | 100 | | | 100 (0) | 100 | | |
| 2 | 2.24 | 5 | 2.24 | 90 (32) | 97 | 100 (0) | 100 | | | 100 (0) | 100 | | |
| 2 | .56 | 13 | .14 | 78 (7) | 90 | 100 (0) | 100 | | | 100 (0) | 95 | | |
| 2 | .56 | 13 | .56 | 70 (13) | 90 | 100 (0) | 100 | | | 100 (0) | 95 | | |
| 2 | .56 | 13 | 2.24 | 40 (22) | 90 | 98 (2) | 100 | | | 95 (0) | 95 | | |
| 2 | 1.12 | 13 | .14 | 93 (55) | 93 | 100 (0) | 100 | | | 98 (2) | 100 | | |
| 2 | 1.12 | 13 | .56 | 65 (0) | 93 | 100 (0) | 100 | | | 100 (0) | 100 | | |
| 2 | 1.12 | 13 | 2.24 | 28 (30) | 93 | 100 (0) | 100 | | | 100 (0) | 100 | | |
| 2 | 2.24 | 13 | .14 | 98 (69) | 97 | 100 (0) | 100 | | | 100 (0) | 100 | | |
| 2 | 2.24 | 13 | .56 | 85 (0) | 97 | 100 (0) | 100 | | | 100 (0) | 100 | | |
| 2 | 2.24 | 13 | 2.24 | 83 (12) | 97 | 100 (0) | 100 | | | 100 (0) | 100 | | |
| 2 | .56 | 6 | .14 | 63 (14) | 90 | 100 (0) | 100 | | | 90 (5) | 95 | | |
| 2 | .56 | 6 | .14 | 30 (30) | 95 | 100 (0) | 100 | | | 100 (0) | 100 | | |
| 2 | .56 | 6 | .56 | 55 (68) | 95 | 100 (0) | 100 | | | 100 (0) | 100 | | |
| 2 | .56 | 6 | .56 | 40 (42) | 90 | 100 (0) | 100 | | | 100 (0) | 95 | | |
|  |  |  |  | (55) |  | (0) |  | | | (0) |  | | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 2 | .56 | 6 | 2.24 | 18 (80) | 90 | 100 (0) | 100 | | | 98 (0) | 95 | | |
| 2 | .56 | 6 | 2.24 | 60 (36) | 95 | 100 (0) | 100 | | | 100 (0) | 100 | | |
| 2 | 1.12 | 6 | .14 | 63 (32) | 93 | 100 (0) | 100 | | | 100 (0) | 100 | | |
| 2 | 1.12 | 6 | .14 | 50 (50) | 100 | 100 (0) | 100 | | | 100 (0) | 100 | | |
| 2 | 1.12 | 6 | .56 | 55 (45) | 100 | 100 (0) | 100 | | | 100 (0) | 100 | | |
| 2 | 1.12 | 6 | .56 | 20 (78) | 93 | 100 (0) | 100 | | | 100 (0) | 100 | | |
| 2 | 1.12 | 6 | 2.24 | 58 (37) | 93 | 100 (0) | 100 | | | 98 (2) | 100 | | |
| 2 | 1.12 | 6 | 2.24 | 28 (72) | 100 | 100 (0) | 100 | | | 100 (0) | 100 | | |
| 2 | 2.24 | 6 | .14 | 73 (27) | 100 | 100 (0) | 100 | | | 100 (0) | 100 | | |
| 2 | 2.24 | 6 | .14 | 60 (38) | 97 | 100 (0) | 100 | | | 100 (0) | 100 | | |
| 2 | 2.24 | 6 | .56 | 80 (20) | 100 | 100 (0) | 100 | | | 100 (0) | 100 | | |
| 2 | 2.24 | 6 | .56 | 40 (58) | 97 | 100 (0) | 100 | | | 100 (0) | 100 | | |
| 2 | 2.24 | 6 | 2.24 | 45 (53) | 97 | 100 (0) | 100 | | | 100 (0) | 100 | | |
| 2 | 2.24 | 6 | 2.24 | 60 (40) | 100 | 100 (0) | 100 | | | 100 (0) | 100 | | |
| 2 | .56 | 27 | .14 | 78 (15) | 92 | 100 (0) | 100 | | | 100 (0) | 100 | | |
| 2 | .56 | 27 | .56 | 30 (67) | 92 | 100 (0) | 100 | | | 100 (0) | 100 | | |
| 2 | .56 | 27 | 2.24 | 18 (80) | 92 | 100 (0) | 100 | | | 100 (0) | 100 | | |
| 2 | 1.12 | 27 | .14 | 88 (7) | 95 | 100 (0) | 100 | | | 100 (0) | 100 | | |
| 2 | 1.12 | 27 | .56 | 55 (42) | 95 | 100 (0) | 100 | | | 100 (0) | 100 | | |
| 2 | 1.12 | 27 | 2.24 | 10 (89) | 95 | 100 (0) | 100 | | | 98 (2) | 100 | | |
| 2 | 2.24 | 27 | .14 | 88 (10) | 98 | 100 (0) | 100 | | | 100 (0) | 100 | | |
| 2 | 2.24 | 27 | .56 | 83 (15) | 98 | 100 (0) | 100 | | | 100 (0) | 100 | | |
| 2 | 2.24 | 27 | 2.24 | 50 (48) | 98 | 100 (0) | 100 | | | 100 (0) | 100 | | |
| 2 | .56 | 7 | .14 | 10 (89) | 92 | 100 (0) | 100 | | | 100 (0) | 100 | | |
| 2 | .56 | 7 | .56 | 13 (85) | 92 | 98 (2) | 100 | | | 100 (0) | 100 | | |
| 2 | .56 | 7 | 2.24 | 10 (89) | 92 | 100 (0) | 100 | | | 100 (0) | 100 | | |
| 2 | 1.12 | 7 | .14 | 33 (65) | 95 | 100 (0) | 100 | | | 100 (0) | 100 | | |
| 2 | 1.12 | 7 | .56 | 30 (68) | 95 | 100 (0) | 100 | | | 100 (0) | 100 | | |
| 2 | 1.12 | 7 | 2.24 | 15 (84) | 95 | 100 (0) | 100 | | | 98 (2) | 100 | | |
| 2 | 2.24 | 7 | .14 | 83 (15) | 98 | 100 (0) | 100 | | | 100 (0) | 100 | | |
| 2 | 2.24 | 7 | .56 | 20 (79) | 98 | 100 (0) | 100 | | | 100 (0) | 100 | | |
| 2 | 2.24 | 7 | 2.24 | 20 (79) | 98 | 100 (0) | 100 | | | 100 (0) | 100 | | |
| 2 | .56 | 8 | .14 | 20 (78) | 92 | 100 (0) | 100 | | | 95 (5) | 100 | | |
| 2 | .56 | 8 | .56 | 13 (85) | 92 | 100 (0) | 100 | | | 98 (2) | 100 | | |
| 2 | .56 | 8 | 2.24 | 5 (94) | 92 | 100 (0) | 100 | | | 100 (0) | 100 | | |
| 2 | 1.12 | 8 | .14 | 5 (94) | 95 | 100 (0) | 100 | | | 100 (0) | 100 | | |
| 2 | 1.12 | 8 | .56 | 28 (70) | 95 | 100 (0) | 100 | | | 100 (0) | 100 | | |
| 2 | 1.12 | 8 | 2.24 | 60 (36) | 95 | 100 (0) | 100 | | | 100 (0) | 100 | | |
| 2 | 2.24 | 8 | .14 | 33 | 98 | 100 | 100 | | | 100 | 100 | | |

TABLE 4-continued

| | | | | % PLANT INHIBITION AND % SAFENING EFFECT ( ) | | | | | | | | |
|---|---|---|---|---|---|---|---|---|---|---|---|---|
| | | ANTIDOTE | | Sorghum | | Foxtail Green | | Crabgrass Large | | Barnyard Grass | | Corn |
| HERB. NO. | RATE | NO. | RATE | W | WO | W | WO | W | WO | W | WO | W WO |
| 2 | 2.24 | 8 | .56 | 20 (66) | 98 | 100 (0) | 100 | | | 100 (0) | 100 | |
| 2 | 2.24 | 8 | 2.24 | 25 (79) | 98 | 98 (0) | 100 | | | 100 (0) | 100 | |
| 2 | .56 | 9 | .07 | 23 (74) | 58 | 100 (2) | 100 | | | 100 (0) | 100 | |
| 2 | .56 | 9 | .14 | 38 (60) | 58 | 100 (0) | 100 | | | 100 (0) | 100 | |
| 2 | .56 | 9 | .14 | 0 (34) | 77 | 100 (0) | 100 | | | 100 (0) | 100 | |
| 2 | .56 | 9 | .56 | 15 (100) | 58 | 100 (0) | 100 | | | 100 (0) | 100 | |
| 2 | .56 | 9 | .56 | 10 (74) | 77 | 100 (0) | 100 | | | 100 (0) | 100 | |
| 2 | .56 | 9 | 2.24 | 10 (87) | 77 | 100 (0) | 100 | | | 100 (0) | 100 | |
| 2 | 1.12 | 9 | .07 | 30 (87) | 72 | 100 (0) | 98 | | | 100 (0) | 100 | |
| 2 | 1.12 | 9 | .14 | 13 (58) | 90 | 100 (0) | 100 | | | 100 (0) | 100 | |
| 2 | 1.12 | 9 | .14 | 18 (85) | 72 | 100 (0) | 98 | | | 100 (0) | 100 | |
| 2 | 1.12 | 9 | .56 | 15 (75) | 90 | 100 (0) | 100 | | | 100 (0) | 100 | |
| 2 | 1.12 | 9 | .56 | 25 (83) | 72 | 100 (0) | 98 | | | 100 (0) | 100 | |
| 2 | 1.12 | 9 | 2.24 | 5 (65) | 90 | 100 (0) | 100 | | | 100 (0) | 100 | |
| 2 | 2.24 | 9 | .07 | 63 (94) | 97 | 100 (0) | 100 | | | 100 (0) | 100 | |
| 2 | 2.24 | 9 | .14 | 53 (35) | 97 | 100 (0) | 100 | | | 100 (0) | 100 | |
| 2 | 2.24 | 9 | .14 | 25 (45) | 97 | 100 (0) | 100 | | | 100 (0) | 100 | |
| 2 | 2.24 | 9 | .56 | 25 (74) | 97 | 100 (0) | 100 | | | 100 (0) | 100 | |
| 2 | 2.24 | 9 | .56 | 33 (74) | 97 | 100 (0) | 100 | | | 100 (0) | 100 | |
| 2 | 2.24 | 9 | 2.24 | 5 (65) | 97 | 100 (0) | 100 | | | 100 (0) | 100 | |
| 2 | .56 | 20 | .03 | 25 (94) | 87 | 100 (0) | 100 | | | 100 (0) | 100 | |
| 2 | .56 | 20 | .04 | 23 (71) | 88 | 95 (5) | 100 | | | 100 (0) | 100 | |
| 2 | .56 | 20 | .07 | 5 (73) | 58 | 100 (0) | 100 | | | 100 (0) | 100 | |
| 2 | .56 | 20 | .07 | 23 (91) | 95 | 100 (0) | 100 | | | 100 (0) | 100 | |
| 2 | .56 | 20 | .14 | 23 (75) | 95 | 95 (5) | 100 | | | 100 (0) | 100 | |
| 2 | .56 | 20 | .14 | 5 (75) | 77 | 100 (0) | 100 | | | 100 (0) | 100 | |
| 2 | .56 | 20 | .14 | 35 (93) | 58 | 100 (0) | 100 | | | 100 (0) | 100 | |
| 2 | .56 | 20 | .14 | 15 (39) | 87 | 100 (0) | 100 | | | 100 (0) | 100 | |
| 2 | .56 | 20 | .14 | 8 (82) | 88 | 100 (0) | 100 | | | 100 (0) | 100 | |
| 2 | .56 | 20 | .56 | 10 (90) | 88 | 98 (2) | 100 | | | 100 (0) | 100 | |
| 2 | .56 | 20 | .56 | 5 (88) | 77 | 100 (0) | 100 | | | 100 (0) | 100 | |
| 2 | .56 | 20 | .56 | 0 (93) | 95 | 98 (2) | 100 | | | 100 (0) | 100 | |
| 2 | .56 | 20 | .56 | 10 (100) | 87 | 100 (0) | 100 | | | 100 (0) | 100 | |
| 2 | .56 | 20 | .56 | 0 (88) | 58 | 100 (0) | 100 | | | 100 (0) | 100 | |
| 2 | .56 | 20 | 2.24 | 15 (100) | 77 | 100 (0) | 100 | | | 100 (0) | 100 | |
| 2 | 1.12 | 20 | .03 | 63 (80) | 95 | 100 (0) | 100 | | | 100 (0) | 100 | |
| 2 | 1.12 | 20 | .04 | 40 (33) | 87 | 100 (0) | 100 | | | 100 (0) | 100 | |
| 2 | 1.12 | 20 | .07 | 20 (54) | 72 | 100 (0) | 98 | | | 100 (0) | 100 | |

TABLE 4-continued

| | | ANTIDOTE | | Sorghum | | Foxtail Green | | Crabgrass Large | | Barnyard Grass | | Corn | |
|---|---|---|---|---|---|---|---|---|---|---|---|---|---|
| HERB. NO. | RATE | NO. | RATE | W | WO | W | WO | W | WO | W | WO | W | WO |
| 2 | 1.12 | 20 | .07 | 53 (44) | 95 | 100 (0) | 100 | | | 100 (0) | 100 | | |
| 2 | 1.12 | 20 | .14 | 10 (88) | 87 | 100 (0) | 100 | | | 100 (0) | 100 | | |
| 2 | 1.12 | 20 | .14 | 8 (88) | 72 | 100 (0) | 98 | | | 100 (0) | 100 | | |
| 2 | 1.12 | 20 | .14 | 40 (57) | 95 | 95 (5) | 100 | | | 100 (0) | 100 | | |
| 2 | 1.12 | 20 | .14 | 38 (60) | 95 | 100 (0) | 100 | | | 100 (0) | 100 | | |
| 2 | 1.12 | 20 | .14 | 0 (100) | 90 | 100 (0) | 100 | | | 100 (0) | 100 | | |
| 2 | 1.12 | 20 | .56 | 0 (100) | 87 | 98 (2) | 100 | | | 100 (0) | 100 | | |
| 2 | 1.12 | 20 | .56 | 5 (94) | 95 | 100 (0) | 100 | | | 100 (0) | 100 | | |
| 2 | 1.12 | 20 | .56 | 28 (70) | 95 | 100 (0) | 100 | | | 100 (0) | 100 | | |
| 2 | 1.12 | 20 | .56 | 25 (65) | 72 | 100 (0) | 98 | | | 100 (0) | 100 | | |
| 2 | 1.12 | 20 | .56 | 15 (83) | 90 | 100 (0) | 100 | | | 100 (0) | 100 | | |
| 2 | 1.12 | 20 | 2.24 | 13 (85) | 90 | 100 (0) | 100 | | | 100 (0) | 100 | | |
| 2 | 2.24 | 20 | .03 | 65 (32) | 97 | 100 (0) | 100 | | | 100 (0) | 100 | | |
| 2 | 2.24 | 20 | .04 | 43 (28) | 60 | 100 (0) | 100 | | | 98 (2) | 100 | | |
| 2 | 2.24 | 20 | .07 | 30 (69) | 97 | 100 (0) | 100 | | | 100 (0) | 100 | | |
| 2 | 2.24 | 20 | .07 | 83 (16) | 99 | 100 (0) | 100 | | | 100 (0) | 100 | | |
| 2 | 2.24 | 20 | .14 | 25 (74) | 97 | 100 (0) | 100 | | | 100 (0) | 100 | | |
| 2 | 2.24 | 20 | .14 | 18 (81) | 97 | 100 (0) | 100 | | | 100 (0) | 100 | | |
| 2 | 2.24 | 20 | .14 | 58 (40) | 97 | 100 (0) | 100 | | | 100 (0) | 100 | | |
| 2 | 2.24 | 20 | .14 | 38 (61) | 99 | 100 (0) | 100 | | | 100 (0) | 100 | | |
| 2 | 2.24 | 20 | .14 | 35 (41) | 60 | 100 (0) | 100 | | | 100 (0) | 100 | | |
| 2 | 2.24 | 20 | .56 | 18 (81) | 97 | 100 (0) | 100 | | | 100 (0) | 100 | | |
| 2 | 2.24 | 20 | .56 | 25 (74) | 99 | 100 (0) | 100 | | | 100 (0) | 100 | | |
| 2 | 2.24 | 20 | .56 | 25 (58) | 60 | 100 (0) | 100 | | | 100 (0) | 100 | | |
| 2 | 2.24 | 20 | .56 | 53 (45) | 97 | 100 (0) | 100 | | | 100 (0) | 100 | | |
| 2 | 2.24 | 20 | .56 | 28 (71) | 97 | 100 (0) | 100 | | | 100 (0) | 100 | | |
| 2 | 2.24 | 20 | 2.24 | 25 (74) | 97 | 100 (0) | 100 | | | 100 (0) | 100 | | |
| 2 | .56 | 12 | .03 | 28 (67) | 87 | 100 (0) | 100 | | | 100 (0) | 100 | | |
| 2 | .56 | 12 | .07 | 13 (86) | 95 | 100 (0) | 100 | | | 100 (0) | 100 | | |
| 2 | .56 | 12 | .14 | 17 (80) | 87 | 100 (0) | 100 | | | 100 (0) | 100 | | |
| 2 | .56 | 12 | .14 | 20 (78) | 95 | 98 (2) | 100 | | | 100 (0) | 100 | | |
| 2 | .56 | 12 | .56 | 5 (94) | 87 | 100 (0) | 100 | | | 100 (0) | 100 | | |
| 2 | .56 | 12 | .56 | 10 (89) | 95 | 98 (2) | 100 | | | 100 (0) | 100 | | |
| 2 | 1.12 | 12 | .03 | 88 (7) | 95 | 100 (0) | 100 | | | 100 (0) | 100 | | |
| 2 | 1.12 | 12 | .07 | 53 (44) | 95 | 100 (0) | 100 | | | 100 (0) | 100 | | |
| 2 | 1.12 | 12 | .14 | 33 (65) | 95 | 100 (0) | 100 | | | 100 (0) | 100 | | |
| 2 | 1.12 | 12 | .14 | 28 (70) | 95 | 100 (0) | 100 | | | 100 (0) | 100 | | |
| 2 | 1.12 | 12 | .56 | 20 (78) | 95 | 100 (0) | 100 | | | 100 (0) | 100 | | |
| 2 | 1.12 | 12 | .56 | 18 | 95 | 100 | 100 | | | 100 | 100 | | |

TABLE 4-continued

| | | | | \% PLANT INHIBITION AND \% SAFENING EFFECT ( ) | | | | | | | | |
|---|---|---|---|---|---|---|---|---|---|---|---|---|
| | | | | Sorghum | | Foxtail Green | | Crabgrass Large | | Barnyard Grass | | Corn |
| HERB. NO. | RATE | ANTIDOTE NO. | RATE | W | WO | W | WO | W | WO | W | WO | W WO |
| 2 | 2.24 | 12 | .03 | 98 (81) | 97 | 100 (0) | 100 | | | 100 (0) | 100 | |
| 2 | 2.24 | 12 | .07 | 75 (24) | 99 | 100 (0) | 100 | | | 100 (0) | 100 | |
| 2 | 2.24 | 12 | .14 | 85 (14) | 99 | 100 (0) | 100 | | | 100 (0) | 100 | |
| 2 | 2.24 | 12 | .14 | 88 (9) | 97 | 100 (0) | 100 | | | 100 (0) | 100 | |
| 2 | 2.24 | 12 | .56 | 60 (38) | 97 | 100 (0) | 100 | | | 100 (0) | 100 | |
| 2 | 2.24 | 12 | .56 | 23 (76) | 99 | 100 (0) | 100 | | | 100 (0) | 100 | |
| 2 | .56 | 24 | .03 | 18 (51) | 37 | 100 (0) | 100 | | | 100 (0) | 100 | |
| 2 | .56 | 24 | .04 | 5 (94) | 88 | 95 (5) | 100 | | | 100 (0) | 100 | |
| 2 | .56 | 24 | .14 | 15 (82) | 88 | 95 (5) | 100 | | | 100 (0) | 100 | |
| 2 | .56 | 24 | .14 | 0 (100) | 37 | 98 (2) | 100 | | | 98 (2) | 100 | |
| 2 | .56 | 24 | .56 | 0 (100) | 37 | 98 (2) | 100 | | | 98 (2) | 100 | |
| 2 | .56 | 24 | .56 | 5 (94) | 88 | 100 (0) | 100 | | | 100 (0) | 100 | |
| 2 | 1.12 | 24 | .03 | 25 (61) | 65 | 100 (0) | 100 | | | 100 (0) | 100 | |
| 2 | 1.12 | 24 | .04 | 25 (71) | 87 | 100 (0) | 100 | | | 100 (0) | 100 | |
| 2 | 1.12 | 24 | .14 | 8 (87) | 65 | 100 (0) | 100 | | | 98 (2) | 100 | |
| 2 | 1.12 | 24 | .14 | 10 (88) | 87 | 100 (0) | 100 | | | 100 (0) | 100 | |
| 2 | 1.12 | 24 | .56 | 30 (65) | 87 | 100 (0) | 100 | | | 100 (0) | 100 | |
| 2 | 1.12 | 24 | .56 | 20 (69) | 65 | 98 (2) | 100 | | | 100 (0) | 100 | |
| 2 | 2.24 | 24 | .03 | 23 (74) | 90 | 100 (0) | 100 | | | 100 (0) | 100 | |
| 2 | 2.24 | 24 | .04 | 50 (16) | 60 | 100 (0) | 100 | | | 100 (0) | 100 | |
| 2 | 2.24 | 24 | .14 | 10 (83) | 60 | 100 (0) | 100 | | | 100 (0) | 100 | |
| 2 | 2.24 | 24 | .14 | 55 (38) | 90 | 98 (2) | 100 | | | 100 (0) | 100 | |
| 2 | 2.24 | 24 | .56 | 8 (86) | 60 | 100 (0) | 100 | | | 100 (0) | 100 | |
| 2 | 2.24 | 24 | .56 | 28 (68) | 90 | 100 (0) | 100 | | | 100 (0) | 100 | |
| 2 | .56 | 26 | .04 | 18 (79) | 88 | 100 (0) | 100 | | | 100 (0) | 100 | |
| 2 | .56 | 26 | .14 | 0 (100) | 88 | 100 (0) | 100 | | | 100 (0) | 100 | |
| 2 | .56 | 26 | .56 | 15 (82) | 88 | 98 (2) | 100 | | | 100 (0) | 100 | |
| 2 | 1.12 | 26 | .04 | 20 (77) | 87 | 100 (0) | 100 | | | 98 (2) | 100 | |
| 2 | 1.12 | 26 | .14 | 8 (90) | 87 | 100 (0) | 100 | | | 100 (0) | 100 | |
| 2 | 1.12 | 26 | .56 | 13 (85) | 87 | 98 (2) | 100 | | | 100 (0) | 100 | |
| 2 | 2.24 | 26 | .04 | 45 (25) | 60 | 100 (0) | 100 | | | 100 (0) | 100 | |
| 2 | 2.24 | 26 | .14 | 25 (58) | 60 | 100 (0) | 100 | | | 100 (0) | 100 | |
| 2 | 2.24 | 26 | .56 | 8 (86) | 60 | 100 (0) | 100 | | | 100 (0) | 100 | |
| 2 | .56 | 23 | .04 | 18 (79) | 88 | 98 (2) | 100 | | | 100 (0) | 100 | |
| 2 | .56 | 23 | .14 | 10 (88) | 88 | 100 (0) | 100 | | | 100 (0) | 100 | |
| 2 | .56 | 23 | .56 | 5 (94) | 88 | 98 (2) | 100 | | | 98 (2) | 100 | |
| 2 | 1.12 | 23 | .04 | 20 (77) | 87 | 98 (2) | 100 | | | 100 (0) | 100 | |
| 2 | 1.12 | 23 | .14 | 13 (85) | 87 | 100 (0) | 100 | | | 98 (2) | 100 | |

TABLE 4-continued

| | | | | % PLANT INHIBITION AND % SAFENING EFFECT ( ) | | | | | | | | | |
|---|---|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 2 | 1.12 | 23 | .56 | 23 (73) | 87 | 100 (0) | 100 | | | 100 (0) | 100 | | |
| 2 | 2.24 | 23 | .04 | 58 (3) | 60 | 100 (0) | 100 | | | 100 (0) | 100 | | |
| 2 | 2.24 | 23 | .14 | 40 (33) | 60 | 100 (0) | 100 | | | 100 (0) | 100 | | |
| 2 | 2.24 | 23 | .56 | 30 (50) | 60 | 100 (0) | 100 | | | 100 (0) | 100 | | |
| 13 | 4.48 | 2 | .14 | | | 100 (0) | 100 | | | 100 (0) | 100 | 8 (87) | 63 |
| 13 | 4.48 | 2 | .56 | | | 100 (0) | 100 | | | 100 (0) | 100 | 15 (76) | 63 |
| 13 | 4.48 | 2 | 2.24 | | | 100 (0) | 100 | | | 100 (0) | 100 | 5 (92) | 63 |
| 13 | 6.72 | 2 | .14 | | | 100 (0) | 100 | | | 100 (0) | 100 | 50 (43) | 88 |
| 13 | 6.72 | 2 | .56 | | | 100 (0) | 100 | | | 100 (0) | 100 | 28 (68) | 88 |
| 13 | 6.72 | 2 | 2.24 | | | 100 (0) | 100 | | | 100 (0) | 100 | 25 (71) | 88 |
| 13 | 8.96 | 2 | .14 | | | 100 (0) | 100 | | | 100 (0) | 100 | 15 (83) | 90 |
| 13 | 8.96 | 2 | .56 | | | 100 (0) | 100 | | | 100 (0) | 100 | 13 (85) | 90 |
| 13 | 8.96 | 2 | 2.24 | | | 100 (0) | 100 | | | 100 (0) | 100 | 15 (83) | 90 |
| 13 | 4.48 | 3 | .14 | | | 100 (0) | 100 | | | 100 (0) | 100 | 8 (87) | 63 |
| 13 | 4.48 | 3 | .14 | | | | | | | 100 (0) | 100 | 0 (100) | 53 |
| 13 | 4.48 | 3 | .56 | | | | | | | 100 (0) | 100 | 0 (100) | 53 |
| 13 | 4.48 | 3 | .56 | | | 100 (0) | 100 | | | 100 (0) | 100 | 5 (92) | 63 |
| 13 | 4.48 | 3 | 2.24 | | | | | | | 100 (0) | 100 | 5 (90) | 53 |
| 13 | 4.48 | 3 | 2.24 | | | 100 (0) | 100 | | | 100 (0) | 100 | 5 (92) | 63 |
| 13 | 6.72 | 3 | .14 | | | 100 (0) | 100 | | | 100 (0) | 100 | 23 (73) | 88 |
| 13 | 6.72 | 3 | .14 | | | | | | | 100 (0) | 100 | 5 (92) | 70 |
| 13 | 6.72 | 3 | .56 | | | | | | | 100 (0) | 100 | 5 (92) | 70 |
| 13 | 6.72 | 3 | .56 | | | 100 (0) | 100 | | | 100 (0) | 100 | 20 (77) | 88 |
| 13 | 6.72 | 3 | 2.24 | | | 100 (0) | 100 | | | 100 (0) | 100 | 23 (73) | 88 |
| 13 | 6.72 | 3 | 2.24 | | | | | | | 100 (0) | 100 | 5 (92) | 70 |
| 13 | 8.96 | 3 | .14 | | | | | | | 100 (0) | 100 | 10 (88) | 85 |
| 13 | 8.96 | 3 | .14 | | | 100 (0) | 100 | | | 100 (0) | 100 | 13 (85) | 90 |
| 13 | 8.96 | 3 | .56 | | | | | | | 100 (0) | 100 | 0 (100) | 85 |
| 13 | 8.96 | 3 | .56 | | | 100 (0) | 100 | | | 100 (0) | 100 | 13 (85) | 90 |
| 13 | 8.96 | 3 | 2.24 | | | 100 (0) | 100 | | | 100 (0) | 100 | 8 (91) | 90 |
| 13 | 8.96 | 3 | 2.24 | | | | | | | 100 (0) | 100 | 0 (100) | 85 |
| 13 | 4.48 | 20 | .14 | | | 100 (0) | 100 | | | 100 (0) | 100 | 10 (84) | 63 |
| 13 | 4.48 | 20 | .14 | | | | | | | 100 (0) | 100 | 5 (90) | 53 |
| 13 | 4.48 | 20 | .56 | | | | | | | 100 (0) | 100 | 0 (100) | 53 |
| 13 | 4.48 | 20 | .56 | | | 100 (0) | 100 | | | 100 (0) | 100 | 28 (55) | 63 |
| 13 | 4.48 | 20 | 2.24 | | | | | | | 100 (0) | 100 | 0 (100) | 53 |
| 13 | 4.48 | 20 | 2.24 | | | 100 (0) | 100 | | | 100 (0) | 100 | 18 (71) | 63 |
| 13 | 6.72 | 20 | .14 | | | | | | | 100 (0) | 100 | 0 (100) | 70 |
| 13 | 6.72 | 20 | .14 | | | 100 | 100 | | | 100 | 100 | 25 | 88 |

TABLE 4-continued

| | | | | % PLANT INHIBITION AND % SAFENING EFFECT ( ) | | | | | | | |
|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 13 | 6.72 | 20 | .56 | | | 100 (0) | 100 | | | 100 (0) | 100 | 35 (71) | 88 |
| 13 | 6.72 | 20 | .56 | | | | | | | 100 (0) | 100 | 0 (60) | 70 |
| 13 | 6.72 | 20 | 2.24 | | | | | | | 100 (0) | 100 | 0 (100) | 70 |
| 13 | 6.72 | 20 | 2.24 | | | 100 (0) | 100 | | | 100 (0) | 100 | 23 (73) | 88 |
| 13 | 8.96 | 20 | .14 | | | 100 (0) | 100 | | | 100 (0) | 100 | 35 (61) | 90 |
| 13 | 8.96 | 20 | .14 | | | | | | | 100 (0) | 100 | 5 (94) | 85 |
| 13 | 8.96 | 20 | .56 | | | | | | | 100 (0) | 100 | 0 (100) | 85 |
| 13 | 8.96 | 20 | .56 | | | 100 (0) | 100 | | | 100 (0) | 100 | 28 (68) | 90 |
| 13 | 8.96 | 20 | 2.24 | | | | | | | 100 (0) | 100 | 0 (100) | 85 |
| 13 | 8.96 | 20 | 2.24 | | | 100 (0) | 100 | | | 100 (0) | 100 | 30 (66) | 90 |
| 13 | 4.48 | 24 | .14 | | | | | | | 100 (0) | 100 | 5 (90) | 53 |
| 13 | 4.48 | 24 | .56 | | | | | | | 100 (0) | 100 | 5 (90) | 53 |
| 13 | 4.48 | 24 | 2.24 | | | | | | | 100 (0) | 100 | 0 (100) | 53 |
| 13 | 6.72 | 24 | .14 | | | | | | | 100 (0) | 100 | 10 (85) | 70 |
| 13 | 6.72 | 24 | .56 | | | | | | | 100 (0) | 100 | 5 (92) | 70 |
| 13 | 6.72 | 24 | 2.24 | | | | | | | 100 (0) | 100 | 10 (85) | 70 |
| 13 | 8.96 | 24 | .14 | | | | | | | 100 (0) | 100 | 13 (84) | 85 |
| 13 | 8.96 | 24 | .56 | | | | | | | 100 (0) | 100 | 5 (94) | 85 |
| 13 | 8.96 | 24 | 2.24 | | | | | | — | 100 (0) | 100 | 5 (94) | 85 |
| 4 | 1.12 | 1 | .14 | 98 (2) | 100 | | | 98 (2) | 100 | | | 0 (100) | 80 |
| 4 | 1.12 | 1 | .56 | 100 (0) | 100 | | | 100 (0) | 100 | | | 10 (87) | 80 |
| 4 | 1.12 | 1 | 2.24 | 100 (0) | 100 | | | 100 (0) | 100 | | | 0 (100) | 80 |
| 4 | 2.24 | 1 | .14 | 100 (0) | 100 | | | 100 (0) | 98 | | | 5 (94) | 87 |
| 4 | 2.24 | 1 | .56 | 100 (0) | 100 | | | 100 (0) | 98 | | | 0 (100) | 87 |
| 4 | 2.24 | 1 | 2.24 | 100 (0) | 100 | | | 100 (0) | 98 | | | 0 (100) | 87 |
| 4 | 4.48 | 1 | .14 | 100 (0) | 100 | | | 100 (0) | 100 | | | 23 (77) | 100 |
| 4 | 4.48 | 1 | .56 | 100 (0) | 100 | | | 100 (0) | 100 | | | 0 (100) | 100 |
| 4 | 4.48 | 1 | 2.24 | 100 (0) | 100 | | | 100 (0) | 100 | | | 0 (100) | 100 |
| 4 | 1.12 | 2 | .14 | 100 (0) | 98 | | | 98 (0) | 98 | | | 0 (100) | 15 |
| 4 | 1.12 | 2 | .14 | 100 (0) | 100 | | | 100 (0) | 100 | | | 0 (100) | 80 |
| 4 | 1.12 | 2 | .56 | 100 (0) | 100 | | | 100 (0) | 100 | | | 0 (100) | 80 |
| 4 | 1.12 | 2 | .56 | 100 (0) | 98 | | | 95 (3) | 98 | | | 18 (0) | 15 |
| 4 | 1.12 | 2 | 2.24 | 100 (0) | 98 | | | 100 (0) | 98 | | | 8 (46) | 15 |
| 4 | 1.12 | 2 | 2.24 | 100 (0) | 100 | | | 100 (0) | 100 | | | 0 (100) | 80 |
| 4 | 2.24 | 2 | .14 | 100 (0) | 100 | | | 100 (0) | 100 | | | 0 (100) | 48 |
| 4 | 2.24 | 2 | .14 | 100 (0) | 100 | | | 100 (0) | 98 | | | 0 (100) | 87 |
| 4 | 2.24 | 2 | .56 | 100 (0) | 100 | | | 95 (5) | 100 | | | 0 (100) | 48 |
| 4 | 2.24 | 2 | .56 | 100 (0) | 100 | | | 100 (0) | 98 | | | 0 (100) | 87 |

TABLE 4-continued

% PLANT INHIBITION AND % SAFENING EFFECT ( )

| HERB. NO. | RATE | ANTIDOTE NO. | RATE | Sorghum W | Sorghum WO | Foxtail Green W | Foxtail Green WO | Crabgrass Large W | Crabgrass Large WO | Barnyard Grass W | Barnyard Grass WO | Corn W | Corn WO |
|---|---|---|---|---|---|---|---|---|---|---|---|---|---|
| 4 | 2.24 | 2 | 2.24 | | | 100 | 100 | | | 98 (2) | 100 | 0 (100) | 48 |
| 4 | 2.24 | 2 | 2.24 | | | 100 (0) | 100 | | | 100 (0) | 98 | 18 (79) | 87 |
| 4 | 4.48 | 2 | .14 | | | 100 (0) | 100 | | | 100 (0) | 100 | 0 (100) | 92 |
| 4 | 4.48 | 2 | .14 | | | 100 (0) | 100 | | | 100 (0) | 100 | 13 (87) | 100 |
| 4 | 4.48 | 2 | .56 | | | 100 (0) | 100 | | | 98 (2) | 100 | 0 (100) | 92 |
| 4 | 4.48 | 2 | .56 | | | 100 (0) | 100 | | | 100 (0) | 100 | 8 (92) | 100 |
| 4 | 4.48 | 2 | 2.24 | | | 100 (0) | 100 | | | 100 (0) | 100 | 0 (100) | 92 |
| 4 | 4.48 | 2 | 2.24 | | | 100 (0) | 100 | | | 100 (0) | 100 | 5 (95) | 100 |
| 4 | 1.12 | 3 | .14 | | | 100 (0) | 100 | | | 100 (0) | 100 | 8 (90) | 80 |
| 4 | 1.12 | 3 | .56 | | | 98 (2) | 100 | | | 100 (0) | 100 | 5 (93) | 80 |
| 4 | 1.12 | 3 | 2.24 | | | 98 (2) | 100 | | | 100 (0) | 100 | 0 (100) | 80 |
| 4 | 2.24 | 3 | .14 | | | 100 (0) | 100 | | | 100 (0) | 98 | 20 (77) | 87 |
| 4 | 2.24 | 3 | .56 | | | 100 (0) | 100 | | | 100 (0) | 98 | 5 (94) | 87 |
| 4 | 2.24 | 3 | 2.24 | | | 100 (0) | 100 | | | 100 (0) | 98 | 0 (100) | 87 |
| 4 | 4.48 | 3 | .14 | | | 100 (0) | 100 | | | 100 (0) | 100 | 5 (95) | 100 |
| 4 | 4.48 | 3 | .56 | | | 100 (0) | 100 | | | 100 (0) | 100 | 0 (100) | 100 |
| 4 | 4.48 | 3 | 2.24 | | | 100 (0) | 100 | | | 100 (0) | 100 | 5 (95) | 100 |
| 4 | 1.12 | 4 | .14 | | | 100 (0) | 100 | | | 100 (0) | 100 | 0 (100) | 90 |
| 4 | 1.12 | 4 | .14 | | | 100 (0) | 100 | | | 100 (0) | 100 | 0 (100) | 80 |
| 4 | 1.12 | 4 | .56 | | | 100 (0) | 100 | | | 100 (0) | 100 | 0 (100) | 90 |
| 4 | 1.12 | 4 | .56 | | | 100 (0) | 100 | | | 100 (0) | 100 | 10 (87) | 80 |
| 4 | 1.12 | 4 | 2.24 | | | 100 (0) | 100 | | | 100 (0) | 100 | 0 (100) | 80 |
| 4 | 1.12 | 4 | 2.24 | | | 100 (0) | 100 | | | 100 (0) | 100 | 0 (100) | 90 |
| 4 | 2.24 | 4 | .14 | | | 100 (0) | 100 | | | 100 (0) | 100 | 5 (94) | 85 |
| 4 | 2.24 | 4 | .14 | | | 100 (0) | 100 | | | 100 (0) | 98 | 0 (100) | 87 |
| 4 | 2.24 | 4 | .56 | | | 100 (0) | 100 | | | 100 (0) | 98 | 5 (94) | 87 |
| 4 | 2.24 | 4 | .56 | | | 100 (0) | 100 | | | 100 (0) | 100 | 0 (100) | 85 |
| 4 | 2.24 | 4 | 2.24 | | | 100 (0) | 100 | | | 100 (0) | 100 | 8 (90) | 85 |
| 4 | 2.24 | 4 | 2.24 | | | 100 (0) | 100 | | | 100 (0) | 98 | 5 (94) | 87 |
| 4 | 4.48 | 4 | .14 | | | 100 (0) | 100 | | | 100 (0) | 100 | 0 (100) | 100 |
| 4 | 4.48 | 4 | .14 | | | 100 (0) | 100 | | | 100 (0) | 100 | 13 (86) | 98 |
| 4 | 4.48 | 4 | .56 | | | 100 (0) | 100 | | | 100 (0) | 100 | 5 (95) | 100 |
| 4 | 4.48 | 4 | .56 | | | 100 (0) | 100 | | | 100 (0) | 100 | 13 (86) | 98 |
| 4 | 4.48 | 4 | 2.24 | | | 100 (0) | 100 | | | 100 (0) | 100 | 10 (90) | 100 |
| 4 | 4.48 | 4 | 2.24 | | | 100 (0) | 100 | | | 100 (0) | 100 | 25 (74) | 98 |
| 4 | 1.12 | 5 | .14 | | | 100 (0) | 100 | | | 100 (0) | 100 | 5 (93) | 80 |
| 4 | 1.12 | 5 | .56 | | | 100 (0) | 100 | | | 100 (0) | 100 | 8 (90) | 80 |
| 4 | 1.12 | 5 | 2.24 | | | 100 (0) | 100 | | | 100 (0) | 100 | 0 (100) | 80 |
| 4 | 2.24 | 5 | .14 | | | 100 | 100 | | | 100 | 98 | 15 | 87 |

TABLE 4-continued

| | | | | % PLANT INHIBITION AND % SAFENING EFFECT ( ) | | | | | | | |
|---|---|---|---|---|---|---|---|---|---|---|---|
| | | ANTIDOTE | | Sorghum | | Foxtail Green | | Crabgrass Large | | Barnyard Grass | | Corn | |
| HERB. NO. | RATE | NO. | RATE | W | WO | W | WO | W | WO | W | WO | W | WO |
| 4 | 2.24 | 5 | .56 | | | 100 (0) | 100 | | | 100 (0) | 98 | 0 (82) (100) | 87 |
| 4 | 2.24 | 5 | 2.24 | | | 100 (0) | 100 | | | 100 (0) | 98 | 0 (100) | 87 |
| 4 | 4.48 | 5 | .14 | | | 100 (0) | 100 | | | 100 (0) | 100 | 68 (32) | 100 |
| 4 | 4.48 | 5 | .56 | | | 100 (0) | 100 | | | 100 (0) | 100 | 8 (92) | 100 |
| 4 | 4.48 | 5 | 2.24 | | | 100 (0) | 100 | | | 100 (0) | 100 | 5 (95) | 100 |
| 4 | 1.12 | 13 | .14 | | | 100 (0) | 100 | | | 100 (0) | 100 | 15 (81) | 80 |
| 4 | 1.12 | 13 | .56 | | | 100 (0) | 100 | | | 100 (0) | 100 | 0 (100) | 80 |
| 4 | 1.12 | 13 | 2.24 | | | 100 (0) | 100 | | | 100 (0) | 100 | 0 (100) | 80 |
| 4 | 2.24 | 13 | .14 | | | 100 (0) | 100 | | | 100 (0) | 98 | 53 (39) | 87 |
| 4 | 2.24 | 13 | .56 | | | 100 (0) | 100 | | | 100 (0) | 98 | 35 (59) | 87 |
| 4 | 2.24 | 13 | 2.24 | | | 100 (0) | 100 | | | 100 (0) | 98 | 8 (90) | 87 |
| 4 | 4.48 | 13 | .14 | | | 100 (0) | 100 | | | 100 (0) | 100 | 95 (5) | 100 |
| 4 | 4.48 | 13 | .56 | | | 100 (0) | 100 | | | 100 (0) | 100 | 75 (25) | 100 |
| 4 | 4.48 | 13 | 2.24 | | | 100 (0) | 100 | | | 100 (0) | 100 | 28 (72) | 100 |
| 4 | 1.12 | 6 | .14 | | | 95 (5) | 100 | | | 100 (0) | 100 | 0 (100) | 80 |
| 4 | 1.12 | 6 | .56 | | | 98 (2) | 100 | | | 98 (2) | 100 | 5 (93) | 80 |
| 4 | 1.12 | 6 | 2.24 | | | 100 (0) | 100 | | | 100 (0) | 100 | 0 (100) | 80 |
| 4 | 2.24 | 6 | .14 | | | 100 (0) | 100 | | | 100 (0) | 98 | 0 (100) | 87 |
| 4 | 2.24 | 6 | .56 | | | 100 (0) | 100 | | | 100 (0) | 98 | 0 (100) | 87 |
| 4 | 2.24 | 6 | 2.24 | | | 100 (0) | 100 | | | 100 (0) | 98 | 0 (100) | 87 |
| 4 | 4.48 | 6 | .14 | | | 100 (0) | 100 | | | 100 (0) | 100 | 23 (77) | 100 |
| 4 | 4.48 | 6 | .56 | | | 100 (0) | 100 | | | 100 (0) | 100 | 5 (95) | 100 |
| 4 | 4.48 | 6 | 2.24 | | | 100 (0) | 100 | | | 100 (0) | 100 | 0 (100) | 100 |

Example 42

The following procedure was used to determine the interaction between a herbicide and antidote when the herbicide is topically applied to the soil surface and the antidote is applied to crop seed. Crop plant seed was treated with the antidote either by contacting the seed with antidote in powder form or by contacting the seed with a solution or suspension of antidote compound dissolved or suspended in a suitable solvent, typically methylene chloride or toluene. Relative amounts of antidote compound and seed were used to provide an antidote-on-seed concentration, on a percent weight/weight basis. Containers were filled and compacted with fumigated silt loam type soil to a depth of about 1.3 cm from the top of the container. A first container was designated as an untreated control, a second container was designated as a herbicide control, and a third container was designated as a herbicide+antidote test container. Untreated crop seed was placed in the first and second containers. Antidote-treated crop seed was placed in the third container. Then, each of the second and third containers was filled and leveled with a cover layer of soil having incorporated therein the selected herbicide at a predetermined concentration. The first container was filled and leveled with soil containing no herbicide. All containers were given about 0.6 cm of overhead water to simulate an activating rainfall. The containers were placed on a greenhouse bench and sub-irrigated as required for the duration of the test. Plant response was observed about three weeks after initial treatment. Results are set forth in Table 5. Herbicide rate is given in kg/ha and antidote rate is given in percent weight/weight of antidote/seed.

TABLE 5

| | | | | | % PLANT INHIBITION AND % SAFENING EFFECT ( ) | | | |
|---|---|---|---|---|---|---|---|---|
| HERB. NO. | RATE | ANTI-DOTE NO. | RATE | Sorghum Grain W | | Sorghum Grain WO | Foxtail Green W | Foxtail Green WO |
| 2 | .56 | 3 | .03 | 0 (100) | | 22 | 98 (2) | 100 |
| 2 | .56 | 3 | .06 | 0 (100) | | 22 | 98 (2) | 100 |
| 2 | .56 | 3 | .13 | 15 (31) | | 22 | 95 (5) | 100 |
| 2 | 1.12 | 3 | .03 | 5 (90) | | 50 | 98 (2) | 100 |
| 2 | 1.12 | 3 | .06 | 0 (100) | | 50 | 100 (0) | 100 |
| 2 | 1.12 | 3 | .13 | 5 (90) | | 50 | 100 (0) | 100 |
| 2 | 2.24 | 3 | .03 | 5 (92) | | 65 | 98 (2) | 100 |
| 2 | 2.24 | 3 | .06 | 15 (76) | | 65 | 100 (0) | 100 |
| 2 | 2.24 | 3 | .13 | 5 (92) | | 65 | 100 (0) | 100 |
| 2 | .56 | 20 | .03 | 0 (100) | | 22 | 98 (2) | 100 |
| 2 | .56 | 20 | .06 | 5 (77) | | 22 | 100 (0) | 100 |
| 2 | .56 | 20 | .13 | 0 (100) | | 22 | 100 (0) | 100 |
| 2 | 1.12 | 20 | .03 | 8 (84) | | 50 | 100 (0) | 100 |
| 2 | 1.12 | 20 | .06 | 0 (100) | | 50 | 100 (0) | 100 |
| 2 | 1.12 | 20 | .13 | 5 (90) | | 50 | 100 (0) | 100 |
| 2 | 2.24 | 20 | .03 | 0 (100) | | 65 | 100 (0) | 100 |
| 2 | 2.24 | 20 | .06 | 10 (84) | | 65 | 100 (0) | 100 |
| 2 | 2.24 | 20 | .13 | 10 (84) | | 65 | 100 (0) | 100 |

Following the same procedures described above in Examples 40 and 42, additional tests were conducted in order to exemplify the safening, antidotal properties of the compounds of Examples 33–38 with a plurality of herbicides from diverse classes of chemicals including some of those in the above list of Herbicide Nos. 1–14 previously tested with the safener compounds of Examples 1–32 (see Tables 2–5). Additional herbicides include the following compounds:

| Herb No. | Name |
|---|---|
| 15 | 2-Methoxy-3,6-dichlorobenzoic acid, dimethylamine salt. |
| 16 | As-triazine-5(4H)one,4-amino-, 6-tert-butyl-,3-(methylthio)-; |
| 17 | 4-Chloro-5-(methylamino)-2-(alpha,alpha,alpha-trifluoro-m-tolyl)-3(2H)-pyridazionone; |
| 18 | Benzeneamine,N-(1-ethylpropyl)-3, 4-dimethyl-2,6-dinitro- |
| 19 | Benzenesulfonamide,2-chloro-N-[[(4-methoxy-6-methyl-1,3,5-triazin-2-yl)amino]carbonyl]-; |
| 20 | Benzoic acid,2-[[[[(4,6-dimethyl-2-pyrimidinyl)amino]carbonyl]amino]sulfonyl]-, methyl ester; |
| 21 | Benzoic acid,2-[[[[(4,6-dimethoxy-2-pyrimidinyl)amino]carbonyl]amino]sulfonyl]methyl]-, methyl ester; |
| 22 | 3-Quinolinecarboxylic acid,2-[4, 5-dihydro-4-methyl-4-(1-methyl-ethyl)-5-oxo-1h-imidazol-2-YL]-; |
| 23 | 3-Quinolinecarboxylic acid,2-[4, 5,-dihydro-4-methyl-4-(1-methyl-ethyl)-5-oxo-1H-imidazol-2-yl]-; |
| 24 | 3-Pyridinecarboxylic acid,2-(difluoromethyl)-5-(4,5-dihydro-2-thiazolyl)-4-(2-methylpropyl)-6-(trifluoromethyl)-,methyl ester; |
| 25 | 3-Pyridinecarboxylic acid,2-[4,5-dihydro-4-methyl-4-(1-methylethyl)-5-oxo-1H-imidazol-2-yl]-; |
| 26 | Benzoic acid,2-[[[[(4-methoxy-6-methyl-1,3,5-triazin-2-YL)amino]carbonyl]amino]sulfonyl]-,methyl ester; |
| 27 | 3-Pyridinecarboxylic acid,5-ethyl-2-[4,5-dihydro-4-(1-methylethyl)-5-oxo-1H-imidazol-2-yl]-; |
| 28 | Benzoic acid, 2-[[[[(4-chloro-6-methoxy-2-pyrimidinyl)amino]-carbonyl]amino]sulfonyl]-,ethyl ester; |
| 29 | Benzenesulfonamide,2-(2-chloroethoxy)-N-[[(4-methoxy-6-methyl-1,3,5-triazin-2-yl)amino]carbonyl]-; |
| 30 | 2-Thiophenecarboxylic acid,3-[[[[(4, 6-dimethoxy-1,3,5-triazin-2-yl)-amino]carbonyl]amino]sulfonyl]-, methyl ester; |
| 31 | 3-Pyridinecarboxylic acid,2-[4,5-dihydro-4-methyl-4-(1-methylethyl)-5-oxo-1H-imidazol-2-yl] -5-methyl-, ammonium salt; |
| 32 | Benzoic acid, 2-[4,5-dihydro-4-methyl-4-(1-methylethyl)-5-oxo-1H-imidazol-2-yl]-4(OR 5)-methyl-; |
| 33 | 2-Imidazolidinone,3-[5-(1,1-dimethylethyl)-3-isoxazolyl]-4-hydroxy-1-methyl-; |

Example 43

Following the test procedure described in Example 40, the antidotal properties of compounds listed in Table 1, mostly Antidote Nos. 33–38, were tested in combinations with a wide variety of herbicidal compounds, particularly Herbicide Nos. 15–33. Results are shown in Table 6.

TABLE 6

% PLANT INHIBITION AND % SAFENING EFFECT ( )

| HERB. NO. | RATE | ANTI-DOTE NO. | RATE | Corn W | Corn WO | Barnyard Grass W | Barnyard Grass WO | Sorghum (Grain) W | Sorghum (Grain) WO | Foxtail Green W | Foxtail Green WO | Pigweed Redroot W | Pigweed Redroot WO | Velvet Leaf W | Velvet Leaf WO | Soybean W | Soybean WO | Wheat W | Wheat WO | Rice W | Rice WO | Hemp Sesbania W | Hemp Sesbania WO | Indian Mustard W | Indian Mustard WO | Tartary Buckwheat W | Tartary Buckwheat WO |
|---|---|---|---|---|---|---|---|---|---|---|---|---|---|---|---|---|---|---|---|---|---|---|---|---|---|---|---|
| 6 | 8.96 | 1 | 0.14 | 5 (62) | 13 | 95 (0) | 95 | | | | | | | | | | | | | | | | | | | | |
| 6 | 11.20 | 1 | 0.14 | 0 (100) | 30 | 95 (0) | 95 | | | | | | | | | | | | | | | | | | | | |
| 6 | 8.96 | 1 | 0.56 | 5 (62) | 13 | 90 (6) | 95 | | | | | | | | | | | | | | | | | | | | |
| 6 | 11.20 | 1 | 0.56 | 0 (100) | 30 | 90 (6) | 95 | | | | | | | | | | | | | | | | | | | | |
| 6 | 8.96 | 1 | 2.24 | 5 (62) | 13 | 85 (11) | 95 | | | | | | | | | | | | | | | | | | | | |
| 6 | 11.20 | 1 | 2.24 | 0 (100) | 30 | 85 (11) | 95 | | | | | | | | | | | | | | | | | | | | |
| 2 | 0.56 | 1 | 0.03 | | | | | 75 (24) | 98 | 95 (5) | 100 | | | | | | | | | | | | | | | | |
| 2 | 2.24 | 1 | 0.03 | | | | | 98 (0) | 98 | 100 (0) | 100 | | | | | | | | | | | | | | | | |
| 2 | 0.56 | 1 | 0.14 | | | | | 90 (9) | 98 | 100 (0) | 100 | | | | | | | | | | | | | | | | |
| 2 | 2.24 | 1 | 0.14 | | | | | 83 (16) | 98 | 100 (0) | 100 | | | | | | | | | | | | | | | | |
| 2 | 0.56 | 1 | 0.56 | | | | | 70 (29) | 98 | 100 (0) | 100 | | | | | | | | | | | | | | | | |
| 2 | 2.24 | 1 | 0.56 | | | | | 85 (14) | 98 | 100 (0) | 100 | | | | | | | | | | | | | | | | |
| 15 | 1.12 | 1 | 0.56 | 10 (0) | 10 | | | 0 (100) | 10 | | | 25 (73) | 90 | | | | | | | | | | | | | | |
| 15 | 1.12 | 1 | 0.56 | 35 (0) | 35 | | | | | | | 60 | 50 | | | | | | | | | | | | | | |
| 15 | 4.48 | 1 | 0.56 | | | | | | | | | 100 | 50 | | | | | | | | | | | | | | |
| 15 | 4.48 | 1 | 0.56 | | | | | 60 (20) | 75 | | | 85 (15) | 100 | | | | | | | | | | | | | | |
| 15 | 1.12 | 1 | 2.24 | 5 (30) | 10 | | | | | | | 65 | 50 | | | | | | | | | | | | | | |
| 15 | 1.12 | 1 | 2.24 | | | | | 10 (0) | 10 | | | 95 | 90 | | | | | | | | | | | | | | |
| 15 | 4.48 | 1 | 2.24 | 15 (58) | 35 | | | | | | | 95 | 50 | | | | | | | | | | | | | | |
| 15 | 4.48 | 1 | 2.24 | | | | | 40 (47) | 75 | | | 100 (0) | 100 | | | | | | | | | | | | | | |
| 15 | 1.12 | 1 | 8.96 | | | | | 0 (100) | 10 | | | 90 (0) | 90 | | | | | | | | | | | | | | |
| 15 | 1.12 | 1 | 8.96 | 0 (100) | 10 | | | | | | | 35 (30) | 50 | | | | | | | | | | | | | | |
| 15 | 4.48 | 1 | 8.96 | | | | | 45 (40) | 75 | | | 100 (0) | 100 | | | | | | | | | | | | | | |
| 15 | 4.48 | 1 | 8.96 | 5 | 35 | | | | | | | 60 | 50 | | | | | | | | | | | | | | |

-continued

| | | | | | | | | | | | | |
|---|---|---|---|---|---|---|---|---|---|---|---|---|
| 7 | 0.14 | 1 | 0.56 | (86) | | | | | | | | |
| 7 | 0.56 | 1 | 0.56 | | | | | | | | | |
| 7 | 1.12 | 1 | 0.56 | 85 | 72 | 100 | 100 | 80 | 90 | 80 | 90 | |
| 7 | 4.48 | 1 | 0.56 | 100 | 95 | 100 (0) | 100 (0) | (12) 100 (0) | 100 (0) | (12) 100 (0) | 100 (0) | |
| 7 | 0.14 | 1 | 2.24 | | | | | | | | | |
| 7 | 0.56 | 1 | 2.24 | | | | | | | | | |
| 7 | 1.12 | 1 | 2.24 | 80 | 72 | 100 | 100 | 45 | 90 | | | |
| 7 | 4.48 | 1 | 2.24 | 95 | 95 (0) | 100 (0) | 100 (0) | (50) 100 (0) | 100 (0) | | | |
| 7 | 0.14 | 1 | 8.96 | | | | | | | | | |
| 7 | 0.56 | 1 | 8.96 | | | | | | | | | |
| 7 | 1.12 | 1 | 8.96 | 85 | 72 | 100 | 100 | 80 | 90 | | | |
| 7 | 4.48 | 1 | 8.96 | 100 | 95 | 100 (0) | 100 (0) | (12) 100 (0) | 100 (0) | | | |
| 16 | 0.56 | 1 | 0.56 | 35 | 20 | 100 | 100 | 10 | 40 | | | |
| 16 | 2.24 | 1 | 0.56 | 0 (100) | (0) | 100 (0) | 100 (0) | (75) 90 | 95 | | | |
| 16 | 0.56 | 1 | 2.24 | 0 | 20 | | | 45 | 40 | | | |
| 16 | 2.24 | 1 | 2.24 | 35 | | | | (6) 100 | 95 | | | |
| 16 | 0.56 | 1 | 8.96 | 5 | | | | 20 | 40 | | | |
| 16 | 2.24 | 1 | 8.96 | 20 | 20 (0) | | | (50) 90 | 95 | | | |
| 17 | 0.14 | 1 | 0.56 | 90 | 88 | 100 (0) | 100 | (6) | | | | |
| 17 | 1.68 | 1 | 0.14 | 80 | 95 | 100 (0) | 100 | | | | | |
| 17 | 3.36 | 1 | 0.14 | (16) 90 | 88 | 100 (0) | 100 | | | 100 | 90 | |
| 17 | 1.68 | 1 | 0.56 | 88 | 95 | 100 (0) | 100 | | | 100 (0) | 100 | |
| 17 | 3.36 | 1 | 0.56 | 85 (8) | 88 | 100 (0) | 100 | | | 100 (0) | 90 | |
| 17 | 1.68 | 1 | 2.24 | 83 (4) | 95 | 100 (0) | 100 | | | 100 (0) | 100 | |
| 17 | 3.36 | 1 | 2.24 | (13) | | | | | | 100 (0) | 90 | |
| 18 | 0.56 | 1 | 0.56 | 55 | 42 | 100 (0) | 100 | 95 | 78 | 100 (0) | 100 | |
| 18 | 1.12 | 1 | 0.56 | | | | | 97 (3) | 0 (100) | | | |
| 18 | 2.24 | 1 | 0.56 | | | | | 95 | 100 (0) | | | |

-continued

| | | | | | | | | | |
|---|---|---|---|---|---|---|---|---|---|
| 18 | 4.48 | 1 | 0.56 | 65 (19) | 100 (0) | | 90 (0) 90 | | 95 88 |
| 18 | 0.56 | 1 | 2.24 | | 100 (0) | | | | |
| 18 | 1.12 | 1 | 2.24 | 40 (5) | 100 (0) | | 95 (0) 95 | | 95 95 (0) |
| 18 | 2.24 | 1 | 2.24 | | 100 (0) | | 90 (0) 90 | | |
| 18 | 4.48 | 1 | 2.24 | 70 (13) | 100 (0) | | 90 (0) 95 | | 95 88 |
| 18 | 0.56 | 1 | 8.96 | | | | 90 (0) 90 | | |
| 18 | 1.12 | 1 | 8.96 | 60 42 | | | 95 (0) 95 | | 95 95 (0) |
| 18 | 2.24 | 1 | 8.96 | 80 | | | 90 (0) 90 | | |
| 18 | 4.48 | 1 | 8.96 | 90 | | | 70 (18) 85 | | |
| 19 | 0.009 | 1 | 1.12 | 25 (73) | | | 90 (0) 90 | | |
| 19 | 0.01 | 1 | 1.12 | | | | 100 95 | | |
| 19 | 0.03 | 1 | 1.12 | 45 (54) | | 10 30 (67) | 95 90 | | 30 27 |
| 19 | 0.03 | 1 | 1.12 | 97 | | | 95 95 | | |
| 19 | 0.07 | 1 | 1.12 | 5 (95) | | 65 70 (8) | | | |
| 19 | 0.14 | 1 | 4.48 | 90 | | | | | |
| 19 | 0.009 | 1 | 4.48 | 80 (18) | | 0 30 (100) | | | 25 42 (41) |
| 19 | 0.01 | 1 | 4.48 | 97 | | 10 70 (86) 15 22 (32) | 95 95 0 (100) 70 (100) | 25 30 10 | 0 (100) |
| 19 | 0.03 | 1 | 4.48 | | | | | | |
| 19 | 0.03 | 1 | 1.12 | 0 (100) 12 45 38 | | 35 73 (53) | 50 (100) 75 | 40 35 | |
| 20 | 0.004 | 1 | 1.12 | | | | | | |
| 20 | 0.004 | 1 | 1.12 | | | | 80 60 | 60 | |
| 20 | 0.009 | 1 | 1.12 | | | | 60 | 10 | 25 68 (64) |
| 20 | 0.009 | 1 | 1.12 | | | | | | |
| 20 | 0.004 | 1 | 4.48 | 12 (100) | | | | | |

-continued

| Ex. | | | | | | | | | |
|---|---|---|---|---|---|---|---|---|---|
| 20 | 0.004 | 1 | 4.48 | | | 10 (55) | 22 | 85 | 10 (0) | 10 |
| 20 | 0.004 | 1 | 4.48 | | | | | 70 | 25 | |
| 20 | 0.009 | 1 | 4.48 | | | | | 90 | 30 | |
| 20 | 0.009 | 1 | 4.48 | 0 (100) | 38 | | | 75 | 35 | |
| 20 | 0.009 | 1 | 4.48 | | | 65 (11) | 73 | 50 | 60 40 | 60 (12) | 68 |
| 21 | 0.28 | 1 | 0.14 | | | | | | | | 35 | 47 (26) | 45 | 35 |
| 21 | 0.56 | 1 | 0.14 | | | | | | | | 75 | 68 (33) | 35 | 30 |
| 21 | 1.12 | 1 | 0.14 | | | | | | | | 45 | 67 | 45 | 30 |
| 21 | 0.28 | 1 | 0.56 | | | | | | | | 0 (100) | 47 (49) | 30 (15) | 35 |
| 21 | 0.56 | 1 | 0.56 | | | | | | | | 35 | 68 | 45 | 30 |
| 21 | 1.12 | 1 | 0.56 | | | | | | | | 70 (100) | 67 | 35 | 30 |
| 21 | 0.28 | 1 | 2.24 | | | | | | | | 0 | 47 | 15 (58) | 35 |
| 21 | 0.56 | 1 | 2.24 | | | | | | | | 45 (34) | 68 | 35 | 30 |
| 21 | 1.12 | 1 | 2.24 | | | | | | | | 25 (63) | 67 (17) | 25 | 30 |
| 21 | 0.28 | 1 | 8.96 | | | | | | | | 10 (79) | 47 (43) | 20 | 35 |
| 21 | 0.56 | 1 | 8.96 | | | | | | | | 55 (86) | 68 | 50 | 30 |
| 21 | 1.12 | 1 | 8.96 | | | | | | | | (18) | 67 | 80 | 30 |
| 22 | 1.12 | 1 | 0.03 | 33 (22) | 42 | | | | | | | | | |
| 22 | 2.24 | 1 | 0.03 | 63 | 60 | | 5 (75) | 20 | 100 | 98 | | | | |
| 22 | 0.28 | 1 | 0.14 | | 17 | | | | 100 (0) | 100 | | | | |
| 22 | 0.28 | 1 | 0.14 | 5 (71) | 17 | | | | 95 | 90 | 10 (50) | 20 | | |
| 22 | 0.56 | 1 | 0.14 | 10 (17) | 12 | | 90 | 78 | 100 (20) | 85 | | | | |
| 22 | 1.12 | 1 | 0.14 | 10 (74) | 38 | | | | 80 | 100 | | | | |
| 22 | 1.12 | 1 | 0.14 | 75 (24) | 98 | | | | 100 (0) | 100 | | | | |
| 22 | 1.12 | 1 | 0.14 | | | | | | 100 (0) | 98 | 75 (22) | 95 | | |
| 22 | 1.12 | 1 | 0.14 | 30 (29) | 42 | | | | 100 | 100 | | | | |
| 22 | 2.24 | 1 | 0.14 | 43 (29) | 60 | | 5 (75) | 20 | 95 | 90 | 10 (50) | 20 | | |
| 22 | 0.28 | 1 | 0.56 | | 17 | | | | | | | | | |
| 22 | 0.28 | 1 | 0.56 | 15 | | | | | | | | | | |

-continued

| | | | | | | | | | | |
|---|---|---|---|---|---|---|---|---|---|---|
| 22 | 0.56 | 1 | 0.56 | 5 (12) | 12 | | | | | |
| 22 | 1.12 | 1 | 0.56 | 0 (59) | 38 | | | | 80 85 (6) | |
| 22 | 1.12 | 1 | 0.56 | 0 (100) | 100 | | | | 100 100 (0) | |
| 22 | 1.12 | 1 | 0.56 | 45 (55) | 98 | | | | 100 100 (0) | |
| 22 | 1.12 | 1 | 0.56 | 10 (77) | 42 | | | | 100 98 | |
| 22 | 2.24 | 1 | 0.56 | | | | 80 78 | | | |
| 22 | 0.28 | 1 | 0.56 | 30 (50) | 60 | | | | | |
| 22 | 0.28 | 1 | 2.24 | 5 (71) | 17 | | | | | |
| 22 | 0.56 | 1 | 2.24 | 0 (100) | 12 | | | | | |
| 22 | 1.12 | 1 | 2.24 | 10 (74) | 38 | | 10 (50) 20 | | | 25 (74) 95 |
| 22 | 1.12 | 1 | 2.24 | 30 (70) | 98 | | | | 100 100 (0) | 10 (50) 20 |
| 22 | 1.12 | 1 | 2.24 | | 99 | | | | 100 100 (0) | 90 90 (0) |
| 23 | 0.14 | 1 | 0.56 | 38 (62) | 99 | 0 45 (23) 58 | 70 (11) 78 | 0 55 50 (0) 50 10 (87) 75 | 90 (0) 85 | 100 (0) 100 |
| 23 | 0.56 | 1 | 0.56 | 99 (1) | 100 | | | | 60 55 70 (0) 70 | 85 95 (11) |
| 23 | 0.03 | 1 | 1.12 | 0 | | | | | | |
| 23 | 0.03 | 1 | 1.12 | | | | | | | |
| 23 | 0.14 | 1 | 1.12 | 0 | 68 | 10 58 (83) | | | 75 55 70 (0) 70 | 15 (40) 25 85 83 |
| 23 | 0.14 | 1 | 1.12 | 0 (100) | 99 | | | 0 10 15 75 (100) (34) 50 | | |
| 23 | 0.14 | 1 | 2.24 | 53 (47) | 99 | | | | 60 55 70 (0) 70 | 5 (80) 25 80 (4) 83 |
| 23 | 0.56 | 1 | 2.24 | 99 (1) | 100 | | | | | |
| 23 | 0.03 | 1 | 4.48 | | | | | | | |
| 23 | 0.03 | 1 | 4.48 | | | | | | | 80 63 95 |
| 23 | 0.14 | 1 | 4.48 | 5 (93) | 68 | | | | | 95 95 |
| 23 | 0.14 | 1 | 4.48 | 73 (27) | 99 | | | | | |
| 23 | 0.56 | 1 | 8.96 | 99 (1) | 100 | | | | | |
| 24 | 0.28 | 1 | 8.96 | 25 | 15 | | | | | |
| 24 | 1.12 | 1 | 0.14 | 95 | 92 | 100 (0) 100 | | | | |
| | | | 0.14 | | | 100 100 | | | | |

-continued

| Ex. | | | | | | | | | | |
|---|---|---|---|---|---|---|---|---|---|---|
| 24 | 0.28 | 1 | 0.56 | 40 | 15 | 100 (0) | | | | |
| 24 | 1.12 | 1 | 0.56 | 85 | 92 | 100 (0) | | | | |
| 24 | 0.28 | 1 | 2.24 | 10 (8) | 15 | 100 (0) | | | | |
| 24 | 1.12 | 1 | 2.24 | 70 (34) | 92 | 100 (0) | | | | |
| 25 | 0.14 | 1 | 0.56 | (24) | | | 10 (84) | 60 | 55 (0) | 63 |
| 25 | 0.14 | 1 | 0.56 | | | | 50 | 35 | 95 (13) | 95 |
| 25 | 0.56 | 1 | 0.56 | | | | 95 | 85 | 75 (0) | 63 |
| 25 | 0.56 | 1 | 0.56 | | | | 95 | 80 | | |
| 25 | 0.14 | 1 | 1.12 | | | | 15 (69) | 48 | 95 (0) | 95 |
| 25 | 0.56 | 1 | 1.12 | 10 (77) | 43 | | 90 | 95 | 35 (8) | 38 |
| 25 | 0.14 | 1 | 2.24 | 95 (0) | 95 | | 35 (42) | 60 | | 90 (3) 92 |
| 25 | 0.56 | 1 | 2.24 | 80 | 23 | | 60 | 35 | 95 | 95 (0) 95 |
| 25 | 0.14 | 1 | 2.24 | 95 (0) | 95 | | 90 | 85 | | 90 | 52 |
| 25 | 0.56 | 1 | 4.48 | 35 (19) | 43 | | 95 | 80 | | 95 (0) | 95 |
| 25 | 0.14 | 1 | 4.48 | 95 (0) | 95 | | 0 (100) | 48 | 70 | 38 |
| 25 | 0.56 | 1 | 8.96 | 25 | 23 | | 95 (0) | 95 | | 90 | 77 |
| 25 | 0.14 | 1 | 8.96 | 95 (0) | 95 | | 45 (25) | 60 | | 90 (3) 92 |
| 25 | 0.56 | 1 | 8.96 | 0 (100) | 43 | | 0 (100) | 35 | | 100 | 95 |
| 25 | 0.56 | 1 | 8.96 | 65 | 95 (32) | | 70 (13) | 80 | | 85 | 52 |
| 26 | 0.03 | 1 | 1.12 | | | | 10 (89) | 85 | 45 | 38 |
| 26 | 0.07 | 1 | 1.12 | 15 (85) 80 | 95 | | | | 85 | 77 |
| 26 | 0.07 | 1 | 1.12 | (16) | | | | | 95 (0) | 95 (0) 92 |
| 26 | 0.14 | 1 | 1.12 | | | | | | 80 | 60 |
| 26 | 0.28 | 1 | 1.12 | 90 (6) | 95 | | | | 100 | 83 | 10 (90) 95 |
| 26 | 0.28 | 1 | 1.12 | 95 | 100 (5) | | | | 95 (4) | 98 | 95 (0) |
| 26 | 0.03 | 1 | 4.48 | | | | | | 100 | 97 | 10 |
| 26 | 0.07 | 1 | 4.48 | 5 | 95 | | | | 90 | 55 | 35 (49) 68 |
| 26 | | | | | | | | | 95 (0) | 95 | |
| 26 | | | | | | | | | 75 | 83 | 0 |

-continued

| | | | | | | | | | | | | | |
|---|---|---|---|---|---|---|---|---|---|---|---|---|---|
| 26 | 0.07 | 1 | 4.48 | 10 (90) | 95 | | | | | | | | |
| 26 | 0.14 | 1 | 4.48 | | | | | | | (95) | | | |
| 26 | 0.28 | 1 | 4.48 | | | | | | | | | | |
| 26 | 0.28 | 1 | 4.48 | 90 (10) | 100 | | 70 (0) 70 (5) | 70 73 (63) | 15 40 | | 20 (10) 60 (67) | | | |
| 27 | 0.14 | 1 | 0.56 | 0 (100) | 8 | | 70 | 65 | | | 95 (4) 100 | 98 97 | | |
| 27 | 0.56 | 1 | 0.56 | 88 (10) | 97 | | | | | | 90 | 55 | | |
| 27 | 1.12 | 1 | 0.56 | | | | | | | 0 (100) | 70 (0) 80 | 70 85 (6) | 95 95 (0) | |
| 27 | 2.24 | 1 | 0.56 | | | | | | | | | | | |
| 27 | 0.14 | 1 | 1.12 | 0 (100) | 12 | | 60 (15) 100 | 70 73 | 40 | | | | 0 (100) 0 | 7 30 (100) |
| 27 | 0.56 | 1 | 1.12 | 75 (0) | 53 | | 45 | | | | | | 40 | |
| 27 | 0.14 | 1 | 2.24 | | 8 | | 75 | 65 | | | | | | |
| 27 | 0.56 | 1 | 2.24 | 43 (100) | 97 | | | | | | | | | |
| 27 | 1.12 | 1 | 2.24 | | (56) | | | | | | 70 (0) 85 | 70 85 (0) | 0 (100) 0 | 7 30 (100) |
| 27 | 2.24 | 1 | 2.24 | | | | | | | | | | | |
| 27 | 0.14 | 1 | 4.48 | 30 (100) | 12 | | | | | | | | | |
| 27 | 0.56 | 1 | 4.48 | (44) | 53 | | | | | | | | | |
| 27 | 0.14 | 1 | 8.96 | | 8 | | 80 | 70 73 | 70 | | | | | |
| 27 | 0.56 | 1 | 8.96 | 8 (100) | 97 | 10 43 (77) | 90 (65) | | 75 | | | | | |
| 27 | 1.12 | 1 | 8.96 | | (92) | 75 95 (22) | 25 80 | | | | 75 | 70 (12) | 20 35 | 7 30 |
| 27 | 2.24 | 1 | 8.96 | | | | | | | | | | | |
| 28 | 0.00 | 1 | 1.12 | | | | 85 | 75 | | | | | | |
| 28 | 0.01 | 1 | 1.12 | 5 (50) | 10 | | 90 | 88 | | | | | | |
| 28 | 0.01 | 1 | 1.12 | 5 (90) | 48 | | 95 (4) 100 (0) | 98 100 | | | | | 5 (0) 50 (17) | 5 60 |
| 28 | 0.07 | 1 | 1.12 | | | 5 43 (89) | | | | | | | | |
| 28 | 0.28 | 1 | 1.12 | | | 60 (37) | 95 | | | | | | | |
| 28 | 1.12 | 1 | 1.12 | | | | 95 | 70 | | | | | 0 (100) 15 | 18 75 (80) |
| 28 | 0.004 | 1 | 4.48 | | | | | | | | | | 65 (14) | 18 75 |
| 28 | 0.01 | 1 | 4.48 | | | | 80 | 75 | | | | | | |
| 28 | 0.01 | 1 | 4.48 | 0 | 10 | | 75 | 75 | | | | | 0 (100) | |

-continued

| | | | | | | | | | | | |
|---|---|---|---|---|---|---|---|---|---|---|---|
| 28 | 0.07 | 1 | 4.48 | (100) 10 48 (80) | 90 (0) 88 95 (4) 98 100 (0) 100 | | | | | | |
| 28 | 0.28 | 1 | 4.48 | | | | | | | | |
| 28 | 1.12 | 1 | 4.48 | | | | | | | | |
| 29 | 0.01 | 1 | 1.12 | | | | | | | | |
| 29 | 0.07 | 1 | 1.12 | 10 63 (85) | | 0 27 (100) 85 | 15 5 55 60 (9) | | | | |
| 29 | 0.28 | 1 | 1.12 | | | | | | | | |
| 29 | 0.56 | 1 | 1.12 | | 95 95 (0) | 70 55 | 95 73 (0) | | | | |
| 29 | 1.12 | 1 | 1.12 | 65 93 (31) | 90 95 (6) | 100 100 90 (0) 100 98 | 95 95 (0) | | | | |
| 29 | 1.12 | 1 | 1.12 | | | | | | | | |
| 29 | 0.01 | 1 | 4.48 | | | | | 35 10 | | | |
| 29 | 0.07 | 1 | 4.48 | | | | | | | | |
| 29 | 0.28 | 1 | 4.48 | 5 63 (93) | 10 95 60 95 (90) (37) | 50 27 25 70 (65) 70 55 | 85 73 95 90 (6) | 0 12 (100) | | | |
| 29 | 0.56 | 1 | 4.48 | | | 70 100 100 98 (30) | | | | | |
| 29 | 1.12 | 1 | 4.48 | 20 93 (79) | | 100 90 | | | | | |
| 29 | 1.12 | 1 | 4.48 | | | | | | | | |
| 30 | 0.01 | 1 | 0.14 | | | 40 40 50 50 (0) | 15 7 0 (100) 25 (100) | 0 10 (100) 10 12 (17) | | | |
| 30 | 0.03 | 1 | 0.14 | | | 0 40 | 0 12 | | | | |
| 30 | 0.01 | 1 | 0.56 | | | 0 50 (100) | 0 (100) | | | | |
| 30 | 0.03 | 1 | 0.56 | | | | | | | | |
| 30 | 1.12 | 1 | 1.12 | 30 93 (68) | 35 88 (61) | 20 40 (50) | 15 7 | 5 40 (88) | | | |
| 30 | 1.12 | 1 | 1.12 | | | 30 50 (40) | 10 12 (17) | 45 50 (10) | | | |
| 30 | 4.48 | 1 | 1.12 | 30 97 (70) | 85 93 (9) | | | | | | |
| 30 | 4.48 | 1 | 1.12 | | | | | | | | |
| 30 | 0.01 | 1 | 2.24 | | | | | | | | |
| 30 | 0.03 | 1 | 2.24 | | | | | | | | |
| 30 | 1.12 | 1 | 4.48 | 10 93 (90) | 55 88 (38) | | | 0 40 (100) | | | |
| 30 | 1.12 | 1 | 4.48 | | | | | | | | |

-continued

| | | | | | | | | | | | | |
|---|---|---|---|---|---|---|---|---|---|---|---|---|
| 30 | 4.48 | 1 | 4.48 | | | 100 100<br>(0) | | | | | | |
| 30 | 4.48 | 1 | 4.48 | 65 97<br>(33) | 80 93<br>(14) | 100<br>(0) | | | | | | |
| 31 | 0.14 | 1 | 0.56 | 0 | | 80 85<br>(6) | | | | | | |
| 31 | 0.14 | 1 | 0.56 | 0 | | 40 35<br>(25) | | | | | | |
| 31 | 0.14 | 1 | 0.56 | 30 75<br>(60) | | 80 60<br>(25) | | | | | | |
| 31 | 0.56 | 1 | 0.56 | | | 60 80 | | | | | | |
| 31 | 0.56 | 1 | 0.56 | | | 90 90<br>(0) | | | | | | |
| 31 | 0.14 | 1 | 0.56 | 0 | | 95 90 | | 25 50<br>(50) | | | | |
| 31 | 0.14 | 1 | 2.24 | | | 35 35 | | | | | | |
| 31 | 0.14 | 1 | 2.24 | | | 0 60<br>(100) | 0 28<br>(100) | | | | | |
| 31 | 0.14 | 1 | 2.24 | | | 60 85<br>(30) | | 35 32 | | | | |
| 31 | 0.56 | 1 | 2.24 | | | 85 90<br>(6) | | | | | | |
| 31 | 0.56 | 1 | 2.24 | 0 75<br>(100) | | 90 90<br>(0) | 30 50<br>(40) | 60 95<br>(37) | | | | |
| 31 | 0.14 | 1 | 8.96 | | | 35 80<br>(57) | | 50 32 | | | | |
| 31 | 0.14 | 1 | 8.96 | | | 35 60<br>(42) | 80 28 | 70 95<br>(27) | | | | |
| 31 | 0.14 | 1 | 8.96 | | | 55 35<br>(18) | | | | | | |
| 31 | 0.56 | 1 | 8.96 | | | 70 85 | 45 50<br>(10) | 10 32<br>(69) | | | | |
| 31 | 0.56 | 1 | 8.96 | 0 75<br>(100) | | 95 90 | | 55 95<br>(43) | | | | |
| 31 | 0.56 | 1 | 1.12 | | 20 58 | 95 90<br>(13) | | 30 25<br>(82) | | | | |
| 31 | 0.56 | 1 | 1.12 | | 35<br>(40) | 70 80 | 60 28 | 90 83 | | | | |
| 23 | 0.03 | 2 | | | 0 | 40 15<br>(50) | | 35 25 | | | | |
| 23 | 0.14 | 2 | | | | 65 | 65 50 | 15 83 | | | | |
| 23 | 0.03 | 2 | 4.48 | | 35 58<br>(40) | 0 15<br>(100) | | 85 52<br>(95) | | | | |
| 23 | 0.14 | 2 | 4.48 | | 25 23<br>(0) | 55 50 | | | | | | |
| 25 | 0.14 | 2 | 1.12 | | 25 23<br>(0) | 75 48<br>(11) | | 90 52<br>(0) | | | | |
| 25 | 0.56 | 2 | 1.12 | | | 85 95 | | 95 95<br>(0) | | | | |
| 25 | 0.14 | 2 | 4.48 | | 90 23<br>(0) | 85 48<br>(11) | | | | | | |
| 25 | 0.56 | 2 | 4.48 | | 95 95<br>(0) | 95 95<br>(0) | | | | | | |
| 27 | 0.14 | 2 | 1.12 | 0 12<br>(100) | 65 40 | | | | | | | |
| 27 | 0.56 | 2 | 1.12 | 60 53 | | 70 65 | | | | | | |
| 27 | 0.14 | 2 | 4.48 | 0 12 | | 70 40 | | | | | | |

-continued

| | | | | | | | | | | | | | | | |
|---|---|---|---|---|---|---|---|---|---|---|---|---|---|---|---|
| 27 | 0.56 | 2 | 4.48 | | (100) | 53 | | | | | | | | | 75 65 |
| 6 | 8.96 | 3 | 0.14 | 5 | (91) | 13 | 95 | (0) | 95 | | | | | | |
| 6 | 11.20 | 3 | 0.14 | 5 | (62) | 30 | 95 | (0) | 95 | | | | | | |
| 6 | 8.96 (24) | 3 | 0.56 | 5 | (84) | 13 | 95 | (0) | 95 | | | | | | |
| 6 | 11.20 | 3 | 0.56 | 10 | (0) | 30 | 95 | (0) | 95 | | | | | | |
| 6 | 8.96 | 3 | 2.24 | 0 | (100) | 13 | 95 | (0) | 95 | | | | | | |
| 6 | 11.20 | 3 | 2.24 | 0 | (100) | 30 | 95 | (0) | 95 | | | | | | |
| 2 | 0.56 | 3 | 0.03 | | | | | | | 75 | (24) | 98 | 98 | (2) | 100 |
| 2 | 0.56 | 3 | 0.03 | | | | | | | 75 | (24) | 98 | 95 | (5) | 100 |
| 2 | 2.24 | 3 | 0.03 | | | | | | | 95 | (4) | 98 | 100 | (0) | 100 |
| 2 | 2.24 | 3 | 0.03 | | | | | | | 93 | (6) | 98 | 100 | (0) | 100 |
| 2 | 0.28 | 3 | 0.14 | | | | | | | 0 | (100) | 85 | 90 | (10) | 100 |
| 2 | 0.56 | 3 | 0.14 | | | | | | | 10 | (90) | 93 | 100 | (0) | 100 |
| 2 | 0.56 | 3 | 0.14 | | | | | | | 85 | (14) | 98 | 100 | (0) | 100 |
| 2 | 0.56 | 3 | 0.14 | | | | | | | 43 | (57) | 98 | 100 | (0) | 100 |
| 2 | 0.56 | 3 | 0.14 | | | | | | | 5 | (94) | 75 | 100 | (0) | 98 |
| 2 | 2.24 | 3 | 0.14 | | | | | | | 55 | (44) | 98 | 100 | (0) | 100 |
| 2 | 2.24 | 3 | 0.14 | | | | | | | 95 | (4) | 98 | 100 | (0) | 100 |
| 2 | 2.24 | 3 | 0.14 | | | | | | | 95 | (4) | 98 | 100 | (0) | 100 |
| 2 | 2.24 | 3 | 0.14 | | | | | | | 25 | (75) | 97 | 100 | (0) | 100 |
| 2 | 0.28 | 3 | 0.56 | | | | | | | 0 | (100) | 85 | 95 | (5) | 100 |
| 2 | 0.56 | 3 | 0.56 | | | | | | | 20 | (79) | 93 | 95 | (5) | 100 |
| 2 | 0.56 | 3 | 0.56 | | | | | | | 78 | (21) | 98 | 98 | (2) | 100 |
| 2 | 0.56 | 3 | 0.56 | | | | | | | 55 | (44) | 98 | 100 | (0) | 100 |
| 2 | 0.56 | 3 | 0.56 | | | | | | | 5 | (94) | 75 | 90 | (9) | 98 |
| 2 | 0.56 | 3 | 0.56 | | | | | | | 55 | (24) | 72 | 100 | | 95 |
| 2 | 2.24 | 3 | 0.56 | | | | | | | 5 | | 100 | 95 | | 100 |

-continued

| | | | | | | | | | | | |
|---|---|---|---|---|---|---|---|---|---|---|---|
| 2 | 2.24 | 3 | 0.56 | | | 50 (95) | 98 | (5) | 100 | | |
| 2 | 2.24 | 3 | 0.56 | | | 95 (49) | 98 | 100 (0) | 100 | | |
| 2 | 2.24 | 3 | 0.56 | | | 90 (4) | 98 | 100 (0) | 100 | | |
| 2 | 2.24 | 3 | 0.56 | | | 55 (9) | 97 | 100 (0) | 100 | | |
| 2 | 0.28 | 3 | 0.56 | | | 5 (44) | 85 | 50 (5) | 100 | | |
| 2 | | 3 | 2.24 | | | | | 95 | 100 | | |
| 2 | 0.56 | 3 | 2.24 | | | 0 (100) | 93 | 100 (0) | 100 | | |
| 2 | 0.56 | 3 | 2.24 | | | 15 (80) | 75 | 95 (4) | 98 | | |
| 2 | 0.56 | 3 | 2.24 | | | 10 (87) | 72 | 90 (6) | 95 | | |
| 2 | 2.24 | 3 | 2.24 | | | 20 (80) | 100 | 95 (5) | 100 | | |
| 2 | 2.24 | 3 | 2.24 | | | 10 (90) | 98 | 100 (0) | 100 | | |
| 2 | 2.24 | 3 | 2.24 | | | 50 (49) | 97 | 100 (0) | 100 | | |
| 2 | 0.56 | 3 | 8.96 | | | 20 (73) | 72 | 100 (0) | 95 | | |
| 2 | 2.24 | 3 | 8.96 | | | 25 (75) | 100 | 100 (0) | 100 | | |
| 15 | 1.12 | 3 | 0.56 | 10 | (0) | 0 (100) | 10 | | | 60 | 50 |
| 15 | 1.12 | 3 | 0.56 | | | | | | | 100 | 90 |
| 15 | 4.48 | 3 | 0.56 | 15 (58) | 35 | | | | | 75 | 50 |
| 15 | 4.48 | 3 | 0.56 | | | 35 (54) | 75 | | | 100 | 100 |
| 15 | 1.12 | 3 | 2.24 | | | 10 | 10 | | | 80 (12) | 90 |
| 15 | 1.12 | 3 | 2.24 | 0 (100) | 10 | | | | | 75 | 50 |
| 15 | 4.48 | 3 | 2.24 | 25 (29) | 35 | | | | | 90 | 50 |
| 15 | 4.48 | 3 | 2.24 | | | 30 (60) | 75 | | | 100 (0) | 100 |
| 15 | 1.12 | 3 | 8.96 | | | 0 (100) | 10 | | | 55 (39) | 90 |
| 15 | 1.12 | 3 | 8.96 | 0 (100) | 10 | | | | | 25 (50) | 50 |
| 15 | 4.48 | 3 | 8.96 | 0 (100) | 35 | | | | | 30 (40) | 50 |
| 15 | 4.48 | 3 | 8.96 | | | 20 (74) | 90 | | | 95 (5) | 100 |
| 7 | 0.14 | 3 | 0.56 | | | | | 90 | 100 | | |
| 7 | 0.56 | 3 | 0.56 | | | 95 | 100 | 100 | 100 | | |

-continued

| Ex. | Dose A | N | Dose B | %1 | %2 | %3 | %4 | %5 | %6 | %7 | %8 | %9 | %10 |
|-----|--------|---|--------|------|------|------|------|------|------|------|------|------|------|
| 7 | 1.12 | 3 | 0.56 | 70 | 72 | 100 (0) | 100 (0) |  |  |  |  |  |  |
| 7 | 4.48 | 3 | 0.56 | 95 | 95 | 100 (0) | 100 (0) |  |  |  |  |  |  |
| 7 | 0.14 | 3 | 2.24 | 90 | 72 | 100 (0) | 100 (0) | 70 | 90 (23) | 100 | 95 | 90 (0) | 100 |
| 7 | 0.56 | 3 | 2.24 | 100 | 95 | 100 (0) | 100 (0) |  |  |  |  |  |  |
| 7 | 1.12 | 3 | 8.96 | 90 | 72 | 100 (0) | 100 (0) | 75 | 90 (17) | 100 | 100 | 90 (0) | 100 |
| 7 | 4.48 | 3 | 8.96 |  |  |  |  |  |  |  |  |  |  |
| 7 | 0.14 | 3 | 8.96 | 90 | 72 | 100 (0) | 100 (0) | 100 | 90 (0) | 100 | 100 | 90 (0) | 100 |
| 7 | 0.56 | 3 | 8.96 | 100 | 95 | 100 (0) | 100 (0) |  |  |  |  |  |  |
| 7 | 1.12 | 3 | 0.56 | 10 |  | 100 (0) | 100 (0) | 20 | 40 (50) | 95 | 95 | 95 (0) | 100 |
| 7 | 4.48 | 3 | 0.56 | 35 | 20 | 100 (0) | 100 (0) |  |  |  |  |  |  |
| 16 | 0.56 | 3 | 2.24 | 0 |  | 100 (0) | 100 (0) | 35 | 40 (13) | 95 | 85 | 95 (0) | 100 |
| 16 | 2.24 | 3 | 2.24 | 30 | 20 | 100 (0) | 100 (0) |  |  |  |  |  |  |
| 16 | 0.56 | 3 | 8.96 | 5 |  | 100 (0) | 100 (0) | 0 | 40 (100) | 100 | 90 | 95 (6) | 100 |
| 16 | 2.24 | 3 | 8.96 | 50 | 20 | 100 (0) | 100 (0) |  |  |  |  |  |  |
| 17 | 1.68 | 3 | 0.14 | 88 | 88 | 100 (0) | 100 (0) |  |  |  |  |  |  |
| 17 | 3.36 | 3 | 0.14 | 93 | 95 (3) | 98 (2) | 100 (0) |  |  |  |  |  |  |
| 17 | 1.68 | 3 | 0.56 | 60 | 88 (32) | 100 (0) | 100 (0) |  |  |  |  |  |  |
| 17 | 3.36 | 3 | 0.56 | 90 | 95 (6) | 100 (0) | 100 (0) |  |  |  |  |  |  |
| 17 | 1.68 | 3 | 2.24 | 88 | 88 (0) | 100 (0) | 100 (0) |  |  |  |  |  |  |
| 17 | 3.36 | 3 | 2.24 | 95 | 95 (0) | 100 (0) | 100 (0) |  |  |  |  |  |  |
| 18 | 0.56 | 3 | 0.56 | 60 | 42 | 100 (0) | 100 (0) | 100 | 100 | 78 | 100 | 95 (3) | 100 |
| 18 | 1.12 | 3 | 0.56 |  |  | 100 (0) | 100 (0) |  |  |  |  |  |  |
| 18 | 2.24 | 3 | 0.56 | 80 |  | 100 (0) | 100 (0) | 100 | 100 | 97 | 100 | 100 (0) | 100 |
| 18 | 4.48 | 3 | 0.56 | 70 (13) |  | 100 (0) | 100 (0) |  |  |  |  |  |  |
| 18 | 0.56 | 3 | 2.24 |  |  | 100 (0) | 100 (0) | 30 | 78 | 97 | 100 | 97 |  |

-continued

| 18 | 1.12  | 3 | 2.24       | 45       | 42       |              |              |              |              |              |
|----|-------|---|------------|----------|----------|--------------|--------------|--------------|--------------|--------------|
| 18 | 2.24  | 3 | 2.24       |          |          | 100 100 (0)  |              |              |              |              |
| 18 | 4.48  | 3 | 2.24       | 65       | 80 (19)  | 100 100 (0)  | 95 97 (3)    |              |              |              |
| 18 | 0.56  | 3 | 8.96       |          |          | 100 100 (0)  | 95 78        |              |              |              |
| 18 | 1.12  | 3 | 8.96       | 60       | 42       |              |              |              |              |              |
| 18 | 2.24  | 3 | 8.96       |          |          | 100 100 (0)  | 90 97 (8)    |              |              |              |
| 18 | 4.48  | 3 | 8.96       | 70       | 80 (13)  |              |              |              |              |              |
| 19 | 0.009 | 3 | 1.12       |          |          |              | (62)         | 85 90 (6)    | 60 88 (32)   |              |
| 19 | 0.01  | 3 | 1.12       | 5        | 90 (95)  |              |              | 90 85        |              |              |
| 19 | 0.03  | 3 | 1.12       |          |          |              |              | 95 90        | 95 (0)       |              |
| 19 | 0.03  | 3 | 1.12       |          |          |              |              | 95 95        |              |              |
| 19 | 0.07  | 3 | 1.12       | 35       | 97 (64)  |              |              | 85 90 (6)    |              |              |
| 19 | 0.14  | 3 | 1.12       |          |          |              |              | 95 95        | 80 88 (10)   |              |
| 19 | 0.009 | 3 | 4.48       |          |          |              | 0 (100)      | 95 90        | 95 (0)       |              |
| 19 | 0.01  | 3 | 4.48       | 10       | 90 (89)  |              | 65 70 (8)    | 95 85        |              |              |
| 19 | 0.03  | 3 | 4.48       |          |          |              |              | 95 90        |              |              |
| 19 | 0.03  | 3 | 4.48       |          |          |              | 0 (100)      | 90 95        |              |              |
| 19 | 0.07  | 3 | 4.48       | 15       | 97 (85)  |              | 10 70 (86)   | 90 90        | 25 27 (8)    |              |
| 19 | 0.14  | 3 | 4.48       |          |          |              | 0 (100)      | 95 95 (0)    | 45 42        |              |
| 20 | 0.004 | 3 | 1.12       | 10       | 12 (17)  |              |              | 60 10        |              |              |
| 20 | 0.004 | 3 | 1.12       |          |          |              | 0 (22) (100) | 65 25        |              |              |
| 20 | 0.004 | 3 | 1.12       |          |          |              | 95 73        | 60 30        |              |              |
| 20 | 0.009 0.009 | 3 | 1.12 1.12 | 0 0   | 38 (100) 12 (100) |      |              | 90 90 60 35  |              |              |
| 20 | 0.009 | 3 | 4.48       |          |          |              |              |              | 0 10 (100)   |              |
| 20 | 0.004 | 3 | 4.48       |          |          |              |              | 70 40        | 40 68 (42)   |              |
| 20 | 0.004 | 3 | 4.48       |          |          |              | 15 22 (32)   | 70 10        |              |              |
| 20 | 0.004 | 3 | 4.48       |          |          |              |              | 70 25        | 0 10 (100)   |              |
| 20 | 0.004 | 3 | 4.48       |          |          |              |              | 100 30       |              |              |

-continued

| | | | | | | | | | | | | | | |
|---|---|---|---|---|---|---|---|---|---|---|---|---|---|---|
| 20 | 0.009 | 3 | 4.48 | | 75 | 73 | | | | | 10 68 (86) | | | |
| 20 | 0.009 | 3 | 4.48 | | | | | | | | | | | |
| 20 | 0.009 | 3 | 4.48 45 | 38 | | | | | 90 | | | | 35 47 (26) | 10 35 (72) 30 |
| 21 | 0.28 | 3 | 0.14 | | | | | | 90 95 | 55 42 | | | 50 68 (27) | 30 30 (0) |
| 21 | 0.56 | 3 | 0.14 | | | | | | | | | | 65 67 (3) | 55 30 |
| 21 | 1.12 | 3 | 0.14 | | | | | | | | | | 50 47 | 15 35 (58) |
| 21 | 0.28 | 3 | 0.56 | | | | | | | | | | 25 68 (64) | 65 30 |
| 21 | 0.56 | 3 | 0.56 | | | | | | | | | | 80 67 (79) | 60 30 |
| 21 | 1.12 | 3 | 0.56 | | | | | | | | | | 10 47 (56) | 15 35 (58) |
| 21 | 0.28 | 3 | 2.24 | | | | | | | | | | 30 68 | 35 30 |
| 21 | 1.12 | 3 | 2.24 | | | | | | | | | | 70 67 (15) | 25 30 (17) |
| 21 | 0.28 | 3 | 8.96 | | | | | | | | | | 40 47 (12) | 25 35 (29) |
| 21 | 0.56 | 3 | 8.96 | | | | | | | | | | 60 68 (67) | 10 30 |
| 21 | 1.12 | 3 | 8.96 | | | | | 35 60 40 | | | | | 15 67 (78) | 65 30 |
| 22 | 1.12 | 3 | 0.03 20 (53) | 42 | | | | | | | 70 20 | | | |
| 22 | 2.24 | 3 | 0.03 40 (34) | 60 | | | | | | | | | | |
| 22 | 0.28 | 3 | 0.14 5 (71) | 17 | | | | | 100 98 100 (0) | | 45 78 (43) | 25 20 | | |
| 22 | 0.28 | 3 | 0.14 10 (17) | 12 | | | | | 100 90 | | | | | |
| 22 | 0.56 | 3 | 0.14 15 (61) | 38 | | | | | 100 85 | | | | | |
| 22 | 1.12 | 3 | 0.14 | | | | | | 90 100 (10) | | | 35 95 (64) | | |
| 22 | 1.12 | 3 | 0.14 35 (65) | 98 | | | | | 100 100 (0) | | | | | |
| 22 | 1.12 | 3 | 0.14 35 (17) | 42 | | | | | 100 98 | | | | | |
| 22 | 2.24 | 3 | 0.14 58 (4) | 60 | | | | | 100 100 (0) | | 10 78 (88) | 25 20 | | |
| 22 | 0.28 | 3 | 0.56 15 (12) | 17 | | | | | 90 90 (0) | | 10 20 (50) | | | |
| 22 | 0.28 | 3 | 0.56 | | | | | | | | | | | |
| 22 | 0.56 | 3 | 0.56 5 (39) | 12 | | | | | 90 85 | | | 35 95 (64) | | |
| 22 | 1.12 | 3 | 0.56 | | | | | | | | | | | |

-continued

| Ex | Dose | | Dose (%) | | | | | | |
|----|------|---|----------|---|---|---|---|---|---|
| 22 | 1.12 | 3 | 0.56 10 (74) 38 | | | | 100 100 (0) | | |
| 22 | 1.12 | 3 | 0.56 85 (14) 98 | | | | 100 100 (0) | | |
| 22 | 1.12 | 3 | 0.56 5 (89) 42 | | | | 100 98 | | |
| 22 | 1.12 | 3 | 0.56 38 (37) 60 | | | | 100 100 (0) | | |
| 22 | 2.24 | 3 | 0.56 0 (100) 17 | | | | 90 90 (0) | | |
| 22 | 0.28 | 3 | 2.24 0 | | 10 (50) 20 | | | | |
| 22 | 0.28 | 3 | 2.24 0 (100) 12 | | | | 100 85 | | |
| 22 | 0.56 | 3 | 2.24 10 (74) 38 | | 75 (4) 78 | | 100 100 | | |
| 22 | 1.12 | 3 | 2.24 | | | 25 (29) 35 | | 95 | 15 (25) 20 |
| 22 | 1.12 | 3 | 2.24 40 (60) 98 | | | 25 (74) 95 | 100 100 (0) | 100 | |
| 22 | 1.12 | 3 | 0.56 10 (60) 25 | | | | | 95 65 | |
| 23 | 0.03 | 3 | 0.56 | | | | 60 | 100 90 | 80 95 (16) |
| 23 | 0.03 | 3 | 0.56 | | | | 70 (0) | | |
| 23 | 0.14 | 3 | 0.56 58 (42) 99 | | | 0 20 (66) 58 | 60 55 | 0 15 50 | 15 45 (67) 97 |
| 23 | 0.14 | 3 | 0.56 70 (13) 80 | | | | 70 (0) | 35 75 (54) | 85 (13) |
| 23 | 0.14 | 3 | 0.56 90 (10) 100 | | | 10 35 (72) | | 80 65 | |
| 23 | 0.56 | 3 | 1.12 5 | | | | | | 5 25 (80) |
| 23 | 0.03 | 3 | 1.12 | | | | | | |
| 23 | 0.03 | 3 | 1.12 | | | | | | |
| 23 | 0.14 | 3 | 1.12 5 (93) 68 | | | | | | 50 50 (0) |
| 23 | 0.03 | 3 | 2.24 | | | | 35 55 (37) | | 35 25 83 (52) |
| 23 | 0.03 | 3 | 2.24 5 (80) 25 | | | | | | 40 |
| 23 | 0.14 | 3 | 2.24 70 (13) 80 | | | 90 95 (6) | | 100 90 | 0 45 (100) |
| 23 | 0.14 | 3 | 2.24 23 (77) 99 | | | | 70 (0) | | 100 97 |
| 23 | 0.14 | 3 | 2.24 | | | 5 | | 50 15 | 5 25 (80) |
| 23 | 0.56 | 3 | 2.24 85 (15) 100 | | | | | 60 | 30 50 (40) |
| 23 | 0.03 | 3 | 4.48 0 | | | 0 58 | | 40 50 | 0 25 (100) |
| 23 | 0.03 | 3 | 4.48 | | | | | | 85 83 |
| 23 | 0.14 | 3 | 4.48 | | | | | | |

-continued

| | | | | | | | | | | |
|---|---|---|---|---|---|---|---|---|---|---|
| 23 | 0.14 | 3 | 4.48 | 0 (100) | 68 | | (100) | | | |
| 23 | 0.03 | 3 | 8.96 | 15 (40) | 25 | | | | | |
| 23 | 0.03 | 3 | 8.96 | | | | | (20) 15 (80) | 75 | |
| 23 | 0.14 | 3 | 8.96 | | | | 15 35 (58) 55 (43) 95 | | 80 100 | 65 90 |
| 23 | 0.14 | 3 | 8.96 | 55 (32) | 80 | | | | | 80 63 95 |
| 23 | 0.14 | 3 | 8.96 | 12 (88) | 99 | | | | | 60 (5) 95 63 |
| 23 | 0.56 | 3 | 8.96 | 95 | 100 | | | | | 80 (0) 95 63 |
| 24 | 0.28 | 3 | 0.14 | 15 (5) | 15 | | | | | 40 95 (0) 38 |
| 24 | 1.12 | 3 | 0.14 | 70 (24) | 92 | | | 50 55 (10) 70 (0) | | |
| 24 | 0.28 | 3 | 0.56 | 15 (0) | 15 | | | | | |
| 24 | 1.12 | 3 | 0.56 | 95 (0) | 92 | | | | | |
| 24 | 0.28 | 3 | 2.24 | 10 (34) | 15 | | | | | 65 92 (30) |
| 24 | 1.12 | 3 | 2.24 | 95 (0) | 92 | | | | | |
| 25 | 0.14 | 3 | 0.56 | | | 30 43 (31) | | 55 60 (9) 35 | 95 | |
| 25 | 0.14 | 3 | 0.56 | | | 95 95 (0) | | 75 98 | 95 77 | |
| 25 | 0.28 | 3 | 0.56 | 82 | 92 | | | 100 50 (17) 60 | | |
| 25 | 0.28 | 3 | 0.56 | 95 70 (24) | 92 | | | 75 80 | | |
| 25 | 0.56 | 3 | 0.56 | | | | | 90 (7) 85 100 | 95 | |
| 25 | 0.56 | 3 | 0.56 | 95 (0) | 100 | 70 23 | | 100 (0) 100 | | 90 52 |
| 25 | 1.12 | 3 | 0.56 | 100 (0) | 100 | 100 95 | | 80 70 | | 95 (0) 95 |
| 25 | 1.12 | 3 | 1.12 | | | 0 (100) 43 | | 20 48 (59) | | 25 92 (73) |
| 25 | 0.56 | 3 | 1.12 | | | | | (16) 95 | | |
| 25 | 0.14 | 3 | 2.24 | | | | | 10 35 (72) | | |
| 25 | 0.14 | 3 | 2.24 | 90 (4) | 82 | | | 100 60 | 40 38 | |
| 25 | 0.28 | 3 | 2.24 | | | | | 95 98 | | |
| 25 | 0.28 | 3 | 2.24 | 90 (3) | 92 | | | 85 60 | 85 77 | |
| 25 | 0.56 | 3 | 2.24 | | | | | 80 (6) 85 | | |

-continued

| | | | | | | | | | | | |
|---|---|---|---|---|---|---|---|---|---|---|---|
| 25 | 0.56 | 3 | | | | | | | 95 | 95 | 95 (0) |
| 25 | 1.12 | 3 | 2.24 | | 90 | 80 | | | | | |
| 25 | 1.12 | 3 | 2.24 | 100 (0) | 95 | 100 (5) | | | | | |
| 25 | | 3 | 2.24 | 100 (0) | 80 | 70 | | | | | |
| 25 | 0.14 | 3 | 4.48 | | 75 | 48 | 80 | 23 | | | |
| 25 | 0.56 | 3 | 4.48 | | 85 | 95 | 95 | 95 (0) | | | |
| 25 | 0.14 | 3 | 8.96 | | 75 | 35 | 30 | 43 (31) | 30 | 38 (22) | 95 95 (0) |
| 25 | 0.14 | 3 | 8.96 | | | | | | | | 95 95 50 (0) 92 (46) |
| 25 | 0.14 | 3 | 8.96 | | 90 | 60 | | | | | |
| 25 | 0.28 | 3 | 8.96 | 92 | 85 | 60 | 85 | 95 (11) | | | |
| 25 | 0.28 | 3 | 8.96 | 82 | 95 | 98 | | | 80 | 77 | 95 95 (0) |
| 25 | 0.56 | 3 | 8.96 | | 90 | 80 | | | | | |
| 25 | 0.56 | 3 | 8.96 | 100 (0) | 90 | 85 | | | | | |
| 25 | 1.12 | 3 | 8.96 | 100 (0) | 100 | 100 (4) | | | | | |
| 25 | 1.12 | 3 | 8.96 | | 80 | 70 | | | | | |
| 32 | 2.24 | 3 | 0.56 | 20 (0) | 15 | 55 (73) | 15 | 95 (85) | | | |
| 32 | 4.48 | 3 | 0.56 | 15 (63) | 60 | 55 | | | | | |
| 32 | 2.24 | 3 | 2.24 | 40 | 75 | 55 | 95 | 95 (0) | | | 15 |
| 32 | 4.48 | 3 | 2.24 | 10 (75) | 70 | 55 | | | | | |
| 32 | 2.24 | 3 | 8.96 | 20 (63) | 80 | 55 | | | | | 90 95 70 83 (6) (16) 75 60 95 95 95 (0) 40 68 (42) |
| 32 | 4.48 | 3 | 8.96 | 15 | 80 | 55 | 20 | 95 (79) | | | 95 98 95 97 (4) (3) 75 55 95 95 (0) |
| 26 | 0.03 | 3 | 1.12 | | | | | | | | 95 95 0 83 (0) (100) 80 60 95 95 (0) 10 |
| 26 | 0.07 | 3 | 1.12 | | | | | | | | 95 98 100 55 (4) |
| 26 | 0.07 | 3 | 1.12 | 10 (90) | | | | | | | |
| 26 | 0.14 | 3 | 1.12 | 95 | | | | | | | |
| 26 | 0.28 | 3 | 1.12 | | | | | | | | |
| 26 | 0.28 | 3 | 1.12 | 95 (5) | | | | | | | |
| 26 | 0.03 | 3 | 4.48 | 100 | | | | | | | |
| 26 | 0.07 | 3 | 4.48 | | | | | | | | |
| 26 | 0.07 | 3 | 4.48 | 5 (95) | | | | | | | |
| 26 | 0.14 | 3 | 4.48 | 95 | | | | | | | |
| 26 | 0.28 | 3 | 4.48 | 90 | 100 | | | | | | |

-continued

| | | | | | | | | |
|---|---|---|---|---|---|---|---|---|
| 26 | 0.28 | 3 | 4.48 | (10) | 90 95 (6) 90 98 (9) | 100 97 | | 5 68 (93) 90 98 (9) |
| 27 | 0.14 | 3 | 0.56 | | | | | |
| 27 | 0.14 | 3 | 0.56 | 0 8 (100) | 95 100 (5) | 75 70 | | 95 100 (5) |
| 27 | 0.56 | 3 | 0.56 | | | | | |
| 27 | 0.56 | 3 | 0.56 | 53 97 (46) | | 70 80 (13) 85 80 | 85 85 (0) | |
| 27 | 0.56 | 3 | 0.56 | 60 90 (34) | | 80 70 | 70 70 (0) | |
| 27 | 1.12 | 3 | 0.56 | 85 97 (13) | | 70 73 (5) 75 40 | 80 85 (6) | |
| 27 | 1.12 | 3 | 0.56 | | | 60 65 (8) | | |
| 27 | 2.24 | 3 | 0.56 | | | 95 95 (0) | | |
| 27 | 0.14 | 3 | 1.12 | 0 12 (100) | 95 98 (4) | 100 100 (0) | 70 70 (0) | 95 98 (4) |
| 27 | 0.56 | 3 | 1.12 | 10 53 (82) | | 90 80 | 80 85 (6) | |
| 27 | 0.14 | 3 | 2.24 | 0 8 (100) | 100 100 (0) | 70 80 (13) 90 70 | | 0 7 (100) 20 30 (34) |
| 27 | 0.14 | 3 | 2.24 | | | | | |
| 27 | 0.56 | 3 | 2.24 | 15 97 (85) | | 65 73 (11) 60 40 | 75 70 | |
| 27 | 0.56 | 3 | 2.24 | 65 90 (28) | | 75 65 | 85 85 (0) | |
| 27 | 1.12 | 3 | 2.24 | 75 97 (23) | | 100 95 | | |
| 27 | 1.12 | 3 | 2.24 | | | | | |
| 27 | 2.24 | 3 | 2.24 | | | | | |
| 27 | 0.14 | 3 | 4.48 | 0 12 (100) | 100 98 | 100 100 (0) | 75 70 | 95 98 (4) |
| 27 | 0.56 | 3 | 4.48 | 20 53 (63) | | 70 80 (13) 95 80 | 85 85 (0) | |
| 27 | 0.14 | 3 | 8.96 | 0 8 (100) | 100 100 (0) | | | 90 98 (9) |
| 27 | 0.56 | 3 | 8.96 | 28 97 (72) | | | | |
| 27 | 0.56 | 3 | 8.96 | | | | | 5 7 (29) 20 30 (34) |
| 27 | 0.56 | 3 | 8.96 30 90 (67) | | | | | 100 100 (0) |
| 27 | 1.12 | 3 | 8.96 90 97 | | | | | |

-continued

| Ex. | | | | | | | | |
|---|---|---|---|---|---|---|---|---|
| 27 | 1.12 | 3 | 8.96 | (8) | | | | |
| 27 | 2.24 | 3 | 8.96 | | 40 43 (7) | 75 70 (11) 65 73 | | |
| 28 | 0.004 | 3 | 1.12 | 0 (100) | | 70 70 (0) 60 75 | | |
| 28 | 0.01 | 3 | 1.12 | | 65 95 (32) | 85 75 | | |
| 28 | 0.01 | 3 | 1.12 | 5 48 (90) | | 85 88 (4) | | |
| 28 | 0.07 | 3 | 1.12 | | 10 43 (77) | 95 98 | 0 27 (100) 75 90 | 20 7 30 (34) |
| 28 | 0.28 | 3 | 1.12 | | 85 95 (11) | 100 100 (0) | 70 55 | |
| 28 | 1.12 | 3 | 4.48 | | | 85 70 | | 10 18 (45) |
| 28 | 0.004 | 3 | 4.48 | 0 10 (100) | | 90 75 | | 25 75 (67) |
| 28 | 0.01 | 3 | 4.48 | 0 48 (100) | | 70 75 (7) | | |
| 28 | 0.07 | 3 | 4.48 | | | 90 88 | | |
| 28 | 0.28 | 3 | 4.48 | | | 95 98 (4) | 100 100 (0) 100 98 | 5 5 (0) 5 60 (92) |
| 28 | 1.12 | 3 | 1.12 | | | 95 100 (5) | 80 90 (12) 70 80 | |
| 29 | 0.01 | 3 | 1.12 | | 70 95 (27) 80 95 (16) | | 27 70 (100) 55 | 5 5 (0) 60 |
| 29 | 0.07 0.28 | 3 3 | 1.12 1.12 | 0 63 (100) | | | | |
| 29 | 0.56 | 3 | 1.12 | | | | 100 100 (0) 100 98 | 75 95 100 |
| 29 | 1.12 | 3 | 1.12 | 30 93 (68) | | | 80 90 | 73 95 (0) |
| 29 | 1.12 | 3 | 1.12 | 5 63 (93) | 80 95 (16) 85 95 (11) | | 27 70 (100) 55 | 75 73 95 |
| 29 | 0.01 0.07 | 3 3 | 4.48 4.48 | | | | | |
| 29 | 0.28 | 3 | 4.48 | | | | 100 100 (0) 100 98 | | 0 10 (100) 0 12 (100) |
| 29 | 0.56 | 3 | 4.48 | | | | 80 90 | |
| 29 | 1.12 | 3 | 4.48 | | | | | 20 7 (0) 0 12 (100) |
| 29 | 1.12 | 3 | 4.48 | 15 93 (84) | | | 0 40 (100) 50 50 (0) | 0 10 (100) 0 12 (100) |
| 30 | 0.01 | 3 | 0.14 | | | | | |
| 30 | 0.03 | 3 | 0.14 | | | | | |

-continued

| | | | | | 35 50 (30) | 60 40 20 7 12 | |
|---|---|---|---|---|---|---|---|
| 30 | 0.01 | 3 | 0.56 | | | | |
| 30 | 0.03 | 3 | 0.56 | | | 100 100 (0) | |
| 30 | 1.12 | 3 | 1.12 | | | 100 100 (0) | |
| 30 | 1.12 | 3 | 1.12 | 30 93 (68) | | 100 100 (0) | |
| 30 | 4.48 | 3 | 1.12 | | | 100 100 (0) | |
| 30 | 4.48 | 3 | 1.12 | 50 97 (49) | | 100 100 (0) | 5 40 (88) |
| 30 | 0.01 | 3 | 2.24 | | | | 55 50 |
| 30 | 0.03 | 3 | 2.24 | | | | |
| 30 | 1.12 | 3 | 4.48 | 5 93 (95) | | | |
| 30 | 1.12 | 3 | 4.48 | | 70 88 (21) | 100 100 (0) | 0 40 (100) 0 7 (100) 70 50 25 12 |
| 30 | 4.48 | 3 | 4.48 | 45 97 (54) | | 100 100 (0) | |
| 30 | 4.48 | 3 | 4.48 | | 95 93 | 100 100 (0) | |
| 31 | 0.14 | 3 | 0.56 | | | 60 60 (0) | |
| 31 | 0.14 | 3 | 0.56 | 0 | | 90 85 (17) | |
| 31 | 0.14 | 3 | 0.56 | 15 75 | | 75 35 | 75 50 |
| 31 | 0.56 | 3 | 0.56 | 10 (87) | | 70 80 | 10 32 (69) |
| 31 | 0.56 | 3 | 0.56 | | | 90 90 (13) | 45 28 |
| 31 | 0.56 | 3 | 2.24 | | | 95 90 (0) | 80 50 |
| 31 | 0.14 | 3 | 2.24 | | | 95 85 (0) | 5 28 (83) |
| 31 | 0.14 | 3 | 2.24 | 0 | | 60 60 (17) | 95 95 (0) 32 |
| 31 | 0.56 | 3 | 2.24 | 15 75 (80) | | 65 35 | 40 32 |
| 31 | 0.56 | 3 | 2.24 | | | 80 60 | 30 50 (40) |
| 31 | 0.14 | 3 | 8.96 | | | 90 90 (0) | 80 28 |
| 31 | 0.14 | 3 | 8.96 | 0 | | 75 90 (17) | 100 100 (0) |
| 31 | 0.14 | 3 | 8.96 | 25 75 (67) | | 50 60 | 90 50 |
| 31 | 0.56 | 3 | 8.96 | | | 90 85 (19) | 30 50 95 95 (0) |
| 31 | 0.56 | 3 | 8.96 | | | 65 35 65 80 | 0 (100) 100 100 (0) 10 8 85 (15) |
| 33 | 0.56 | 3 | 0.56 | 0 17 (100) | | 95 90 90 (0) | 90 95 (6) 30 7 100 100 (0) 13 25 (48) |

-continued

| | | | | | | | | | | | | |
|---|---|---|---|---|---|---|---|---|---|---|---|---|
| 33 | 1.12 | 3 | 0.56 | 10 | (89) | 85 | | | 0 | 45 (23) | 58 | 50 | 95 (5) | 100 | 40 | 17 | 30 (15) | 35 | 58 (26) | 78 |
| 33 | 2.24 | 3 | 0.56 | 60 (32) | 87 | | | 65 | | | 100 | 100 (0) | 95 | 13 | 50 | 32 | 100 (0) | 100 |
| 33 | 0.56 | 3 | 2.24 | 10 | 17 | | | 40 | 0 | | | 95 (0) | 40 | (57) 7 | 0 (100) | 8 | (60) 25 |
| 33 | 1.12 | 3 | 2.24 | 45 (42) | 85 | | | 35 (30) | 10 (83) | 58 | 50 | 100 (0) | 40 | 17 | 55 | 35 | 58 (26) | 78 |
| 33 | 2.24 | 3 | 2.24 | 63 (48) | 87 | | | 25 (48) | 10 (57) | 23 | 48 | 100 (38) | 73 | 93 | 35 | 32 | 100 (0) | 100 |
| 33 | 0.56 | 3 | 8.96 | 13 (28) | 17 | | | 90 (6) | 95 | 95 | 95 | 95 (0) | 10 | 7 | 13 | (22) | (0) |
| 33 | 1.12 | 3 | 8.96 | 10 (89) | 85 | | | 50 | 20 (14) | 23 | 48 | 100 (0) | 0 | 17 | 40 | 8 | 40 | 25 |
| 33 | 2.24 | 3 | 8.96 | 25 (72) | 87 | | | 75 (22) | 95 (0) | 95 | 95 | 100 (0) | 40 (57) | 93 | 10 (69) | 35 92 | 58 (26) | 78 |
| 23 | 0.03 | 13 | 1.12 | | | | | 65 | | | 40 | | | | 40 | | | |
| 23 | 0.14 | 13 | 1.12 | | | | | 80 | | | 65 | | | | 90 | | 32 73 | 100 (27) |
| 23 | 0.03 | 13 | 4.48 | | | | | 70 | | | 40 | | | | 25 | | 25 | |
| 23 | 0.14 | 13 | 4.48 | | | | | 75 | | | 65 | | | | 80 (0) | | 83 | |
| 25 | 0.14 | 13 | 1.12 | | | | | 90 | 0 (100) | 30 | 90 | | | 75 88 (15) | 35 (4) | 52 | |
| 25 | 0.56 | 13 | 1.12 | | | | | 70 (18) | | | 85 | | | | 35 (33) | 95 (0) | 95 | |
| 25 | 0.14 | 13 | 4.48 | | | | | 90 | 85 | 70 | 90 | | | 95 (0) | 90 | 52 | |
| 25 | 0.56 | 13 | 4.48 | | | | | 95 (0) | | | 95 | | | | 95 (0) | | 95 | |
| 27 | 0.14 | 13 | 1.12 | 0 (100) | 12 | | | 85 (6) | | | 90 | | | | 95 (0) | | 95 | |
| 27 | 0.56 | 13 | 1.12 | 25 (53) | 53 | | | 95 (0) | | | 95 | | | | | | | |
| 27 | 0.14 | 13 | 4.48 | 0 (100) | 12 | | | 85 (6) | | | 90 | | | | | | | |
| 27 | 0.56 | 13 | 4.48 | 5 (91) | 53 | | | 85 | | | 85 | | | | | | | |
| 19 | 0.009 | 27 | 1.12 | 0 (100) | 90 | | | | | | | | | | | | | |
| 19 | 0.01 | 27 | 1.12 | 5 (95) | 97 | | | | | | | | | | | | | |
| 19 | 0.03 | 27 | 1.12 | | | | | | | | | | | | | | | |
| 19 | 0.03 | 27 | 1.12 | | | | | | | | | | | | | | | |
| 19 | 0.07 | 27 | 1.12 | | | | | | | | | | | | | | | |
| 19 | 0.14 | 27 | 1.12 | | | | | | | | | | | | | | | |
| 19 | 0.009 | 27 | 4.48 | 10 | 90 | | | | | | | | | | | | | |
| 19 | 0.01 | 27 | 4.48 | | | | | | | | | | | | | | | |

-continued

| | | | | | | | | | | |
|---|---|---|---|---|---|---|---|---|---|---|
| 19 | 0.03 | 27 | 4.48 | (89) | | 95 (0) | 90 | | | |
| 19 | .03 | 27 | 4.48 | | | 95 (0) | 95 | | | |
| 19 | 0.07 | 27 | 4.48 25 | 97 (75) | | 85 (6) | 90 | | | |
| 19 | 0.14 | 27 | 4.48 | | | 90 (6) | 95 | | | |
| 20 | 0.004 | 27 | 1.12 | | | 15 (40) | 25 | | | |
| 20 | 0.004 | 27 | 1.12 0 | 12 (100) | | 40 | 10 | | | |
| 20 | 0.004 | 27 | 1.12 | | | 65 | 30 | | | |
| 20 | 0.009 | 27 | 1.12 | | | 60 | 35 | | | |
| 20 | 0.009 | 27 | 1.12 0 | 38 (100) | | 25 (59) 55 | 60 | 35 | 0 (100) | |
| 20 | 0.004 | 27 | 4.48 | | | 40 | 30 | 50 | | |
| 20 | 0.004 | 27 | 4.48 0 | 12 (100) | | 25 | 10 | | | |
| 20 | 0.004 | 27 | 4.48 | | | 0 (100) | 25 | 45 | | |
| 20 | 0.009 | 27 | 4.48 0 | 38 (100) | | 50 | 40 | | | |
| 20 | 0.009 | 27 | 4.48 | | 0 (100) | 55 | 35 | | | 0 (100) | 10 |
| 20 | 0.009 | 27 | 4.48 | | | 55 (9) | 60 | 35 42 | 30 (56) | 68 |
| 20 | 0.03 | 27 | 1.12 | | 95 73 | | 80 (16) 100 | (17) 95 95 (0) | | |
| 26 | 0.07 | 27 | 1.12 15 | 95 (85) | 90 95 (6) | | 95 | 60 | 15 (78) | |
| 26 | 0.07 | 27 | 1.12 | | | | 95 (4) 100 | 83 | | |
| 26 | 0.14 | 27 | 1.12 | | 95 95 (0) | | 95 | 98 95 (0) | 15 | |
| 26 | 0.28 | 27 | 1.12 85 | 100 (15) | | | 95 | 97 | | |
| 26 | 0.28 | 27 | 4.48 | | 50 95 (48) | | 95 (0) 100 | 55 | 0 (100) | |
| 26 | 0.03 | 27 | 4.48 | | | | 95 | 95 95 (0) | 15 | |
| 26 | 0.07 | 27 | 4.48 15 | 95 (85) | | | 100 | 83 | | |
| 26 | 0.07 | 27 | 4.48 | | 95 95 (0) | | 95 (4) | 98 95 (0) | 15 (78) | 68 |
| 26 | 0.14 | 27 | 4.48 | | | | 90 (8) | 97 | | |
| 26 | 0.28 | 27 | 4.48 | | | | 65 | 55 | | |
| 26 | 0.28 | 27 | 4.48 65 | 100 | | | | | | |

-continued

| Ex | | | | | | | | |
|---|---|---|---|---|---|---|---|---|
| 28 | 0.004 | 27 | 1.12 | (35) | | 75 | | |
| 28 | 0.01 | 27 | 1.12 | | 40 43 (7) 80 95 (16) | 75 (0) | 70 | 10 18 (45) 0 (100) 75 |
| 28 | 0.01 | 27 | 1.12 0 (100) | | 50 (34) | 75 | | |
| 28 | 0.07 | 27 | 1.12 45 (7) | | 95 | 88 | | |
| 28 | 0.28 | 27 | 1.12 | | 95 (4) | 98 | | |
| 28 | 1.12 | 27 | 1.12 | | 100 (0) | 100 | 0 5 (100) 35 60 (42) | |
| 28 | 0.004 | 27 | 4.48 | | 80 | 70 | | 10 18 (100) 0 (100) 75 |
| 28 | 0.01 | 27 | 4.48 | | 85 | 75 | | |
| 28 | 0.01 | 27 | 4.48 10 (0) | | 65 (14) | 75 | | |
| 28 | 0.07 | 27 | 4.48 10 48 (80) | | 90 | 88 | | |
| 28 | 0.28 | 27 | 4.48 | | 95 (4) | 98 | | |
| 28 | 1.12 | 27 | 4.48 | 15 43 (66) 60 95 (37) | 95 (5) | 100 | | |
| 29 | 0.01 | 27 | 1.12 | | | 70 0 (100) 85 | 27 80 5 (0) (6) 60 90 55 | |
| 29 | 0.07 | 27 | 1.12 | | | | 70 55 | |
| 29 | 0.28 | 27 | 1.12 5 (93) | | 95 (5) | 100 | 100 | 10 (100) 10 (17) 12 |
| 29 | 0.56 | 27 | 1.12 | 90 95 (6) 95 (0) | 100 | 100 | 98 | |
| 29 | 1.12 | 27 | 1.12 | | 100 | 100 | 90 | |
| 29 | 1.12 | 27 | 1.12 20 93 (79) | | 20 (26) 65 (8) 50 (10) 100 (0) | 100 | 27 95 73 70 95 95 (0) | 10 (0) 12 |
| 29 | 0.01 | 27 | 4.48 | 85 95 (11) | | 100 | 55 | |
| 29 | 0.07 | 27 | 4.48 | | | 100 | 100 | |
| 29 | 0.28 | 27 | 4.48 5 63 (93) | | | 100 | 90 | |
| 29 | 0.56 | 27 | 4.48 | 90 95 (6) | 95 (4) | 100 | 98 | |
| 29 | 1.12 | 27 | 4.48 10 93 (90) | | | | | 10 (75) 40 |
| 30 | 1.12 | 27 | 4.48 | | 95 (5) | 100 | | |
| 30 | 1.12 | 27 | 1.12 15 93 (84) | 75 88 (15) | 95 (5) | 100 | | |
| 30 | 4.48 | 27 | 1.12 75 97 (23) | | 100 (0) | 100 | | |

-continued

| | | | | | | | | | | |
|---|---|---|---|---|---|---|---|---|---|---|
| 30 | 4.48 | 27 | | | 95 | 93 | 100 (0) | 100 | | | |
| 30 | 1.12 | 27 | | | | | 95 (5) | 100 | | | |
| 30 | 1.12 | 27 | | | 60 (32) | 88 | 100 (0) | 100 | | | |
| 30 | 4.48 | 27 | | | 95 | 93 | 100 (0) | 100 | | | |
| 30 | 4.48 | 27 | 1.12 | | | | 100 (0) | 100 | | | |
| 19 | 0.009 | 7 | 4.48 | 0 (100) | 93 | | 85 (6) | 90 | 85 (4) | 88 | 70 50 |
| 19 | 0.01 | 7 | 4.48 | | | | 85 (0) | 85 | | | |
| 19 | 0.03 | 7 | 4.48 | 70 (28) | 97 | | 95 (0) | 95 | 95 (0) | 95 | 0 (100) 40 55 50 |
| 19 | 0.03 | 7 | 1.12 | | | 25 30 (17) | 95 (0) | 90 | | | |
| 19 | 0.03 | 7 | 1.12 | 10 (89) | 90 | | 90 (0) | 90 | 95 (0) | 88 | |
| 19 | 0.07 | 7 | 1.12 | | | 65 70 (8) | 90 (0) | 95 | | | |
| 19 | 0.07 | 7 | 1.12 | 55 (44) | 97 | | 90 (0) | 90 | 95 (0) | 95 | |
| 19 | 0.14 | 7 | 1.12 | | | | 100 | 95 | | | |
| 19 | 0.009 | 7 | 4.48 | | | 0 (100) | 95 | 90 | | | |
| 19 | 0.01 | 7 | 4.48 | 10 (89) | 90 | | 90 (6) | 95 | | | |
| 19 | 0.03 | 7 | 4.48 | | | 0 70 (100) | 20 (20) | 25 | | | |
| 19 | 0.03 | 7 | 4.48 | | | 0 22 (100) | 60 | 30 | | | |
| 19 | 0.07 | 7 | 4.48 | 40 (59) | 97 | | 10 (0) | 10 | | | |
| 19 | 0.14 | 7 | 4.48 | | | | 10 (75) | 40 | 20 27 (26) | | 0 (100) 10 |
| 20 | 0.004 | 7 | 1.12 | | | | 0 (100) | 60 | | | |
| 20 | 0.004 | 7 | 1.12 | | | | 75 (40) | 35 | 70 | 42 | |
| 20 | 0.004 | 7 | 1.12 | 0 (100) | 12 | | 15 (100) | 25 | | | |
| 20 | 0.009 | 7 | 1.12 | 0 (100) | 38 | 85 73 | 10 (40) | 10 | | | |
| 20 | 0.009 | 7 | 1.12 | | | 5 22 (78) | 0 (100) | 30 | 35 | 27 | 80 68 10 (0) 10 |
| 20 | 0.009 | 7 | 1.12 4.48 | | | | 60 (0) | 60 | 40 (5) | 42 | |
| 20 | 0.004 | 7 | 4.48 | 0 (100) | 12 | | 30 | 40 | | | |
| 20 | 0.004 | 7 | 4.48 | | | | | | | | |
| 20 | 0.009 | 7 | 4.48 | | | | | | | | |
| 20 | 0.009 | 7 | 4.48 | 0 | 38 | | | | | | |

-continued

| | | | | | | | | | | | | | | | |
|---|---|---|---|---|---|---|---|---|---|---|---|---|---|---|---|
| 20 | 0.009 | 7 | | | | | | | | | | 90 | 73 | | |
| 23 | 0.03 | 7 | 4.48 | | (100) | | | | | | | | | | |
| 23 | 0.14 | 7 | 1.12 | 5 | | | | | | (25) | | | | 85 | |
| 23 | 0.14 | 7 | 1.12 | 5 | (93) | | | | | 10 (72) | | | | | 68 |
| 23 | 0.03 | 7 | 4.48 | 0 | | | | | | 55 | | | | | |
| 23 | 0.14 | 7 | 4.48 | 70 | | | | | | 55 (27) | 35 | | | | 68 |
| 26 | 0.03 | 7 | 1.12 | | | | | | | 0 | 75 | | | | |
| 26 | 0.07 | 7 | 1.12 | | | | | | | 75 (0) | 75 | | | | |
| 26 | 0.07 | 7 | 1.12 | 60 | (37) | | | | | | 80 (16) 100 | 95 95 83 | 95 (0) | | |
| 26 | 0.14 | 7 | 1.12 | | | | | | | | | | | 35 | |
| 26 | 0.28 | 7 | 1.12 | | | | | 85 | 95 (11) | | 60 | 60 | | | |
| 26 | 0.28 | 7 | 1.12 | 95 | (5) | | | | | | 85 (14) 100 | 98 95 97 | 95 (0) | | |
| 26 | 0.03 | 7 | 4.48 | | | | | 95 | 95 (0) | | 70 | 55 | | 30 | 68 |
| 26 | 0.07 | 7 | 4.48 | 10 | (90) | | | | | | | | | (56) | |
| 26 | 0.07 | 7 | 4.48 | | | | | 10 | 95 (90) | | 85 (11) 100 | 95 95 60 | 95 (0) | | |
| 26 | 0.14 | 7 | 4.48 | | | | | | | | 85 | 83 | | 0 | |
| 26 | 0.28 | 7 | 4.48 | 75 | (25) | | | 85 | 95 (11) 20 43 (54) | | 95 (4) 100 | 98 100 55 | 95 | | |
| 26 | 0.28 | 7 | 4.48 | | | | | | | | 100 | 97 | | | |
| 28 | 0.004 | 7 | 1.12 | | | | | | | | 70 | | | 15 (78) | 68 |
| 28 | 0.01 | 7 | 1.12 | 0 | (100) | | | 70 | 95 (27) | | 70 (0) | | | 0 (100) | 18 |
| 28 | 0.01 | 7 | 1.12 | | | | | | | | 75 | | | | |
| 28 | 0.07 | 7 | 1.12 | 5 | (90) | | | | | | 88 | | | 40 (47) | 75 |
| 28 | 0.28 | 7 | 1.12 | | | | | 15 | 43 (66) | | 98 (5) 100 | 60 25 | 5 60 (59) | | |
| 28 | 1.12 | 7 | 1.12 | | | | | 40 | 95 (58) | | 95 | | | | |
| 28 | 0.004 | 7 | 4.48 | | | | | | | | 90 | | | 0 (100) | 18 |
| 28 | 0.01 | 7 | 4.48 | | | | | | | | 80 | | | 5 (94) | 75 |
| 28 | 0.01 | 7 | 4.48 | 5 | (50) | | | | | | 80 | | | | |
| 28 | 0.07 | 7 | 4.48 | 5 | (90) | | | | | | 88 | | | | |
| 28 | 0.28 | 7 | 4.48 | | | | | | | | 98 | | | 55 65 | |
| 28 | 1.12 | 7 | 4.48 | | | | | | | | 100 | | | 5 60 | |

| | | | | | | | |
|---|---|---|---|---|---|---|---|
| 29 | 0.01 | 7 | 1.12 | | | 0 (0) | |
| 29 | 0.07 | 7 | 1.12 | | | | |
| 29 | 0.28 | 7 | 1.12 | 0 (100) | 90 (6) 95 (0) | 0 27 100 73 95 (100) 95 (0) 90 55 | 0 (100) 0 (100) 10 12 |
| 29 | 0.56 | 7 | 1.12 | | | | |
| 29 | 1.12 | 7 | 1.12 | | | 100 100 98 90 | |
| 29 | 1.12 | 7 | 1.12 25 (74) 93 | 80 (16) 95 (16) | 80 (12) 100 0 (100) 27 90 73 95 (0) 25 (65) 55 | 10 (0) 15 0 (100) 10 12 |
| 29 | 0.01 | 7 | 4.48 | | | | |
| 29 | 0.07 | 7 | 4.48 | | 80 (16) 88 (10) | 95 (5) 100 98 | |
| 29 | 0.28 | 7 | 4.48 0 (100) 63 | | | 95 (4) 90 | |
| 29 | 0.56 | 7 | 4.48 | 95 93 | | 100 | |
| 29 | 1.12 | 7 | 4.48 5 (95) 93 | 85 88 (4) | 100 | 95 88 0 (100) 40 50 |
| 30 | 1.12 | 7 | 1.12 | | 95 | 100 | 95 |
| 30 | 1.12 | 7 | 1.12 60 (36) 93 | | | 100 | |
| 30 | 1.12 | 7 | 1.12 95 (3) 97 | | | 100 | 95 95 0 (100) 50 40 |
| 30 | 4.48 | 7 | 1.12 | | | 100 | |
| 30 | 4.48 | 7 | 4.48 | | | 100 | |
| 30 | 1.12 | 7 | 4.48 55 (41) | | | 100 | 90 88 |
| 30 | 4.48 | 7 | 4.48 | | | 90 (0) | |
| 30 | 4.48 | 7 | 4.48 90 (8) 97 | 10 30 (67) | | 85 (0) | |
| 19 | 0.009 | 28 | 1.12 | | | 95 (0) | |
| 19 | 0.01 | 28 | 1.12 10 (89) 90 | | | 90 (6) | |
| 19 | 0.03 | 28 | 1.12 | | | 90 (0) | |
| 19 | 0.03 | 28 | 1.12 | | | 85 (0) | |
| 19 | 0.07 | 28 | 1.12 | 50 70 (29) | | 90 (6) | |
| 19 | 0.14 | 28 | 1.12 60 (39) 97 | | | 95 (6) | |
| 19 | 0.009 | 28 | 4.48 | | | 90 | |

-continued

| | | | | | | | | | |
|---|---|---|---|---|---|---|---|---|---|
| 19 | 0.01 | 28 | 4.48 | | | 90 (0) | 85 | | |
| 19 | 0.03 | 28 | 4.48 | 10 (89) | | 95 (0) | 95 | | |
| 19 | 0.03 | 28 | 4.48 | | | 95 (0) | 90 | | |
| 19 | 0.07 | 28 | 4.48 | 15 (85) | 30 70 (58) | 90 (0) | 90 | | |
| 19 | 0.14 | 28 | 4.48 | | | 95 (0) | 95 | | |
| 20 | 0.004 | 28 | 1.12 | | | 60 | 30 | | |
| 20 | 0.004 | 28 | 1.12 | 0 (100) | 0 (100) | 0 (100) | 10 | | |
| 20 | 0.004 | 28 | 1.12 | | | 0 (100) | 25 | 95 95 (0) | |
| 20 | 0.009 | 28 | 1.12 | 30 (22) | | 20 (50) | 40 | | |
| 20 | 0.009 0.009 | 28 | 1.12 1.12 | | 80 73 | 90 25 (29) | 60 35 | 10 27 (63) | 25 |
| 20 | 0.004 | 28 | 4.48 | | | 0 (100) | 30 | | |
| 20 | 0.004 | 28 | 4.48 | | 55 22 | 0 (100) | 25 | 45 42 | 20 (71) |
| 20 | 0.004 | 28 | 4.48 | 12 | | 20 | 10 | 40 27 | 5 (50) |
| 20 | 0.009 | 28 | 4.48 | 0 (100) | | 45 | 40 | | |
| 20 | 0.009 0.009 | 28 | 4.48 4.48 | 15 (61) | 80 73 | 70 60 | 60 35 | 75 42 | 60 (12) |
| 23 | 0.03 0.14 | 28 | 1.12 1.12 | 0 10 (86) | | 0 (34) | 75 | | |
| 23 | 0.03 0.14 | 28 | 4.48 4.48 | 0 40 (42) | | 0 (14) 65 | 75 | | |
| 26 | 0.03 | 28 | 1.12 | | 85 95 (11) | 70 (27) 50 (17) | | 95 95 (0) | 35 |
| 26 | 0.07 | 28 | 1.12 | 10 68 (68) | | 95 | | 60 | |
| 26 | 0.07 | 28 | 1.12 | | 95 95 (0) | 100 | | 83 | 30 (56) |
| 26 | 0.14 | 28 | 1.12 | | | 100 | | 98 95 (0) | 68 |
| 26 | 0.28 | 28 | 1.12 | 95 | | 85 | | 97 | |
| 26 | 0.28 | 28 | 1.12 95 (5) | | | 95 (0) | | 55 | |
| 26 | 0.03 | 28 | 4.48 | | | 100 | | 95 95 (0) | 35 |
| 26 | 0.07 | 28 | 4.48 | | 55 95 | | | 83 | 10 |

| Ex | Dose1 | Dose2 | Dose3 | Data |
|---|---|---|---|---|
| 26 | 0.07 | 28 | 4.48 | 10 95 (90) |
| 26 | 0.14 | 28 | 4.48 | |
| 26 | 0.28 | 28 | 4.48 | |
| 26 | 0.28 | 28 | 4.48 | 85 100 28 (15) 0.004 28 |
| 28 | 0.01 | 28 | 1.12 | 5 10 (50) |
| 28 | 0.01 | 28 | 1.12 | 5 48 (90) |
| 28 | 0.07 | 28 | 1.12 | |
| 28 | 0.28 | 28 | 1.12 | |
| 28 | 1.12 | 28 | 1.12 | |
| 28 | 0.004 | 28 | 4.48 | |
| 28 | 0.01 | 28 | 4.48 | 5 10 (50) |
| 28 | 0.01 | 28 | 4.48 | 30 48 (38) |
| 28 | 0.07 | 28 | 4.48 | |
| 28 | 0.28 | 28 | 4.48 | |
| 28 | 1.12 | 28 | 4.48 | |
| 29 | 0.01 | 28 | 1.12 | |
| 29 | 0.07 | 28 | 1.12 | 5 63 (93) |
| 29 | 0.28 | 28 | 1.12 | |
| 29 | 0.56 | 28 | 1.12 | |
| 29 | 1.12 | 28 | 1.12 | 15 93 (84) |
| 29 | 1.12 | 28 | 4.48 | |
| 29 | 0.01 | 28 | 4.48 | |
| 29 | 0.07 | 28 | 4.48 | 0 63 (100) |
| 29 | 0.28 | 28 | 4.48 | |
| 29 | 0.56 | 28 | 4.48 | |
| 29 | 1.12 | 28 | 4.48 | 25 93 (74) |

-continued

| | | | | | | | | | |
|---|---|---|---|---|---|---|---|---|---|
| 29 | 1.12 | 28 | 4.48 | 95 | 90 (6) | 95 (4) | | | |
| 30 | 1.12 | 28 | 1.12 | 55 (41) | 93 | 100 (0) | 98 | | |
| 30 | 1.12 | 28 | 1.12 | 90 (8) | 97 | 100 (0) | 100 | | |
| 30 | 4.48 | 28 | 1.12 | | 88 | 100 (0) | 100 | | |
| 30 | 4.48 | 28 | 1.12 | 15 (84) | 93 | 100 (0) | 100 | 10 (17) | 12 |
| 30 | 1.12 | 28 | 4.48 | | 65 (27) | 100 (0) | 100 | 0 (100) | 40 |
| 30 | 1.12 | 28 | 4.48 | 60 (39) | 97 | 100 (0) | 100 | | 80 |
| 30 | 4.48 | 28 | 4.48 | | 95 | 100 (0) | 100 | | 50 |
| 30 | 4.48 | 28 | 1.12 | 10 (89) | 90 | 90 (0) | 90 | 0 (100) | 40 |
| 19 | 0.009 | 8 | 1.12 | | | 85 (0) | 85 | 65 | 50 |
| 19 | 0.01 | 8 | 1.12 | 45 (54) | 97 | 90 (0) | 90 | | |
| 19 | 0.03 | 8 | 1.12 | | | 100 (0) | 95 | 95 | 88 |
| 19 | 0.03 | 8 | 1.12 | 5 (95) | 90 | 90 (0) | 90 | 95 (0) | 95 |
| 19 | 0.07 | 8 | 4.48 | | 30 (0) | 90 (6) | 95 | | |
| 19 | 0.14 | 8 | 4.48 | | 30 (58) | 85 (0) | 85 | | |
| 19 | 0.009 | 8 | 4.48 | 5 (95) | | 90 (0) | 90 | 95 | 88 |
| 19 | 0.01 | 8 | 4.48 | | | 85 (0) | 85 | 95 (0) | 95 |
| 19 | 0.03 | 8 | 1.12 | 30 (0) | | 95 (0) | 95 | | |
| 19 | 0.03 | 8 | 1.12 | 5 (95) | 97 | 90 (0) | 90 | | |
| 19 | 0.07 | 8 | 4.48 | | 30 | 90 (0) | 90 | | |
| 19 | 0.14 | 8 | 4.48 | 0 (100) | 70 | 90 (6) | 90 | | |
| 20 | 0.004 | 8 | 1.12 | 0 (100) | 20 (72) | 15 | 10 | | |
| 20 | 0.004 | 8 | 1.12 | | | 95 (0) | 95 | 70 | 27 |
| 20 | 0.004 | 8 | 1.12 | | 0 (100) | 0 (100) | 30 | | 0 (100) |
| 20 | 0.009 | 8 | 1.12 | 0 (100) | 70 (73) | 0 (100) | 25 | 60 | 90 |
| 20 | 0.009 | 8 | 1.12 | | | 40 | 35 | | 68 |
| 20 | 0.009 | 8 | 1.12 | 0 (5) | | 0 (100) | 60 | | 42 |
| 20 | 0.009 | 8 | 1.12 | 40 | 22 | 50 | 40 | | 0 |
| 20 | 0.004 | 8 | 4.48 | 38 | 0 | 0 | 25 | | 10 |

| Cmpd | Dose A | Dose B | Dose C | Col 5 | Col 6 | Col 7 |
|---|---|---|---|---|---|---|
| 20 | 0.004 | 8 | 4.48 | | | (100) |
| 20 | 0.004 | 8 | 4.48 | | 50 | 27 |
| 20 | 0.009 | 8 | 4.48 | | (100) 65 50 | 30 10 |
| 20 | 0.009 | 8 | 4.48 10 (17) | | 60 | 40 |
| 20 | 0.009 | 8 | 4.48 20 38 (48) | | 80 | 42 |
| 20 | 0.03 | 8 | 4.48 | 45 73 (39) | 20 60 | 55 68 (20) 20 25 |
| 23 | 0.03 | 8 | 1.12 | 0 | 15 35 (58) 70 15 | |
| 23 | 0.14 | 8 | 1.12 | 35 58 (40) | 0 55 | 25 83 (70) |
| 23 | 0.14 | 8 | 4.48 5 | 10 | 30 75 | |
| 23 | 0.03 | 8 | 1.12 15 68 (78) | | 45 15 | 0 25 |
| 23 | 0.03 | 8 | 4.48 | | 0 75 | |
| 23 | 0.14 | 8 | 4.48 0 15 68 (78) | 20 58 (66) | 45 (40) 30 50 | 35 83 (58) 35 (33) |
| 23 | 0.14 | 8 | 4.48 | 35 23 | 0 48 | 95 95 |
| 25 | 0.56 | 8 | 1.12 | 90 95 | 0 (100) 90 95 | 80 |
| 25 | 0.14 | 8 | 1.12 | 35 23 | 0 48 | 95 95 (0) |
| 25 | 0.56 | 8 | 1.12 | 95 95 (0) | 0 (100) 85 95 (11) | 95 |
| 25 | 0.03 | 8 | 4.48 | 85 95 (11) | 80 (16) 100 | 95 95 (0) 83 60 15 |
| 26 | 0.07 | 8 | 1.12 | | 75 | 98 95 (0) 97 55 |
| 26 | 0.07 | 8 | 1.12 20 95 (79) | 90 95 (6) | 100 | 15 (73) 85 (11) 95 95 (0) 60 |
| 26 | 0.14 | 8 | 1.12 | | 100 | 40 68 (42) |
| 26 | 0.28 | 8 | 1.12 80 100 (20) | | 90 | 98 95 (0) 83 55 |
| 26 | 0.28 | 8 | 1.12 | | 95 (4) 100 | 20 |
| 26 | 0.03 | 8 | 4.48 | | | |
| 26 | 0.07 | 8 | 4.48 10 95 (90) | | | 95 |
| 26 | 0.07 | 8 | 4.48 | 30 95 (69) | | |
| 26 | 0.14 | 8 | 4.48 | | | |
| 26 | 0.28 | 8 | 4.48 25 100 (75) | | | 95 |

-continued

| Ex. | Dose | | Dose | | | | | | | |
|---|---|---|---|---|---|---|---|---|---|---|
| 26 | 0.28 | 8 | 4.48 | 85 95 (11) | | | | 100 | | 97 |
| 27 | 0.14 | 8 | 1.12 | 0 12 (100) | | | | | | |
| 27 | 0.56 | 8 | 1.12 | 5 53 (91) | 30 43 (31) | | | | | |
| 27 | 0.14 | 8 | 4.48 | 0 12 (100) | 55 95 (43) | | | | | |
| 27 | 0.56 | 8 | 4.48 | 30 53 (44) | | | | | | |
| 28 | 0.004 | 8 | 1.12 | | | 55 40 | | | | |
| 28 | 0.01 | 8 | 1.12 | | | 75 65 | | | | |
| 28 | 0.01 | 8 | 1.12 | 10 10 (0) | | 55 40 | | | | |
| 28 | 0.07 | 8 | 1.12 | 15 48 (69) | | 75 65 | | | | |
| 28 | 0.28 | 8 | 1.12 | | | 80 70 | | | | |
| 28 | 1.12 | 8 | 1.12 | | | 85 75 | | | | |
| 28 | 0.004 | 8 | 4.48 | | | 95 75 | | | | |
| 28 | 0.01 | 8 | 4.48 | 5 10 (50) | 15 43 (66) | 60 75 (20) | | | | |
| 28 | 0.01 | 8 | 4.48 | | | 50 75 (34) | | | | |
| 28 | 0.07 | 8 | 4.48 | 5 48 (90) | 55 95 (43) | 85 88 (4) | | | | |
| 28 | 0.28 | 8 | 4.48 | | | 100 98 | | | | |
| 28 | 1.12 | 8 | 4.48 | | | 100 100 (0) | | 5 | | |
| 29 | 0.01 | 8 | 1.12 | 0 63 (100) | 80 95 (16) | 85 70 | 0 (100) | 5 70 | | |
| 29 | 0.07 | 8 | 1.12 | 15 93 (84) | 90 95 (6) | 95 75 | | | | |
| 29 | 0.28 | 8 | 1.12 | | | 80 98 | 30 (46) | 27 90 55 | 0 (100) 55 (9) | 0 18 (100) |
| 29 | 0.56 | 8 | 1.12 | | | 90 85 | 100 | 70 95 100 | 0 (100) | 0 75 (100) |
| 29 | 1.12 | 8 | 1.12 | | | 80 | 100 | 55 | | |
| 29 | 0.01 / 0.07 | 8 | 4.48 / 4.48 | | | 95 85 | 95 | 90 | | |
| 29 | 0.28 | 8 | 4.48 | 85 95 | | 80 | 95 | 27 95 70 95 | 0 (100) (0) | 73 95 0 10 (100) |
| 29 | 0.56 | 8 | 4.48 | 60 95 (37) | | 95 (5) | | 55 | | 0 (100) |
| 29 | 1.12 | 8 | 4.48 | 10 63 (85) | | 100 | 98 | 100 | | 95 12 |

-continued

| | | | | | | | | |
|---|---|---|---|---|---|---|---|---|
| 29 | 1.12 | 8 | 4.48 | 10 (90) | 93 | | 95 (5) | 100 |
| 30 | 1.12 | 8 | 1.12 | 10 (90) | 93 | | 100 (0) | 100 |
| 30 | 1.12 | 8 | 1.12 | | | | 100 (0) | 100 |
| 30 | 4.48 | 8 | 1.12 | 80 (18) | 97 | | 100 (0) | 100 |
| 30 | 4.48 | 8 | 1.12 | 0 (100) | 93 | | 100 (0) | 100 |
| 30 | 1.12 | 8 | 4.48 | | | | 100 (0) | 100 | 10 (75) | 40 | 50 |
| 30 | 1.12 | 8 | 4.48 | 40 (59) | 97 | | 100 (0) | 100 | 90 | | |
| 30 | 4.48 | 8 | 4.48 | | | | 100 (0) | 100 | 10 (75) | 40 | 50 |
| 30 | 4.48 | 8 | 4.48 | | | | 35 | 15 | 70 | 50 | |
| 23 | 0.03 | 29 | 1.12 | 25 | 75 | | 25 | 75 | 10 (60) | 25 | |
| 23 | 0.03 | 29 | 1.12 | 75 (0) | | | 50 (0) | 50 | 60 (28) | 83 | |
| 23 | 0.14 | 29 | 1.12 | 50 (0) | 68 | | | | 0 | 0 | 25 |
| 23 | 0.14 | 29 | 4.48 | 40 (0) | | | 40 (0) | 15 | | | |
| 23 | 0.03 | 29 | 4.48 | 0 (100) | 58 | | 0 | 75 | 80 (4) | 83 | |
| 23 | 0.03 | 29 | 4.48 | 0 | | | 30 (60) | 50 | 30 (43) | 52 | |
| 23 | 0.14 | 29 | 4.48 | | | | 50 (0) | 48 | 95 (0) | 95 | |
| 25 | 0.14 | 29 | 1.12 | 10 (83) | 58 | | 55 | | 80 (0) | 52 | 95 |
| 25 | 0.14 | 29 | 1.12 | 10 (57) | 23 | | 95 (0) | 95 | 95 (0) | 95 | |
| 25 | 0.56 | 29 | 4.48 | 95 (0) | 95 | | 60 (0) | 48 | | | |
| 27 | 0.14 | 29 | 1.12 | 45 (0) | 23 | | 80 (16) | 95 | | | |
| 27 | 0.56 | 29 | 1.12 | 95 (0) | 95 | | 0 (100) | 40 | | | |
| 27 | 0.14 | 29 | 4.48 | | | | 70 | 65 | | | |
| 27 | 0.56 | 29 | 4.48 | | | | 50 | 40 | | | |
| 19 | 0.009 | 14 | 1.12 | 30 (100) | 12 | | 65 (0) | 65 | | 90 | |
| 19 | 0.01 | 14 | 1.12 | 0 (100) | 53 (44) | | 80 (12) | 90 | | | 88 |
| 19 | 0.03 | 14 | 1.12 | 10 (89) | 90 | | 80 (6) | 85 | | 95 (0) | 95 |
| | | | | | | | 95 | 90 | | | |

(11)    (100)    (100)

-continued

| Ex | Rate | Days | Rate2 | | | | | | | | | | | | |
|---|---|---|---|---|---|---|---|---|---|---|---|---|---|---|---|
| 19 | 0.03 | 14 | 1.12 | | | | | 100 | 95 | | | | | | |
| 19 | 0.07 | 14 | 1.12 | 10 | 97 (90) | | | 95 | 90 | | | | | | |
| 19 | 0.14 | 14 | 1.12 | | | | | 100 | 85 | | | | | | |
| 19 | 0.009 | 14 | 4.48 | | | | | 90 | 90 | | | | | | |
| 19 | 0.01 | 14 | 4.48 | 5 | 90 (95) | | | 80 (6) | 85 | | | | | | |
| 19 | 0.03 | 14 | 4.48 | | | | | 95 | 90 | | | | | | |
| 19 | 0.03 | 14 | 4.48 | | | 0 (100) | | 95 (0) | 95 | | 95 | | | | |
| 19 | 0.07 | 14 | 4.48 | 30 | 97 (70) | | | 95 (0) | 90 | | | | | | |
| 19 | 0.14 | 14 | 4.48 | | 85 | 70 | | 100 | 95 | | | 88 | | | |
| 20 | 0.004 | 14 | 1.12 | | | | | 0 (100) | 25 | | | | | | |
| 20 | 0.004 | 14 | 1.12 | | 15 | 70 (79) | 22 | 0 (100) | 30 | | 95 | | | | |
| 20 | 0.004 | 14 | 1.12 | | | | | 0 (100) | 10 | | 95 (0) | | | | |
| 20 | 0.004 | 14 | 1.12 | | | | | 0 (100) | 30 | | | | | | |
| 20 | 0.009 | 14 | 1.12 | 0 | 12 (100) | | | 35 (13) | 40 | | | | | | |
|  |  |  |  |  | 20 | 38 (48) |  |  |  |  |  |  |  |  |  |
| 20 | 0.009 | 14 | 4.48 | | 90 | 73 | | 60 | 35 | | | | | | |
| 20 | 0.009 | 14 | 4.48 | | | | | 70 | 60 | | 40 | | | | |
| 20 | 0.004 | 14 | 4.48 | | | | | 80 | 30 | | | | | | |
| 20 | 0.004 | 14 | 4.48 | | 0 | 22 | | 0 (100) | 25 | | | 27 | | | |
|  |  |  |  |  | (100) |  |  |  |  |  |  |  |  |  |  |
| 20 | 0.004 | 14 | 4.48 | | | | | 0 (100) | 10 | | | 42 | 45 (34) | 68 | |
| 20 | 0.009 | 14 | 4.48 | 0 | 12 (100) | | | 30 (25) | 40 | | | 27 | | | |
|  |  |  |  | 25 | 38 (35) |  |  |  |  |  |  |  |  |  |  |
| 20 | 0.009 | 14 | 4.48 | | | | | 60 | 60 | | | | | | |
| 20 | 0.009 | 14 | 4.48 | | 85 | 73 | | 20 (43) | 35 | 95 | 60 | | | 10 | |
|  |  |  |  |  |  |  |  |  |  | (0) |  |  |  | (100) |  |
| 26 | 0.03 | 14 | 1.12 | | | | | | | 95 95 | | | | | |
|  |  |  |  |  |  |  |  |  |  | (0) |  |  |  |  |  |
| 26 | 0.07 | 14 | 1.12 | 65 | 95 (32) | 85 | 95 (11) | 100 | | 0 (100) | 60 | 42 | | 0 | |
| 26 | 0.07 | 14 | 1.12 | | | | | 100 | | 100 | 83 | | 10 | 95 | |
|  |  |  |  |  |  |  |  |  |  |  |  |  | (86) |  |  |
| 26 | 0.14 | 14 | 1.12 | | | | | 80 | 55 | 98 | 97 | | | 95 (0) | |
| 26 | 0.28 | 14 | 1.12 | | | 85 | 95 (11) | | | | | | | 0 | |
| 26 | 0.28 | 14 | 1.12 | 95 | 100 (5) | 95 | 95 (0) | 80 | | | | | 15 | 95 | 68 (78) |
| 26 | 0.03 | 14 | 4.48 | | | | | 80 | | | | 95 | | 95 | |

-continued

| | | | | | | | | | | | |
|---|---|---|---|---|---|---|---|---|---|---|---|
| 26 | 0.07 | 14 | 4.48 | | | 25 95 (74) | | 95 (16) | 83 | (0) | 0 |
| 26 | 0.07 | 14 | 4.48 | 35 95 (64) | | | | 50 (17) | 60 | | |
| 26 | 0.14 | 14 | 4.48 | | | | | 90 (9) | 98 | 95 | |
| 26 | 0.28 | 14 | 4.48 | 85 100 (15) | | | | 100 | 55 | (0) | 95 |
| 26 | 0.28 | 14 | 4.48 | | | | | | | | |
| 26 | 0.28 | 14 | 4.48 | | | | | 100 | 97 | | |
| 28 | 0.004 | 14 | 1.12 | | | 90 95 (6) | 65 70 (8) 95 | | | | |
| 28 | 0.01 | 14 | 1.12 | | | 35 43 (19) | 65 75 (14) 85 88 (4) | | | | |
| 28 | 0.01 | 14 | 1.12 | | | 90 95 (6) | 100 98 | | | | |
| 28 | 0.07 | 14 | 1.12 | | | | 95 100 (5) | 0 (100) | 40 (34) | | |
| 28 | 0.28 | 14 | 1.12 | | | | 70 70 (0) 80 75 | | | | 5 |
| 28 | 1.12 | 14 | 4.48 | | | | | | | | 60 |
| 28 | 0.004 | 14 | 4.48 | | | 10 43 (77) | 80 75 | | | | |
| 28 | 0.01 | 14 | 4.48 | 0 10 (100) | | 85 95 (11) | 80 88 (10) | 0 (100) 75 | 5 (0) 45 (25) | | 5 |
| 28 | 0.01 | 14 | 4.48 | 15 48 (69) | | | 100 98 | 60 | 27 80 | | 60 |
| 28 | 0.07 | 14 | 4.48 | | | | 95 100 (5) | 85 (15) | 70 95 | (0) | 73 |
| 28 | 0.28 | 14 | 4.48 | | | | | 95 (4) | 55 | | 95 |
| 28 | 1.12 | 14 | 4.48 | | | | | 95 | 100 | | |
| 29 | 0.01 | 14 | 1.12 | 5 63 (93) | | | | 60 | 98 | | 40 68 (42) |
| 29 | 0.07 | 14 | 1.12 | | | | | | 90 | | 0 (100) |
| 29 | 0.28 | 14 | 1.12 | 40 93 (57) | | | | | | | 20 75 (74) |
| 29 | 0.56 | 14 | 1.12 | | | | | | | | |
| 29 | 1.12 | 14 | 1.12 | | | 90 95 (6) | | 60 95 | 27 100 70 95 (0) | | 10 10 (0) 35 |
| 29 | 1.12 | 14 | 4.48 | | | 85 95 (11) | | | | | 0 18 (100) 30 |
| 29 | 0.01 0.07 | 14 | 4.48 4.48 | | | | | 90 | 55 | | (60) |
| 29 | 0.28 | 14 | 4.48 | 5 63 (93) | | | | | | | 73 |
| 29 | 0.56 | 14 | 4.48 | | | 85 95 (11) | | 100 (0) | 100 | (0) | 0 10 (100) |

-continued

| | | | | | | | | |
|---|---|---|---|---|---|---|---|---|
| 29 | 1.12 | 14 | 4.48 | 10 (90) 93 | 90 95 (6) | 100 100 (0) | 95 (4) 98 | 15 12 |
| 29 | 1.12 | 14 | 4.48 | | 70 88 (21) | 95 100 (5) | | 0 (100) 40 |
| 30 | 1.12 | 14 | 1.12 | 50 (47) 93 | 95 93 | 100 100 (0) | | 90 50 |
| 30 | 1.12 | 14 | 1.12 | 95 (3) 97 | | 95 100 (5) | | 0 (100) 40 |
| 30 | 4.48 | 14 | 1.12 | | 55 88 (38) | 100 100 (0) | | 60 50 |
| 30 | 4.48 | 14 | 4.48 | 15 (84) 93 | 95 93 | 100 100 (0) | | 0 25 |
| 30 | 1.12 | 14 | 4.48 | 95 (3) 97 | | 100 100 (0) | | 65 (100) 83 (22) |
| 30 | 4.48 | 14 | 4.48 | | | 100 100 (0) | | 55 25 |
| 30 | 4.48 | 14 | 1.12 | | 0 | 65 15 | | 90 83 |
| 23 | 0.03 | 30 | 1.12 | | 30 58 (49) | 70 50 | | 75 52 |
| 23 | 0.14 | 30 | 4.48 | | 0 75 | 45 15 50 | | 95 (0) 95 |
| 23 | 0.03 | 30 | 4.48 | 0 (100) 12 | 20 23 (14) | 75 48 | | 25 (52) 52 |
| 23 | 0.14 | 30 | 1.12 | 30 (44) 53 | 95 95 (0) | 95 95 | | 90 95 (6) |
| 25 | 0.14 | 30 | 1.12 | | 60 23 | 65 48 | | |
| 25 | 0.56 | 30 | 4.48 | 0 (100) 12 | 95 (0) 95 | 65 95 (32) | | |
| 25 | 0.14 | 30 | 4.48 | 40 (25) 53 | | 10 40 (75) | | |
| 25 | 0.56 | 30 | 1.12 | | | 75 65 | | 0 25 |
| 27 | 0.14 | 30 | 1.12 | 0 (100) 12 | 20 58 (66) | 10 40 (75) | | 0 (100) |
| 27 | 0.56 | 30 | 1.12 | 10 (86) 68 | 5 | 70 65 | | |
| 27 | 0.14 | 30 | 4.48 | | | 45 15 | | 45 83 |
| 27 | 0.56 | 30 | 4.48 | | 30 58 | 10 0 (100) 75 | | (46) |
| 27 | 0.14 | 30 | 1.12 | 0 | | 55 50 | | 30 25 |
| 23 | 0.03 | 15 | 1.12 | | | 0 (100) 15 | | |
| 23 | 0.03 | 15 | 1.12 | | | 0 50 | | |
| 23 | 0.14 | 15 | 1.12 | | | 55 | | |
| 23 | 0.14 | 15 | 4.48 | | | | | |
| 23 | 0.03 | 15 | 4.48 | | | | | 85 83 |
| 23 | 0.03 | 15 | 4.48 | | | | | |
| 23 | 0.14 | 15 | | | | | | |

-continued

| | | | | | | | | | |
|---|---|---|---|---|---|---|---|---|---|
| 23 | 0.14 | 15 | 4.48 | 30 | (49) | 68 | 55 | (27) | 75 |
| 25 | 0.14 | 15 | 1.12 | | | | 70 | | 48 |
| 25 | 0.56 | 15 | 1.12 | | 20 (14) | 23 | 80 (16) | | 95 |
| 25 | 0.14 | 15 | 4.48 | | 80 (16) | 95 | 70 | | 48 |
| 25 | 0.56 | 15 | 4.48 | | 10 (57) | 23 | 70 (27) | | 95 |
| 25 | 0.14 | 15 | 1.12 | 10 (17) | 35 (64) | 95 | 35 (13) | | 40 |
| 27 | 0.56 | 15 | 1.12 | 0 (100) | | | 60 (8) | | 65 |
| 27 | 0.14 | 15 | 4.48 | 0 (100) | | | 65 | | 40 |
| 27 | 0.56 | 15 | 4.48 | 35 (34) | | | 75 | | 65 |
| 27 | 0.14 | 15 | 1.12 | | | | 15 | | 15 |
| 23 | 0.03 | 16 | 1.12 | | 0 | | 70 | | 50 |
| 23 | 0.14 | 16 | 4.48 | | 45 (23) | 58 | 0 (100) | | 15 |
| 23 | 0.03 | 16 | 4.48 | | 0 | | 25 (50) | | 50 |
| 25 | 0.14 | 16 | 1.12 | | 35 (40) | 58 | 70 | | 48 |
| 25 | 0.14 | 16 | 1.12 | | 70 | 23 | 95 | | 95 |
| 25 | 0.56 | 16 | 4.48 | | 95 | 95 | 95 (0) | | 48 | 0 (100) | 25 |
| 25 | 0.56 | 16 | 4.48 | | 45 (6) | 23 | 80 | | 95 | 90 | 83 |
| 27 | 0.14 | 16 | 1.12 | 0 (100) | 90 | 95 | 50 (16) | | 40 | 60 | 25 |
| 27 | 0.56 | 16 | 1.12 | 65 (100) | | | 70 | | 65 | 90 | 83 |
| 27 | 0.14 | 16 | 4.48 | 0 (100) | | | 70 | | 40 | 50 (4) | 52 |
| 27 | 0.56 | 16 | 4.48 | 75 | | | 75 (0) | | 65 | 95 (0) | 95 |
| 19 | 0.009 | 10 | 1.12 | | | | 90 | | 90 | 95 | 95 |
| 19 | 0.01 | 10 | 1.12 | 10 | | | 75 (12) | | 85 | | |
| 19 | 0.03 | 10 | 1.12 | (89) | | | 95 | | 90 | 95 (0) | 88 |
| 19 | 0.03 | 10 | 1.12 | | 30 (0) | 30 | 90 (6) | | 95 | | |
| 19 | 0.07 | 10 | 1.12 | 15 (85) | | | 80 | | 90 | | |
| 19 | 0.14 | 10 | 1.12 | | | | 100 (12) | | 95 | 95 | 88 |
| 19 | 0.009 | 10 | 4.48 | | | 97 | 85 | | 90 | | |
| 19 | 0.01 | 10 | 4.48 | 10 | | 90 | 90 (6) | | 85 | | |

-continued

| | | | | | | | | | | | |
|---|---|---|---|---|---|---|---|---|---|---|---|
| 19 | 0.03 | 10 | | | 0 | 30 | 85 | 90 | | 95 | |
| 19 | 0.03 | 10 | 4.48 | (89) | | | 95 (6) | 95 (0) | | | |
| 19 | 0.07 | 10 | 4.48 | | 10 | 70 | 90 | 90 | | | |
| 19 | 0.14 | 10 | 4.48 | 45 97 (54) | 0 | (86) 22 | 95 (0) | 95 (0) | | | |
| 20 | 0.004 | 10 | 1.12 | | | | 0 (100) | 25 (100) | | | 0 10 (100) |
| 20 | 0.004 | 10 | 1.12 | | 90 | 73 | 0 (100) | 30 (100) | | | |
| 20 | 0.004 | 10 | 1.12 | 25 12 | | | 55 | 10 | | 65 | 27 |
| 20 | 0.009 | 10 | 1.12 | 30 38 (22) | | | 50 | 40 | | | |
| 20 | 0.009 | 10 | 1.12 | | 0 | 22 | 40 | 35 | | | 55 68 |
| 20 | 0.004 | 10 | 4.48 | | (100) | | 30 (50) | 60 (60) | | 55 | 42 (20) |
| 20 | 0.004 | 10 | 4.48 | 5 12 | | | 0 (100) | 30 | | | |
| 20 | 0.004 | 10 | 4.48 | 0 38 (59) (100) | | | 10 (0) | 25 (75) | | | |
| 20 | 0.009 | 10 | 4.48 | | | | 10 | 10 | | 60 | 27 |
| 20 | 0.009 | 10 | 4.48 | | 20 | 73 | 10 (75) | 40 (42) | | | 0 10 (100) |
| 20 | 0.009 | 10 | 4.48 | | | (73) | 35 | 60 | | | |
| 23 | 0.03 | 10 | 1.12 | 0 | 0 | | 70 (80) | 35 | | | 10 68 (86) |
| 23 | 0.03 | 10 | 1.12 | 15 68 | | | 0 | 15 | | 45 | 42 |
| 23 | 0.14 | 10 | 1.12 | | 30 | 58 | 65 | 50 | | | 25 25 (0) |
| 23 | 0.14 | 10 | 1.12 | 15 (78) | | (49) | 15 (30) | 75 | | | 55 83 (34) |
| 23 | 0.03 | 10 | 4.48 | 5 | 0 45 | 58 (23) | 0 (100) | 15 50 | 80 (16) | | 35 25 60 83 (28) |
| 23 | 0.03 | 10 | 4.48 | | | | 85 (11) | 75 | 100 | | |
| 23 | 0.14 | 10 | 4.48 | 5 | 25 95 | 23 95 | 85 | 48 95 | | 95 95 (0) | 90 52 95 95 (0) |
| 25 | 0.14 | 10 | 1.12 | (93) | 35 | 0 23 | 0 | 48 | | 83 | 70 52 |
| 25 | 0.56 | 10 | 1.12 | | 80 | 95 (16) | (100) | 95 (0) | | | 95 95 (0) |
| 25 | 0.14 | 10 | 4.48 | | | | 75 | | | | |
| 25 | 0.56 | 10 | 4.48 | | | | 95 | | | 95 | 95 |
| 26 | 0.03 | 10 | 1.12 | | 90 | 95 | | | | | 10 |
| 26 | 0.07 | 10 | 1.12 | | | | | | | | |

-continued

| Ex | Dose | n | Conc | | | | |
|----|------|----|------|---|---|---|---|
| 26 | 0.07 | 10 | 1.12 | 20 95 (79) | | | |
| 26 | 0.14 | 10 | 1.12 | | | | |
| 26 | 0.28 | 10 | 1.12 | 95 100 (5) | (6) | | 90 60 |
| 26 | 0.28 | 10 | 1.12 | | | | 95 (4) 98 95 (0) 95 |
| 26 | 0.03 | 10 | 4.48 | | | | 95 55 |
| 26 | 0.07 | 10 | 4.48 | 25 95 (74) | | | 90 (8) 97 |
| 26 | 0.07 | 10 | 4.48 | | | | 50 (48) 95 95 (0) 95 |
| 26 | 0.14 | 10 | 4.48 | 90 100 (10) | 95 95 (0) | 65 40 | 55 (34) 83 |
| 26 | 0.28 | 10 | 4.48 | | 45 95 (53) | 65 (0) 65 40 | 100 60 |
| 26 | 0.28 | 10 | 4.48 | | | 65 40 | 95 (4) 98 95 (0) 95 30 68 (56) |
| 27 | 0.14 | 10 | 1.12 | 10 12 (17) | 95 95 (0) | 65 (0) 65 | 100 55 |
| 27 | 0.56 | 10 | 1.12 | 10 53 (82) | | 40 (43) 70 | 97 0 |
| 27 | 0.14 | 10 | 4.48 | 0 12 (100) | 5 43 (89) | 80 75 | |
| 27 | 0.56 | 10 | 4.48 | 15 53 (72) | 65 95 (32) | 55 75 (27) 90 88 | 15 68 (78) 95 |
| 28 | 0.004 | 10 | 1.12 | | | 100 98 (5) 70 | |
| 28 | 0.01 | 10 | 1.12 | 5 10 (50) | 10 43 (77) | 70 (0) 75 | 20 0 18 45 (100) |
| 28 | 0.01 | 10 | 1.12 | 0 48 (100) | 60 95 (37) | 70 75 (7) 75 | (25) 10 75 (87) |
| 28 | 0.07 | 10 | 1.12 | | | 80 75 | |
| 28 | 0.28 | 10 | 1.12 | | | 80 88 (10) | 5 0 18 |
| 28 | 1.12 | 10 | 1.12 | | | 95 98 (4) | 35 (0) 60 0 (100) 0 (100) |
| 28 | 0.004 | 10 | 4.48 | 0 10 (100) | | 100 100 (0) | 27 90 5 60 |
| 28 | 0.01 | 10 | 4.48 | 5 48 (90) | | 50 95 | 70 95 35 (42) 73 95 |
| 28 | 0.01 | 10 | 4.48 | | | | |
| 28 | 0.07 | 10 | 4.48 | | | | |
| 28 | 0.28 | 10 | 4.48 | | | | |
| 28 | 1.12 | 10 | 4.48 | | | | |
| 29 | 0.01 | 10 | 1.12 | | | | |
| 29 | 0.07 | 10 | 1.12 | | | | |

-continued

| | | | | | | | | Ln |
|---|---|---|---|---|---|---|---|---|
| 29 | 0.28 | 10 | 1.12 | | 85 95 (11) | 100 100 (0) | 65 100 (0) | 10 10 (0) |
| 29 | 0.56 | 10 | 1.12 | 0 63 (100) | 80 95 (16) | 100 100 (0) | 55 100 | 10 10 20 12 |
| 29 | 1.12 | 10 | 1.12 | | | 100 100 (0) | 100 98 | |
| 29 | 1.12 | 10 | 4.48 | 45 93 (52) | | 100 100 (0) | 90 | 73 95 |
| 29 | 0.01 | 10 | 4.48 | | 90 95 (6) | 100 100 (0) | 55 100 (86) | |
| 29 | 0.07 | 10 | | 5 63 (93) | | | 27 95 70 95 (0) | |
| 29 | 0.28 | 10 | 4.48 | | 90 95 (6) | 100 100 (0) | 55 98 | 10 10 (0) |
| 29 | 0.56 | 10 | 4.48 | | 65 88 (27) | 100 100 (0) | 100 90 | 0 12 (100) |
| 29 | 1.12 | 10 | 4.48 | 20 93 (79) | | | 95 (4) | |
| 29 | 1.12 | 10 | 4.48 | 30 93 (68) | 0 93 (100) | 100 100 (0) | 100 | 10 40 (75) |
| 30 | 1.12 | 10 | 1.12 | | | 100 100 (0) | | |
| 30 | 1.12 | 10 | 1.12 | 95 97 (3) | 95 88 | 100 100 (0) | | 25 50 (50) |
| 30 | 4.48 | 10 | 4.48 | | | 50 15 | | 15 40 (63) |
| 30 | 4.48 | 10 | 4.48 | 25 93 (74) | 45 93 (52) | 75 50 | | |
| 30 | 1.12 | 10 | 4.48 | | | 25 15 | | 0 50 (100) |
| 30 | 1.12 | 10 | 4.48 | | 0 | 65 50 | | 0 25 (100) |
| 30 | 4.48 | 10 | 1.12 | 85 97 (13) | 25 58 (57) | 90 48 | | 85 83 |
| 30 | 4.48 | 10 | 1.12 | | 15 58 (75) | 85 95 (11) | | 30 25 50 83 (40) |
| 30 | 0.03 | 11 | | | 15 58 | | | |
| 30 | 0.14 | 11 | | | 35 23 (35) | 90 48 | | 90 52 95 (0) |
| 23 | 0.03 | 11 | 4.48 | | 90 95 (6) | | | |
| 23 | 0.14 | 11 | 4.48 | | 15 23 (35) | 90 95 (6) | | 85 52 |
| 25 | 0.14 | 11 | 1.12 | | | 40 40 (0) | | |
| 25 | 0.56 | 11 | 1.12 | | 95 95 (0) | 65 65 (0) | | 95 95 (0) |
| 25 | 0.14 | 11 | 4.48 | | | | | |
| 27 | 0.14 | 11 | 1.12 | 0 12 (100) | | | | |
| 27 | 0.56 | 11 | 1.12 | 45 53 (16) | | | | |

-continued

| | | | | | | | | |
|---|---|---|---|---|---|---|---|---|
| 27 | 0.14 | 11 | 4.48 | 0 (100) | 12 | | 60 | |
| 27 | 0.56 | 11 | 4.48 | 65 | 53 | | 75 | 65 |
| 19 | 0.009 | 17 | 1.12 | 5 (95) | 90 | | 95 | 90 |
| 19 | 0.01 | 17 | 1.12 | | | | 90 | 85 |
| 19 | 0.03 | 17 | 1.12 | | | | 95 | 90 |
| 19 | 0.03 | 17 | 1.12 | | | 90 | 95 (0) | 95 |
| 19 | 0.07 | 17 | 1.12 | 90 (8) | 97 | | 90 (0) | 90 |
| 19 | 0.14 | 17 | 1.12 | | | | 95 (0) | 95 |
| 19 | 0.009 | 17 | 4.48 | 90 (0) | 90 | | 90 (0) | 90 |
| 19 | 0.01 | 17 | 4.48 | | | | 90 (0) | 85 |
| 19 | 0.03 | 17 | 4.48 | | | | 90 (0) | 90 |
| 19 | 0.03 | 17 | 4.48 | | | 95 | 95 (0) | 95 |
| 19 | 0.07 | 17 | 4.48 | 95 (3) | 97 | | 95 (0) | 90 |
| 19 | 0.14 | 17 | 4.48 | | | | 95 | 95 |
| 20 | 0.004 | 17 | 1.12 | | | 65 30 | 10 25 | 35 27 |
| 20 | 0.004 | 17 | 1.12 | | | | (60) 30 | |
| 20 | 0.004 | 17 | 1.12 | 15 | 12 | 75 70 | 25 (17) 40 | |
| 20 | 0.009 | 17 | 1.12 | 20 (48) | 38 | | 45 10 85 40 | |
| 20 | 0.009 | 17 | 1.12 | | | | 55 (9) 60 | |
| 20 | 0.009 | 17 | 4.48 | | | 20 30 (34) | 85 35 0 25 (100) | 25 42 (41) |
| 20 | 0.004 | 17 | 4.48 | 0 (100) | 12 | 50 (29) 70 22 | 0 10 (100) | |
| 20 | 0.004 | 17 | 4.48 | | | 5 (78) | 0 30 (100) | 35 27 |
| 20 | 0.009 | 17 | 4.48 | 35 (8) | 38 | | 0 40 (100) | |
| 20 | 0.009 | 17 | 4.48 | | | 90 73 10 22 (55) | 25 40 (38) 35 | 50 42 |
| 20 | 0.009 | 17 | 4.48 | | | | 45 35 | |
| 23 | 0.03 | 17 | 1.12 | 0 | 45 | 0 (100) 73 | 0 60 (100) | 10 10 (0) |
| 23 | 0.14 | 17 | 1.12 | (34) | 68 | | 55 75 | 85 68 |
| 23 | 0.03 | 17 | 4.48 | 5 25 (64) | 38 | | 70 75 (7) | 0 (100) 10 |
| 23 | 0.14 | 17 | 4.48 | | 68 | | 0 50 75 (34) | 10 68 (86) |

-continued

| | | | | | | | |
|---|---|---|---|---|---|---|---|
| 26 | 0.03 | 17 | 1.12 | | | | |
| 26 | 0.07 | 17 | 1.12 | 75 95 (22) | 95 95 (0) | 40 (58) 95 95 | |
| 26 | 0.07 | 17 | 1.12 | | | 15 (75) 60 | |
| 26 | 0.14 | 17 | 1.12 | | | 100 83 | 0 |
| 26 | 0.28 | 17 | 1.12 | 95 100 (5) | 95 95 (0) | 100 98 95 (0) 90 55 | 95 |
| 26 | 0.28 | 17 | 1.12 | | | | 0 |
| 26 | 0.03 | 17 | 4.48 | | | 100 97 | 95 |
| 26 | 0.07 | 17 | 4.48 | | 0 95 (100) | 95 (0) 95 95 (0) | 0 |
| 26 | 0.07 | 17 | 4.48 | 90 95 (6) | | 90 83 | 95 |
| 26 | 0.14 | 17 | 4.48 | | | 100 60 | |
| 26 | 0.28 | 17 | 4.48 | 95 100 (5) | 95 95 (0) 10 43 (77) 35 95 (64) | 95 (4) 98 95 (0) 100 55 | 0 68 (100) 0 18 (100) 10 75 (87) |
| 26 | 0.28 | 17 | 4.48 | | | 100 97 | |
| 26 | 1.12 | 17 | 1.12 | | | | |
| 28 | 0.004 | 17 | 1.12 | 10 10 (0) 48 (100) | | | |
| 28 | 0.01 | 17 | 1.12 | 0 (100) | | 0 (100) 35 (42) | 5 60 |
| 28 | 0.01 | 17 | 1.12 | | | | |
| 28 | 0.07 | 17 | 1.12 | | | | |
| 28 | 0.28 | 17 | 1.12 | | 20 43 (54) 90 95 (6) | | |
| 28 | 1.12 | 17 | 1.12 | | | | |
| 28 | 0.004 | 17 | 4.48 | 0 10 (100) | | 0 (100) 45 (25) 90 95 (0) | 0 18 (100) 0 75 (100) |
| 28 | 0.01 | 17 | 4.48 | 0 48 (100) | | 27 70 95 55 | 5 60 73 95 |
| 28 | 0.01 | 17 | 4.48 | | | | |
| 28 | 0.07 | 17 | 4.48 | | | 0 (100) 15 (79) 70 | |
| 28 | 0.28 | 17 | 4.48 | | | | |
| 29 | 1.12 | 17 | 1.12 | | | | |
| 29 | 0.01 | 17 | 1.12 | | | | |
| 29 | 0.07 | 17 | 1.12 | | | | |
| 29 | 0.28 | 17 | 1.12 | 25 63 (61) | | | |

-continued

| | | | | | | | | | | |
|---|---|---|---|---|---|---|---|---|---|---|
| 29 | 0.56 | 17 | 1.12 | | | 90 95 (6) 95 (0) | 100 (0) 100 | | | |
| 29 | 1.12 | 17 | 1.12 | | | | 85 (6) | 100 | | |
| 29 | 1.12 | 17 | 1.12 | 85 93 (9) | | | 90 | 98 | | |
| 29 | 0.01 | 17 | 4.48 | | | | 10 (63) | 27 60 (18) | 0 (100) | |
| 29 | 0.07 | 17 | 4.48 | | | | 0 (100) | 70 95 | 10 (17) | |
| 29 | 0.28 | 17 | 4.48 | 25 63 (61) | | | 95 | (0) 55 | | |
| 29 | 0.56 | 17 | 4.48 | | | | 100 | 100 | | |
| 29 | 1.12 | 17 | 4.48 | 95 93 | | | | | | |
| 29 | 1.12 | 17 | 4.48 | | | 90 95 (6) 95 (0) | | 90 | | |
| 30 | 1.12 | 17 | 1.12 | | | 95 95 (0) 88 (15) | | 98 | 15 | 10 10 |
| 30 | 1.12 | 17 | 1.12 | 90 93 (4) | | 75 | | | | |
| 30 | 1.12 | 17 | 1.12 | 100 97 | | | | | 5 (88) | 10 12 |
| 30 | 4.48 | 17 | 4.48 | 95 | | 25 93 (72) | | | 85 | |
| 30 | 1.12 | 17 | 4.48 | | | 95 93 | | | | |
| 30 | 1.12 | 17 | 4.48 | | 95 95 (0) | | | | | |
| 30 | 4.48 | 17 | 4.48 | 95 97 (3) | 5 (0) 90 (6) | | | | | |
| 30 | 4.48 | 17 | 4.48 | 5 13 (62) | 95 95 (0) | | | | 0 (100) | 50 |
| 6 | 8.96 | 20 | 0.14 | 5 30 (84) | 95 95 (0) | | | | 20 | 50 |
| 6 | 11.20 | 20 | 0.14 | 15 13 | 90 95 (6) | | | | | |
| 6 | 8.96 | 20 | 0.56 | 5 30 (84) | 95 95 (0) | | | | | |
| 6 | 11.20 | 20 | 0.56 | 10 13 (24) | 95 95 (0) | | | 100 | (60) | |
| 6 | 8.96 | 20 | 2.24 | 15 30 (50) | 90 95 (6) | | | | | |
| 6 | 11.20 | 20 | 2.24 | | 95 95 (0) | | | | | |
| 2 | 0.28 | 20 | 0.14 | | | 5 85 (95) | 95 (5) 100 | | | 100 |
| 2 | 0.56 | 20 | 0.14 | | | 5 93 (95) | 100 (0) | | | 100 |
| 2 | 0.56 | 20 | 0.14 | | | 20 75 (74) | 100 | | | 98 |
| 2 | 2.24 | 20 | 0.14 | | | 40 98 (60) | 100 (0) | | | 100 |
| 2 | 2.24 | 20 | 0.14 | | | 32 97 | 100 | | | 100 |

-continued

| | | | | | | | |
|---|---|---|---|---|---|---|---|
| 2 | 0.28 | 20 | 0.56 | | 0 (68) 85 | (0) 100 | 100 |
| 2 | 0.56 | 20 | 0.56 | | 30 (100) 93 | 90 (0) | 100 |
| 2 | 0.56 | 20 | 0.56 | | 15 (68) 72 | 95 (10) | 95 |
| 2 | 0.56 | 20 | 0.56 | | 20 (80) 75 | 100 (0) | 98 |
| 2 | 2.24 | 20 | 0.56 | | 30 (74) 100 | 100 (0) | 100 |
| 2 | 2.24 | 20 | 0.56 | | 25 (70) 98 | 100 (0) | 100 |
| 2 | 2.24 | 20 | 0.56 | | 15 (75) 97 | 100 (0) | 100 |
| 2 | 0.28 | 20 | 2.24 | | 0 (85) | 100 (0) | 100 |
| 2 | 0.56 | 20 | 2.24 | | 10 (100) 93 | 95 (5) | 95 |
| 2 | 0.56 | 20 | 2.24 | | 10 (90) 72 | 80 (16) | 98 |
| 2 | 0.56 | 20 | 2.24 | | 0 (87) 75 | 95 (4) | 100 |
| 2 | 2.24 | 20 | 2.24 | | 20 (100) 98 | 100 (0) | 100 |
| 2 | 2.24 | 20 | 2.24 | | 30 (80) 100 | 100 (0) | 100 |
| 2 | 2.24 | 20 | 8.96 | | 30 (70) 97 | 100 (0) | 95 |
| 2 | 0.56 | 20 | 8.96 | | 20 (70) 72 | 90 (6) | 100 |
| 2 | 2.24 | 20 | 8.96 | | 15 (73) 100 | 100 (0) | 100 |
| 15 | 1.12 | 20 | 0.56 | | 0 (85) | | 55 |
| 15 | 1.12 | 20 | 0.56 | 0 (100) 10 | 0 (100) 10 | | 85 (6) 50 |
| 15 | 4.48 | 20 | 0.56 | 10 (72) 35 | | 95 | 90 |
| 15 | 4.48 | 20 | 0.56 | | 20 (74) 75 | (0) 100 | 50 |
| 15 | 1.12 | 20 | 2.24 | 0 (100) 10 | | 95 | 100 |
| 15 | 1.12 | 20 | 2.24 | | 0 (100) 10 | 75 (17) 100 | 50 |
| 15 | 4.48 | 20 | 2.24 | | 45 (40) 75 | | 85 |
| 15 | 4.48 | 20 | 2.24 | 10 (72) 35 | | 90 | 90 |
| 15 | 1.12 | 20 | 8.96 | 10 (0) 10 | | 100 | 100 |
| 15 | 1.12 | 20 | 8.96 | | 0 (100) 10 | | 50 |
| 15 | 4.48 | 20 | 8.96 | 10 35 | | 95 | 95 |

-continued

| | | | | | | | | | |
|---|---|---|---|---|---|---|---|---|---|
| 15 | 4.48 | 20 | 8.96 | (72) | | | | 100 | |
| 7 | 0.14 | 20 | 0.56 | | | 0 (100) | | | |
| 7 | 0.56 | 20 | 0.56 | 90 | 100 (0) | 75 | 90 (0) | | |
| 7 | 1.12 | 20 | 0.56 | 90 | 100 (0) | 100 | 100 (0) | | |
| 7 | 4.48 | 20 | 0.56 | (6) | | | | | |
| 7 | 0.14 | 20 | 2.24 | 80 | | 90 | 90 (0) | | |
| 7 | 0.56 | 20 | 2.24 | 70 | | 95 | 100 (0) | | |
| 7 | 1.12 | 20 | 2.24 | (27) | | | | | |
| 7 | 4.48 | 20 | 2.24 | 80 | | 90 | 90 (0) | | |
| 7 | 0.14 | 20 | 8.96 | 100 | 100 (0) | 95 | 90 (0) | 90 | 100 |
| 7 | 0.56 | 20 | 8.96 | 100 | 100 (0) | 100 | 100 (0) | | |
| 7 | 1.12 | 20 | 8.96 | 80 | | 95 | 90 (0) | | |
| 7 | 4.48 | 20 | 8.96 | 100 | | 95 | 95 (0) | | |
| 16 | 0.56 | 20 | 0.56 | 5 | | | | | |
| 16 | 2.24 | 20 | 0.56 | 10 (50) | 20 | 25 | 40 (38) | | |
| 16 | 0.56 | 20 | 2.24 | 20 | | 85 | 95 (11) | | |
| 16 | 2.24 | 20 | 2.24 | 0 (100) | 20 | 5 | 40 (88) | | |
| 16 | 0.56 | 20 | 8.96 | 10 | | 75 | 95 (22) | | |
| 16 | 2.24 | 20 | 8.96 | 25 | 20 | 15 | 40 (63) | | |
| 17 | 1.68 | 20 | 0.14 | 88 | 100 (0) | 95 | 95 (0) | 100 | 100 (0) |
| 17 | 3.36 | 20 | 0.14 | 95 | 100 (0) | | | 100 | 100 (0) |
| 17 | 1.68 | 20 | 0.56 | 78 (12) | 100 (0) | | | 95 | 95 (0) |
| 17 | 3.36 | 20 | 0.56 | 80 (16) | 100 (0) | | | 100 | 100 (0) |
| 17 | 1.68 | 20 | 2.24 | 68 (23) | 98 (2) | | | 95 | 95 (0) |
| 17 | 3.36 | 20 | 2.24 | 88 (8) | 100 (0) | 70 (11) | 78 | 100 | 100 (0) |
| 18 | 0.56 | 20 | 0.56 | | | | | 95 (3) | 97 |
| 18 | 1.12 | 20 | 0.56 | 30 (29) | 100 (0) | | | 95 | 97 |
| 18 | 2.24 | 20 | 0.56 | 42 | | | | 100 | |

-continued

| | | | | | | | | | | |
|---|---|---|---|---|---|---|---|---|---|---|
| 18 | 4.48 | 20 | 4.48 | 80 (0) | 100 | 100 (0) | 70 78 (11) (3) | 100 | 97 | | |
| 18 | 0.56 | 20 | 0.56 | 80 | 100 | 100 (0) | 95 97 (3) | 100 (0) | 97 | | |
| 18 | 1.12 | 20 | 1.12 | 45 | | | | | | | |
| 18 | 2.24 | 20 | 2.24 | 42 | | | | | | | |
| 18 | 4.48 | 20 | 4.48 | 40 (50) | 100 | 100 (0) | 95 78 (3) | 100 | 97 | | |
| 18 | 0.56 | 20 | 0.56 | 35 | | | | | | | |
| 18 | 1.12 | 20 | 1.12 | (17) | | | | | | | |
| 18 | 2.24 | 20 | 2.24 | 80 | 100 | 100 (0) | 85 97 (13) | 100 (0) | 97 | | |
| 18 | 4.48 | 20 | 4.48 | 90 | | | | | | | |
| 19 | 0.009 | 20 | 1.12 | 0 (100) | | 0 30 (100) | | | 85 (6) | 90 | 85 (4) 88 |
| 19 | 0.01 | 20 | 1.12 | | | | | | 95 | 85 | |
| 19 | 0.03 | 20 | 1.12 | | | | | | 100 | 95 | |
| 19 | 0.03 | 20 | 1.12 | 60 (39) | | 20 70 (72) | | | 90 (0) | 90 | 95 (0) 88 |
| 19 | 0.07 | 20 | 1.12 | 97 | | | | | 85 (6) | 90 | |
| 19 | 0.14 | 20 | 1.12 | 5 (95) | | | | | 95 (0) | 95 | |
| 19 | 0.009 | 20 | 4.48 | 90 | | 10 30 (67) | | | 95 (0) 70 (18) | 90 85 | 95 88 |
| 19 | 0.01 | 20 | 4.48 | | | | | | | | |
| 19 | 0.03 | 20 | 4.48 | 35 (64) | | | | | 95 (0) | 95 | |
| 19 | 0.03 | 20 | 4.48 | 97 | | 10 70 (86) 65 | 22 | | 95 (0) | 90 | 95 (0) 95 |
| 19 | 0.07 | 20 | 4.48 | | | | | | 85 (6) | 90 | |
| 19 | 0.14 | 20 | 1.12 | 0 (100) 25 | 12 | | | | 95 (0) | 95 | |
| 20 | 0.004 | 20 | 1.12 | 38 (35) | | | | | 15 (40) 55 | 25 30 | 40 27 |
| 20 | 0.004 | 20 | 1.12 | | | | | | 15 | 10 | |
| 20 | 0.004 | 20 | 1.12 | | | 65 73 (11) | | | 20 (50) 35 (42) | 40 60 | 55 42 |
| 20 | 0.009 | 20 | 1.12 | | | | | | | | |
| 20 | 0.009 | 20 | 1.12 | | | | | | 65 | 35 | |
| 20 | 0.009 | 20 | 1.12 | | | | | | 35 | 10 | 30 68 (56) |
| 20 | 0.004 | 20 | 4.48 | 0 (100) 12 | | | | | | | |

-continued

| | | | | | | | | | | | | |
|---|---|---|---|---|---|---|---|---|---|---|---|---|
| 20 | 0.004 | 20 | 4.48 | | 0 (100) | | | | | | | |
| 20 | 0.004 | 20 | 4.48 | | 22 | | | | | | | |
| 20 | 0.009 | 20 | 4.48 | | 45 (39) | | | | | | | |
| 20 | 0.009 | 20 | 4.48 | | 73 | | | | | | | |
| 20 | 0.009 | 20 | 4.48 | 0 (100) | | | | | | | | |
| 20 | 0.28 | 20 | 0.14 | 38 | | | | | | | | |
| 21 | 0.56 | 20 | 0.14 | | 20 (20) | 25 | | | 5 (50) | | | |
| 21 | 1.12 | 20 | 0.14 | | 60 | 30 | 60 | | 27 | | | |
| 21 | 0.28 | 20 | 0.56 | | 25 (29) | 35 | 40 (5) | | 85 | | | |
| 21 | 0.56 | 20 | 0.56 | | 20 (67) | 60 | 42 | | 68 | | | |
| 21 | 1.12 | 20 | 0.56 | | 15 (63) | 40 | | | | 30 | 47 | 10 (72) 35 |
| 21 | 2.24 | 20 | 2.24 | | | | | | | 55 | 68 | 30 30 |
| 21 | 1.12 | 20 | 2.24 | | | | | | | 80 (20) | 67 | 40 (0) 30 |
| 21 | 0.28 | 20 | 8.96 | | | | | | | 15 | 47 | 5 35 |
| 21 | 0.56 | 20 | 8.96 | | | | | | | 65 (69) | 68 | (86) |
| 21 | 1.12 | 20 | 8.96 | | | | | | | 5 | | 35 30 |
| 21 | 1.12 | 20 | 0.03 | | | | | | | 75 | 67 | 80 30 |
| 22 | 2.24 | 20 | 0.03 | 20 (53) | | | | | | 45 (5) | 47 | 30 35 |
| 22 | 0.28 | 20 | 0.14 | 42 | | | | | | 60 | 68 | 45 30 |
| 22 | 0.28 | 20 | 0.14 | 60 (34) | 60 | | 98 | | | 20 (12) | 67 | 30 30 |
| 22 | 0.56 | 20 | 0.14 | 10 (42) 17 | | | 100 | 100 (0) | | 10 (71) | 47 | (0) 35 |
| 22 | 1.12 | 20 | 0.14 | 10 (17) 12 | | 90 | 100 | 100 | | 90 | 68 | 5 30 |
| 22 | 1.12 | 20 | 0.14 | 25 (75) 98 | | 78 | 100 | 85 | 10 (50) 20 | (79) | | (86) |
| 22 | 1.12 | 20 | 0.14 | 10 (74) 38 | | | 100 | 100 | | 75 | 67 | 55 30 |
| 22 | 1.12 | 20 | 0.14 | 42 | | | 100 (0) | 100 | | | | 70 30 |
| 22 | 2.24 | 20 | 0.14 | 25 (41) | | 20 | 100 | 98 | 25 (74) 95 | | | |
| 22 | 0.28 | 20 | 0.56 | 10 (84) 60 | 65 | | 100 (0) | 100 | | | | |
| 22 | 0.28 | 20 | 0.56 | 10 (42) 17 | | | 95 | 90 | 15 (25) 20 | | | |
| 22 | 0.56 | 20 | 0.56 | 0 12 | | | 75 | 85 | | | | |

-continued

| Ex. | Dose | | Dose | Results | | | | | | |
|---|---|---|---|---|---|---|---|---|---|---|
| 22 | 1.12 | 20 | 0.56 | 45 (100) 98 | | | | | | |
| 22 | 1.12 | 20 | 0.56 | 5 (87) 38 | | | | | | |
| 22 | 1.12 | 20 | 0.56 | 5 (89) 42 | | | | | | |
| 22 | 1.12 | 20 | 0.56 | 0 (100) 60 | | | | | | |
| 22 | 2.24 | 20 | 0.56 | | | | 100 (12) 100 | | | |
| 22 | 0.28 | 20 | 0.56 | 10 (42) 17 | 20 (75) 78 | | 100 (0) 100 | | | |
| 22 | 0.28 | 20 | 2.24 | 0 (100) 12 | | | 100 (0) 98 | | 40 (58) 95 | |
| 22 | 0.56 | 20 | 2.24 | 10 (74) 38 | | | 100 (0) 100 | | | |
| 22 | 1.12 | 20 | 2.24 | 15 (85) 98 | 10 (50) 20 | | 100 90 | 25 20 | | |
| 22 | 1.12 | 20 | 2.24 | 85 (15) 99 | | | 70 (18) 85 | | 60 (37) 95 | |
| 23 | 0.14 | 20 | 0.56 | 95 99 (1) 100 | 75 (4) 78 | 15 50 75 | 100 (0) 100 | 55 70 | 10 (60) 25 | 85 83 |
| 23 | 0.56 | 20 | 0.56 | 0 | | 20 50 | 100 (0) 100 | | | |
| 23 | 0.03 | 20 | 1.12 | | | 45 (10) 50 | 55 (0) 55 | 60 55 | | |
| 23 | 0.03 | 20 | 1.12 | | | 0 (100) 75 | 65 (8) 70 | 80 70 | | |
| 23 | 0.14 | 20 | 1.12 | 15 (78) 68 | | | | | | |
| 23 | 0.14 | 20 | 2.24 | 75 (25) 99 | | | | | | |
| 23 | 0.56 | 20 | 2.24 | 95 (5) 100 | | 15 50 75 | | | 45 (22) 25 83 | |
| 23 | 0.03 | 20 | 4.48 | 0 | 15 (75) 58 | 0 60 30 | | | 65 | |
| 23 | 0.03 | 20 | 4.48 | | | 35 (54) 40 | 70 75 | 55 70 | | |
| 23 | 0.14 | 20 | 4.48 | 20 (71) 68 | | | | | | |
| 23 | 0.14 | 20 | 8.96 | 85 (15) 99 | | | | | | |
| 23 | 0.56 | 20 | 8.96 | 95 (5) 100 | | | 100 (0) 100 | | | |
| 24 | 0.28 | 20 | 0.14 | 35 | 15 (75) 58 | | 100 (0) 100 | 75 | 63 | |
| 24 | 1.12 | 20 | 0.14 | 85 (8) 92 | | | 100 (0) 100 | 95 (0) 95 | | |
| 24 | 0.28 | 20 | 0.56 | 25 | 15 (92) 58 | | 100 (0) 100 | 70 | 63 | |

-continued

-continued

| | | | | | | | | | | | | |
|---|---|---|---|---|---|---|---|---|---|---|---|---|
| 25 | 1.12 | 20 | 8.96 | | | | 70 (0) | | | | | |
| 32 | 2.24 | 20 | 0.56 | 100 (0) | | | 70 | | | | | |
| 32 | 4.48 | 20 | 0.56 | 0 (100) | 100 | | 15 | | | | | |
| 32 | 2.24 | 20 | 2.24 | 10 (75) | 10 (73) | | 25 (55) | | | | | |
| 32 | 4.48 | 20 | 2.24 | 10 (0) | 40 | | 0 | | | | | |
| 32 | 2.24 | 20 | 8.96 | 5 (88) | 10 (100) | | 85 | | | | | |
| 32 | 4.48 | 20 | 8.96 | 10 (0) | 10 | | 90 | | | | | |
| 32 | 2.24 | 20 | 4.48 | 20 (50) | 40 | | 50 (10) | | | | | |
| 26 | 0.03 | 20 | 1.12 | | | | 55 | | | | | |
| 26 | 0.07 | 20 | 1.12 | | | 85 95 (11) | 55 | 95 (0) 100 | 95 95 (0) 83 | 95 0 60 | | |
| 26 | 0.07 | 20 | 1.12 | 20 (79) | 95 | | | 65 | | | | |
| 26 | 0.14 | 20 | 1.12 | | | | | 95 (4) 95 | 98 95 (0) 55 | 95 97 | | |
| 26 | 0.28 | 20 | 1.12 | 95 (5) | 100 | 95 (0) | | 100 | 95 95 (0) 83 | 95 0 60 | | |
| 26 | 0.28 | 20 | 1.12 | | | 25 (74) | | 75 (22) 100 | | | | |
| 26 | 0.03 | 20 | 4.48 | | | | | 85 | | | | |
| 26 | 0.07 | 20 | 4.48 | 15 (85) | 95 | 95 (0) 95 (4) | | 95 (4) 100 | 98 95 (0) 55 | 95 50 (27) | 68 20 | |
| 26 | 0.14 | 20 | 4.48 | | | | | 100 | | | | |
| 26 | 0.28 | 20 | 4.48 | 65 (35) | 100 | | | 70 (0) 80 (6) | 97 70 | | | |
| 26 | 0.28 | 20 | 4.48 | | | 100 100 (0) | 95 | | 85 | | | |
| 27 | 0.14 | 20 | 0.56 | 0 (100) | 8 | | 100 | | | | | |
| 27 | 0.14 | 20 | 0.56 | 75 (23) | 97 | | 75 (7) | | | | | |
| 27 | 0.56 | 20 | 0.56 | 15 (84) | 90 | | 80 (20) | | 20 | 95 40 (42) 85 (14) | 68 98 | |
| 27 | 0.56 | 20 | 0.56 | | | | 65 (8) | | 5 | | | |
| 27 | 0.56 | 20 | 0.56 | | | | 70 (13) | | | 7 | 95 (5) | 100 |
| 27 | 1.12 | 20 | 0.56 | | | | 70 | | | 30 | | |
| 27 | 1.12 | 20 | 0.56 | 80 (18) | 97 | | 73 | | | | | |
| 27 | 2.24 | 20 | 0.56 | | | | | | | | | |

| | | | | | | | | | | | |
|---|---|---|---|---|---|---|---|---|---|---|---|
| 27 | 0.14 | 20 | 1.12 | 5 (59) | 12 | | 0 (5) | 40 | | | 80 (19) 98 |
| 27 | 0.56 | 20 | 1.12 | 5 (91) | 53 | | 65 (100) | 65 (0) | | | |
| 27 | 0.14 | 20 | 2.24 | 0 (100) | 8 | | 100 | 95 | 85 (0) | | |
| 27 | 0.14 | 20 | 2.24 | 85 (13) | 97 | 95 (4) | 85 | 70 | | | |
| 27 | 0.56 | 20 | 2.24 | 25 (73) | 90 | | 95 (5) | 80 | 85 | 0 (100) | 100 100 (0) |
| 27 | 0.56 | 20 | 2.24 | | | | 70 (0) | 100 | | | |
| 27 | 0.56 | 20 | 2.24 | | | | 90 | 70 | | | 7 |
| 27 | 1.12 | 20 | 2.24 | | | | 75 | 80 | | 20 (34) | 30 |
| 27 | 1.12 | 20 | 2.24 | 85 (13) | 97 | | 25 (38) | 73 | | | |
| 27 | 2.24 | 20 | 2.24 | | | | 80 | 40 | | | |
| 27 | 0.14 | 20 | 4.48 | 0 (100) | 12 | | 95 (0) | 65 | 60 (15) | | 95 (4) |
| 27 | 0.56 | 20 | 4.48 | 40 (25) | 53 | 95 (4) | | 95 | 80 (6) | | |
| 27 | 0.14 | 20 | 8.96 | 0 (100) | 8 | 100 100 (0) | 90 | 80 | 70 | 0 (100) | 100 100 (0) |
| 27 | 0.14 | 20 | 8.96 | 12 (88) | 97 | | 100 | 100 | 85 | | |
| 27 | 0.56 | 20 | 8.96 | 35 (62) | 90 | | 65 (8) | 70 | | | 7 |
| 27 | 0.56 | 20 | 8.96 | | | 95 (5) | 90 | 80 | | 20 (34) | 30 |
| 27 | 0.56 | 20 | 8.96 | 60 (39) | 97 | | 65 (11) | 73 | | | |
| 27 | 1.12 | 20 | 8.96 | | | | 90 | 70 | | | |
| 28 | 0.004 | 20 | 1.12 | | | 10 43 (77) | 95 | 75 | | | 10 18 (45) 75 |
| 28 | 0.01 | 20 | 1.12 | 5 (50) | 10 | 80 (16) 95 | 60 (20) | 75 | | 5 (0) | 45 (40) |
| 28 | 0.01 | 20 | 1.12 | 5 (90) | 48 | | 85 (4) | 88 | | 40 (34) | 5 60 |
| 28 | 0.07 | 20 | 1.12 | | | | 100 | 98 | | | |
| 28 | 0.28 | 20 | 1.12 | | | | 100 (0) | 100 | | | |
| 28 | 1.12 | 20 | 1.12 | | | | 90 | 70 | | | 15 18 |
| 28 | 0.004 | 20 | 4.48 | | | 15 43 | | | | | |

-continued

| | | | | | | | | | | | | | | |
|---|---|---|---|---|---|---|---|---|---|---|---|---|---|---|
| 28 | 0.01 | 20 | | | 85 | | | | | | 50 (66) | 95 (48) | | |
| 28 | 0.01 | 20 | 4.48 | | 80 | 75 | | | | | | | | |
| 28 | 0.07 | 20 | 4.48 | 5 | 80 (10) | 75 | | | | | | | | |
| 28 | 0.28 | 20 | 4.48 | 20 (50) (59) | 95 (4) | 88 | | | | | | | | |
| 28 | 1.12 | 20 | 4.48 | | 100 (0) | 98 | | 20 | 5 | | | | | |
| 29 | 0.01 | 20 | 1.12 | | | 100 | 50 (0) | 27 100 (9) 70 95 (0) | 55 60 | 73 95 | | | | (17) 75 45 (40) |
| 29 | 0.07 | 20 | 1.12 | | | | 25 (55) | 55 | | | | | | |
| 29 | 0.28 | 20 | 1.12 | 0 (100) | | | 100 (0) | 100 | | | 85 95 | (11) 95 | | |
| 29 | 0.56 | 20 | 1.12 | | | | 95 (4) | 98 | | | 75 (11) (22) | 95 | | |
| 29 | 1.12 | 20 | 1.12 | | | | 80 (12) | 90 | | | | | | |
| 29 | 1.12 | 20 | 4.48 | 15 (84) | 63 | | 0 (100) | 27 85 70 95 (0) | 55 | 73 | | | | |
| 29 | 0.01 | 20 | 4.48 | | | | 85 | 55 | | | | | | |
| 29 | 0.07 | 20 | 4.48 | 0 (100) | | | 75 | 100 | | | | | | |
| 29 | 0.28 | 20 | 4.48 | | | | 100 | 100 (0) 0 (100) | | | | | 10 10 (0) 0 (100) | 12 |
| 29 | 0.56 | 20 | 4.48 | | | | | 98 | | | 85 95 (11) | | | |
| 29 | 1.12 | 20 | 4.48 | 10 (90) | 93 | | 90 (0) | 90 | | | 85 (11) | 95 | | |
| 30 | 0.01 | 20 | 0.14 | | | 100 (0) | 0 (100) | 40 0 (100) | 7 | | | | 0 0 (100) | 10 12 |
| 30 | 0.03 | 20 | 0.14 | | | 100 (0) | 0 (100) | 50 0 (100) | 12 | | | | | |
| 30 | 0.01 | 20 | 0.56 | | | 100 (0) | 0 (100) | 40 30 | 7 | | | | | |
| 30 | 0.03 | 20 | 0.56 | | | 100 (0) | 0 (100) | 50 0 (100) | 12 | | | | 30 (25) | 40 |
| 30 | 1.12 | 20 | 1.12 | | | | 35 (30) | | | | 50 (44) | 88 | 70 | 50 |
| 30 | 1.12 | 20 | 1.12 | 20 (79) | 93 | | | | | | 95 | 93 | | |
| 30 | 4.48 | 20 | 1.12 | 95 (3) | 97 | | 45 | | | | | | | |
| 30 | 4.48 | 20 | 2.24 | | | | 50 (0) | 40 0 (100) 50 0 (100) | 7 12 | | | | | |
| 30 | 0.01 | 20 | 2.24 | | | | | | | | | | | |
| 30 | 0.03 | 20 | | | | | | | | | | | | |

-continued

| | | | | | | | | | | | | | | |
|---|---|---|---|---|---|---|---|---|---|---|---|---|---|---|
| 30 | 1.12 | 20 | 1.12 | | | | 100 (0) | 100 | | | | | | |
| 30 | 1.12 | 20 | 4.48 | 35 (63) | 93 | | 100 (0) | 100 | | | | | | |
| 30 | 4.48 | 20 | 4.48 | 65 (33) | 97 | | 100 (0) | 100 | | | | | | |
| 30 | 4.48 | 20 | 4.48 | | | | 95 (5) | 85 | 80 | | | 40 | | |
| 31 | 0.14 | 20 | 0.56 | 0 | | 10 | 75 (12) | 35 | | | | | | |
| 31 | 0.14 | 20 | 0.56 | | | 89 | 60 | 60 | | | | | | |
| 31 | 0.14 | 20 | 0.56 | | | 88 | 85 | | | | 0 (100) | 0 | | |
| 31 | 0.56 | 20 | 0.56 | 0 | | | 95 | 90 | | | | | | |
| 31 | 0.56 | 20 | 0.56 | 30 (60) | 75 | | 70 (13) | 80 | 50 (0) | | 28 | 30 (7) | 32 100 (0) | 100 95 (0) | 100 100 |
| 31 | 0.56 | 20 | 2.24 | | | | 85 (6) | 90 | 40 | | | | 32 95 (5) | 100 (0) | 100 |
| 31 | 0.14 | 20 | 2.24 | | | | 90 25 (59) | 85 60 | | | | | | | |
| 31 | 0.14 | 20 | 2.24 | 0 | | | 55 90 | 35 90 | 35 (30) | | 50 | 30 (7) | 32 95 (0) | 95 100 (0) | 100 100 |
| 31 | 0.14 | 20 | 2.24 | 5 (94) | 75 | 90 (4) | 90 (0) | 90 | | | 28 | 95 (0) | | | |
| 31 | 0.14 | 20 | 8.96 | 0 | | 93 | 70 (13) | 80 | 30 | | 50 | 30 (7) | 32 80 (20) | 100 100 (0) | 100 |
| 31 | 0.14 | 20 | 8.96 | 10 (87) | 75 | | 65 25 (59) | 35 60 | 30 (40) | | | 90 (6) | 95 100 (0) | 100 | |
| 31 | 0.56 | 20 | 8.96 | 35 | 17 | | 95 95 | 85 90 | | | 50 | | | | |
| 31 | 0.56 | 20 | 8.96 | 50 (42) | 85 | | 90 (0) | 90 | 95 48 | 100 | 7 8 (0) | 7 (0) | 8 90 | 25 | 78 |
| 33 | 0.56 | 20 | 0.56 | 20 (78) | 87 | | 75 (7) | 80 | 100 35 | 100 (0) | 17 5 (86) | | 35 55 (30) | 90 | 25 |
| 33 | 1.12 | 20 | 0.56 | 8 (53) | 17 | | | | 100 83 | 100 (0) | 93 60 | | 32 93 (7) | | 100 |
| 33 | 2.24 | 20 | 2.24 | 0 (100) | 85 | | | | 95 0 | 95 (0) | 7 13 | 17 45 | 8 95 (0) | | 25 |
| 33 | 0.56 | 20 | 2.24 | 93 | 87 | | | | 100 35 | 100 (0) | | | 35 100 (0) | 100 | 78 |
| 33 | 1.12 | 20 | 2.24 | | | | | | 100 50 | 85 (11) | 93 16 (50) | | 32 35 (65) | 100 | 100 |
| 33 | 2.24 | 20 | 8.96 | 8 (53) | 17 | | | | 95 33 (47) | 100 | 7 10 | | 8 70 | 25 | 25 |
| 33 | 0.56 | 20 | 8.96 | 68 | 85 | | | | 100 25 | | 17 15 | | 35 95 | | 78 |

-continued

| Ex. | Dose | Time | Dose | % (%) | % | % | % (%) | % | % (%) | % |
|---|---|---|---|---|---|---|---|---|---|---|
| 33 | 2.24 | 20 | 8.96 | (20) 23 (74) | | | | | | 87 |
| 19 | 0.009 | 12 | 1.12 | 15 (84) | | | | | | 90 |
| 19 | 0.01 | 12 | 1.12 | | | 80 (12) | 90 | 100 (0) | | |
| 19 | 0.03 | 12 | 1.12 | 90 (8) | | 95 | 85 | 100 (0) | | 97 |
| 19 | 0.03 | 12 | 1.12 | | | 95 (0) | 90 95 | (20) | | |
| 19 | 0.07 | 12 | 1.12 | | | 85 (6) | 95 | 75 (40) | 93 33 (58) | |
| 19 | 0.14 | 12 | 1.12 | 0 (100) | 10 (67) 30 | 95 (0) | 90 | 85 (4) | 88 | 90 |
| 19 | 0.009 | 12 | 4.48 | | 10 (86) 70 | 75 (17) | 90 | | | |
| 19 | 0.01 | 12 | 4.48 | | | 95 | 85 | | | |
| 19 | 0.03 | 12 | 4.48 | 0 (100) | | 95 | 90 | 90 88 | | |
| 19 | 0.03 | 12 | 4.48 | | | 90 (6) | 95 | | | 97 |
| 19 | 0.07 | 12 | 4.48 | 15 (85) | 35 (50) 30 | 95 | 90 | 95 (0) | 95 | |
| 19 | 0.14 | 12 | 4.48 | | 10 (55) 70 22 | 100 | 95 | | | |
| 20 | 0.004 | 12 | 1.12 | | | 70 | 25 | | | 12 |
| 20 | 0.004/0.004 | 12 | 1.12/1.12 | 0 (100) 35 | | 65 10 (0) | 30 10 | 35 | 5 (50) 27 | 38 |
| 20 | 0.009 | 12 | 1.12 | | | 10 (75) | 40 | | 10 | |
| 20 | 0.009 | 12 | 1.12 | 15 (61) | | 80 | 60 | 25 (41) | 42 | |
| 20 | 0.009/0.004 | 12 | 1.12/4.48 | | 80 73 22 | 80 (0) | 35 25 | | 95 5 (50) | 12 |
| 20 | 0.004 | 12 | 4.48 | 0 (100) | 0 (100) | 65 | 10 | | | |
| 20 | 0.004 | 12 | 4.48 | | | 25 | 30 | 40 | 27 | 38 |
| 20 | 0.009 | 12 | 4.48 | | | 30 (0) | 40 | | | |
| 20 | 0.009 | 12 | 4.48 | 15 (61) | 0 73 | 35 (13) 50 | 35 | 40 (5) | 40 (42) 42 | 68 10 |
| 20 | 0.03 | 12 | 1.12 | | | 60 (0) | 60 | | | |
| 23 | 0.03 | 12 | 1.12 | | 0 | 65 | 15 | 40 | 10 (60) | 68 |
| 23 | 0.03/0.14 | 12 | 1.12/1.12 | 0 (100) | | 15 50 (34) | 75 | | 42 | 25 |

-continued

| Ex | A | B | C | D | E | F | G | H | I | J |
|----|----|----|----|----|----|----|----|----|----|----|
| 23 | 0.14 | 12 |  |  |  | 60 | 55 | 50 |  |  |
| 23 | 0.03 | 12 | 4.48 |  |  | 15 | 40 (80) | 15 | 80 (4) | 83 |
| 23 | 0.03 | 12 | 4.48 | 5 |  |  | 20 (38) |  | 45 | 25 |
| 23 | 0.14 | 12 | 4.48 |  | 58 | 20 (66) | 65 | 50 | 75 (10) | 83 |
| 23 | 0.14 | 12 | 4.48 | 10 (86) | 58 |  | 30 |  |  |  |
| 25 | 0.14 | 12 | 1.12 | 68 |  | 15 (35) | 15 | 75 | 40 (24) | 52 |
| 25 | 0.14 | 12 | 1.12 |  | 23 | 90 (6) | 48 |  | 90 (6) | 95 |
| 25 | 0.56 | 12 | 1.12 |  | 95 | 35 | 95 |  | 95 (0) | 52 |
| 25 | 0.14 | 12 | 4.48 |  | 23 | 70 (27) | 48 |  |  | 95 |
| 25 | 0.56 | 12 | 4.48 |  | 95 | 0 (100) | 95 | 85 (11) 100 | 95 95 (0) 60 |  |
| 26 | 0.03 | 12 | 1.12 | 95 |  |  |  | 100 | 98 95 (0) 83 | 68 |
| 26 | 0.07 | 12 | 1.12 | 50 (48) |  | 85 (11) |  | 95 (4) 100 | 95 97 | 40 |
| 26 | 0.07 | 12 | 1.12 |  | 95 |  |  | 100 | 55 |  |
| 26 | 0.14 | 12 | 1.12 | 100 |  | 55 (43) |  | 95 (0) 70 | 95 95 (0) 60 | 25 (64) |
| 26 | 0.28 | 12 | 1.12 | 95 (5) |  |  |  | 90 | 83 | 68 |
| 26 | 0.28 | 12 | 4.48 | 50 (48) |  | 35 (64) | 95 | 95 (4) 100 | 98 95 (0) 97 | 0 |
| 26 | 0.03 | 12 | 4.48 |  |  | 80 (16) |  | 95 | 55 | 80 |
| 26 | 0.07 | 12 | 4.48 |  |  |  |  |  |  |  |
| 26 | 0.07 | 12 | 4.48 |  |  |  |  |  |  |  |
| 26 | 0.14 | 12 | 4.48 | 95 (5) | 100 |  | 40 |  |  |  |
| 26 | 0.28 | 12 | 4.48 | 0 (100) 12 |  | 5 (89) 85 (11) | 65 |  |  |  |
| 27 | 0.28 | 12 | 1.12 | 0 (100) 12 |  |  | 40 |  |  |  |
| 27 | 0.14 | 12 | 1.12 | 10 (82) 53 |  |  | 65 |  |  |  |
| 27 | 0.56 | 12 | 4.48 | 0 (100) 12 |  |  | 70 |  |  | 15 (17) |
| 27 | 0.14 | 12 | 4.48 | 0 (100) 53 |  | 43 | 80 |  |  | 18 |
| 28 | 0.56 | 12 | 4.48 |  |  | 80 | 75 |  |  | 65 (14) |
| 28 | 0.004 | 12 | 1.12 |  |  |  |  |  |  |  |
| 28 | 0.01 | 12 | 1.12 |  | 95 | 80 | 70 |  |  |  |
| 28 | 0.01 | 12 | 1.12 | 0 (100) 10 | 95 | 85 | 75 |  |  | 75 |

-continued

| Ex. | | | | | | | | | |
|---|---|---|---|---|---|---|---|---|---|
| 28 | 0.07 | 12 | | | 80 (10) | 88 | | | |
| 28 | 0.28 | 12 | 1.12 | 30 (38) | 95 (4) | 98 | | | 25 (42) 43 |
| 28 | 1.12 | 12 | 1.12 | | 100 (0) | 100 | | | 65 (32) 95 |
| 28 | 0.004 | 12 | 1.12 | | 75 | 70 | 20 | 5 | |
| 28 | 0.01 | 12 | 4.48 | | 95 | 75 | 15 (75) | 60 | |
| 28 | 0.01 | 12 | 4.48 | 5 (50) | 70 (7) | 75 | | 10 (45) | 18 |
| 28 | 0.01 | 12 | 4.48 | 10 (80) | 80 (10) | 88 | | 0 (100) | 75 |
| 28 | 0.07 | 12 | 4.48 | | 100 (0) | 98 | | | |
| 28 | 0.28 | 12 | 4.48 | | 100 (0) | 100 | | | |
| 28 | 1.12 | 12 | 1.12 | | | | | | |
| 29 | 0.01 | 12 | 1.12 | | 10 (63) | 10 | 5 (0) | 5 | |
| 29 | 0.07 | 12 | 1.12 | 0 (100) | 0 (100) | 0 | 25 (59) | 60 | |
| 29 | 0.28 | 12 | 1.12 | | 10 (82) | 10 | 27 95 | 73 | 85 (11) 95 |
| 29 | 0.56 | 12 | 1.12 | | 100 (0) | 100 | 70 100 | 95 | 95 (0) 95 |
| 29 | 1.12 | 12 | 1.12 | 30 (68) | 100 | 98 | 55 | | |
| 29 | 1.12 | 12 | 4.48 | | 65 (28) | 90 | | 0 (100) | 10 |
| 29 | 0.01 | 12 | 4.48 | 0 (100) | 0 (100) | 0 | 27 95 | 73 | 80 (16) 95 |
| 29 | 0.07 | 12 | 4.48 | | 0 (100) | 0 | 70 95 | 95 | 85 (11) 95 |
| 29 | 0.28 | 12 | 4.48 | | 65 | 55 | 0 (0) | 15 | |
| 29 | 0.56 | 12 | 4.48 | 35 (63) | 100 | 100 | 0 (100) | 0 | |
| 29 | 1.12 | 12 | 4.48 | | 100 | 90 | | | |
| 29 | 1.12 | 12 | 4.48 | | 100 | 98 | (100) | 12 | |

| | | | | | | | | | |
|---|---|---|---|---|---|---|---|---|---|
| 30 | 1.12 | 12 | 1.12 | | | 90 | | 100 100 (0) | 0 40 (100) |
| 30 | 1.12 | 12 | 1.12 | 80 93 (14) | | 88 | | 100 100 (0) 95 (5) | |
| 30 | 4.48 | 12 | 1.12 | | | | | 100 100 (0) | 70 50 |
| 30 | 4.48 | 12 | 1.12 | 95 97 (3) | | 93 | | 100 100 (0) | |
| 30 | 1.12 | 12 | 4.48 | | | 90 | | 100 100 (0) | 10 40 (75) |
| 30 | 1.12 | 12 | 4.48 | 60 93 (36) | | 88 | | 100 100 (0) | |
| 30 | 4.48 | 12 | 4.48 | | | | | 100 100 (0) | 90 50 |
| 30 | 4.48 | 12 | 4.48 | 95 97 (3) | | 93 | | 100 100 (0) | |
| 19 | 0.009 | 18 | 1.12 | | | | | 90 90 (0) | |
| 19 | 0.01 | 18 | 1.12 | 5 90 (95) | | | | 95 85 | |
| 19 | 0.03 | 18 | 1.12 | | | | | 95 90 | |
| 19 | 0.03 | 18 | 1.12 | | | 25 30 (17) | | 95 95 (0) | |
| 19 | 0.07 | 18 | 1.12 | 80 97 (18) | | | | 90 90 (0) | 95 88 |
| 19 | 0.14 | 18 | 1.12 | | | 60 70 (15) | | 100 95 | |
| 19 | 0.009 | 18 | 4.48 | | | | | 85 90 | 95 (0) |
| 19 | 0.01 | 18 | 4.48 | 5 90 (95) | | | | 85 85 (6) | |
| 19 | 0.03 | 18 | 4.48 | | | 0 30 (100) | | 85 (0) | 90 88 |
| 19 | 0.03 | 18 | 4.48 | 20 97 (80) | | | | 100 95 | |
| 19 | 0.07 | 18 | 4.48 | | | 40 70 (43) | | 95 90 | 95 (0) |
| 19 | 0.14 | 18 | 1.12 | | | 20 22 (10) | | 90 90 (0) | |
| 20 | 0.004 | 18 | 1.12 | 0 12 (100) | | | | 95 (0) | 0 10 (100) |
| 20 | 0.004 | 18 | 1.12 | | | | | 25 25 (0) | |
| 20 | 0.004 | 18 | 1.12 | 10 38 (74) | | 10 73 (87) | | 15 10 | 25 27 (8) |
| 20 | 0.009 | 18 | 1.12 | | | | | 55 30 | 10 42 (77) |
| 20 | 0.009 | 18 | 1.12 | | | | | 20 40 (50) | 10 68 (86) |
| 20 | 0.009 | 18 | 1.12 | | | | | 25 35 (29) | 20 27 (26) |
| 20 | 0.004 | 18 | 4.48 | | | | | 65 60, 15 30 (50) | |

-continued

| Cpd | Dose | | Rate | | | | | | | |
|---|---|---|---|---|---|---|---|---|---|---|
| 20 | 0.004 | 18 | 4.48 | 0 (100) | | | 0 (100) 85 | | | |
| 20 | 0.004 | 18 | 4.48 | | | 0 (100) 22 | 30 (50) | | | |
| 20 | 0.009 | 18 | 4.48 | 12 | | 80 73 | 10 (72) 35 | | | 45 42 |
| 20 | 0.009 | 18 | 4.48 | | | | 0 (100) 40 | | | |
| 20 | 0.009 | 18 | 4.48 | 30 (22) | | | | | | |
| 26 | 0.03 | 18 | 1.12 | 38 | | 90 (6) 95 | | 95 (0) 95 83 | | |
| 26 | 0.07 | 18 | 1.12 | | | | | 100 60 | 95 | 0 |
| 26 | 0.07 | 18 | 1.12 | 60 (37) 95 | | 90 (6) 95 | | 100 98 | 95 (0) | 0 68 (100) |
| 26 | 0.14 | 18 | 1.12 | | | | | 95 55 | 95 | |
| 26 | 0.28 | 18 | 1.12 | 95 (5) 100 | | 15 (85) 95 | | 95 (3) 97 | 95 | 0 |
| 26 | 0.28 | 18 | 1.12 | | | | | 90 (6) 95 | 95 (0) | |
| 26 | 0.03 | 18 | 4.48 | | | 95 (0) 95 | | 90 60 | 95 | 0 68 (100) |
| 26 | 0.07 | 18 | 4.48 | 45 (53) 95 | | 40 (7) 43 | | 35 (58) 83 | 95 (0) | 0 |
| 26 | 0.07 | 18 | 4.48 | | | 95 (0) 95 | | 95 (4) 98 | 95 | 30 (56) 68 |
| 26 | 0.14 | 18 | 4.48 | | | | | 100 55 | | 0 (100) 18 |
| 26 | 0.28 | 18 | 4.48 | 95 (5) 100 | | | 75 70 | 100 97 | | 35 (54) 75 |
| 26 | 0.28 | 18 | 4.48 | | | | 80 75 | | | |
| 28 | 0.004 | 18 | 1.12 | | | | 75 | | | |
| 28 | 0.01 | 18 | 1.12 | 0 (100) 10 | | | 55 (27) 75 | | 5 (0) 5 | |
| 28 | 0.01 | 18 | 1.12 | 5 (90) 48 | | | 80 (10) 88 | | 15 (75) 60 | |
| 28 | 0.07 | 18 | 1.12 | | | | 95 (4) 98 | | | |
| 28 | 0.28 | 18 | 1.12 | | | | 100 (0) 100 | | | |
| 28 | 1.12 | 18 | 1.12 | | | 10 (77) 43 | 60 (15) 70 | | | 0 (100) 18 |
| 28 | 0.004 | 18 | 4.48 | | | | 85 75 | | | |
| 28 | 0.01 | 18 | 4.48 | 5 (50) 10 | | | 85 75 | | | |
| 28 | 0.01 | 18 | 4.48 | | | 30 (69) 95 | | | | 0 (100) 75 |
| 28 | 0.07 | 18 | 4.48 | 10 (80) 48 | | | 95 88 | | | |

| Ex. | Dose | Time | Dose | Result 1 | Result 2 | Result 3 |
|---|---|---|---|---|---|---|
| 28 | 0.28 | 18 | 4.48 | | | 95, 98 (4) |
| 28 | 1.12 | 18 | 4.48 | | | 100 (0) |
| 29 | 0.01 | 18 | 1.12 | | | |
| 29 | 0.07 | 18 | 1.12 | | | |
| 29 | 0.28 | 18 | 1.12 | 0, 63 (100) | 0, 27 (100) | 20, 5 |
| 29 | 0.56 | 18 | 1.12 | 15, 93 (84) | 0, 70 (100) | 70, 60 |
| 29 | 1.12 | 18 | 1.12 | 90, 95 (6) | 75, 95 | 95, 73 |
| 29 | 1.12 | 18 | 4.48 | 95, 95 (0) | 55 | 80, 95 (16) |
| 29 | 0.01 | 18 | 4.48 | | 100, 100 | |
| 29 | 0.07 | 18 | 4.48 | | 100, 98 | |
| 29 | 0.28 | 18 | 4.48 | | 95, 90 | |
| 29 | 0.56 | 18 | 4.48 | 10, 63 (85) | 25, 27 (8) | 85, 73 |
| 29 | 1.12 | 18 | 4.48 | 30, 93 (68) | 85, 70 (0) | 90, 95 (6) |
| 30 | 1.12 | 18 | 1.12 | 85, 93 (9) | 85, 55 | 0, 10 (100) |
| 30 | 1.12 | 18 | 1.12 | | 100, 100 | 0, 12 (100) |
| 30 | 1.12 | 18 | 1.12 | 25, 93 (74) | 100 (0) | |
| 30 | 1.12 | 18 | 1.12 | 95, 97 (3) | 95, 90 | |
| 30 | 4.48 | 18 | 4.48 | | 95 (5) | |
| 30 | 4.48 | 18 | 4.48 | | 100 (0) | |
| 30 | 1.12 | 18 | 4.48 | 25, 93 (74) | 100 (0) | 0, 10 (100) |
| 30 | 1.12 | 18 | 4.48 | 95, 97 (3) | 100 (0) | 0, 12 (100) |
| 19 | 0.009 | 24 | 1.12 | | 95 (5) | 0, 40 (100) |
| 19 | 0.01 | 24 | 1.12 | | 100 (0) | |
| 19 | 0.03 | 24 | 1.12 | 15, 30 (50) | 80, 90 (12) | 95, 50 |
| 19 | 0.03 | 24 | 1.12 | | 95, 85 | 15, 40 (63) |
| 19 | 0.07 | 24 | 1.12 | 80, 97 (18) | 100, 95 | 100, 50 |
| 19 | | 24 | | | 95, 90 | 85, 88 (4) |
| 19 | | 24 | | | 95, 90 | 95, 95 (0) |

-continued

| Cmpd | Dose | Time | Conc. | Col 5 | Col 6 | Col 7 | Col 8 |
|------|------|------|-------|-------|-------|-------|-------|
| 19 | 0.14 | 24 | 1.12 | | 75 | 100 90 (0) | 75 |
| 19 | 0.00 | 24 | 4.48 | | 70 | 95 90 | 70 |
| 19 | 0.01 | 24 | 4.48 | | | 100 85 | |
| 19 | 0.03 | 24 | 4.48 | 0 (100) | 30 | 100 95 | |
| 19 | 0.03 | 24 | 4.48 | | | 90 90 | 95 (0) |
| 19 | 0.07 | 24 | 4.48 | 30 (58) | 70 | 85 90 (6) | |
| 19 | 0.14 | 24 | 4.48 | 0 (100) | 22 | 100 95 | 95 88 |
| 20 | 0.004 | 24 | 1.12 | | | 25 25 (0) | 0 (100) 10 |
| 20 | 0.004 | 24 | 1.12 | | | 25 30 (17) | |
| 20 | 0.004 | 24 | 1.12 1.12 | 15 (85) | | 25 10 | |
| 20 | 0.009 | 24 | 4.48 4.48 | 30 (22) | 20 (73) | 70 60 | 60 (12) 10 |
| 20 | 0.009 | 24 | 1.12 | | 0 (100) | 55 40 (43) | 5 (50) |
| 20 | 0.009 | 24 | 4.48 | 0 (100) | 22 | 20 35 (60) | |
| 20 | 0.004 | 24 | 4.48 | | | 10 25 | |
| 20 | 0.004 | 24 | 4.48 | | | 30 30 | |
| 20 | 0.004 | 24 | 4.48 | 0 (100) | | 0 10 (0) | 50 27 |
| 20 | 0.009 | 24 | 4.48 | 0 (100) | 40 (46) | 50 40 | 60 42 |
| 20 | 0.009 | 24 | 4.48 | | | 50 35 | 50 68 (27) |
| 20 | 0.009 | 24 | 4.48 | 5 (68) | 0 | 15 60 (75) | 0 (100) |
| 23 | 0.03 | 24 | 1.12 | 0 (100) | | 40 15 | 0 25 (100) |
| 23 | 0.03 | 24 | 1.12 1.12 | | 20 (66) | 0 75 (87) | |
| 23 | 0.14 | 24 | | | 20 | 70 50 | 40 83 (52) |
| 23 | 0.14 | 24 | 4.48 | | | 45 15 | 0 25 (100) |
| 23 | 0.03 | 24 | 4.48 4.48 | 15 (78) | 20 (66) | 10 75 (67) | 0 83 |
| 23 | 0.03 | 24 | 4.48 | | 0 (100) | 45 50 (10) | 85 52 |
| 25 | 0.14 | 24 | 1.12 | | 35 (64) | 75 48 | 85 |
| 25 | 0.56 | 24 | 1.12 | | | 90 95 (6) | 95 95 (0) |

-continued

| Cpd | Dose | Hr | Dose | Data |
|---|---|---|---|---|
| 25 25 | 0.14 | 24 | 4.48 | 25 23 95; 85 48 95 (48); 85 52 95 (0) |
| 25 | 0.56 | 24 | 4.48 | 85 95 (11); 50; 95 |
| 26 | 0.03 | 24 | 1.12 | 85 95 (11) |
| 26 | 0.07 | 24 | 1.12 | 55 95 (43); 90 95 (6); 85 95 (0) |
| 26 | 0.07 | 24 | 1.12 | 70 83 (16) 100 60 |
| 26 | 0.14 | 24 | 1.12 | 95 (5); 100 98; 95 95 (0) |
| 26 | 0.28 | 24 | 1.12 | 95 100 (5); 100 97; 95 95 (0) |
| 26 | 0.28 | 24 | 1.12 | 10 95 (90); 100 55; 0 |
| 26 | 0.03 | 24 | 4.48 | 95 100; 85 95 (11) 75; 0 68 (100) |
| 26 | 0.07 | 24 | 4.48 | 80 95 (16); 90 83 |
| 26 | 0.07 | 24 | 4.48 | 95 98 (4) 100 97; 0 68 |
| 26 | 0.14 | 24 | 4.48 | 90 95 (6); 90 55; 25 68 (64) |
| 26 | 0.28 | 24 | 4.48 | 95 (5) 12 |
| 27 | 0.14 | 24 | 1.12 | 0 (100) 5 53 (91); 10 43 (77); 15 (63) 65 (0); 0 18 (100) |
| 27 | 0.56 | 24 | 1.12 | 0 12; 40 43 (58); 30 (40) 65 (25); 10 75 (87) |
| 27 | 0.14 | 24 | 4.48 | 0 (100) 35 53 (34); 65 (0) 70 |
| 27 | 0.56 | 24 | 4.48 | 5 10 (50); 20 43 (54); 60 75 (20); 0 18 (100) |
| 28 | 0.004 | 24 | 1.12 | 45 75 (40); 0 5 (100) |
| 28 | 0.01 | 24 | 1.12 | 80 98 (10); 40 60 (34) |
| 28 | 0.01 | 24 | 1.12 | 5 48 (90); 100 98; 10 75 (100) |
| 28 | 0.07 | 24 | 1.12 | 100 100 |
| 28 | 0.28 | 24 | 1.12 | 50 43 (48); 85 70; 0 18 (100) |
| 28 | 1.12 | 24 | 1.12 | 70 (7) 75 |
| 28 | 0.004 | 24 | 4.48 | 0 (100) 10; 90 75; 0 75 (100) |
| 28 | 0.01 | 24 | 4.48 | 80 88 |
| 28 | 0.01 | 24 | 4.48 | 5 48 |
| 28 | 0.07 | 24 | 4.48 | |

| Ex | Dose1 | Time | Dose2 | Result A | Result B | Result C | Result D |
|---|---|---|---|---|---|---|---|
| 28 | 0.28 | 24 | 4.48 | (90) | | | |
| 28 | 1.12 | 24 | 4.48 | | 95 (10) 95 (4) 98 100 (5) | | |
| 29 | 0.01 | 24 | 1.12 | | | | |
| 29 | 0.07 | 24 | 1.12 | | | | |
| 29 | 0.28 | 24 | 1.12 | 0 (100) | 90 (6) 95 95 (0) | 0 (100) 80 | 5 5 30 (0) 60 (50) |
| 29 | 0.56 | 24 | 1.12 | 30 (68) | | 27 70 55 | |
| 29 | 1.12 | 24 | 1.12 | | | 100 100 | 90 95 (0) 73 |
| 29 | 1.12 | 24 | 4.48 | 20 (69) | | 100 (0) 98 | 95 (0) |
| 29 | 0.01 | 24 | 4.48 | | | 80 (12) | |
| 29 | 0.07 | 24 | 4.48 | | | 0 (100) 80 | |
| 29 | 0.28 | 24 | 4.48 | 55 (41) | 90 (6) 95 95 (0) | 27 70 55 | |
| 29 | 0.56 | 24 | 4.48 | 90 (4) | | 100 100 | 90 95 (0) 73 |
| 30 | 1.12 | 24 | 4.48 | | 70 88 (21) | 95 (0) 95 90 | 10 10 (0) 10 12 (17) |
| 30 | 1.12 | 24 | 1.12 | 30 93 (68) | 95 | 95 100 100 (5) 100 (0) 100 (0) | 10 10 (0) 10 12 (17) |
| 30 | 1.12 | 24 | 1.12 | | 85 88 (4) | 100 (0) 100 (0) 100 (0) 95 100 | |
| 30 | 1.12 | 24 | 1.12 | 95 97 (3) | | 100 (0) 50 | 5 40 (88) |
| 30 | 4.48 | 24 | 4.48 | | 93 | 10 75 (87) | 100 50 |
| 30 | 4.48 | 24 | 4.48 | 35 93 (63) | 95 | 0 25 75 (67) | 0 40 (100) |
| 30 | 1.12 | 24 | 4.48 | 95 97 (3) | 93 | 10 70 15 | 60 50 |
| 30 | 1.12 | 24 | 4.48 | | | | |
| 23 | 0.03 | 26 | 1.12 | 5 | | | |
| 23 | 0.14 | 26 | 1.12 | 35 68 (49) | | | |
| 23 | 0.03 | 26 | 4.48 | 0 | 0 | | |
| 23 | 0.14 | 26 | 4.48 | 30 68 (56) | | | |
| 23 | 0.03 | 26 | 1.12 | 5 | | | 5 25 (80) |
| 23 | 0.03 | 19 | 1.12 | | | | |

-continued

| | | | | | | | | | | | |
|---|---|---|---|---|---|---|---|---|---|---|---|
| 23 | 0.14 | 19 | 1.12 | | | | | 70 | 50 | 95 | 83 |
| 23 | 0.14 | 19 | 1.12 | 15 (78) | 68 | 20 (66) | 58 | 55 (27) | 75 | | |
| 23 | 0.03 | 19 | 4.48 | 0 | | 0 | | 50 | 15 | 0 (100) | 25 |
| 23 | 0.03 | 19 | 4.48 | | | | | 60 | | 90 | 83 |
| 23 | 0.14 | 19 | 4.48 | | | 10 (83) | 58 | 40 | 50 | | |
| 23 | 0.14 | 19 | 4.48 | 35 (49) | 68 | | | 40 (20) | 75 | 80 | 52 |
| 25 | 0.14 | 19 | 1.12 | | | 20 (14) | 23 | 65 (47) | 48 | 95 | 95 |
| 25 | 0.56 | 19 | 1.12 | | | 95 (0) | 95 | 95 | 95 | 90 (0) | 52 |
| 25 | 0.14 | 19 | 4.48 | | | 80 (0) | 23 | 60 (0) | 48 | 95 | 95 |
| 25 | 0.56 | 19 | 4.48 | | | 90 | 95 | 95 | 95 | | |
| 27 | 0.14 | 19 | 1.12 | 0 (100) | 12 | | (6) | 60 | 40 | | |
| 27 | 0.56 | 19 | 1.12 | 70 | 53 | | | 80 | 65 | | |
| 27 | 0.14 | 19 | 4.48 | 0 (100) | 12 | | | 60 | 40 | | |
| 27 | 0.56 | 19 | 4.48 | 85 | 53 | | | 90 | 65 | 95 | 88 |
| 19 | 0.009 | 23 | 1.12 | | | | | 90 | 90 | | |
| 23 | 0.01 | 23 | 1.12 | 10 (89) | 90 | 0 (100) | 30 | 85 (0) | 85 | | |
| 23 | 0.03 | 23 | 1.12 | | | | | 95 (0) | 95 | 95 (0) | 95 |
| 23 | 0.03 | 23 | 1.12 | | | 75 | 70 | 95 | 90 | | |
| 23 | 0.07 | 23 | 1.12 | 30 (70) | 97 | | | 80 (12) | 90 | | |
| 23 | 0.14 | 23 | 1.12 | | | | | 95 (0) | 95 | 95 | 88 |
| 23 | 0.009 | 23 | 4.48 | | | | | 90 (0) | 90 | | |
| 23 | 0.01 | 23 | 4.48 | 0 (100) | 90 | 0 (100) | 30 | 90 (0) | 85 | 95 (0) | 95 |
| 23 | 0.03 | 23 | 4.48 | | | | | 90 (0) | 90 | | |
| 23 | 0.03 | 23 | 4.48 | | | 30 (58) | 70 | 90 (0) | 95 | | |
| 23 | 0.07 | 23 | 4.48 | 35 (64) | 97 | 10 (55) | 22 | 100 (0) | 95 | | |
| 23 | 0.14 | 23 | 4.48 | | | | | 100 | 90 | | |
| 20 | 0.004 | 23 | 1.12 | | | | | 100 | 95 | | |
| 20 | 0.004 | 23 | 1.12 | | | | | 0 (100) | 25 | 0 (100) | 10 |
| 20 | 0.004 | 23 | 1.12 | 0 (100) | 12 | | | 0 (100) | 30 | | |
| | | | | | | | | 0 (100) | 10 | 20 (26) | 27 |

-continued

| | | | | | | | | | |
|---|---|---|---|---|---|---|---|---|---|
| 20 | 0.009 | 23 | 1.12 | | | 40 40 / 90 (0) 35 | | | |
| 20 | 0.009 | 23 | 1.12 | 10 38 / (74) | 65 73 / (11) 22 | 20 60 / (67) 35 25 | | 60 68 / (12) | |
| 20 | 0.009 | 23 | 1.12 | | 0 22 / (100) | 30 30 / (0) 10 | 55 42 | 5 10 / (50) | |
| 20 | 0.004 | 23 | 4.48 | | | 0 10 / (100) 60 40 | | | |
| 20 | 0.004 | 23 | 4.48 | 0 12 / (100) | | 0 60 / (100) 65 35 | 0 27 / (100) | | |
| 20 | 0.004 | 23 | 4.48 | 15 38 / (61) | | 10 15 / (34) | | | |
| 20 | 0.009 | 23 | 4.48 | | 65 73 / (11) | 0 75 / (54) | | 15 68 / (78) | |
| 20 | 0.009 | 23 | 4.48 | | | 35 50 65 | 55 42 | 10 25 / (60) | |
| 20 | 0.009 | 23 | 4.48 | | 55 58 / (6) | 30 15 | | | |
| 20 | 0.03 | 23 | 1.12 | | 0 | 0 75 / (100) | 75 42 | 80 83 / (4) | |
| 23 | 0.03 | 23 | 1.12 | 0 68 | 30 58 / (49) 23 | 0 55 / (27) 50 | | 5 25 / (80) | |
| 23 | 0.14 | 23 | 1.12 | 5 / (93) | 25 | 15 48 / (70) | | | |
| 23 | 0.14 | 23 | 1.12 | | 90 95 / (6) 23 | 0 95 / (100) | | 85 83 | |
| 23 | 0.03 | 23 | 4.48 | 0 68 | 50 23 | 85 95 / (11) | | 75 52 | |
| 23 | 0.03 | 23 | 4.48 | 15 / (78) | 95 95 / (0) | 0 48 / (100) | | | |
| 23 | 0.14 | 23 | 4.48 | | | 90 95 / (6) | | 95 95 / (0) | 95 (0) |
| 25 | 0.14 | 23 | 1.12 | | | | | 95 95 / (0) | 95 (0) |
| 25 | 0.56 | 23 | 1.12 | | | | | 70 52 | |
| 25 | 0.14 | 23 | 4.48 | | | | | 95 95 / (0) | 95 (0) |
| 25 | 0.56 | 23 | 4.48 | | | | | 0 | |
| 26 | 0.03 | 23 | 1.12 | | 65 95 / (32) | 90 95 85 (6) 60 | | | |
| 26 | 0.07 | 23 | 1.12 | 10 95 / (90) | | 100 83 | | | |
| 26 | 0.07 | 23 | 1.12 | | | 100 98 | | | |
| 26 | 0.14 | 23 | 1.12 | | | 100 97 | | | |
| 26 | 0.28 | 23 | 1.12 | | | 100 55 | | 5 68 / (93) | |
| 26 | 0.28 | 23 | 1.12 | 90 100 / (10) | 85 95 / (11) | 90 95 / (6) | | | |
| 26 | 0.03 | 23 | 4.48 | | | | | | |

-continued

| | | | | | | | | | | | | |
|---|---|---|---|---|---|---|---|---|---|---|---|---|
| 26 | 0.07 | 23 | 4.48 | | | | | 90 | 83 | | 0 | |
| 26 | 0.07 | 23 | 4.48 | 15 (85) | 95 | 0 (100) | 95 | | | | | |
| 26 | 0.14 | 23 | 4.48 | | | | | 0 (100) | 60 | | | |
| 26 | 0.28 | 23 | 4.48 | | | | | 95 (4) | 98 | 95 (0) | 95 | |
| 26 | 0.28 | 23 | 4.48 | 80 (20) | 100 | 80 (16) | 95 | 90 (8) | 97 | | | |
| 27 | 0.14 | 23 | 1.12 | 0 (100) | 12 | | | 85 | 55 | | 0 (100) | 68 |
| 27 | 0.56 | 23 | 1.12 | 0 (100) | 53 | | | | | | | |
| 27 | 0.14 | 23 | 4.48 | 0 (100) | 12 | | | | | | | |
| 27 | 0.56 | 23 | 4.48 | 5 (91) | 53 | | | | | | | |
| 28 | 0.004 | 23 | 1.12 | | | | | 10 (75) | 40 | | | |
| 28 | 0.01 | 23 | 1.12 | 5 (50) | 10 | 10 (77) | 43 | 85 | 65 | | | |
| 28 | 0.01 | 23 | 1.12 | | | | | 30 (25) | 40 | | | |
| 28 | 0.07 | 23 | 1.12 | 5 (90) | 48 | 55 (43) | 95 | 70 | 65 | | | |
| 28 | 0.28 | 23 | 1.12 | | | | | 55 (22) | 70 | | 0 (100) | 18 |
| 28 | 1.12 | 23 | 1.12 | | | | | 95 | 75 | | | |
| 28 | 0.004 | 23 | 4.48 | | | | | 60 (20) | 75 | | 0 (100) | 75 |
| 28 | 0.01 | 23 | 4.48 | 5 (50) | 10 | 10 (77) | 43 | 80 (10) | 88 | 30 | 5 | |
| 28 | 0.01 | 23 | 4.48 | | | | | 95 (4) | 98 | 30 (50) | 60 | |
| 28 | 0.07 | 23 | 4.48 | 5 (90) | 48 | 40 (58) | 95 | 100 (0) | 100 | | | |
| 28 | 0.28 | 23 | 4.48 | | | | | 70 (0) | 70 | | 0 (100) | 18 |
| 28 | 1.12 | 23 | 4.48 | | | | | 80 | 75 | | | |
| 29 | 0.01 | 23 | 1.12 | 0 (100) | 63 | | | 50 (34) | 75 | 25 | 5 | |
| 29 | 0.07 | 23 | 1.12 | | | | | 85 (4) | 88 | 40 (34) | 60 | 0 (100) | 75 |
| 29 | 0.28 | 23 | 1.12 | | | 90 (6) | 95 | 95 (4) | 98 | 95 (0) | 95 | |
| 29 | 0.56 | 23 | 1.12 | | | 95 (0) | 95 | 95 (4) | 100 | | | |
| 29 | 1.12 | 23 | 1.12 | | | | | 50 (5) | 27 | | 0 (100) | 10 |
| 29 | 1.12 | 23 | 1.12 | | | | | | | | 0 (100) | 12 |
| 29 | 0.01 | 23 | 4.48 | 5 (95) | 93 | | | | | | | |

| | | | | 80 | 73 | | | | |
|---|---|---|---|---|---|---|---|---|---|
| | | | | 95 | 70 | | | | |
| | | | | 0 (100) | 55 | | | | |
| | | | | 100 | 100 | | | | |
| | | | | 100 (0) | 98 | | | | |
| | | | | 90 | 90 | | | | |
| | | | | 0 | 27 | 95 | 73 | | |

-continued

| | | | | | | | |
|---|---|---|---|---|---|---|---|
| 29 | 0.07 | 23 | 4.48 | | | 15 70 95 (100) (79) (0) 60 55 | |
| 29 | 0.28 | 23 | 4.48 | 0 (100) | 85 95 (11) | 100 100 (0) (0) 100 100 | |
| 29 | 0.56 | 23 | 4.48 | 63 | 85 95 (11) | | 10 10 (0) 0 12 (100) |
| 29 | 1.12 | 23 | 4.48 | | | 100 100 (0) (0) | |
| 29 | 1.12 | 23 | 4.48 | 93 | 55 88 (38) 95 93 | 100 100 (0) (0) 100 100 (0) (0) 90 85 (0) 80 (6) | 95 95 (0) |
| 30 | 1.12 | 23 | 1.12 | 0 (100) 15 (84) | 25 88 (72) | 100 100 (0) (0) 90 85 (0) | 0 40 (100) 70 50 |
| 30 | 1.12 | 23 | 1.12 | 85 93 (13) | 95 93 | 80 (6) 95 90 (0) | |
| 30 | 1.12 | 23 | 4.48 | 97 | | 95 90 | 88 |
| 30 | 4.48 | 23 | 1.12 | 0 (100) | 85 30 | 90 (6) 90 85 | 90 |
| 30 | 4.48 | 23 | 1.12 | 93 | | 80 (6) 95 | 95 (0) |
| 30 | 1.12 | 23 | 4.48 | 90 | 85 70 | 95 90 | 0 40 (100) |
| 30 | 4.48 | 23 | 1.12 | 97 (18) | | 90 (6) 90 85 (0) | 88 |
| 30 | 4.48 | 23 | 1.12 | 90 (0) | 40 30 | 80 (6) 95 | |
| 19 | 0.009 | 22 | 4.48 | 15 (84) | | 95 90 | 95 (0) |
| 19 | 0.01 | 22 | 1.12 | | | | 60 |
| 19 | 0.03 | 22 | 1.12 | 97 (3) | 85 70 | 95 90 | 95 |
| 19 | 0.03 | 22 | 1.12 | | | | |
| 19 | 0.07 | 22 | 1.12 | 90 (0) | | 95 | 0 10 (100) |
| 19 | 0.14 | 22 | 4.48 | 90 | 80 70 22 | 100 95 60 25 | |
| 19 | 0.009 | 22 | 4.48 | 95 (3) | 10 (55) | 0 10 (100) | |
| 19/20 | 0.14/0.004 | 22 | 4.48/1.12 | 97 | | | |
| 20 | 0.004 | 22 | 1.12 | 12 (100) | | | |

| | | | | | | | | | | | | | |
|---|---|---|---|---|---|---|---|---|---|---|---|---|---|
| 20 | 0.004 | 22 | 1.12 | | | | | 20 | 30 (34) | | | | |
| 20 | 0.009 | 22 | 1.12 | 30 | 38 (22) | | | 10 | 40 (75) | | | | |
| 20 | 0.009 | - 22 | 1.12 | | | | | 60 | 35 | | | | |
| 20 | 0.009 | 22 | 1.12 | | | | | 30 | 60 (50) | | | | |
| 20 | 0.004 | 22 | 4.48 | | | | | 35 | 10 | | | | |
| 20 | 0.004 | 22 | 4.48 | 0 | 12 (100) | | | 15 | 25 (40) | | | 65 | 68 (5) |
| 20 | 0.004 | 22 | 4.48 | | | | | 70 | 30 | | | | |
| 20 | 0.009 | 22 | 4.48 | | | | | 95 | 35 | | | 65 | 68 |
| 20 | 0.009 | 22 | 4.48 | | | 55 | 42 | 65 | 60 | | | | |
| 20 | 0.009 | 22 | 4.48 | 60 | 38 | | | 40 | 40 | | | 40 | 10 |
| 23 | 0.03 | 22 | 1.12 | | | | | 20 | 15 | | | | |
| 23 | 0.03 | 22 | 1.12 | 0 | | | | 0 | | | | | |
| 23 | 0.14 | 22 | 1.12 | 45 | 68 (34) | | | 50 | 75 (34) | 60 | 27 | 80 | 83 |
| 23 | 0.14 | 22 | 1.12 | | | | | 80 | 50 | | | | |
| 23 | 0.03 | 22 | 4.48 | 0 | | | | 35 | 15 | | | 45 | 25 |
| 23 | 0.03 | 22 | 4.48 | | | | | 35 | | | | | |
| 23 | 0.14 | 22 | 4.48 | | | | | 40 | 50 | 80 | 42 | 80 | 83 (4) |
| 23 | 0.14 | 22 | 4.48 | 15 | 68 (78) | | | 35 | 75 (20) | | | | |
| 25 | 0.14 | 22 | 1.12 | 30 | 23 | | | 50 | 48 (54) | | | 85 | 52 |
| 25 | 0.56 | 22 | 1.12 | 95 | 95 | | | 85 | 95 | | | 95 | 95 (0) |
| 25 | 0.14 | 22 | 4.48 | | | | | 80 | 48 (11) | | | 95 | 52 |
| 25 | 0.56 | 22 | 4.48 | 40 | 23 | | | 90 | 95 (6) | | | 95 | 95 (0) |
| 26 | 0.03 | 22 | 1.12 | | | | | | | 75 | 95 | | |
| 26 | 0.07 | 22 | 1.12 | 95 | 95 (0) | | | | | 90 | 60 (22) | | |
| 26 | 0.07 | 22 | 1.12 | | | | | | | 100 | 83 | | 5 |
| 26 | 0.14 | 22 | 1.12 | | | | | | | 95 | 98 (4) | | |
| 26 | 0.28 | 22 | 1.12 | 100 | 100 (0) | | | | | 100 | 97 | 95 | 95 (0) |
| 26 | 0.28 | 22 | 1.12 | | | | | | | 100 | 55 | | |
| 26 | 0.03 | 22 | 4.48 | | | | | | | 95 | 95 | | |
| 26 | 0.07 | 22 | 4.48 | 90 | 95 (6) | | | | | 85 | 60 (0) | | 95 |
| 26 | 0.07 | 22 | 4.48 | | | | | | | 100 | 83 | | 65 |
| 26 | 0.14 | 22 | 4.48 | 95 | 95 (0) | | | | | 100 | 98 | 95 | 95 (0) |

-continued

| | | | | | | | | | | |
|---|---|---|---|---|---|---|---|---|---|---|
| 26 | 0.28 | 22 | 4.48 | 100 (0) | 100 | | 95 (0) | 95 | | 95 | |
| 26 | 0.28 | 22 | 4.48 | | | 60 | | | 100 | 55 | 68 (20) |
| 27 | 0.14 | 22 | 1.12 | 5 (59) | 12 | 70 55 | 65 40 | | | | |
| 27 | 0.56 | 22 | 1.12 | 75 | 53 | 80 | 65 | | | | |
| 27 | 0.14 | 22 | 4.48 | 0 (100) | 12 | | | | | | |
| 27 | 0.56 | 22 | 4.48 | 30 (44) | 53 | 90 | 70 | | | | |
| 28 | 0.004 | 22 | 1.12 | | | 80 | 75 | 65 | 43 | | 5 18 (73) |
| 28 | 0.01 | 22 | 1.12 | 5 (50) | 10 | 85 | 75 | 80 (16) | 95 | | 70 75 (7) |
| 28 | 0.01 | 22 | 1.12 | | | 80 (10) | 88 | | | | |
| 28 | 0.07 | 22 | 1.12 | 10 (80) | 48 | 95 (4) | 98 | | | 20 5 | 0 18 (100) |
| 28 | 0.28 | 22 | 1.12 | | | 100 (0) | 100 | 40 (7) | 43 95 | 80 | 95 75 |
| 28 | 1.12 | 22 | 1.12 | | | 70 (0) | 70 | 90 (6) | 95 | | |
| 28 | 0.004 | 22 | 4.48 | | | 80 (0) | 75 | | | | |
| 28 | 0.01 | 22 | 4.48 | 5 (50) | 10 | 80 | 75 | | | 25 5 | 0 10 (100) |
| 28 | 0.01 | 22 | 4.48 | 15 (69) | 48 | 95 | 88 | | | 55 60 | 15 |
| 28 | 0.07 | 22 | 4.48 | | | 100 (0) | 98 | | | 90 73 (9) | |
| 28 | 0.28 | 22 | 4.48 | | | 100 (0) | 100 | | | 95 95 (0) | |
| 29 | 0.01 | 22 | 1.12 | | | 80 | | 95 | 95 | 95 (100) | 73 |
| 29 | 0.07 | 22 | 1.12 | | | 90 | 27 | (0) | | 0 95 | 20 10 |
| 29 | 0.28 | 22 | 1.12 | 60 (5) | 63 | 60 | 55 | | | 60 95 | |
| 29 | 0.56 | 22 | 1.12 | | | 100 (0) | 100 | 95 (0) | 95 | 100 (0) | |
| 29 | 1.12 | 22 | 1.12 | | | 100 | 98 | | | 90 98 (9) | 10 12 (17) |
| 29 | 1.12 | 22 | 1.12 | 95 | 93 | | | | | | |
| 29 | 0.01 | 22 | 4.48 | | | | | | | | |
| 29 | 0.07 | 22 | 4.48 | | | | | | | | |
| 29 | 0.28 | 22 | 4.48 | 55 (13) | 63 | | | 95 (0) | 95 | | |
| 29 | 0.56 | 22 | 4.48 | | | | | 95 (0) | 95 | | |
| 29 | 1.12 | 22 | 4.48 | | | | | | | | |

-continued

| Ex. | Dose | Day | Dose | Result A | Result B | Result C | Result D |
|-----|------|-----|------|----------|----------|----------|----------|
| 29 | 1.12 | 22 | 4.48 | 95 93 | | 80 88 (10) 95 93 | 95 100 (5) 100 |
| 30 | 1.12 | 22 | 1.12 | 95 93 | | | 100 100 (0) 100 |
| 30 | 1.12 | 22 | 1.12 | 95 97 | | 75 88 (15) 95 93 | 100 100 (0) 100 |
| 30 | 4.48 | 22 | 1.12 | 100 | | | 100 100 (0) 100 |
| 30 | 4.48 | 22 | 1.12 | 100 95 | | | 100 100 (0) 100 |
| 30 | 1.12 | 22 | 4.48 | | 93 | | 100 100 (0) 100 |
| 30 | 1.12 | 22 | 4.48 | | | | 100 100 (0) 100 |
| 30 | 4.48 | 22 | 4.48 | | | | 100 100 (0) 100 |
| 30 | 4.48 | 22 | 4.48 | 100 | 97 | | 100 100 (0) 100 |
| 19 | 0.009 | 21 | 1.12 | 0 (100) | 90 | 10 30 (67) | 85 90 (6) 85 88 (4) 95 100 (5) 100 35 (13) 40 90 50 |
| 19 | 0.01 | 21 | 1.12 | | | | 80 85 (6) 95 (0) |
| 19 | 0.03 | 21 | 1.12 | | | | 100 95 |
| 19 | 0.03 | 21 | 1.12 | 35 (64) | 97 | 15 70 (79) | 90 90 (0) 95 95 (0) 35 (13) 40 95 50 |
| 19 | 0.07 | 21 | 1.12 | | | | 95 90 |
| 19 | 0.14 | 21 | 4.48 | | | | 100 95 |
| 19 | 0.009 | 21 | 4.48 | 5 (95) | 90 | 10 30 (67) | 80 90 (12) 85 88 (4) |
| 19 | 0.01 | 21 | 4.48 | | | 5 70 (93) | 80 85 (6) 95 (0) |
| 19 | 0.03 | 21 | 4.48 | | | 0 22 (100) | 90 90 (0) |
| 19 | 0.03 | 21 | 4.48 | 55 (44) | 97 | | 95 95 (0) |
| 19 | 0.07 | 21 | 4.48 | | | 70 73 (5) | 90 90 (0) |
| 19 | 0.14 | 21 | 4.48 | | | | 100 95 |
| 20 | 0.004 | 21 | 1.12 | 0 (100) | 12 | | 0 25 (100) 20 27 (26) 0 10 (100) |
| 20 | 0.004 | 21 | 1.12 | | | | 10 30 (67) |
| 20 | 0.004 | 21 | 1.12 | | | | 0 10 (100) |
| 20 | 0.009 | 21 | 1.12 | | | | 0 35 (100) |
| 20 | 0.009 | 21 | 1.12 | 25 (35) | 38 | | 50 60 (17) 15 42 (65) 35 68 (49) |
| 20 | 0.009 | 21 | 1.12 | 20 | 12 | | 60 40 |
| 20 | 0.004 | 21 | 4.48 | | | | 55 10 |

-continued

| Ex. | Dose | | | Result 1 | Result 2 | Result 3 | Result 4 | Result 5 | Result 6 | Result 7 |
|-----|------|---|---|----------|----------|----------|----------|----------|----------|----------|
| 20 | 0.004 | 21 | | | | 0 (22) | | | 10 10 (0) | |
| 20 | 0.004 | 21 | | 4.48 | | | 10 25 (60) | | | |
| 20 | 0.009 | 21 | | 4.48 | | 73 | 25 30 (17) | | | |
| 20 | 0.009 | 21 | | 4.48 5 (87) | | 85 | 85 35 | | 15 27 (45) | 95 |
| 20 | 0.009 | 21 | | 4.48 | | | 25 40 | | | 68 |
| 23 | 0.03 | 21 | | 4.48 | 38 | | 55 60 (38) | | 42 | |
| 23 | 0.03 | 21 | | 1.12 0 | | | 55 (9) | | 55 | |
| 23 | 0.14 | 21 | | 1.12 35 (49) | | 0 | 0 40 (47) | | | 0 (100) |
| 23 | 0.14 | 21 | | 1.12 | 68 | | 50 75 (34) | | | 80 (4) |
| 23 | 0.03 | 21 | | 4.48 | | 90 58 | 80 50 | | | 5 25 (80) |
| 23 | 0.03 | 21 | | 4.48 0 | | 0 | 15 15 (0) | | | 80 (4) |
| 23 | 0.14 | 21 | | 4.48 0 (100) | | 30 58 (49) | 0 40 (20) | | | 90 52 |
| 23 | 0.14 | 21 | | 1.12 | | 0 (100) | 40 75 (47) | | | 95 95 (0) |
| 25 | 0.56 | 21 | | 1.12 | | 95 95 (0) | 70 48 | | 95 95 (0) | 75 95 (0) |
| 25 | 0.14 | 21 | | 4.48 45 (53) | | 90 23 95 (0) | 85 95 (11) | | | 45 |
| 25 | 0.56 | 21 | | 4.48 | 95 | | 65 48 (6) | | | |
| 25 | 0.03 | 21 | | 1.12 | | 90 95 (6) | 90 95 (0) | 95 95 (0) | 100 98 | |
| 26 | 0.07 | 21 | | 1.12 90 100 (10) | | | | | 100 97 | 75 |
| 26 | 0.07 | 21 | | 1.12 | | 95 95 (0) | | | 95 55 | |
| 26 | 0.14 | 21 | | 1.12 | | | | 95 95 (0) | 95 95 (0) | |
| 26 | 0.28 | 21 | | 1.12 | | | | | 100 83 | 5 |
| 26 | 0.28 | 21 | | 4.48 25 95 (74) | | 65 95 (32) | | | 30 60 (50) | |
| 26 | 0.03 | 21 | | 4.48 | | | | 95 95 (0) | 100 98 | |
| 26 | 0.07 | 21 | | 4.48 | | | | | | 55 68 (20) |
| 26 | 0.07 | 21 | | 4.48 | | 95 95 (0) | | 95 95 (0) | 100 97 | |
| 26 | 0.14 | 21 | | 4.48 | | | | | 100 55 | |
| 26 | 0.28 | 21 | | 4.48 75 100 (25) | | | | | | |

-continued

| Ex | | | | | | | | | | | | | |
|---|---|---|---|---|---|---|---|---|---|---|---|---|---|
| 27 | 0.14 | 21 | 1.12 | 0 (100) | 12 | | | 70 | 40 | | | | |
| 27 | 0.56 | 21 | 1.12 | 45 (16) | 53 | | | 80 | 65 | | | | |
| 27 | 0.14 | 21 | 4.48 | 0 (100) | 12 | | | 55 | 40 | | | | |
| 27 | 0.56 | 21 | 4.48 | 25 (53) | 53 | | | 70 | 65 | | | | |
| 28 | 0.004 | 21 | 1.12 | | | 15 (66) | 43 | 70 | 70 | | | 0 (100) | 18 |
| 28 | 0.01 | 21 | 1.12 | | | 85 | 95 (11) | 80 | 75 | | | 25 (67) | 75 |
| 28 | 0.01 | 21 | 1.12 | 35 | 10 | | | 65 | 75 | | | | |
| 28 | 0.07 | 21 | 1.12 | 5 (90) | 48 | | | 95 (14) | 88 | | | | |
| 28 | 0.28 | 21 | 1.12 | | | | | 100 | 98 | 0 (100) | 5 | | |
| 28 | 1.12 | 21 | 1.12 | | | | | 100 | 100 | 55 | 60 (9) | | |
| 28 | 0.004 | 21 | 4.48 | | | 10 (77) | 43 | 80 | 70 | | | 10 (45) | 18 |
| 28 | 0.01 | 21 | 4.48 | 5 (50) | 10 | | | 70 | 75 | | | | |
| 28 | 0.01 | 21 | 4.48 | | | 65 (32) | 95 | 90 | 75 | | | | |
| 28 | 0.07 | 21 | 4.48 | 5 (90) | 48 | | | 80 (10) | 88 | | | 0 (100) | 75 |
| 28 | 0.28 | 21 | 4.48 | | | | | 95 (4) | 98 | | | | |
| 28 | 1.12 | 21 | 4.48 | | | | | 100 | 100 (0) | | | | |
| 29 | 0.01 | 21 | 1.12 | 0 (100) | 63 | | | | | 55 (65) | 27 | 70 | 55 |
| 29 | 0.07 | 21 | 1.12 | | | | | | | 25 | 60 | | |
| 29 | 0.28 | 21 | 1.12 | | | 95 | 95 (0) | | | 100 (0) | 100 | | |
| 29 | 0.56 | 21 | 1.12 | 5 (95) | 93 | | | | | 100 | 90 | | |
| 29 | 1.12 | 21 | 1.12 | | | 95 | 95 (0) | | | 100 | 98 | 0 (100) | 10 |
| 29 | 1.12 | 21 | 1.12 | | | | | | | 0 (100) | 27 | 5 (59) | 12 |
| 29 | 0.01 | 21 | 4.48 | 0 (100) | 63 | | | | | 0 (100) | 70 | | |
| 29 | 0.07 | 21 | 4.48 | | | | | | | 80 | 55 | 85 | 73 |
| 29 | 0.28 | 21 | 4.48 | | | 80 (16) | 95 | | | 95 (5) | 100 | 95 | 95 (0) |
| 29 | 0.56 | 21 | 4.48 | 15 (84) | 93 | | | | | 90 (0) | 90 | 0 (100) | 10 |
| 29 | 1.12 | 21 | 4.48 | | | 85 | 95 | | | 100 | 98 | 0 | 12 |

-continued

| Ex. | Dose | Ex. | Dose | | | | | | |
|---|---|---|---|---|---|---|---|---|---|
| 30 | 1.12 | 21 | 1.12 | | | | (11) | | |
| 30 | 1.12 | 21 | 1.12 | 35 93 (63) | 75 88 (15) | 100 100 (0) | | | |
| 30 | 4.48 | 21 | 1.12 | | 95 93 | 100 100 (0) | | | |
| 30 | 4.48 | 21 | 1.12 | 95 97 (3) | | 100 100 (0) | | | |
| 30 | 1.12 | 21 | 4.48 | | 25 88 (72) | 95 100 (5) | | | |
| 30 | 1.12 | 21 | 4.48 | 10 93 (90) | | 100 100 (0) | (100) | | |
| 30 | 4.48 | 21 | 4.48 | | 95 93 | 95 100 (5) | 25 40 (38) | | |
| 30 | 4.48 | 21 | 4.48 | 85 97 (13) | 80 85 (6) | 100 100 (0) | 50 50 (0) | | |
| 2 | 0.28 | 31 | 0.56 | | 95 93 | 100 100 (0) | 5 40 (88) | | |
| 2 | 0.56 | 31 | 0.56 | | 95 97 (3) | 100 100 (0) | 70 50 | | |
| 2 | 2.24 | 31 | 0.56 | | 60 85 (30) | 100 100 (0) | | | |
| 2 | 0.28 | 31 | 2.24 | | 80 93 (14) | 100 100 (0) | | | |
| 2 | 0.56 | 31 | 2.24 | | 95 97 (3) | 100 100 (0) | | | |
| 2 | 2.24 | 31 | 2.24 | | 15 85 (83) | 85 100 (15) | | | |
| 2 | 0.28 | 31 | 8.96 | | 15 93 (84) | 95 100 (5) | | | |
| 2 | 0.56 | 31 | 8.96 | | 70 97 (28) | 100 100 (0) | | | |
| 2 | 2.24 | 31 | 8.96 | | | | | | |
| 19 | 0.009 | 31 | 1.12 | | 15 30 (50) | 90 90 (0) | 95 | | |
| 19 | 0.01 | 31 | 1.12 | 35 90 (62) | | 90 85 | 88 | | |
| 19 | 0.03 | 31 | 1.12 | | | 95 95 (0) | | | |
| 19 | 0.03 | 31 | 1.12 | | | 95 90 | 95 | | |
| 19 | 0.07 | 31 | 1.12 | 45 97 (54) | 85 70 | 80 90 (12) | | | |
| 19 | 0.14 | 31 | 1.12 | | 30 22 | 100 95 | | | |
| 20 | 0.004 | 31 | 1.12 | | | 45 25 | | | |
| 20 | 0.004 | 31 | 1.12 | | | 35 30 | | 10 10 (0) | |
| 20 | 0.004 | 31 | 1.12 | | | 20 10 | | | |
| 20 | 0.009 | 31 | 1.12 | 0 12 (100) | | 55 60 (9) | 40 27 | | |
| 20 | 0.009 | 31 | 1.12 | | 70 73 | 0 35 | 0 42 (100) | 50 68 | |

-continued

| | | | | | | | | | | |
|---|---|---|---|---|---|---|---|---|---|---|
| 20 | 0.009 | 31 | | | | | (5) | | | |
| 23 | 0.03 | 31 | 1.12 | 30 | 38 | | | (100) | 30 | 40 |
| 23 | 0.14 | 31 | 1.12 | 0 | 68 | | | (25) | 25 | |
| 23 | 0.03 | 31 | 4.48 | | | (22) | | (47) | 40 | 75 |
| 23 | 0.14 | 31 | 4.48 | 0 | 68 | (86) | | (60) | 50 | 75 |
| 28 | 0.004 | 31 | 1.12 | 45 | | (34) | 65 | 43 | 30 | 75 |
| 28 | 0.01 | 31 | 1.12 | 5 | 10 | (50) | | | 85 | 70 |
| 28 | 0.01 | 31 | 1.12 | | | | | | 80 | 75 |
| 28 | 0.07 | 31 | 1.12 | 15 | 48 | (69) | 90 | 95 | 90 | 75 |
| 28 | 0.28 | 31 | 1.12 | | | | | (6) | 85 | 88 |
| 29 | 1.12 | 31 | 1.12 | | | | | | 95 | 98 (4) |
| 29 | 0.01 | 31 | 1.12 | 0 | 63 | (100) | | | 100 | 100 (0) |
| 29 | 0.07 | 31 | 1.12 | | | | 95 | 95 (0) | 0 | 27 (100) |
| 29 | 0.28 | 31 | 1.12 | | | | 95 | 95 (0) | 95 | 70 |
| 29 | 0.56 | 31 | 1.12 | | | | | | 70 | 55 |
| 30 | 1.12 | 31 | 1.12 | 45 | 93 (52) | | 95 | 88 | 100 100 (0) | 100 100 (0) |
| 30 | 1.12 | 31 | 1.12 | 75 | 93 (20) | | | | 100 100 (0) | 98 (0) |
| 30 | 1.12 | 31 | 1.12 | 95 | 97 (3) | | 95 | 93 | 100 100 (0) | 90 |
| 30 | 4.48 | 31 | 1.12 | | | | | | 90 | |
| 19 | 4.48 | 31 | 1.12 | 35 | 90 (62) | | | | 90 (0) | |
| 19 | 0.009 | 34 | 1.12 | | | | 10 | 30 (67) | 65 | 85 (24) |
| 19 | 0.01 | 34 | 1.12 | | | | | | 95 | 95 (0) |
| 19 | 0.03 | 34 | | | | | | | | 0 10 (100) |
| 19 | 0.03 | 34 | | | | | | | | 40 12 |
| 19 | 0.07 | 34 | 1.12 | 70 | 97 (28) | | 90 | 70 | 65 90 (28) | 5 40 (88) |
| 19 | 0.14 | 34 | 1.12 | | | | | | 95 95 (0) | 90 50 |
| 19 | 0.009 | 34 | 4.48 | | | | | | 90 90 (0) | |

| | | | | | | | | | | | |
|---|---|---|---|---|---|---|---|---|---|---|---|
| 19 | 0.01 | 34 | 4.48 | 0 (100) | 90 | | | 70 (18) | 85 | | |
| 19 | 0.03 | 34 | 4.48 | | | | | 100 | 95 | | |
| 19 | 0.03 | 34 | 4.48 | | | | | 90 (0) | 90 | | |
| 19 | 0.07 | 34 | 4.48 | 95 (3) | 97 | | | 90 (0) | 90 | | |
| 19 | 0.14 | 34 | 4.48 | | | | | 100 | 95 | 95 (0) | 95 |
| 20 | 0.004 | 34 | 1.12 | 0 (100) | 12 | 70 (0) | 70 | 20 (34) | 30 | | |
| 20 | 0.004 | 34 | 1.12 | | | | | 0 (100) | 10 | 0 (100) | 27 |
| 20 | 0.004 | 34 | 1.12 | 70 | 38 | 0 (100) | 22 | 0 (100) | 25 | | |
| 20 | 0.009 | 34 | 1.12 | | | 70 (5) | 73 | 20 (0) | 40 | 0 (100) | 27 |
| 20 | 0.009 | 34 | 1.12 | | | | | 40 (50) | 35 | | |
| 20 | 0.009 | 34 | 1.12 | | | | | 60 (0) | 60 | 30 (29) | 42 |
| 20 | 0.004 | 34 | 4.48 | | | 15 (32) | 22 | 25 (17) | 30 | 40 | 27 |
| 20 | 0.004 | 34 | 4.48 | 10 (17) | 12 | 70 (5) | 73 | 65 | 25 | | |
| 20 | 0.004 | 34 | 4.48 | 30 (22) | 38 | | | 0 (100) | 10 | | |
| 20 | 0.009 | 34 | 4.48 | | | | | 40 (0) | 40 | | |
| 20 | 0.009 | 34 | 4.48 | | | 15 | | 50 | 35 | 35 (17) | 42 |
| 20 | 0.009 | 34 | 4.48 | | | | | 80 | 60 | | |
| 23 | 0.03 | 34 | 1.12 | 0 (100) | 0 | 0 (100) | 58 | 0 | 15 | | |
| 23 | 0.03 | 34 | 1.12 | | | 10 | | 20 | 15 | 0 (100) | 10 |
| 23 | 0.14 | 34 | 1.12 | 0 (78) | 68 | | | 45 (40) | 75 | 15 (40) | 25 |
| 23 | 0.14 | 34 | 1.12 | 15 | | | | 40 (20) | 50 | | |
| 23 | 0.03 | 34 | 4.48 | | | 30 (49) | 58 | 50 (0) | 15 | 0 (100) | 83 |
| 23 | 0.03 | 34 | 4.48 | | | 50 | 23 | 0 | 75 | 30 | 25 |
| 23 | 0.14 | 34 | 4.48 | | | 80 | 95 | 15 (80) | 50 | | |
| 23 | 0.14 | 34 | 4.48 | | | | | 45 (10) | 50 | 90 | 83 |
| 25 | 0.14 | 34 | 1.12 | | | | | 65 | 48 | 90 | 52 |
| 25 | 0.56 | 34 | 1.12 | | | 40 (16) | 23 | 90 | 95 | 95 | 95 |
| 25 | 0.14 | 34 | 4.48 | | | 90 (6) | 95 | 90 (6) | 48 | 95 (0) | 52 |
| 25 | 0.56 | 34 | 4.48 | | | | | 95 (0) | 95 | 95 | 95 |
| 26 | 0.03 | 34 | 1.12 | | | | | 85 | 95 | 95 | |

-continued

-continued

| | | | | | | | | | |
|---|---|---|---|---|---|---|---|---|---|
| 26 | 34 | 0.07 | 1.12 | | | 80 95 (16) | | | |
| 26 | 34 | 0.07 | 1.12 | 90 95 (6) | | | | | |
| 26 | 34 | 0.14 | 1.12 | | | 95 95 (0) | | | |
| 26 | 34 | 0.28 | 1.12 | | | | 100 83 (11) | | |
| 26 | 34 | 0.28 | 1.12 | 100 100 (0) | | | 90 60 | | |
| 26 | 34 | 0.03 | 4.48 | | | | 95 98 (4) | 95 95 (0) | |
| 26 | 34 | 0.07 | 4.48 | 80 95 (16) | | 95 95 (0) | 100 97 | | 20 |
| 26 | 34 | 0.07 | 4.48 | | | | 80 55 | | |
| 26 | 34 | 0.14 | 4.48 | | | 90 95 (6) | 95 95 (0) | 95 95 (0) | |
| 26 | 34 | 0.28 | 4.48 | | | 95 95 (0) | 90 60 | | |
| 26 | 34 | 0.28 | 4.48 | 95 100 (5) | | | 100 83 | | |
| 27 | 34 | 0.14 | 1.12 | 0 12 (100) | | | 100 98 (8) | 95 95 (0) | 60 68 (12) |
| 27 | 34 | 0.56 | 1.12 | 75 53 (17) | | | 80 55 | | |
| 27 | 34 | 0.14 | 4.48 | 0 12 (100) | | 20 43 (54) | | | 0 |
| 27 | 28 | 0.56 | 4.48 1.12 | 75 53 | 70 40 (0) 65 40 | 70 95 (27) | 95 95 (0) | | 50 68 (27) |
| 28 | 34 | 0.01 | 1.12 | 10 10 (0) | 55 40 | | | | |
| 28 | 34 | 0.01 | 1.12 | 40 48 (17) | 75 65 (15) | 30 43 (31) | | | 10 18 (45) |
| 28 | 34 | 0.07 | 1.12 | | 85 70 | 90 95 (6) | 95 95 (0) | 5 5 (0) | 35 75 (54) |
| 28 | 34 | 0.28 | 1.12 | | 80 75 | | 95 95 (0) | 20 60 (67) | |
| 28 | 34 | 1.12 | 1.12 | | 80 75 | | | | |
| 28 | 34 | 0.004 | 4.48 | 5 10 (50) | 75 88 (15) | | | | |
| 28 | 34 | 0.01 | 4.48 | 40 48 (17) | 100 98 (0) | | | | 0 18 (100) |
| 28 | 34 | 0.01 | 4.48 | | 100 100 (0) | | | | 0 75 (100) |
| 28 | 34 | 0.07 | 4.48 | | 85 70 | | | 10 5 (84) | |
| 28 | 34 | 0.28 | 4.48 | | 90 75 | | | 10 60 | |
| 28 | 34 | 0.28 | 4.48 | | 60 75 | | | | |
| 28 | 34 | 1.12 | 4.48 | | 85 88 (20) | | | | |
| 28 | 34 | | 4.48 | | 95 98 (4) | | | | |
| 28 | 34 | | 4.48 | | 100 100 (0) | | | | |

-continued

| | | | | | | | | |
|---|---|---|---|---|---|---|---|---|
| 29 | 0.01 | 34 | 1.12 | | | 95 | | 95 |
| 29 | 0.07 | 34 | 1.12 | | | 95 (0) | | 95 (0) |
| 29 | 0.28 | 34 | 1.12 | 0 (100) | 63 | | | |
| 29 | 0.56 | 34 | 1.12 | | | 90 | | 95 |
| 29 | 1.12 | 34 | 1.12 | | 95 | 95 (6) | | 95 (0) |
| 29 | 1.12 | 34 | 1.12 | | 93 | | 10 | 55 |
| 29 | 0.01 | 34 | 4.48 | | | | 95 (82) | 27 70 |
| 29 | 0.07 | 34 | 4.48 | 5 (93) | 63 | 90 | 100 (0) | 100 |
| 29 | 0.28 | 34 | 4.48 | | | 95 | 100 | 98 |
| 29 | 0.56 | 34 | 4.48 | | | | 90 | 90 |
| 29 | 1.12 | 34 | 4.48 | 75 (20) | 93 | 90 88 | 65 (100) | 27 70 |
| 29 | 1.12 | 34 | 1.12 | 95 | 93 | 95 93 | 0 80 | (0) 55 |
| 30 | 1.12 | 34 | 1.12 | | | | 100 | 90 |
| 30 | 1.12 | 34 | 1.12 | 100 (14) | 97 | 85 88 | 100 (0) | 100 |
| 30 | 4.48 | 34 | 4.48 | 80 (14) | 93 | 95 93 | 100 (5) | 100 |
| 30 | 1.12 | 34 | 1.12 | | | | 95 (5) | 100 |
| 30 | 1.12 | 34 | 4.48 | | | | 100 (5) | 100 |
| 30 | 4.48 | 34 | 4.48 | 100 | 97 | | 100 (0) | 100 |
| 30 | 0.009 | 35 | 1.12 | 25 (73) | 90 | | 95 (0) | |
| 30 | 0.01 | 35 | 1.12 | | | 35 | 75 (12) | |
| 19 | 0.03 | 35 | 1.12 | | | 30 | 90 (0) | |
| 19 | 0.03 | 35 | 1.12 | | | | 95 (0) | 95 88 |
| 19 | 0.07 | 35 | 1.12 | 95 (3) | 97 | 85 | 95 | 95 |
| 19 | 0.14 | 35 | 1.12 | | | | 90 (6) | 95 88 |
| 19 | 0.009 | 35 | 4.48 | | | | 85 (6) | |
| 19 | 0.01 | 35 | 4.48 | 40 (56) | 90 | 70 | 95 | 95 |
| 19 | 0.03 | 35 | 4.48 | | | | 95 | 95 |

-continued

| | | | | | | | | |
|---|---|---|---|---|---|---|---|---|
| 19 | 0.03 | 35 | 4.48 | | | 95 95 | | |
| 19 | 0.07 | 35 | 4.48 | 95 97 (3) | | 95 90 (0) | | |
| 19 | 0.14 | 35 | 4.48 | | | 95 95 (0) | | |
| 20 | 0.004 | 35 | 1.12 | | 5 30 (84) | 10 25 | | 15 10 |
| 20 | 0.004 | 35 | 1.12 | 10 12 (17) | | 0 10 (60) | | |
| 20 | 0.004 | 35 | 1.12 | | | 0 30 (100) | | |
| 20 | 0.009 | 35 | 1.12 | | 50 70 (29) 22 | 0 35 (100) | 5 27 (82) | 80 68 |
| 20 | 0.009 | 35 | 1.12 | | 25 | 90 60 (59) | 25 42 (41) | |
| 20 | 0.009 | 35 | 1.12 | 60 38 | | 25 40 | | |
| 20 | 0.004 | 35 | 4.48 | 30 | | 35 30 (13) | 30 27 | 50 10 |
| 20 | 0.004 | 35 | 4.48 | | 95 73 | 25 10 | | 85 68 |
| 20 | 0.004 | 35 | 4.48 | 45 | | 90 25 | | |
| 20 | 0.009 | 35 | 4.48 | | | 80 40 | | |
| 20 | 0.009 | 35 | 4.48 | | 40 22 | 90 35 | 45 42 | 50 25 |
| 20 | 0.009 | 35 | 4.48 | | 100 73 | 40 60 | | |
| 23 | 0.03 | 35 | 1.12 | | 0 | 60 15 (34) | | 90 83 |
| 23 | 0.03 | 35 | 1.12 | 15 15 (78) | | 50 25 | | 35 25 |
| 23 | 0.14 | 35 | 1.12 | | 55 58 (6) | 85 75 (67) | | 80 83 (4) |
| 23 | 0.14 | 35 | 1.12 | | 15 | 85 50 | | |
| 23 | 0.03 | 35 | 4.48 | 0 | | 35 15 | | 90 52 |
| 23 | 0.03 | 35 | 4.48 | | 10 58 (83) | 70 50 | | 95 95 (0) |
| 23 | 0.14 | 35 | 4.48 | 45 68 (34) | | 55 75 | | 80 52 95 (0) |
| 23 | 0.14 | 35 | 4.48 | | 20 23 (14) | 0 48 (100) | | 90 95 95 (0) |
| 25 | 0.14 | 35 | 1.12 | | 95 95 (0) | 60 95 (37) | 90 95 95 (6) 83 | |
| 25 | 0.56 | 35 | 1.12 | | 35 23 | 50 48 | 100 60 | |
| 25 | 0.14 | 35 | 4.48 | | 100 95 | 85 95 (11) | 70 98 | 25 |
| 25 | 0.56 | 35 | 4.48 | | | | 100 97 | |
| 26 | 0.03 | 35 | 1.12 | | 90 95 (6) | 55 75 | | |
| 26 | 0.07 | 35 | 1.12 | | | 0 48 (100) | | |
| 26 | 0.07 | 35 | 1.12 | 90 95 (6) | | 60 95 | | |
| 26 | 0.14 | 35 | 4.48 | | 95 95 (0) | 50 48 95 | 95 95 (0) | 90 68 |
| 26 | 0.28 | 35 | 1.12 | | | 85 95 (11) | | |

-continued

| | | | | | | | |
|---|---|---|---|---|---|---|---|
| 26 | 0.28 | 35 | 1.12 | | | 85 55 | |
| 26 | 0.03 | 35 | 4.48 | 100 100 (0) | | 90 95 95 (6) (0) | |
| 26 | 0.07 | 35 | 4.48 | | | 90 83 | |
| 26 | 0.07 | 35 | 4.48 | 65 95 (32) | | 0 60 | 0 |
| 26 | 0.14 | 35 | 4.48 | | | 0 (100) | |
| 26 | 0.28 | 35 | 4.48 | | 40 | 95 98 100 95 (4) | 40 68 (42) |
| 26 | 0.28 | 35 | 4.48 | 95 100 (5) | 65 40 | 95 97 (3) | |
| 27 | 0.14 | 35 | 1.12 | 0 (100) 70 0 | 75 30 | 50 55 (10) | |
| 27 | 0.56 | 35 | 1.12 | | | | |
| 27 | 0.14 | 35 | 4.48 | | 0 (100) | | |
| 27 | 0.56 | 35 | 4.48 | 5 53 (91) | 70 65 | | |
| 28 | 0.004 | 35 | 1.12 | | 70 (0) | | 10 18 (45) |
| 28 | 0.01 | 35 | 1.12 | 25 43 (42) | 80 75 | | |
| 28 | 0.01 | 35 | 1.12 | | 85 75 | | 10 75 (87) |
| 28 | 0.07 | 35 | 1.12 | 80 95 (16) | 80 88 | | |
| 28 | 0.28 | 35 | 1.12 | | 80 (10) 100 98 | | |
| 28 | 1.12 | 35 | 1.12 | 30 43 (31) | 100 100 | | |
| 28 | 0.004 | 35 | 4.48 | 80 95 (16) | 90 (0) 70 | 0 5 (100) 5 60 (92) | 0 18 (100) 35 (54) |
| 28 | 0.01 | 35 | 4.48 | | 95 75 | | |
| 28 | 0.01 | 35 | 4.48 | 10 (0) | 80 75 | 5 60 (17) | |
| 28 | 0.07 | 35 | 4.48 | 10 48 (80) | 100 88 | 25 50 73 | |
| 28 | 0.28/1.12 | 35 | 4.48/4.48 | 25 48 (48) | 100 98 (10) 100 100 (0) | 95 95 (0) | 0 27 (100) 15 70 (79) 80 55 |
| 29 | 0.01 | 35 | 1.12 | | | 100 100 | |
| 29 | 0.07 | 35 | 1.12 | 10 (0) | 95 (0) 95 (0) | 100 98 | 0 10 (100) 25 12 |
| 29 | 0.28 | 35 | 1.12 | | | | |
| 29 | 0.56 | 35 | 1.12 | 30 63 (53) | | | |
| 29 | 1.12 | 35 | 1.12 | | | | |

-continued

| Ex. | Dose | N | Dose | Result | Result | Result | Result | Result | Result | Result |
|---|---|---|---|---|---|---|---|---|---|---|
| 29 | 1.12 | 35 | 1.12 | 80 (14) | 93 | | | | 80 (12) | 90 |
| 29 | 0.01 | 35 | | | | | | | 0 (100) | 27 | 90 |
| 29 | 0.07 | 35 | | | | | | | 70 (0) | 70 | 95 |
| 29 | 0.28 | 35 | 4.48 | 5 (93) | 63 | | | | 60 | 55 | 73 (0) |
| 29 | 0.56 | 35 | 4.48 | 75 (22) | 95 | | | | 100 (0) | 100 | 95 | 15 10 |
| 29 | 1.12 | 35 | 4.48 | 55 (41) | 93 | | | | 100 | 90 | 5 12 |
| 29 | 1.12 | 35 | 4.48 | 95 (0) | 95 | | | | 100 | 98 | (59) |
| 30 | 1.12 | 35 | 4.48 | 85 (4) | 88 | | | | | | 15 40 (63) |
| 30 | 1.12 | 35 | 1.12 | 95 | 93 | | | | | | 85 50 |
| 30 | 1.12 | 35 | 1.12 | 100 | 97 | | | | | | 10 40 (75) |
| 30 | 1.12 | 35 | 1.12 | 60 (32) | 88 | | | | | | 55 50 |
| 30 | 4.48 | 35 | 1.12 | 95 | 93 | | | | | | |
| 30 | 1.12 | 35 | 4.48 | 50 (47) | 93 | 95 | 100 (5) | | | | |
| 30 | 1.12 | 35 | 4.48 | | | 100 (0) | 100 | | | | |
| 30 | 4.48 | 35 | 4.48 | 95 (3) | 97 | 95 (0) | 100 | | | | |
| 2 | 0.28 | 32 | 0.14 | | | 100 (0) | 100 | 0 (100) | 85 | | |
| 2 | 0.56 | 32 | 0.14 | | | 95 (5) | 100 | 25 (74) | 93 | | |
| 2 | 2.24 | 32 | 0.14 | | | 100 (0) | 100 | 35 (64) | 97 | | |
| 2 | 0.28 | 32 | 0.56 | | | 95 (5) | 100 | 10 (89) | 85 | | |
| 2 | 0.56 | 32 | 0.56 | | | 95 (5) | 100 | 10 (90) | 93 | | |
| 2 | 2.24 | 32 | 0.56 | | | 100 (0) | 100 | 45 (54) | 97 | | |
| 2 | 0.28 | 32 | 2.24 | | | 95 (5) | 100 | 10 (89) | 85 | | |
| 2 | 0.56 | 32 | 2.24 | | | 100 (0) | 100 | 20 (79) | 93 | | |
| 2 | 2.24 | 32 | 2.24 | | | 100 (0) | 100 | 15 (85) | 97 | | |
| 19 | 0.009 | 32 | 1.12 | 15 (84) | 90 | | | | | 85 (6) | 90 | 95 88 |
| 19 | 0.01 | 32 | 1.12 | | | | | 5 (84) | 30 | 80 (6) | 85 |
| 19 | 0.03 | 32 | 1.12 | | | | | | | 100 (0) | 95 |

-continued

| | | | | | | | | |
|---|---|---|---|---|---|---|---|---|
| 19 | 0.03 | 32 | 1.12 | | | 95 | 90 | 95 95 |
| 19 | 0.07 | 32 | 1.12 | 50 97 (49) | | 90 90 (0) | | (0) |
| 19 | 0.14 | 32 | 1.12 | | | 100 95 | | |
| 20 | 0.004 | 32 | 1.12 | | 0 70 (100) 85 22 | 0 25 (100) 20 10 | | |
| 20 | 0.004 | 32 | 1.12 | 5 12 (59) | | 80 30 | | 5 10 (50) |
| 20 | 0.004 | 32 | 1.12 | | | | 15 27 (45) | |
| 20 | 0.009 | 32 | 1.12 | | | 10 35 (72) 70 60 | 35 42 (17) | |
| 20 | 0.009 | 32 | 1.12 | | 30 73 (59) | 70 40 | | 40 68 (42) |
| 20 | 0.009 | 32 | 1.12 | 25 38 (35) | | 45 75 60 (20) 70 85 | | |
| 23 | 0.03 | 32 | 1.12 | 0 68 | | | | |
| 23 | 0.14 | 32 | 1.12 | 10 (86) | | | | |
| 23 | 0.03 | 32 | 4.48 | 5 (56) | | | | |
| 23 | 0.14 | 32 | 4.48 | 30 | | | | |
| 26 | 0.03 | 32 | 1.12 | | 30 95 (69) | | 95 95 (0) | 0 |
| 26 | 0.07 | 32 | 1.12 | | | | 90 95 83 (6) 100 | |
| 26 | 0.07 | 32 | 1.12 | 15 95 (85) | | | 50 60 (17) 95 98 | |
| 26 | 0.14 | 32 | 1.12 | | | | (4) 100 97 | |
| 26 | 0.28 | 32 | 1.12 | | | | 90 55 | |
| 28 | 0.28 | 32 | 1.12 | 85 100 (15) | | | 95 70 | 95 95 (0) | 50 68 (27) |
| 28 | 0.004 | 32 | 1.12 | | | | 95 75 | |
| 28 | 0.01 | 32 | 1.12 | | 30 43 (31) | | 85 75 | 95 95 (0) | 0 18 (100) |
| 28 | 0.01 | 32 | 1.12 | 5 10 (50) | 70 95 (27) | | 85 88 (4) 100 98 | | 15 75 (80) |
| 28 | 0.07 | 32 | 1.12 | 15 48 (69) | | | 100 100 (0) | | |
| 28 | 0.28 | 32 | 1.12 | | | | | 0 5 (100) | |
| 28 | 1.12 | 32 | 1.12 | | | | | 15 60 (75) | |
| 29 | 0.01 | 32 | 1.12 | | | | 0 27 (100) 0 70 (100) 70 55 | 80 73 | |
| 29 | 0.07 | 32 | 1.12 | | | | | 95 95 (0) | |
| 29 | 0.28 | 32 | 1.12 | 0 63 (100) | | | | | |

-continued

| | | | | | | | | |
|---|---|---|---|---|---|---|---|---|
| 29 | 0.56 | 32 | 1.12 | | 75 95 (22) 90 95 (6) | | | 0 10 (100) 15 12 |
| 29 | 1.12 | 32 | 1.12 | | | | | |
| 29 | 1.12 | 32 | 1.12 | 0 93 (100) 30 93 (68) | | | | |
| 29 | 1.12 | 32 | 1.12 | 90 97 (8) | | | | |
| 30 | 1.12 | 32 | 1.12 | | 10 88 (89) 95 93 | | | 0 40 (100) 95 50 |
| 30 | 1.12 | 32 | 1.12 | | | 100 100 (0) 100 100 | | |
| 30 | 4.48 | 32 | 1.12 | | | 100 100 (0) 100 100 | | |
| 30 | 4.48 | 32 | 1.12 | | | 100 100 (0) 100 100 | | |
| 2 | 0.56 | 36 | 0.56 | | 75 72 100 95 80 100 (20) (5) 65 72 95 100 (10) (0) | | | |
| 2 | 2.24 | 36 | 0.56 | | | | | |
| 2 | 0.56 | 36 | 2.24 | | 70 100 100 100 (30) (6) 25 72 90 100 (66) (0) 85 100 (15) (0) | | | |
| 2 | 2.24 | 36 | 2.24 | | | | | |
| 2 | 0.56 | 36 | 8.96 | | | | | |
| 2 | 2.24 | 36 | 8.96 | | | | | |
| 23 | 0.03 | 36 | 1.12 | | 0 58 45 (23) | | 60 15 50 60 (100) | 30 25 83 50 (40) |
| 23 | 0.14 | 36 | 1.12 | | 0 | | 0 15 25 50 (50) | 10 25 (60) 90 83 |
| 23 | 0.03 | 36 | 4.48 | | 70 58 | | 35 48 (28) 80 95 | |
| 23 | 0.14 | 36 | 4.48 | | 20 23 (14) 70 95 (27) | | 65 48 (16) 95 95 (0) | 15 52 (72) 95 95 |
| 25 | 0.14 | 36 | 1.12 | | 80 23 95 95 (0) | | 25 40 (38) 80 65 25 40 (38) 80 65 | 85 52 95 95 (0) |
| 25 | 0.56 | 36 | 1.12 | | | | | |
| 25 | 0.14 | 36 | 4.48 | | | | | |
| 25 | 0.56 | 36 | 4.48 | | | | | |
| 27 | 0.14 | 36 | 1.12 | 0 12 (100) 90 53 | | | | |
| 27 | 0.56 | 36 | 1.12 | 0 12 (100) 70 53 | | | | |
| 27 | 0.14 | 36 | 4.48 | | | | | |
| 27 | 0.56 | 37 | 4.48 | | 50 72 (31) 100 100 (0) | | 80 95 (16) 95 100 (0) | |
| 2 | 0.56 | 37 | 0.56 | | | | | |
| 2 | 2.24 | 37 | 0.56 | | 55 72 (24) 90 100 (10) | | 95 95 (0) 95 100 (5) | |
| 2 | 0.56 | 37 | 2.24 | | | | | |
| 2 | 2.24 | 37 | 2.24 | | 0 72 | | 90 95 | |
| 2 | 0.56 | 37 | 8.96 | | | | | |

-continued

| | | | | | | | | |
|---|---|---|---|---|---|---|---|---|
| 2  | 2.24 | 37 | 8.96 |  | (100) 65 (35) 10 | 100 (6) 100 (0) |  |  |
| 23 | 0.03 | 37 | 1.12 |  | 70 0 | 58 |  |  |
| 23 | 0.14 | 37 | 1.12 |  | 30 (49) 10 (57) | 58 23 |  |  |
| 23 | 0.03 | 37 | 4.48 |  | 85 (11) | 95 |  |  |
| 23 | 0.14 | 37 | 4.48 |  | 70 95 (0) | 23 95 |  |  |
| 25 | 0.14 | 37 | 1.12 |  |  |  | 50 90 0 (100) | 15 50 |
| 25 | 0.56 | 37 | 1.12 |  |  |  | 0 (100) 75 | 15 48 |
| 25 | 0.14 | 37 | 4.48 |  |  |  | 95 (0) | 95 |
| 25 | 0.56 | 37 | 4.48 |  |  |  | 90 (6) 90 | 48 95 |
| 27 | 0.14 | 37 | 1.12 | 10 (17) 40 (25) | 12 53 |  | 60 | 40 |
| 27 | 0.56 | 37 | 1.12 | 0 (100) 40 (25) | 12 53 |  | 65 50 | 65 40 |
| 27 | 0.14 | 37 | 4.48 |  |  |  | 65 (0) | 65 |
| 27 | 0.56 | 37 | 4.48 |  |  |  |  |  |
| 2 | 0.56 | 33 | 0.03 |  | 85 (14) | 98 (2) |  |  |
| 2 | 2.24 | 33 | 0.03 |  | 98 (0) | 98 (0) |  |  |
| 2 | 0.56 | 33 | 0.14 |  | 93 (6) | 98 (0) |  |  |
| 2 | 2.24 | 33 | 0.14 |  | 90 (9) | 98 (0) |  |  |
| 2 | 0.56 | 33 | 0.56 |  | 68 (31) | 98 (2) |  |  |
| 2 | 2.24 | 33 | 0.56 |  | 95 (4) | 98 (0) |  |  |
| 2 | 0.56 | 33 | 0.03 |  | 95 (4) | 98 (0) |  |  |
| 2 | 2.24 | 33 | 0.03 |  | 90 (9) | 98 (0) |  |  |
| 2 | 0.56 | 33 | 0.14 |  | 95 (4) | 98 (0) |  |  |
| 2 | 2.24 | 33 | 0.14 |  | 98 (0) | 100 (0) |  |  |
| 2 | 0.56 | 33 | 0.56 |  | 90 (9) | 98 (0) |  |  |
| 2 | 2.24 | 33 | 0.56 |  | 95 (4) | 100 (0) |  |  |
| 2 | 0.56 | 3 | 0.14 | 0 (100) 15 (74) 0 | 18 57 18 | 100 100 (0) 100 | 25 90 0 (100) 70 (16) 85 | 25 (0) 83 25 (0) 52 |
| 2 | 2.24 | 3 | 0.14 |  |  | 99 | 95 (0) 85 95 | 95 (0) 52 95 |
| 2 | 0.56 | 3 | 0.56 |  |  |  |  |  |

-continued

| | | | | | | | | | |
|---|---|---|---|---|---|---|---|---|---|
| 2 | 2.24 | 3 | 0.56 | (100) 0 | 57 | 100 | 100 | (0) | 99 |
| 2 | 0.56 | 3 | 2.24 | (100) 0 | 18 | 100 | 100 | (0) | 99 |
| 2 | 2.24 | 3 | 2.24 | (100) 0 | 57 | 100 | 100 | (0) | 99 |
| 2 | 0.56 | 34 | 0.14 | (100) 0 | 18 | 100 | 100 | (0) | 99 |
| 2 | 2.24 | 34 | 0.14 | (100) 60 | 57 | 95 | 95 | (5) | 99 |
| 2 | 0.56 | 34 | 0.56 | (100) 0 | 18 | 95 | 95 | (5) | 99 |
| 2 | 2.24 | 34 | 0.56 | (48) 30 | 57 | 100 | 100 | (0) | 99 |
| 2 | 0.56 | 34 | 2.24 | (100) 0 | 18 | 100 | 100 | (0) | 99 |
| 2 | 2.24 | 34 | 2.24 | (39) 35 | 57 | 100 | 100 | (0) | 99 |
| 2 | 0.56 | 35 | 0.14 | (100) 0 | 18 | 90 | 90 | (10) | 99 |
| 2 | 2.24 | 35 | 0.14 | (100) 0 | 57 | 100 | 100 | (0) | 99 |
| 2 | 0.56 | 35 | 0.56 | (73) 5 | 18 | 100 | 100 | (0) | 99 |
| 2 | 2.24 | 35 | 0.56 | (30) 40 | 57 | 100 | 100 | (0) | 99 |
| 2 | 0.56 | 35 | 2.24 | 20 | 18 | 100 | 100 | (0) | 99 |
| 2 | 2.24 | 35 | 2.24 | 60 | 57 | 100 | 100 | | 100 |
| 2 | 0.28 | 3 | 0.03 | (0) 100 | 100 | 28 | 28 | (55) | 62 |
| 2 | — | 25 | 2.24 | | | 50 | — | 0 | 0 |
| 2 | 2.24 | 25 | 0.14 | | | 0 | 100 | 80 | 100 |
| 2 | 0.56 | 25 | 0.14 | | | 10 | 100 | 42 | 100 |
| 2 | 2.24 | 25 | 0.56 | | | 10 | 100 | 80 | 100 |
| 2 | 0.56 | 25 | 0.56 | | | 5 | 100 | 42 | 100 |
| 2 | 2.24 | 25 | 2.24 | | | 0 | 100 | 80 | 100 |
| 2 | 0.56 | 25 | 2.24 | | | 0 | 100 | 42 | 100 |

Example 44

The procedure described in Example 42 was used to conduct tests for the antidotal activity of the compound of Example 3 (oxazolidine, 3-(dichloroacetyl)-5-(2-furanyl)-2,2-dimethyl-)with a thiocarbamate herbicide (2,3,3-)trichloroalkyl-N,N-diisopropylthiocarbamate, (triallate); Herbicide No. 1) and a herbicidal pyridine compound (3-pyridinecarboxylic acid, 2-(difluoromethyl)-5-(4,5-dihydro-2-thiazolyl)-4-(2-methylpropyl)-6-trifluoromethyl)-, methyl ester; Herbicide No. 24). Results are reported in Table 7.

TABLE 7

% PLANT INHIBITION AND % SAFENING EFFECT( )

| HERB. NO. | RATE | ANTI-DOTE NO. | RATE | Corn W | Corn WO | Barnyard Grass W | Barnyard Grass WO | Sorghum (Grain) W | Sorghum (Grain) WO | Foxtail Green W | Foxtail Green WO | Pigweed Redroot W | Pigweed Redroot WO | Velvet Leaf W | Velvet Leaf WO | Soybean W | Soybean WO | Wheat W | Wheat WO | Rice W | Rice WO | Hemp Sesbania W | Hemp Sesbania WO | Indian Mustard W | Indian Mustard WO | Tartary Buckwheat W | Tartary Buckwheat WO |
|---|---|---|---|---|---|---|---|---|---|---|---|---|---|---|---|---|---|---|---|---|---|---|---|---|---|---|---|
| 1 | 1.12 | 3 | 0.03 | 100 (0) | 100 | 93 (6) | 98 | | | | | | | | | | | | | | | | | | | | |
| 1 | 0.28 | 3 | 0.12 | 98 (2) | 100 | 20 (68) | 62 | | | | | | | | | | | | | | | | | | | | |
| 1 | 1.12 | 3 | 0.12 | 100 (0) | 100 | 95 (4) | 98 | | | | | | | | | | | | | | | | | | | | |
| 1 | 0.28 | 3 | 0.50 | 100 (0) | 100 | 0 (100) | 62 | | | | | | | | | | | | | | | | | | | | |
| 1 | 1.12 | 3 | 0.50 | 100 (0) | 100 | 85 (14) | 98 | | | | | | | | | | | | | | | | | | | | |
| 24 | 0.01 | 3 | 0.03 | 0 | 0 | | | 5 (29) | 7 | 80 | 65 | | | | | | | | | | | | | | | | |
| 24 | 0.07 | 3 | 0.03 | 0 (100) | 10 | | | 15 | | 95 (0) | 95 | | | | | | | | | | | | | | | | |
| 24 | 0.28 | 3 | 0.03 | 0 (100) | 3 | | | 60 | 33 | 100 (0) | 100 | | | | | | | | | | | | | | | | |
| 24 | 0.01 | 3 | 0.03 | 0 (100) | 20 | | | 68 (20) | 85 | 98 (0) | 98 | | | | | | | | | | | | | | | | |
| 24 | 0.07 | 3 | 0.03 | 65 (10) | 72 | | | 90 (8) | 97 | 100 (0) | 100 | | | | | | | | | | | | | | | | |
| 24 | 0.28 | 3 | 0.03 | 100 (0) | 100 | | | 100 (0) | | 100 (0) | 100 | | | | | | | | | | | | | | | | |
| 24 | 0.01 | 3 | 0.12 | 15 (25) | 20 | | | 80 (6) | 85 | 98 (0) | 98 | | | | | | | | | | | | | | | | |
| 24 | 0.01 | 3 | 0.12 | 10 | | | | 28 (24) | 7 | 50 | 65 | | | | | | | | | | | | | | | | |
| 24 | 0.07 | 3 | 0.12 | 0 (100) | 10 | | | 8 | | 95 (0) | 95 | | | | | | | | | | | | | | | | |
| 24 | 0.07 | 3 | 0.12 | 60 (17) | 72 | | | 98 | 97 | 100 (0) | 100 | | | | | | | | | | | | | | | | |
| 24 | 0.28 | 3 | 0.12 | 93 (7) | 100 | | | 100 (0) | 100 | 100 (0) | 100 | | | | | | | | | | | | | | | | |
| 24 | 0.28 | 3 | 0.12 | 0 (100) | 3 | | | 75 | 33 | 100 (0) | 100 | | | | | | | | | | | | | | | | |
| 24 | 0.01 | 3 | 0.50 | 35 | 20 | | | 40 (53) | 85 | 100 (0) | 98 | | | | | | | | | | | | | | | | |
| 24 | 0.01 | 3 | 0.50 | 5 | | | | 20 | 7 | 80 | 65 | | | | | | | | | | | | | | | | |
| 24 | 0.07 | 3 | 0.50 | 30 (59) | 72 | | | 100 | 97 | 100 | 100 | | | | | | | | | | | | | | | | |
| 24 | 0.07 | 3 | 0.50 | 0 (100) | 10 | | | 60 | | 95 (0) | 95 | | | | | | | | | | | | | | | | |
| 24 | 0.28 | 3 | 0.50 | 90 (10) | 100 | | | 98 (2) | 100 | 100 (0) | 100 | | | | | | | | | | | | | | | | |
| 24 | 0.28 | 3 | 0.50 | 0 (100) | 3 | | | 70 | 33 | 95 (5) | 100 | | | | | | | | | | | | | | | | |

Example 45

This example describes the preparation of the herbicidal compound 5-(trifluoromethyl)-4-chloro-3-(3'-[1-ethoxycarbonyl]-ethoxy-4'-nitrophenoxy (-1- methyl-pyrazole (Herbicide No. 34), a heterocycyl phenyl ether compound representative of the class.

961 g (4.80 mol) of 5-trifluoromethyl-4,-chloro-3-hydroxy-1-methylpyrazol, 1317 g (5.12 mol) of ethyl 2-(5-fluoro-2-nitrophenoxy)propanoate, and 380 g (2.75 mol) of potassium carbonate were stirred with 6000 ml of DMSO at 70° C. for 20 hours. Another 100 g (0.72 mol) of potassium carbonate was added. After another 16 hours at 70° C. another 163 g (1.18 mol) of potassium carbonate was added. After stirring another 6 hours at 70° C., the product was isolated from the mixture by extracting twice with ether and combining the ether extracts, washing same 2X with brine, dried with MgSO$_{41}$ decolorized with charcoal, filtered and rotovaped to give a black oil. Purification by silica gel chromatography gave 1733 g of a dark oil. Further, purification by vacuum distillation (molecular still) gave a reddish oil, which on prolonged standing gave a reddish orange solid, m.p. 40°-440° C.

| Elemental Analysis for C$_{16}$H$_{15}$F$_3$Cl$_1$N$_3$O$_6$ | | | |
|---|---|---|---|
| | C | H | N |
| Calculated | 43.90 | 3.45 | 9.60 |
| Found | 43.96 | 3.50 | 9.58 |

The above first-named intermediate, (5-trifluoromethyl)-4-chloro-3-hydroxy-1-methylpyrazole (m.p. 136°-140° C.) may be prepared by various means. A preferred process comprises bubbling ammonia gas through ethyl 4,4,4-trifluoroacetoacetate at an elevated temperature of about 55°-85° C. while removing water to form 3-amino-4,4,4-trifluoro-2-butenoic acid ethyl ester. This ester is then reacted directly with methylhydrazine at about 60°-100° C. to form the 3- and 5- hydroxy isomers mixture of the intermediate pyrazole. The desired 3- isomer may be separated by stirring the isomer mixture in an aqueous solution of sodium bicarbonate wherein the 5-isomer is dissolved while the 3-isomer remains in suspension and is readily separated by filtration. The 5-trifluoromethyl-3-hydroxy methylpyrazole product can be then chlorinated in the 4-position using a suitable chlorinating agent such as chlorine or sulfuryl chloride in a suitable solvent such as acetonitrile or diethyl ether, then poured into ice water containing sodium carbonate, washed with water and extracted with ether, and purified, e.g., by recrystallization.

The above intermediate, ethyl 2-(5-fluoro-2-nitrophenoxy) propanoate can be prepared from 2-hydroxy-4-fluoronitrobenzene which is commercially available or by reacting 2,4-difluoronitrobenzene with sodium hydroxide in dimethylsulfoxide (DMSO) and extracting the product from water with hexane. 2-hydroxy-4-fluoronitrobenzene is reacted with a haloalkylcarboxylate (e.g., ethyl 2-bromo- or 2-chloropropionate in a suitable solvent (e.g., acetone, acetonitrile, DMF or DMSO) in the presence of a base (e.g., KOH or NAOH) for an extended period (e.g., 3 days), then isolating the nitrobenzene product by standard laboratory techniques.

Example 46

This example describes a greenhouse test for the postemergence activity of the compound of Example 3 in combination with the Herbicide No. 34, the compound of the preceding example. The test plants involved were soybeans as the crops and the weeds morningglory and velvetleaf.

The procedure used in conducting the tests of this example involved planting the test plants in separate pots and growing the soybeans to the 1.5 trifoliate stage, then applying the herbicide and tank-mixtures of the herbicide and antidote to the plant canopy (foliage) surface with the track sprayer delivering 20 gal. (75.71 liters) of liquid per acre (0.405 ha). All plants were sprayed when the soybeans reached the 1.5 trifoliate leaf stage. Observations of herbicidal activity were made thirteen (13) days after spraying the plants. Results are shown in Table 8.

TABLE 8

| Treatment Rate (Kg/Ha) | | | | |
|---|---|---|---|---|
| Ex./Antidote #3 | Herb #34 | Soybeans | Morning glory | Velvet leaf |
| 0 | 0 | 0.00 | 0.00 | 0.00 |
| 0 | 0.56 | 21 | 98 | 98 |
| 0 | 2.24 | 43 | 99 | 99 |
| .035 | 0 | 5 | 10 | 1 |
| .035 | .56 | 20 | 98 | 98 |
| .035 | 2.24 | 41 | 98 | 98 |
| .07 | 0 | 9 | 14 | 1 |
| .07 | .56 | 16 | 98 | 99 |
| .07 | 2.24 | 21 | 99 | 99 |
| .14 | 0 | 5 | 8 | 0 |
| .14 | .56 | 16 | 95 | 98 |
| .14 | 2.24 | 21 | 95 | 97 |
| 0.28 | 0 | 8 | 15 | 1 |
| 0.28 | 0.56 | 11 | 89 | 98 |
| 0.28 | 2.24 | 38 | 98 | 99 |
| 0.56 | 0 | 5 | 15 | 1 |
| 0.56 | 0.56 | 19 | 98 | 99 |
| 0.56 | 2.24 | 31 | 99 | 99 |

As noted in the data in Table 8, soybean injury was reduced from about 21% when treated with 0.56 kg/ha of herbicide alone to about 11% when, at the same herbide rate, 0.28 kg/ha of antidote was present. Weed control was excellent for morningglory and velvetleaf. The data also indicates that for Antidote No. 3 rates of 0.28 kg/ha soybean injury due to Herbicide No. 34 was excessive. It was also observed that even at the higher antidote rates, at the time of observation all soybeans were actively growing out of their injury, whereas both weeds were mostly dead.

Example 47

This example describes a field test evaluation of the postemergence activity of the same herbicide/antidote combination used in the greenhouse tests of Example 46.

Velvetleaf and morningglory seed (3.5 gal.; 13.251) were blended together and seeded with a cyclone spreader (setting 1.5) mounted on the tri-motorcycle (spacing every 25 ft; 7.62 meters) and incorporated into the soil (silt loam) with a culti-packer to a depth of 1.0 in. (2.54 cm). A four-row John Deere Maxi-merge planter with 20 in. (50.8 cm) row spacings was used to plant 4 rows of the soybeans (Williams) 1.0 in. (2.54 cm) in the soil.

No overhead irrigation was employed in this test as soil conditions, i.e., hot and humid with excellent soil moisture, were extremely favorable for fast soybean growth.

The soybeans were allowed to grow to the 1.5 trifoliate stage (two weeks) at which time the herbicide alone and tank mixtures of the herbicide/antidote combination were applied to the plant canopy surface with a small plot tractor-mounted sprayer delivering 30 gal. (113.56 l) of liquid per acre (0.405 ha). A randomized block design with three replicates of each treatment was used. Each plot was 12 ft×25 ft (3.66 m×7.62 m)..

Evaluations ("Eval") of herbicidal activity were made 5 and 14 days after treatment (DAT). Results are shown in Table 9, in which the following symbols are used to represent plants.
S = Soybeans
MG = Morningglory
VL = Velvetleaf
P = Purslane
CW = Carpetweed

TABLE 9

| Eval. (DAT) | Treatment Rate (Kg/Ha) Herb No. 34 | Ex./Anti- dote 3 | % Inhibition (Avg. 3 reps) | | | | |
|---|---|---|---|---|---|---|---|
| | | | S | MG | VL | P | CW |
| 5 | 0 | 0 | 0 | 0 | 0 | 0 | 0 |
| 14 | 0 | 0 | 0 | 0 | 0 | 0 | 0 |
| 5 | 0.0175 | 0 | 15 | 75 | 83 | 93 | 96 |
| 14 | 0.0175 | 0 | 10 | 65 | 85 | 87 | 96 |
| 5 | 0.035 | 0 | 20 | 85 | 92 | 95 | 96 |
| 14 | 0.035 | 0 | 18 | 77 | 93 | 95 | 97 |
| 5 | 0.07 | 0 | 27 | 92 | 97 | 97 | 99 |
| 14 | 0.07 | 0 | 23 | 87 | 99 | 95 | 98 |
| 5 | 0.07 | 0.28 | 15 | 90 | 96 | 97 | 99 |
| 14 | 0.07 | 0.28 | 12 | 90 | 93 | 93 | 98 |

The results of the above field test indicate that Herbicide No. 34 is extremely active against noxious weeds even at rates as low as 0.0175 kg/ha (1/64 lb/ac). At 0.035 kg/ha (1/32 lb/ac) and without an antidote, soybean injury is slightly above commercially-desirable levels (15%), whereas weed control is excellent. At 0.07 kg/ha (1/16 lb/ac) Herbicide No. 34 caused injury to soybeans above the commercially-desirable level. However, when 0.28 kg/ha (1/4 lb/ac) of Antidote No. 3 was mixed with 0.07 kg/ha of the herbicide, soybean injury was reduced to commercially-acceptable levels with substantially complete weed control.

Symptomology on the soybeans indicated some initial brown spotting present, but no further development of herbicide injury (severe burn). Results were more dramatic at 5 DAT than at 14 DAT when all soybean plants appeared to outgrow injury.

Example 48

Using the same procedure described in Example 45, but substituting n-butyl 2-(5-fluoro-2-nitrophenoxy) propanoate as the starting alkoxycarbonyl alkoxy nitrobenzene, there was prepared 5-trifluoromethyl-4-chloro-3-(3'-[1-n-butoxycarbonyl]ethoxy-4'-nitrophenoxy)-1-methylpyrazol, N25/D 1.5102. (Herbicide No. 35)

Example 49

Following the procedure described in Example 46, postemergence tests were conducted in the greenhouse to determine the antidotal activity of the compounds of Examples 3 and 20 (Antidote Nos. 3 and 20, respectively) against the heterocycyl phenyl ether prepared in the preceding example, i.e., Herbicide No. 35, in soybeans; no weeds were present in this test. Observations of herbicidal activity on the whole plant were made ten days after treatment (DAT); observation of initial activity at the first trifoliate stage was made the day following treatment. Test results are shown in Table 10.

TABLE 10

| Ex./Anti- dote No. | Rate (Kg/Ha) | Herb #35 (Kg/Ha) | % Soybean Injury (Avg. 2 reps) | |
|---|---|---|---|---|
| | | | 1 DAT | 10 DAT |
| — | — | 0.56 | 80 | 50 |
| — | — | 2.24 | 90 | 50 |
| 3 | 2.24 | — | 15 | 5 |
| 3 | 0.14 | 0.56 | 95 | 50 |
| 3 | 0.14 | 2.24 | 90 | 40 |
| 3 | 0.56 | 0.56 | 80 | 35 |
| 3 | 0.56 | 2.24 | 90 | 35 |
| 3 | 2.24 | 0.56 | 90 | 35 |
| 3 | 2.24 | 2.24 | 90 | 35 |
| 20 | 2.24 | — | 20 | 10 |
| 20 | 0.14 | 0.56 | 90 | 28 |
| 20 | 0.14 | 2.24 | 90 | 25 |
| 20 | 0.56 | 0.56 | 80 | 30 |
| 20 | 0.56 | 2.24 | 90 | 35 |
| 20 | 2.24 | 0.56 | 85 | 25 |
| 20 | 2.24 | 2.24 | 95 | 35 |

Neither antidote reduced initial leaf burn caused by Herbicide No. 35; however, regrowth was enhanced substantially after ten days, particularly when treated with Antidote No. 20. The 50% injury caused by the herbicide 10 DAT at 0.56 kg/ha was reduced to 28% by 0.14 kg/ha of Antidote No. 20. Similar reductions in soybean injury were effected by other herbicide/antidote ratios with Antidote No. 20 and to a lesser extent with Antidote No. 3.

The above specifically mentioned herbicidal compounds are intended merely as exemplary of the classes of herbicides which they represent. However, it is expressly contemplated that many other herbicidal compounds analogous to those represented herein having a variety of equivalent radicals substituted on the central nucleus may similarly be safened to various crop plants to a greater or lesser extent with the antidotal compounds of this invention. For example, other u-haloacetanilide compounds useful as herbicides are described in U.S. Pat. Nos. 3,442,945, 3,547,620, 3,830,841, 3,901,768, 4,517,011, 4,601,745, 4,319,918, 3,586,496 and 3,574,746.

Herbicidally-useful thiocarbamate compounds are described in U.S. Pat. Nos. 2,913,327, 3,330,643 and 3,330,821.

Other herbicidal pyridine compounds are described in U.S. Pat. No. 4,692,184 and copending U.S. Ser. Nos. 07/134,231 (U.S. Pat. No. 4,988,384) and 07/134,232, (U.S. Pat. No. 4,826,532) both of common assignment herewith.

Herbicidally-useful heterocycyl phenyl ethers (especially pyrazolyl aryl ethers) are described in U.S. Pat. No. 4,298,749 and popending U.S. Ser. Nos. 07/175,460 (abandoned), entitled "Substituted 3-(4-Nitrophenoxy) Pyrazoles and Their Use As Herbicides", of common assignment herewith.

Herbicidal diphenyl ethers and nitrophenyl ethers include 2,4-dichlorophenyl 4'-nitrophenyl ether ("nitrofen"), 2-chloro-1-(3'-ethoxy-4'-nitrophenoxy)-4-trifluoromethylbenzene ("Oxyfluorfen"), 2',4'-dichlorophenyl 3-methoxy-4-nitrophenyl ether ("Chlormethoxynil"), methyl 2-[4'-(2", 4"-dichlorophenoxy)-phenoxy]-propionate, N-(2'-phenoxyethyl)

2-[5′-(2″-chloro-4″-trifluoromethylphenoxy)-phenoxy]-propionamide, 2-methoxyethyl 2-[nitro-5-(2-chloro-4-trifluoromethylphenoxy)-phenoxyl-propionate]and 2-chloro-4-trifluoromethylphenyl 3′-oxazolin-2′-yl-4′-nitrophenylether.

Another generic class of agrichemically-important herbicidal compounds specifically contemplated for use in combination with the antidotal compounds of this invention are the ureas and sulfonylurea derivatives. Important herbicidal ureas include 1-(benzothiazol-2-yl)-1,3-dimethylurea; phenylureas, for example: 3-(3-chloro-p-tolyl)-1,1-dimethylurea ("chlorotoluron"), 1,1-dimethyl-3-(α,α,αtrifluoro-m-tolyl) urea ("fluometuron"), 3-(4-bromo-3-chlorophenyl)-methoxy-1-methylurea ("chlorbromuron"), 3-(4-bromophenyl)-1-methoxy-1-methylurea ("metobromuron"), 3-(3,4-dichlorophenyl)-l-methoxy-l-methylurea ("linuron"), 3-(4-chlorophenyl)-1-methoxy-1-methylurea ("lemonolinuron"), 3-(3,4-dichlorophenyl)-1,1-dimethyl-urea ("diuron"), 3-(4-chlorophenyl)-1,1-dimethylurea ("monuron") and 3-(3-chloro-4-methoxyphenyl)-1,1-dimethylurea ("metoxuron");

Important herbicidal sulfonylureas specifically contemplated as useful in compositions with the antidotal compounds of this invention include those disclosed in the following patents: U.S. Pat. Nos. 4,383,113, 4,127,405, 4,481,029, 4,514,212, 4,420,325, 4,638,004, 4,675,046, 4,681,620, 4,741,760, 4,723,123, 4,411,690, 4,718,937, 4,620,868, 4,668,277, 4,592,776, 4,666,508, 4,696,695, 4,731,446 and 4,668,279 and EP Numbers 084224, 173312, 190105, 256396, 264021, 264672, 142152, 244847, 176304, 177163, 187470, 187489, 184385, 232067, 234352, 189069, 224842, 249938, 246984 and 246984.

Among the herbicidal sulfonylureas disclosed in one or more of the above patents which are of particular interest are mentioned the species N-[(4-methoxy-6-methylpyrimidin-2-yl)aminocarbonyl]-3.-chloro-4-methoxycarbonyl-1-methylpyrazole-5-sulfonamide, N-[(4,6-dimethoxypyrimidin-2-yl)aminocarbonyl]-3-chloro-4-methoxycarbonyl-1-methylpyrazole-5-sulfonamid e N-[(4-methoxy-6-methylpyrimidin-2-yl)aminocarbonyl]-3-chloro-4-ethoxycarbonyl-1-methylpyrazole-5, sulfonamide, N-[(4,6-dimethoxypyrimidin-2-yl)aminocarbonyl]-3-chloro-4-ethoxycarbonyl-1-methylpyrazole-5 -sulfonamide, N-[(4,6-dimethoxypyrimidin-2-yl)aminocarbonyl]-3-bromo-4-ethoxycarbonyl-1-methylpyrazole- 5-sulfonamide and N-(methoxycarbonyl-1-phenyl sulfonyl-N′-(bis-difluoromethoxy pyrimidin-2-yl)urea.

Other herbicidal imidazolinone or imidazolidinone or -dione compounds within the purview of this invention which may be safened for use in various crops include the compounds disclosed in the following exemplary publications: EP Numbers 041623, 198552 and 216360; JA 1109-790, JA 1197-580A, GB 2 172 886A, J6 1183-272A and and Australian published Application No. AU 8661-073A and U.S. Pat. Nos. 4,188,487, 4,297,128, 4,647,301, 4,638,068, 4,650,514, 4,562,257, 4,554,013, 4,709,036, 4,749,404 and 4,741,767.

Still other classes of herbicidal compounds contemplated for combination with the antidotes of this invention include the following representative species:

Triazines and triazinones: 2,4-bis-(isopropylamino)-6-methylthio-1,3,5-triazine ("prometryn"), 2,4-bis-(ethylamino)-6-methylthio-1,3,5-triazine ("simetryn"), 2-(1′,2′-dimethylpropylamino)-4-ethylamino-6-methylthio-1,3,5-triazine ("dimethametryn"), 2-chloro-4,6-bis-(ethylamino)-1,3,5-triazine ("simazine"), 2-tert-butylamino-4-chloro-6-ethylamino-1,3,5-triazine ("terbuthylazine"), 2-tert-butylamino-4-ethylamino-6-methoxy-1,3,5-triazine ("terbumeton"), 2-tertbutylamino-4-ethylamino-6-methylthio-1,3,5-triazine ("terbutryn"), 2-ethylamino-4-isopropylamino-6-methylthio-1,3,5-triazine ("ametryn") and 3,4-bis-(methylamino)-6-tert-butyl-4,4-dihydro-1,2,4-triazin-5-one.

Benzoic acid derivatives: 5-(2′-chloro-4′-trifluoromethylphenoxy)-2-nitrobenzoic acid ("Acifluorfen") and 2,6-dichlorobenzonitrile ("dichlobenil"). Oxadiazolones: 5-tert-butyl-3-(2′,4′-dichloro-5′-isopropoxyphenyl)-1,3,4-oxadiazol-2-one ("Oxadiazon").

Phosphates: S-2-methylpiperidinocarbonylmethyl O,O-dipropyl phosphorodithioate ("Piperophos").

Pyrazoles: 1,3-dimethyl-4-(2′,4′-dichlorobenzolyl)-5-(4′-tolylsulfonyloxy)-pyrazole.

Also α-(phenoxyphenoxy)-propionic acid derivatives and α-pyridyl-2-oxyphenoxy)-propionic acid derivatives.

As will be appreciated by those skilled in the art, the practice of this invention comprises the use of the novel antidotal compounds disclosed and claimed herein with any herbicidally-active compound. Obviously, the above listings of exemplary compounds is not intended to be exhaustive, but representative. Again, as noted earlier herein, it is expected that not every combination of herbicide and antidote will result in safening of all crops, but is within the skill of the art to test any given herbicide with an invention antidote in plant screens of any spectrum of plants and note the results.

The foregoing embodiments illustrate that the combinations of herbicide and antidote of this invention are useful in controlling weeds while reducing herbicidal injury to crop plants under greenhouse and field test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8-18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, longchain alcohols usually containing 10-18 carbon atoms, and condensation products of ethylene oxide with fatty acids, alkylphenols, and mercaptans.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

We claim:

1. Compositons comprisinga herbicidally-effective amount of a herbicidal compound selected from the group consisting of 2-haloacetanilides, thiocarbamates, dinitroanilines, sulfonylureas, imidazolidinones, pyridinecarboxylic acid methyl esters, pyrrollidinones, benzoic acid salts and esters, triazinones, pyridazinones, isoxazolidinones, imidazoles and phenoxypyrazoles and an antidotally-effective amount of a compound according to the formula

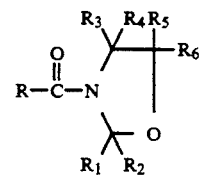

and agriculturally-acceptable salts thereof wherein
R is halomethyl;
$R_1$ is $C_{1-4}$ alkyl, haloalkyl or phenyl;
$R_2$–$R_5$ are H or $C_{1-4}$ alkyl;
$R_6$ is a saturated or unsaturated $C_{5-10}$ oxygen, nitrogen or sulfur atoms, optionally substituted with a $C_{1-4}$ alkyl or haloalkyl radical or halogen atom or with oxygen on a ring nitrogen atom and
$R_5$ and $R_6$ may be combined to form a spiroheterocyclic ring as defined for the $R_6$ radical.

2. Compositions according to claim 1 wherein said herbicidal compound is a thiocarbamate compound.

3. Compositions according to claim 2 wherein said thiocarbamate herbicide is EPTC.

4. Compositions according to claim 1 wherein said herbicidal compound is an α-haloacetanilide compound.

5. Compositions according to claim 4 wherein said α-haloacetanilide is selected from the group consisting of
alachlor,
acetochlor,
butachlor,
metolachlor,
metazochlor,
2-chloro-21-methyl-61-methoxy-N-(isopropoxymethyl)acetanilide,
2-chloro-2'-methyl-61-trifluoromethyl-N-(ethoxymethyl)acetanilide, and
2-chloro-2',6'1-dimethyl-N-(2-methoxyethyl)acetanilide.

6. Composition according to claim 1 wherein said herbicidal compound is a sulfonylurea selected from the group consisting of
benzenesulfonamide, 2-chloro-N-[[(4-methoxy-6-methyl-1,3,5-triazin-2-yl)amino]carbonyl];
benzoic acid, 2-[[[[(4-chloro-6-methoxy-2-pyrimidinyl)amino]carbonyl]amino]sulfonyl]-ethyl ester;
2-thiophenecarboxylic acid, 3-[[[[(4,6-dimethoxy-1,3,5-triazin-2-yl)amino]carbonyl]amino]sulfonyl]-,methyl ester;
benzoic acid, 2-[[[[(4,6-dimethyl-2-pyrimidinyl)amino]carbonyllamino]sulfonyl]methyl ester;
benzenesulfonamide, 2-(2-chloroethoxy)-N-[[(4-methoxy-6-methyl-1,3,5-triazin-2-yl)amino]carbonyl]
benzoic acid, 2-[[[[(4-methoxy-6-methyl-1,3,5-triazin-2-yl)amino]carbonyl]amino]sulfonyl]-,methyl ester;

7. Composition according to claim 1 wherein said herbicidal compound is a heterocycyl phenyl ether selected from the group consisting of 5-(trifluoromethyl)-4-chloro-3-(31-[1-ethoxycarbonyl]-ethoxy-41-nitrophenoxy) -1-methylpyrazol;

1-(trifluoromethyl)-4-chloro-3-(3'-methoxy-4'-nitrophenoxy)-1-methylpyrazole;

5-(trifluoromethyl)-4-chloro-3-(3'-[1-n-butoxycarbonyl]-ethoxy-41-nitrophenoxy) -1-methylpyrazol;

5-(trifluoromethyl)-4-chloro-3-(3'-methylsulfamoylcarbonylpropoxy-4'-nitrophenoxy)-1-methylpyrazo l;

5-(trifluoromethyl)-4-chloro-3-(3'-propoxycarbonylmethyloxime-4'-nitrophenoxy)-1-methylpyrazole and (±)-2-[4-[[5-(trifluoromethyl)-2-pyridinyl]oxy]-phenoxy]propanoic acid.

8. Composition according to claim 1 wherein said herbicidal compound is a pyridine selected from the group consisting of 3-pyridinecarboxylic acid, 2-(difluoromethyl)-5-(4,5-dihyro-2-thiazolyl)-4-(2-methylpropyl)-6-(trifluoromethyl)-, methyl ester;

3-pyridinecarboxylic acid, 2-(difluoromethyl)-4-(2-methylpropyl)-5-(1H-pyrazol-1-ylcarbonyl)-6-(trifluoromethyl)-, methyl ester;

3,5-pyridine dicarbothioic acid, 2-(difluoromethyl)-4-(2-methylpropyl) -6-(trifluoromethyl)-, S,S-dimethyl ester; and 3,5-pyridinedicarboxylic acid, 2-(difluoromethyl)-4-(2-methylpropyl) 6-(trifluoromethyl), dimethyl ester.

9. Composition according to claim 1 wherein said herbicidal compound is selected from the group consisting of 2-chloro-4-(ethylamino)-6-(isopropylamino)-sym-triazine;

4-amino-6-tertbutyl-3-(methylthio)-AS-triazine-5(4H)one;

2-chloro-4-(1-cyano-1-methylethylamino)-6-ethylamino-1,3,5-triazine;

trifluoro-2,6-dinitro-N,N-dipropy)--p-toluidine;

benzeneamine, N-(1-ethylpropyl)-3,4-dimethyl-2,6-dinitro-;

2-pyrrolidinone, 3-chloro-4-(chloromethyl) -1-[3-(trifluoromethyl)phenyl], trans-;

3-isoxazolidinone,2-[(2-chlorophenyl) methyl]-4,4-dimethyl-;

2-imidazolidinone, 3-[5-(1,1-dimethylethyl) -3-isoxazolyl]-4-hydroxy-l-methyl-;

2-methoxy-3,6-dichlorobenzoic acid, dimethylamine salt;

methyl 5-(2,4-dichlorophenoxy)-2-nitrobenzoate;

1'-(carboethoxy)ethyl 5-[2-chloro-4-(trifluoromethyl)phenoxy]-2-nitrobenzoate;

ammonium-DL-homoalanin-4-yl(methyl) phosphinate and 2-(3,4-dichlorphenyl)-4-methyl-1,2,4-oxadiazolidine-3,5-dione. &

10. Compositions according to any one of claimes 1, 2-6, 7, 8 or 9 wherein R in said formula is a dihalomethyl radical.

11. Compositions according to claim 10 wherein said radical is a dichloromethyl radical.

12. Compositions according to claim 11 wherein $R_1$ and $R_2$ are both $C_{1-4}$ alkyl radicals.

13. Compositions according to claim 12 wherein said alkyl radicals are methyl.

14. Compositions according to claim 13 wherein $R_3$, $R_4$ and $R_5$ are hydrogen.

15. Compositions according to claim 14 wherein $R_6$ is a $C_5$ heterocyclic radical containing oxygen as the hetero atom.

16. Compositions according to claim 15 in which the antidotally-effective compound is oxazolidine, 3-(dichloroacetyl)-5-(2-furanyl)-2,2-dimethyl.

17. Compositions according to claim 14 wherein $R_6$ is a $C_6$ heterocyclic radical containing nitrogen as the hetero atom.

18. Compositions according to claim 17 in which the antidotally-effective compound is oxazolidinyl, 3-(dichloroacetyl)-5-(3-pyridyl)-2,2-dimethyl)-.

19. Compositions according to claim 14 wherein $R_6$ is a $C_5$ heterocyclic radical containing sulfur as the hetero atom.

20. Compositions according to claim 14 in which the antidotally-effective compound is oxazolidine, 3-(dichloroacetyl)-5-(2-thienyl)-2,2-dimethyl-.

21. Compositions according to claim 11 wherein $R_1$ is trifluoromethyl and $R_2$ is $C_{1-4}$ alkyl.

22. Compositions according to claim 21 wherein $R_2$ is methyl and $R_3$, $R_4$ and $R_5$ are hydrogen.

23. Compositions according to claim 22 wherein $R_6$ is a $C_5$ heterocyclic radical containing oxygen as the hetero atom.

24. Compositions according to claim 23 in which the antidotally-effective compound is oxazolidine, 3-(dichloroacetyl)-5-(2-furanyl)-2-methyl-2-(tri-fluoromethyl)-.

25. Compositions according to claim 22 wherein $R_6$ is a $C_5$ heterocyclic radical containing sulfur as the hetero atom.

26. Compositions according to Claim 25 wherein the antidotal component comprises a mixture of the cis- and trans-isomers of oxazolidine, 3-(dichloroacetyl)-2-methyl-5-(2-thienyl)-2-trifluoromethyl)-.

27. Composition comprising
(a) a herbicidally-effective amount of a herbicidal compound selected from the group consisting of alachlor,
acetochlor,
metolachlor,
metazochlor,
2-chloro-2'-methyl-6'-methoxy-N-(isopropoxyMethyl)acetanilide,
2-chloro-2'-methyl-6'-trifluoromethyl-N-(ethoxymethyl)acetanilide, and
2-chloro-2',6'-dimethyl-N-(2-methoxyethyl)acetanilide; and
(b) an antidotally-effective amount of a compound selected from the group consisting of
oxazolidine, 3-(dichloroacetyl)-2,2-dimethyl-5-(2-thienyl)-,
oxazolidine, 3-(dichloroacetyl)-5-(2-furanyl)-2,2-dimethyl-, and
oxazolidine, 3-(dichloroacetyl)-5-(3-pyridyl)-2,2-dimethyl-.

28. Composition according to Claim 27 wherein said herbicidal compound is alachlor and said antidotally-effective compound is oxazolidine, 3-(dichloroacetyl)-5-(2-furanyl)-2,2-dimethy-.

29. Composition according to claim 27 wherein said herbicidal compound is acetochlor and said antidotally-effective compound is oxazolidine, 3-(dichloroacetyl)-5-(2-furanyl)-2,2-dimethyl-.

30. Composition according to claim 27 wherein said herbicidal compound is alachlor and said antidotally-effective compound is oxazolidine, 3-(dichloroacetyl)-5-(3-pyridyl)-2,2-dimethyl-.

31. Composition according to claim 27 wherein said herbicidal compound is acetochlor and said antidotally-effective compound is oxazolidine, 3-(dichloroacetyl)-5-(3-pyridyl)-2,2-dimethyl-.

32. Method for reducing phytotoxicity to crop plants due to herbicidal compounds selected from the group consisting of 2-haloacetanilides, thiocarbamates, dinitroanilines, sulfonylureas, imidazolidinones, pyridinecarboxylic acid methyl esters, pyrrollidinones, benzoic acid salts and esters, triazinones, pyridazinones, isoxazolidinones, imidazoles and phenoxypyrazoles which comprises applying to the locus of the crop plant an antidotally-effective amount of a compound according to the formula

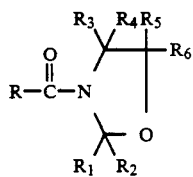

and agriculturally-acceptable salts thereof wherein
R is halomethyl;
$R_1$ is $C_{1-4}$ alkyl, haloalkyl or phenyl;
$R_2$–$R_5$ are H or $C_{1-4}$ alkyl;
$R_6$ is a saturated or unsaturated $C_{5-10}$ heterocyclic radical containing 1 or 2 oxygen, nitrogen or sulfur atoms, optionally substituted with a $C_{1-4}$ alkyl or haloalkyl radical or halogen atom or with oxygen on a ring nitrogen atom and
$R_5$ and $R_6$ may be combined to form a spiroheterocyclic ring as defined for the $R_6$ radical.

33. Method according to claim 32 wherein said herbicidal compound is a thiocarbamate compound.

34. Method according to claim 33 wherein said thiocarbamate herbicide is EPTC.

35. Method according to claim 32 wherein said herbicidal compound is an α-haloacetanilide compound.

36. Method according to claim 35 wherein said α-haloacetanilide is selected from the group consisting of
alachlor,
acetochlor,
butachlor,
metolachlor,
metazochlor,
2-chloro-2'-methyl-6'-methoxy-N-(isopropoxymethyl)acetanilide,
2-chloro-2'-methyl-6'-trifluoromethyl-N-(ethoxymethyl)acetanilide, and
2-chloro-2',6'-dimethyl-N-(2-methoxyethyl)-acetanilide.

37. Method according to claim 32 wherein said herbicidal compound is a sulfonylurea.

38. Method according to claim 32 wherein said herbicidal compound is a heterocycyl phenyl ether.

39. Method according to claim 32 wherein said herbicidal compound is a pyridine.

40. Method according to claim 32 wherein said herbicidal compound is selected from the group consisting of
2-chloro-4-(ethylamino)-6-(isopropylamino)-sym-triazine;
4-amino-6-tertbutyl-3-(methylthio)-AS-triazine-5(4H)one;
2-chloro-4-(l-cyano-l-methylethylamino)-6-ethylamino-1,3,5-triazine;
trifluoro-2,6-dinitro-N,N-dipropy)-p-toluidine;
benzeneamine, N-(1-ethylpropyl)-3,4-dimethyl-2,6-dinitro-;
2-pyrrolidinone, 3-chloro-4-(chloromethyl) -1-[3-(trifluoromethyl)phenyl], trans-;
3-isoxazolidinone,2-[(2-chlorophenyl) methyl]-4,4-dimethyl-;
2-imidazolidinone, 3-[5-(1,1-dimethylethyl) -3-isoxazolyl]-4-hydroxy-l-methyl-;
2-methoxy-3,6-dichlorobenzoic acid, dimethylamine salt;
methyl 5-(2,4-dichlorophenoxy)-2-nitrobenzoate;
1'-(carboethoxy)ethyl 5-[2-chloro-4-(trifluoromethyl)phenoxy]-2-nitrobenzoate;
ammonium-DL-homoalanin-4-yl(methyl) phosphinate [Glufosinate-Ammonium]and
2-(3,4-dichlorphenyl)-4-methyl-1,2,4-oxadiazolidine-3,5-dione.

41. Method according to any of claims 32, 33–37 38, 39, 40, 41, wherein R in said formula is a dihalomethyl radical.

42. Method according to claim 41 wherein said radical is a dichloromethyl radical.

43. Method according to claim 41 wherein $R_1$ and $R_2$ are both $C_{1-4}$ alkyl radicals.

44. Method according to claim 43 wherein said alkyl radicals are methyl.

45. Method according to claim 44 wherein $R_3$, $R_4$ and $R_5$ are hydrogen.

46. Method according to claim 45 wherein $R_6$ is a $C_5$ heterocyclic radical containing oxygen as the hetero atom.

47. Method according to claim 46 in which the antidotally-effective compound is oxazolidine, 3-(dichloroacetyl)-5-(2-furanyl)2,2-dimethyl.

48. Method according to claim 45 wherein $R_6$ is $C_6$ heterocyclic radical containing nitrogen as the hetero atom.

49. Method according to claim 48 in which the antidotally-effective compound is oxazolidine, 3-(dichloroacetyl)-5-(3-pyridyl)-2,2-dimethyl-.

50. Method according to claim 45 wherein $R_6$ is a $C_5$ heterocyclic radical containing sulfur as the hetero atom.

51. Method according to claim 50 in which the antidotally-effective compound is oxazolidine, 3-(dichloroacetyl)-5-(2-thienyl)-2,2-dimethyl-.

52. Method according to claim 42 wherein $R_1$ is trifluoromethyl and $R_2$ is $C_{1-4}$ alkyl.

53. Method according to claim 52 wherein $R_2$ is methyl and $R_3$, $R_4$ and $R_5$ are hydrogen.

54. Method according to claim 53 wherein $R_6$ is a $C_5$ heterocyclic radical containing oxygen as the hetero atom.

55. Method according to claim 54 in which the antidotally-effective compound is oxazolidine, 3-(dichloroacetyl)-5-(2-furanyl)-2-methyl-2-(trifluoromethyl)-.

56. Method according to claim 53 wherein $R_6$ is a $C_5$ heterocyclic radical containing sulfur as the hetero atom.

57. Method according to claim 56 which comprises a mixture of the cis- and trans-isomers of oxazolidine, 3-(dichloroacetyl)-2-methyl-5-(2-thienyl)-2-trifluoromethyl)-.

58. Method according to claim 32 wherein said crop plant includes corn, sorghum, rice and soybeans.

59. Method according to claim 58 wherein said crop plant locus is treated with a composition comprising
   (a) a herbicidally-effective amount of a herbicidal compound selected from the group consisting of
   alachlor,
   acetochlor,
   metolachlor,
   metazochlor,
   2-chloro-2'-methyl-6'-methoxy-N-(isopropoxymethyl)acetanilide,
   2-chloro-2'-methyl-6'-trifluoromethyl-N-(ethoxymethyl)acetanilide,
   2-chlciro-2',6'-dimethyl-N-(2-methoxyethyl)acetanilide, and EPTC; and
   (b) an antidotally-effective amount of a compound selected from the group consisting of
   oxazolidine, 3-(dichloroacetyly-2,2-dimethyl-5-(2-thienyl)-,
   oxazolidine, 3-(dichloroacetyl)-5-(2-furanyl)-2,2-dimethyl-, and
   oxazolidine, 3-(dichloroacetyl)-5-(3-pyridyl)-2,2-dimethyl-.

60. Method according to claim 59 wherein said crop plant is corn.

61. Method according to claim 60 wherein component (b) is oxazolidine, 3-(dichloroacetyl)-5-2-dimethyl- 62. Method according to claim 61 wherein said herbigidal compound is alachlor.

63. Method according to claim 61 wherein said herbicidal compound is acetochlor.

64. Method according to claim 61 wherein said herbicidal compound is metolachlor.

65. Method according to claim 61 wherein said herbicidal compound is metazochlor.

66. Method according to claim 61 wherein said herbicidal compound is EPTC.

67. Method according to claim 59 wherein said crop plant is sorghum.

68. Method according to claim 67 wherein component (b) is oxazolidine, 3-(dichloroacetyl)-5-(2-furanyl)-2,2-dlmethyl-.

69. Method according to claim 69 wherein said herbicidal compound is alachlor.

70. Method according to claim 68 wherein said herbicidal compound is metolachlor.

71. Method according to claim 68 wherein said herbicidal compound is EPTC.

72. Method according to claim 59 wherein said crop plant is soybeans.

73. Method according to claim 72 wherein component (b) is oxazolidine, 3-(dichloroacetyl)-5-(2-furanyl 2-dimethyl-.

74. Method according to claim 73 wherein said herbicidal compound is acetochlor.

75. Composition comprising
   (a) a herbicidally-effective amount of a herbicidal compound selected from the group consisting of
   alachlor,
   acetochlor,
   metolachlor,
   metazachlor
   2-chloro-2'-methyl-6'-methoxy-N-(isopropoxymethyl)acetanilide
   2-chloro-2'-methyl-6'-trifluoromethyl-N-(ethoxymethyl)acetanilide, and
   2-chloro-2', 6'-dimethyl-N-(2-methoxyethyl)acetanilide and
   (b) an antidotally-effective amount of oxazolidine, 3-(dichloroacetyl)-5-(2-furanyl)-2,2-dimethyl-,.

76. Compositon according to claim 75 wherein said herbicidal compound is alachlor.

77. Composition according to claim 75 wherein said herbicidal compound is acetochlor.

78. Method for reducing phytotoxicity to crop plants due to a herbicidal compound selected from the group consisting of
   alachlor,
   acetochlor,
   metolachlor,
   metazachlor
   2-chloro-2'-methyl-6'-methoxy-N-(isopropoxymethyl)acetanilide,
   2-chloro-2'- methyl-6'trifluoromethyl-N-(ethoxymethyl)acetanilide, and
   2-chloro-2', 6'-dimethyl-N-(2-methoxyethyl) acetanilide
which comprises applying to the plant locus a herbicidally-effective amount of oxazolidine, 3-(dichloroacetyl)-5(2-furanyl)-2,2-dimethyl-,.

79. Method according to claim 78 wherein said herbicide is alachlor.

80. Method according to claim 78 wherein said herbicide is acetochlor.

81. Method according to either of claims 79 or 80 wherein said crop plant is corn.

* * * * *